US009255149B2

(12) United States Patent
Himmler et al.

(10) Patent No.: US 9,255,149 B2
(45) **Date of Patent: *Feb. 9, 2016**

(54) CYTOTOXIC IMMUNOGLOBULIN

(71) Applicant: F-star Biotechnologische Forschungs- und Entwicklungsges.m.b.H., Cambridge (GB)

(72) Inventors: Gottfried Himmler, Gross-Enzersdorf (AT); Geert Mudde, Breitenfurt (AT); Anton Bauer, Wagram (AT); Gerda Redl, Gross-Enzersdorf (AT); Maximillian Woisetschlager, Oberwil (CH)

(73) Assignee: F-star Biotechnologische Forschungs- und Entwicklungsges.m.b.H, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/629,760

(22) Filed: Feb. 24, 2015

(65) Prior Publication Data

US 2015/0166665 A1 Jun. 18, 2015

Related U.S. Application Data

(63) Continuation of application No. 14/470,425, filed on Aug. 27, 2014, which is a continuation of application No. 12/990,119, filed as application No. PCT/EP2009/052509 on Mar. 3, 2009, now Pat. No. 8,859,738.

(30) Foreign Application Priority Data

May 2, 2008 (EP) .................................... 08450068

(51) Int. Cl.

| | |
|---|---|
| ***A61K 39/00*** | (2006.01) |
| ***C07K 16/28*** | (2006.01) |
| ***C07K 16/00*** | (2006.01) |
| ***C07K 16/32*** | (2006.01) |
| ***C07K 16/30*** | (2006.01) |

(52) U.S. Cl.

CPC ........... *C07K 16/2863* (2013.01); *C07K 16/005* (2013.01); *C07K 16/30* (2013.01); *C07K 16/32* (2013.01); *C07K 2317/52* (2013.01); *C07K 2317/524* (2013.01); *C07K 2317/526* (2013.01); *C07K 2317/53* (2013.01); *C07K 2317/565* (2013.01); *C07K 2317/73* (2013.01); *C07K 2317/732* (2013.01); *C07K 2317/734* (2013.01); *C07K 2317/76* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 5,223,409 | A | 6/1993 | Ladner et al. | 435/69.7 |
| 5,395,750 | A | 3/1995 | Dillon et al. | 435/5 |
| 5,475,100 | A | 12/1995 | Hashino et al. | 536/23.53 |
| 5,536,814 | A | 7/1996 | Ruoslahti et al. | 530/329 |
| 5,723,323 | A | 3/1998 | Kauffman et al. | 435/172.3 |
| 5,759,817 | A | 6/1998 | Barbas | 435/69.7 |
| 5,763,192 | A | 6/1998 | Kauffman et al. | 435/7.1 |
| 5,814,476 | A | 9/1998 | Kauffman et al. | 435/69.1 |
| 5,817,483 | A | 10/1998 | Kauffman et al. | 435/69.1 |
| 5,824,514 | A | 10/1998 | Kauffman et al. | 435/91.1 |
| 5,844,094 | A | 12/1998 | Hudson et al. | 530/387.3 |
| 5,892,019 | A | 4/1999 | Schlom et al. | 536/23.53 |
| 6,057,098 | A | 5/2000 | Buechler et al. | 435/6 |
| 6,294,654 | B1 | 9/2001 | Bogen et al. | 530/387.3 |
| 6,352,842 | B1 | 3/2002 | Short et al. | 435/69.1 |
| 6,358,709 | B1 | 3/2002 | Short et al. | 435/69.1 |
| 6,361,974 | B1 | 3/2002 | Short et al. | 435/69.1 |
| 6,365,377 | B1 | 4/2002 | Patten et al. | 435/91.1 |
| 6,376,246 | B1 | 4/2002 | Crameri et al. | 435/440 |
| 6,562,617 | B1 | 5/2003 | Anderson et al. | 435/235 |
| 6,602,684 | B1 | 8/2003 | Umana et al. | 435/69.1 |
| 7,442,778 | B2 | 10/2008 | Gegg et al. | 530/391.7 |
| 7,632,497 | B2 | 12/2009 | Stavenhagen | 424/133.1 |
| 7,645,861 | B2 | 1/2010 | Gegg et al. | 530/391.7 |
| 7,655,764 | B2 | 2/2010 | Gegg et al. | 530/391.7 |
| 7,655,765 | B2 | 2/2010 | Gegg et al. | 530/391.7 |
| 7,662,931 | B2 | 2/2010 | Gegg et al. | 530/391.7 |
| 7,750,127 | B2 | 7/2010 | Gegg et al. | 530/391.7 |
| 7,750,128 | B2 | 7/2010 | Gegg et al. | 530/391.7 |
| 7,858,090 | B2 | 12/2010 | Koide | 424/145.1 |
| 8,008,453 | B2 | 8/2011 | Gegg et al. | 530/391.7 |
| 8,580,927 | B2 | 11/2013 | Dimitrov | 530/387.3 |

(Continued)

FOREIGN PATENT DOCUMENTS

| | | | |
|---|---|---|---|
| AU | 2005/289685 | 4/2005 | A61K 47/48 |
| CN | 1606566 | 4/2005 | C07K 5/08 |

(Continued)

OTHER PUBLICATIONS

Adachi, et al., Interaction between the antigen and antibody is controlled by the constant domains: Normal mode dynamics of the HEL-HyHEL-10 complex, Protein Science, 12(10):2125-31, Oct. 2003.

Adib-Conquy et al., Effect of amino acid substitutions in the heavy chain CDR3 of an autoantibody on its reactivity, International Immunology 10:341-346, 1998.

Altschul et al, Local Alignment Statistics. Methods in Enzymology 266, pp. 460-480, 1996.

Amstutz et al., In vitro display technologies: novel developments and applications, Curr. Opin Biotechnol 12, pp. 400-405, 2001.

Arbabi et al., Selection and identification of single domain antibody fragments from camel heavy-chain antibodies, FEBS, 414, 521-526, 1997.

Asano et al., Humanization of the Bispecific Epidermal Growth Factor Receptor × CD3 Diabody and Its Efficacy as a Potential Clinical Reagent. Clinical Cancer Research, vol. 12, No. 13, pp. 4036-4042, 2006.

(Continued)

*Primary Examiner* — Brad Duffy

(74) *Attorney, Agent, or Firm* — Sunstein Kann Murphy & Timbers LLP

(57) ABSTRACT

The invention relates to a cytotoxic modular antibody with a molecular weight of up to 60 kD, specifically binding to a cell surface target with a binding affinity of $Kd<10^{-8}$ M, a method of producing such antibody and its use as a therapeutic.

30 Claims, 27 Drawing Sheets

(56) References Cited

U.S. PATENT DOCUMENTS

Figure 1:
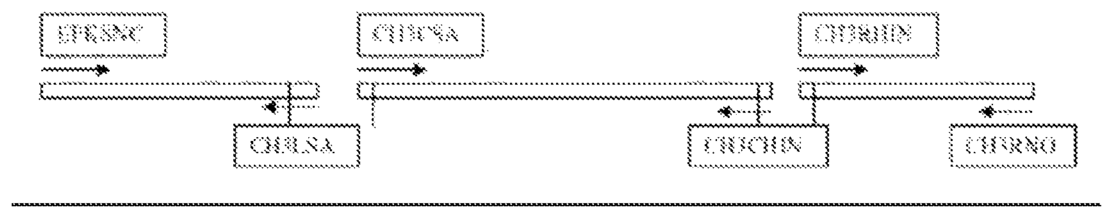

| | | | | |
|---|---|---|---|---|
| 8,921,279 | B2 | 12/2014 | Himmler et al. | 506/9 |
| 9,045,528 | B2 | 6/2015 | Ruker et al. | C07K 16/00 |
| 2002/0103345 | A1 | 8/2002 | Zhu | 530/388.15 |
| 2002/0106370 | A1 | 8/2002 | Cardy et al. | 424/133.1 |
| 2003/0027213 | A1 | 2/2003 | Zhu et al. | 435/7.1 |
| 2003/0129188 | A1 | 7/2003 | Barbas et al. | |
| 2003/0148372 | A1 | 8/2003 | Tomlinson et al. | 435/7.1 |
| 2003/0157091 | A1 | 8/2003 | Hoogenboom | 424/130.1 |
| 2004/0018508 | A1 | 1/2004 | Friedman | 435/6 |
| 2004/0043424 | A1 | 3/2004 | Baughn et al. | 435/7.1 |
| 2004/0063924 | A1 | 4/2004 | Tang et al. | 536/23.5 |
| 2004/0071690 | A1 | 4/2004 | Hudson et al. | 424/130.1 |
| 2004/0082508 | A1 | 4/2004 | Yue et al. | 514/12 |
| 2004/0097711 | A1 | 5/2004 | Yue et al. | 530/387.1 |
| 2004/0101905 | A1 | 5/2004 | Brekke et al. | 435/7.1 |
| 2004/0132101 | A1 | 7/2004 | Lazar et al. | 435/7.1 |
| 2004/0146976 | A1 | 7/2004 | Wittrup et al. | 435/69.1 |
| 2005/0054832 | A1 | 3/2005 | Lazar et al. | 530/387.3 |
| 2005/0069549 | A1 | 3/2005 | Herman | 424/178.1 |
| 2005/0158829 | A1 | 7/2005 | Fandl et al. | 435/69.1 |
| 2005/0244403 | A1 | 11/2005 | Lazar et al. | 424/130.1 |
| 2005/0255548 | A1 | 11/2005 | Lipovsek et al. | 435/69.1 |
| 2005/0266000 | A1 | 12/2005 | Bond et al. | 424/143.1 |
| 2006/0140934 | A1 | 6/2006 | Gegg et al. | 424/133.1 |
| 2008/0227958 | A1 | 9/2008 | Thompson et al. | 530/387.3 |
| 2009/0298195 | A1 | 12/2009 | Ruker et al. | 436/501 |
| 2010/0048877 | A1 | 2/2010 | Ruker et al. | 530/387.3 |
| 2011/0251375 | A1 | 10/2011 | Ruker et al. | 530/387.3 |
| 2012/0010388 | A1 | 1/2012 | Himmler | 530/387.3 |
| 2012/0028839 | A1 | 2/2012 | Ruker et al. | 506/14 |
| 2012/0094874 | A1 | 4/2012 | Ruker et al. | 506/18 |
| 2012/0276104 | A1 | 11/2012 | Woisetschlager | 424/136.1 |
| 2015/0153359 | A1 | 6/2015 | Himmler et al. | G01N 33/6857 |

FOREIGN PATENT DOCUMENTS

| | | | |
|---|---|---|---|
| EP | 1752471 | 2/2007 | C07K 16/00 |
| EP | 1772465 | 4/2007 | C07K 16/00 |
| EP | 1797127 | 6/2007 | A61K 47/48 |
| EP | 2028193 | 2/2009 | C07K 16/00 |
| EP | 1699826 | 11/2009 | |
| EP | 2158220 | 3/2010 | C07K 16/00 |
| EP | 2407487 | 1/2012 | C07K 16/30 |
| EP | 2451838 | 5/2012 | C07K 16/00 |
| JP | 2002-058479 | 2/2002 | C12N 15/09 |
| JP | 2003-518377 | 6/2003 | C12N 15/09 |
| WO | WO 90/07861 | 7/1990 | C12P 21/00 |
| WO | WO 92/09690 | 6/1992 | C12N 15/00 |
| WO | WO 93/08278 | 4/1993 | C12N 15/10 |
| WO | WO 93/23537 | 11/1993 | C12N 15/12 |
| WO | WO 96/22377 | 7/1996 | C12N 15/62 |
| WO | WO 97/20858 | 6/1997 | C07K 16/32 |
| WO | WO 97/34631 | 9/1997 | A61K 39/395 |
| WO | WO 00/42561 | 7/2000 | G06F 19/00 |
| WO | WO 00/71694 | 11/2000 | C12N 15/00 |
| WO | WO 01/01748 | 1/2001 | |
| WO | WO 01/70947 | 9/2001 | C12N 15/10 |
| WO | WO 01/83525 | 11/2001 | C07K 14/00 |
| WO | WO 01/88159 | 11/2001 | C12N 15/62 |
| WO | WO 02/06469 | 1/2002 | C12N 15/62 |
| WO | WO 02/32925 | 4/2002 | |
| WO | WO 02/44215 | 6/2002 | C07K 16/00 |
| WO | WO 02/060919 | 8/2002 | |
| WO | WO 02/088171 | 11/2002 | |
| WO | WO 03/012100 | 2/2003 | C12N 15/10 |
| WO | WO 03/029456 | 4/2003 | C12N 15/00 |
| WO | WO 03/075840 | 9/2003 | |
| WO | WO 2004/018674 | 3/2004 | C12N 15/10 |
| WO | WO 2004-044004 | 5/2004 | C07K 14/705 |
| WO | WO 2004/044011 | 5/2004 | |
| WO | WO 2005/021595 | 3/2005 | C07K 19/00 |
| WO | WO 2005-114215 | 12/2005 | G01N 33/68 |
| WO | WO 2006/033700 | 3/2006 | |
| WO | WO 2006/036834 | 4/2006 | C07K 19/00 |
| WO | WO 2006/072620 | 7/2006 | C07K 16/00 |
| WO | WO 2006/087637 | 8/2006 | C07K 16/32 |
| WO | WO 2008/003103 | 1/2008 | C07K 16/00 |
| WO | WO 2008/003116 | 1/2008 | C12N 15/09 |
| WO | WO 2008/119096 | 10/2008 | C07K 16/00 |
| WO | WO 2009/000006 | 12/2008 | C07K 16/00 |
| WO | WO 2009/099961 | 8/2009 | C07K 16/00 |
| WO | WO 2011/003811 | 1/2011 | C07K 16/00 |
| WO | WO 2012/007167 | 1/2012 | C07K 16/32 |
| WO | WO 2015/049537 | 4/2015 | C12Q 1/68 |

OTHER PUBLICATIONS

Auf Der Maur, Antigen-independent selection of intracellular stable antibody frameworks, Methods, 34:215-224, 2004.

Barbas III et al., Semisynthetic combinatorial antibody libraries: a chemical solution to the diversity problem. Proc. Nat'l. Acad. Sci. USA 89:4457-4461,1992.

Barclay, Membrane proteins with immunoglobulin-like domains—a master superfamily of interaction molecules. Seminars in Immunology,15:215-223, 2003.

Batey et al., Poster: Pre-clinical evaluation of FS102: a HER2 specific Fcab with a novel mechanism of action, AACR-NCI-EORTC International Conference on Molecular Targets and Cancer Therapeutics, 1 page, Oct. 21, 2013.

Batey et al., Abstract B123: Preclinical evaluation of FS102: a HER2-specific Fcab with a novel mechanism of action, Mol Cancer Ther., 12:B123, Nov. 2013.

Benhar et al., Highly efficient selection of phage antibodies Mediated by Display of Antigen as Lpp-OmpA Fusions on Live Bacteria 301, pp. 893-904, 2000.

Berntzen et al., Characterization of an FcgammaRI-binding peptide selected by phage display, Protein Eng Des Sel. 19(3):121-128, 2006.

Berntzen et al., Prolonged and increased expression of soluble Fe receptors, IgG and a TCR-Ig fusion protein by transiently transfected adherent 293E cells, J Immunol Methods. 298(1-2):93-104, 2005.

Berry et al., Development of functional human monoclonal single-chain variable fragment antibody against HIV-1 from human cervical B cells. Hybrid. Hybridomas, 22(2), pp. 97-108, Apr. 2003.

Binz, High-affinity Binders Selected from Designed Ankyrin Repeat Protein Libraries, Nat. Biotechnol 22, pp. 575-582, 2004.

Binz et al., Engineering novel binding proteins from nonimmunoglobulin domains. Nat Biotechnol., 23:1257-1268, 2005.

Boder et al., Yeast Surface Display for Screening Combinatorial Polypeptide Libraries, Nat. Biotechnol15, pp. 553-557, 1997.

Boder et al., Yeast Surface Display for Directed Evolution of Protein Expression, Affinity, and Stability, Methods Enzymol 328, pp. 430-444, 2000.

Boder et al., Directed evolution of antibody fragments with monovalent femtomolar antigen-binding affinity. Proceedings of the National Academy of Science; vol. 97, No. 20, p. 10701-10705, Sep. 2000.

Bork et al., The immunoglobulin fold. Structural classification, sequence patterns and common core, J. Mol. Biol. 242:309-320, 1994.

Bowie et al., Deciphering the message in protein sequences: tolerance to amino acid substitutions. Science, vol. 24 7: 1306-1310, 1990.

Burgess et al., Possible dissociation of the heparin binding and mitogenic activities of heparin binding (acidic fibroblast) growth factor-1 from its receptor binding activities by site directed mutagenesis of a single lysine residue. Journal of Cell Biology, vol. 111, pp. 2129-2138, 1990.

Cabilly et al., Generation of Antibody Activity from Immunoglobulin Polypeptide Chains Produced in *Escherichia coli*, Proc. Natl. Acad. Sci. USA vol. 81, pp. 3273-3277, Jun. 1984.

Caldas et al., Humanization of the anti-CD18 antibody 6.7: an unexpected effect of a framework residue in binding to antigen. Mol. Immunol., 39 (15): 941-952, May 2003.

Carter, Bispecific Human IgG by Design, Journal of Immunological Methods 248, pp. 7-15, 2001.

Carter et al., High level *Escherichia coli* expression and production of a bivalent humanized antibody fragment. Biotechnology (NY), 10(2):163-167, Feb. 1992.

(56) References Cited

OTHER PUBLICATIONS

Chen et al., Isolation of High-Affinity Ligand-Binding Proteins by Periplasmic Expression with Cytometric Screen (PEGS), Nature Biotechnol. vol. 19, pp. 537-542, Jun. 2001.
Chien et al., Significant structural and functional change of an antigen-binding site by a distant amino acid substitution: proposal of a structural mechanism. Proc. Natl. Acad. Sci. USA, 86 (14): 5532-5536, Jul. 1989.
Chirino et al., Minimizing the immunogenicity of protein therapeutics, Drug Discovery Today 9:82-90, 2004.
Cho et al., Structure of the extracellular region of HER2 alone and in complex with the Herceptin Fab. Nature, 13;421 (6924): 756-760, Feb. 2003.
Coco et al., DNA Shuffling Method for Generating Highly Recombined Genes and Evolved Enzymes, Nature Publishing Group, vol. 19, pp. 354-359, Apr. 2001.
Conrath et al., Antigen binding and solubility effects upon the veneering of a camel VHH in framework-2 to mimic a VH. J Mol Biol., 350:112-125, 2005.
Cornish-Bowden, Nomenclature for incompletely specified bases in nucleic acid sequences: recommendations 1984. Nucleic Acids Res., 3(9):3021-30 May 10, 1985.
Cortez-Retamozo et al., Efficient Tumor Targeting by Single-domain Antibody Fragments of Camels, Int. J. Cancer 98, 456-462, 2002.
Crameri et al., DNA Shuffling of a Family of Genes from Diverse Species Accelerates Directed Evolution, Nature vol. 391, pp. 288-291, Jan. 15, 1998.
Dall'Acqua, Modulation of the effector functions of a human IgG1 through engineering of its hinge region. J. Immunol. 177:1129-1138, 2006.
Dall'Acqua et al., Increasing the affinity of a human IgG1 for the neonatal Fc receptor: biological consequences. The Journal of Immunology, 169: 5171-5180, 2002.
De Jager et al., Simultaneous detection of 15 human cytokines in a single sample of stimulated peripheral blood mononuclear cells. Clin. Diagn. Lab. Immunol., 10:133-139, 2003.
Doi et al. Screening of conformationally constrained random polypeptide libraries displayed on a protein scaffold CMLS, Cell Mol Life Sci., 54(5):394-404, 1998.
Dottorini et al., Crystal structure of a human VH: requirements for maintaining a monomeric fragment. Biochemistry, 43:622-628, 2004.
Ewert et al., Stability improvement of antibodies for extracellular and intracellular applications: CDR grafting to stable frameworks and structure-based framework engineering. Methods, 34:184-199, 2004.
F-star, F-star Alpha: A new asset centric company, Feb. 11, 2014.
Felgenhauer et al., Nucleotide Sequences of the cDNAs encoding the V-regions of H-and L-chains of a Human Monoclonal Antibody Specific to HIV-1-gp41, Nucleic Acids Research, vol. 18, No. 16, p. 4927, 1990.
Fellouse et al., Molecular recognition by a binary code. J. Mol. Biol, 348, pp. 1153-1162, 2005.
Fellouse et al., Synthetic antibodies from a four-amino-acid code: a dominant role for tyrosine in antigen recognition. Proc Natl. Acad Sci. 101(34), pp. 12467-12472, Aug. 24, 2004.
Fellouse et al., Tyrosine plays a dominant functional role in the paratope of a synthetic antibody derived from a four amino acid code, J. Mol. Biol. 357:100-114, 2006.
Fields et al., A Novel Genetic System to Detect protein-Protein Interactions, Nature vol. 340, pp. 245-246, Jul. 20, 1989.
Fitzgerald, In vitro display technologies—new tools for drug discovery, DDT, vol. 5, 253-258, 2000.
Foote et al., Antibody framework residues affecting the conformation of the hypervariable loops, J. Mol. Biol. 224: 487-499, 1992.
Gao et al., Making artificial antibodies: a format for phage display of combinatorial heterodimeric arrays. Proceedings of the National Academy of Sciences of USA, vol. 96, 11, 25, pp. 6025-6030, May 1999.
Gonçalves, Chem. Rev 109, Fluorescent Labeling of Biomolecules with Organic Probes, 190-212, 2009.
Georgiou et al., Practical Applications of Engineering Gram-negative Bacterial Cell Surfaces, Elsevier Science Publishers Ltd (UK), vol. 11, pp. 6-10, Jan. 1993.
Georgiou et al., Display of Heterologous Proteins on the Surface of Microorganisms: From the Screening of Combinatorial Libraries to Live Recombinant Vaccines, Nature Biotechnology vol. 15, pp. 29-34, Jan. 1997.
Giusti et al., Somatic diversification of S107 from an antiphosphocholine to an anti-DNA autoantibody is due to a single base change in its heavy chain variable region. Proc. Natl. Acad. Sci. USA, 84 (9): 2926-2930, May 1987.
Gram et al., In vitro selection and affinity maturation of antibodies from a naive combinatorial immunoglobulin library. Proceedings of the National Academy of Sciences of the United States of America, vol. 89, No. 8, pp. 3576-3580, 1992.
Halaby et al., The immunoglobulin fold family: sequence analysis and 3D structure comparisons, Protein Engineering 12: 563-571, 1999.
Hanes et al., In vitro Selection and Evolution of Functional Proteins by Using Ribosome Display, Proc. Natl. Acad. Sci, USA, vol. 94, pp. 4937-4942, May 1997.
Harriman et al., Multiplexed Elispot Assay, J. Immun Meth, 341:127-134, 2009.
Hasenhindl et al., Stability assessment on a library scale: a rapid method for the evaluation of the commutability and insertion of residues in C-terminal loops of the CH3 domains of IgG1-Fc, Protein Engineering, Design and Selection, vol. 26, Issue 10, 675-682, 2013.
Hasenhindl et al., Creating stable stem regions for loop elongation in Fcabs—insights from combining yeast surface display, in silico loop reconstruction and molecular dynamics simulations, Biochimica at Biophysica Acta (BBA), vol. 1844, Issue 9, pp. 1530-1540, Sep. 2014.
Haurum, How to leverage oncogene addiction: targetd biological therapy inducing growth factor receptor internalization and degradation, PEPtalk: The Protein Science Week Jan. 19, 2015.
Hayhurst et al., High-Throughput Antibody Isolation, Curr. Opin. Chem. Biol. vol. 5, pp. 683-689, 2001.
He et al., Structure of a Human Monoclonal Antibody Fab Fragment Against gp41 of Human Immunodeficiency Virus Type 1, Proc. Natl., Acad. Sci. USA. vol. 89, pp. 7154-7158, Aug. 1992.
Hermeling et al., Structure-immunogenicity relationships of therapeutic proteins, Pharm. Res. 21:897-903, 2004.
Holliger et al., Engineered Antibody Fragments and the rise of Single Domains, Nature Biotechnology Vo. 23, No. 9, pp. 1126-1136, Sep. 2005.
Hoogenboom et al., Multi-subunit proteins on the surface of filamentous phage: methodologies for displaying antibody (Fab) heavy and light chains, Nucleic Acids Research, vol. 19, No. 15 pp. 4133-4137, Oxford University Press, 1991.
Hoover et al., DNA Works: an automated method for designing oligonucleotides for PCR-based gene synthesis. Nucleic Acids Res. 30(10):e43, 2002.
Hosse et al., A new generation of protein display scaffolds for molecular recognition. Protein Sci., 15:14-27, 2006.
Hufton et al., Development and application of cytotoxic T lymphocyte-associated antigen 4 as a protein scaffold for the generation of novel binding ligands. FEBS Letters, 475:225, 2000.
Huston et al., Protein engineering of antibody binding sites: recovery of specific activity in an anti-digoxin single-chain Fv analogue produced in *Escherichia coli*., Proc Natl Acad Sci US A. 85:5879-5883, 1988.
Isaac et al., Poster: Pre-clinical evaluation of FS102: a HER2 specific Fcab with novel mechanism of action, AstraZeneca-MedImmune-Cambridge Cancer Centre Symposium, 1 page, Mar. 25, 2014.
Janeway et al., Immunobiology, Garland Science Publishing Chapter 3-5, p. 109, Fig. 3.5, 2005.
Jez et al., "Significant impact of single N-glycan residues on the biological activity of Fe-based antibody-like fragments," Journal of Biological Chemistry, vol. 29, pp. 24313-24319, May 15, 2012.

(56) References Cited

OTHER PUBLICATIONS

Johnsson et al., Split ubiquitin as a sensor of protein interactions in vivo, Proc. Natl. Acad. Sci. USA vol. 91, pp. 10340-10344, Biochemistry, Oct. 1994.
Jones et al., Replacing the complementarity-determining regions in a human antibody with those from a mouse, Nature 321: 522-525, 1986.
Jung et al., Surface display of *Zymomonas mobilis levansucrase* by using the ice-nucleation protein of *Pseudomonas syringae*, Nature Biotechnology vol. 16, p. 576-580, Jun. 1998.
Kainer et al., Correlation between CD16a binding and immune effector functionality of an antigen specific immunoglobin Fc fragment (Fcab), Arch Biochem Biophys, vol. 526, Issue 2, pp. 154-158, Oct. 2012.
Kang et al., Linkage of recognition and replication functions by assembling combinatorial antibody Fab libraries along phage surfaces. Proc Natl Acad Sci USA, 15;88(10):4363-4366, May 1991.
Kang et al., Human neutralizing Fab molecules against severe acute respiratory syndrome coronavirus generated by phage display, Clin Vaccine Immunol., 13(8):953-957, Aug. 2006.
Kashmiri et al., SDR grafting—a new approach to antibody humanization. Methods 36:25-34, 2005.
Kay et al., Phage display of peptides and proteins: a laboratory manual, Academic Press, 1996.
Kettleborough et al. Humanization of a mouse monoclonal antibody by CDR-grafting: the importance of framework residues on loop conformation. Protein Eng., 4:773-783, 1991.
Kikuchi et al., Novel family shuffling methods for the in vitro evolution of enzymes, Gene 236, 159-167, 1999.
Kikuchi et al., An effective family shuffling method using single-stranded DNA, Gene 243, 133-137, 2000.
Kohl et al., Cloning and Expression of an HIV-1 Specific Single-Chain F Region Fused to *Escherichia coli* Alkaline Phosphatase, Ann Ny Acad. Sci, 646, p. 106-114, 1991.
Koide et al., High-affinity single-domain binding proteins with a binary-code interface. PNAS, 104:6632-6637, 2007.
Koivunen et al., "Selection of Peptides Binding to the α5β1 Integrin from Phage Display Library", The Journal of Biological Chemistry, vol. 268, No. 27, pp. 20205-20210, The American Society for Biochemistry and Molecular Biology, Inc., Sep. 25, 1993.
Kolkman et al., Directed evolution of proteins by exon shuffling, 2001 Nature Publishing Group, vol. 19, p. 423-428, May 2001.
Kontermann, Dual targeting strategies with bispecific antibodies, MAbs, 4(2):182-97, Mar./Apr. 2012.
Koren et al., Immune responses to therapeutic proteins in humans—clinical significance, assessment and prediction, Current Pharmaceutical Biotechnology 3:349-360, 2002.
Kunkel, Rapid and efficient site-specific mutagenesis without phenotypic selection. Proc Natl Acad Sci USA, 82(2):488-92, Jan. 1985.
Kufer et al., A revival of bispecific antibodies, Trends in Biotechnology, vol. 22, No. 5, p. 238-244, May 2004.
Laffly et al, Monoclonal and recombinant antibodies, 30 years after . . . Hum Antibodies, 14(1-2):33-55, 2005.
Lauvrak et al., Identification and characterisation of Clq-binding phage displayed peptides, Biol. Chem. 378(12):1509-1519, 1997.
Lazar et al., Transforming growth factor alpha: mutation of aspartic acid 47and leucine 48 results in different biological activities. Molecular and Cellular Biology, vol. 8, pp. 1247-1252, 1988.
Lea & Stewart, Analysis of antigenic surfaces of proteins, FASEB J. 9:87-93, 1995.
Lederman et al., A single amino acid substitution in a common African allele of the CD4 molecule ablates binding of the monoclonal antibody, OKT4. Molecular Immunology 28:1171-1181, 1991.
Lee et al., Surface-displayed viral antigens on *Salmonella* carrier vaccine, Nature Biotechnology, vol. 18, p. 645-648, Jun. 2000.
LeFranc et al., IMGT, The international IMmunoGeneTics database, Nucleic Acids Research, vol. 27, No. 1, p. 209-212, 1999.
LeFranc et al., IMGT, the international ImMunoGeneTics database, Nucleic Acids Research, vol. 29, No. 1, p. 207-209, 2001.
LeFranc et al., IMGT, the international ImMunoGeneTics database, Nucleic Acids Research, vol. 31 , No. 1, p. 307-310, 2003.
LeFranc et al., IMGT unique numbering for immunoglobulin and T cell receptor constant domains and Ig superfamily C-like domains, Developmental and Comparative Immunology 29, 185-203, 2005.
LeFranc et al., IMGT, the International ImMunoGeneTics information system, Nucleic Acids Research, vol. 33, Database issue D593-D597, 2005.
LeFranc et al., IMGT unique numbering for immunoglobulin and T cell receptor variable domains and Ig superfamily V-like domains, Developmental and Comparative Immunology, vol. 27, No. 1, pp. 55-77, Jan. 2003.
Le Gall et al., Effect of linker sequences between the antibody variable domains on the formation, stability and biological activity of a bispecifc tandem diabody, Protein Engineering, Design & Selection vol. 17, No. 4, pp. 357-366, 2004.
Li et al., beta-Endorphin omission analogs: dissociation of immunoreactivity from other biological activities. Proc. Nat'l. Acad. Sci. USA 77:3211-3214, 1980.
Loconte et al., The atomic structure of protein-protein recognition sites, J. Mol. Biol. 285:2177-2198, 1999.
Lowman et al., Selecting High-Affinity Binding Proteins by Monovalent Phage Display, Biochemistry 30:10832-10838, 1991.
Lutz et al., Creating multiple-crossover DNA libraries independent of sequence identity, PNAS, vol. 98, No. 20, p. 11248-11253, Sep. 25, 2001.
Malmborg et al., Selective Phage Infection Mediated by Epitope Expression on F. Pilus, J. Mol. Biol., vol. 273, p. 544-551, 1997.
Marvin et al., Recombinant approaches to IgG-like bispecific antibodies, Acta Pharmacologica Sinica, vol. 26, No. 6, pp. 649-658, 2005.
Masuda et al., The role of interface framework residues in determining antibody V(H)/V(L) interaction strength and antigen-binding affinity. FEBS J., 273:2184-2194, 2006.
Matiheakis et al., An in vitro polysome display system for identifying ligands from very large peptide libraries, Proc. Natl., Acad. Sci. USA vol. 91, pp. 9022-9026, Biochemistry, Sep. 1994.
Maynard et al., Antibody Engineering, Annu. Rev. Biomed. Eng., vol. 2, p. 339-376, 2000.
McCall et al., Increasing the affinity for tumor antigen enhances bispecific antibody cytotoxicity. J. Imm., 166:6112-6117, 2001.
McCall et al., Isolation and characterization of an anti-CD16 single-chain Fv fragment and construction of an anti-HER2/neu/antiCD16 bispecific scFv that triggers CD16-dependent tumor cytolysis. Mol. Imm., 36, 433-445, 1999.
Merz Jr. et al., The Protein Folding Problem and Tertiary Structure Prediction, Birkhauser, Boston, MA, pp. 433, and 492-495, 1994.
Miyazaki et al. Changes in the specificity of antibodies by site-specific mutagenesis followed by random mutagenesis; Protein Eng., 12(5):407-15, May 1999.
Munoz-Olaya, A novel modular antibody technology for generating bispecific antibodies, PEGS Lisbon, Nov. 3-7, 2014.
Nemoto et al., In vitro virus: Bonding of mRNA bearing puromycin at the 3"-terminal ned to the C-terminal end of its encoded protein on the ribosome in vitro, FEBS Letters 414, 405-408, 1997.
Nygren et al., Scaffolds for engineering novel binding sites in proteins, Current Biology, 7:463-469, 1997.
Park et al., Rationally designed anti-HER2/neu peptide mimetic disables P185HER2/neu tyrosine kinases in vitro and in vivo. Nat Biotechnol., 18(2):194-8, Feb. 2000.
Pelletier et al. Oligomerization domain-directed reassembly of active dihydrofolate reductase from rationally designed fragments, Proc. Natl. Acad. Sci USA, vol. 95, pp. 12141-12146, Oct. 1998.
Perosa et al., CD20 Mimicry by a mAb Rituximab-Specific Linear Peptide, Ann. N.Y. Acad. Sci. 1051: 672-683, New York Academy of Sciences, 2005.
Presta et al., Engineering therapeutic antibodies for improved function, Mediation and Modulation of Antibody Function, Biochemical Society, 30(4):487-490, 2002.
Privezentzev, Poster: F-star: Advancing Novel Bispecific Antibody Biologics, Gordon Research Conference; Antibody Biology & Engineering, 1 page, Mar. 2014.

(56) References Cited

OTHER PUBLICATIONS

Riechmann et al., Single domain antibodies: comparison of camel VH and camelised human VH domains. Journal of Immunological Methods, 231:25-38, 1999.
Roberts et al., RNA-peptide fusions for the in vitro selection of peptides and proteins, Proc. Natl. Acad. Sci. USA, vol. 94, pp. 12297-12302, Nov. 1997.
Rondot et al., A helper phage to improve single-chain antibody presentation in phage display. Nat. Biotechnol., (1), pp. 75-78, Jan. 2001.
Roovers et al., Efficient inhibition of EGFR signaling and of tumour growth by antagonistic anti-EFGR Nanobodies. Cancer Immunol. Immunother., 56:303-317, 2007.
Rudikoff et al., Single amino acid substitution altering antigen-binding specificity, Proc. Natl. Acad. Sci. USA, 79(6): 1979-1983, Mar. 1982.
Ruiz et al., IMGT, the international ImMunoGeneTics database, Nucleic Acids Research. vol. 28, No. 1, p. 219-221, 2000.
Ruker et al., Expression of a Human Monoclonal Anti-HIV-1 Antibody in CHO Cells, Ann NY Acad. Sci. 646, p. 212-219, Dec. 27, 1991.
Salfield, Isotype selection in antibody engineering, Nature Biotech. 25(12):1369-1372, 2007.
Saerens et al., Identification of a Universal VHH Framework to Graft Non-canonical Antigen-binding Loops of Camel Single-domain Antibodies, J. Mol. Biol. 352, 597-607, 2005.
Schaffitzel et al., Ribosome display: an in vitro method for selection and evolution of antibodies from libraries, J Immunol Methods 231:119-135, 1999.
Schmittel et al., Application of the IFN-γ ELISPOT assay to quantify T cell responses against proteins, Journal of Immunological Methods 247:17-24, 2001.
Shao et al., Random-priming in vitro recombination: an effective tool for directed evolution, Nucleic Acids Research, vol. 26, No. 2, p. 681-683, 1998.
Shields et al., High Resolution Mapping of the Binding Site on Human IgG1 for FcγRI, FcγRII, FcγRIII, and FcRn and Design of IgG1 Variants with Improved Binding to the FcγR. The Journal of Biological Chemistry, vol. 276, No. 9, pp. 6591-6604, 2001.
Sidhu et al., Synthetic therapeutic antibodies, Nature Chemical Biology, vol. 2, pp. 682-688, 2006.
Simon & Rajwesky, A functional antibody mutant with an insertion in the framework region 3 loop of the VH domain: implications for antibody engineering. Protein Eng., 5:229-234, 1992.
Skolnick & Fetrow, From genes to protein structure and function: novel applications of computational approaches in the genomic era. Trends in Biotechnology, vol. 18, pp. 34-39, 2000.
Smith, Filamentous Fusion Phage: Novel Expression Vectors That Display Cloned Antigens on the Virion Surface, Science, vol. 228 p. 1315-1317, 1985.
Spiridon Camelia I et al., Targeting multiple Her-2 epitopes with monoclonal antibodies results in improved antigrowth activity of a human breast cancer cell line in vitro and in vivo, Clinical Cancer Research, The American Association for Cancer Research, vol. 8, No. 6, pp. 1720-1730, Jun. 1, 2002.
Tangri et al., Rationally engineered therapeutic proteins with reduced immunogenicity, J. Immunol. 174:3187-3196, 2005.
Traxlmayr et al., Directed evolution of Her2/neu-binding IgGl-Fc for improved stability and resistance to aggregation by using yeast surface display, Protein Engineering, Design and Selection, vol. 6, Issue 4, pp. 255-265, 2013.
Traxlmayr et al. Construction of pH-sensitive Her2-binding IgGl-Fc by directed evolution, Biotechnology Journal, vol. 9, Issue 8, pp. 1013-1022, Aug. 2014.
Uhlenbroich, Poster: F-star: Advancing Novel Bispecific Antibody Biologics, Empowered Antibodies Congress, 1 page, Jun. 18, 2014.
Vajdos et al., Comprehensive functional maps of the antigen-binding site of an anti-ErbB2 antibody obtained with shotgun scanning mutagenesis, Journal of Molecular Biology, vol. 320, No. 2, pp. 415-428, Jul. 5, 2002.
Virnekas et al., Trinucleotide phosphoramidites: ideal reagents for the synthesis of mixed oligonucleotides for random mutagenesis, Nucleic Acids Res. 22:5600-5607, 1994.
Visintin et al., Selection of antibodies for intracellular function using a two-hybrid in vivo system, PNAS vol. 96, No. 21, pp. 11723-11728, Oct. 12, 1999.
Vogt et al., Construction of an Artificial Receptor Protein ("Anticalin") Based on the Human Apolipoprotein D. Chembiochem 5(2):191-199, Feb. 6, 2004.
Wang et al., Expression patterns and transcript processing of ftt-1 and ftt-2, two *C. elegans* 14-3-3 homologues, J. Mol. Biol. 268:619-630, 1997.
Wang et al., Retargeting T cells for HER2-positive tumor killing by a bispecific Fv-Fc antibody, PLoS One, vol. 8, Issue 9, e75589, 9 pages, Sep. 23, 2013.
Weaver-Feldhaus et al., Yeast mating for combinatorial Fab library generation and surface display, FEBS Lett. 564(1-2):24-34, Apr. 23, 2004.
Weiner et al., Site-directed mutagenesis of double-stranded DNA by the polymerase chain reaction, Gene, 151(1-2), pp. 119-123, Dec. 30, 1994.
Whitehorn et al., A Generic Method for Expression and Use of "Tagged" Soluble Versions of Cell Surface Receptors, BioTechnology vol. 13, pp. 1215-1219, Nov. 1995.
Winter et al., Humanized antibodies, Immunology Today, vol. 14, No. 6, pp. 243-246, 1993.
Winkler et al., Changing the antigen binding specificity by single point mutations of an anti-p24 (HIV-1) antibody, J. Imm., 265:4505-4514 , 2000.
Wittrup, KD, Protein Engineering by cell-surface display, Current Opinion in Biotechnology, vol. 12:395-399, 2001.
Woisetschlager et al., In vivo and in vitro activity of an immunoglobulin Fc fragment (Fcab) with engineered Her-2/neu binding sites, Biotechnology Journal, vol. 9, Issue 6, pp. 844-851, Jun. 2014.
Wozniak-Knopp, Introducing antigen-binding sites in structural loops of immunoglobulin constant domains: Fc fragments with engineered HER2/neu-binding sites and antibody properties, Protein Eng. & Design & Selection. vol. 23, 289-297, 2010.
Wu et al., Humanization of a murine monoclonal antibody by simultaneous optimization of framework and CDR residues, J. Mol. Biol. 294:151-162, 1999.
Xiao et al., A large library based on a novel (CH2) scaffold: identification of HIV-1 inhibitors, Biochem Biophys Res Commun. 387(2):387-92, Sep. 18, 2009.
Yanez et al., Combinatorial codon-based amino acid substitutions, Nucleic Acids Res. 32(20):e158, Nov. 10, 2004.
Yau et al., Affinity maturation of a VHH by mutational hotspot randomization, Journal of Immunological Methods. vol. 297, vol. 1-2, pp. 213-224, 2005.
Zemlin et al., Expressed murine and human CDR-H3 intervals of equal length exhibit distinct repertoires that differ in their amino acid composition and predicted range of structures, J. Mol. Biol. 334:733-749, 2003.
Zhou et al., A Novel Strategy by the Action of Ricin that Connects Phenotype and Genotype without Loss of the Diversity of Libraries, J. Am. Chem. Soc. vol. 124, No. 4, pp. 538-543, 2002.
Zhao et al., Molecular evolution by staggered extension process (StEP) in vitro recombination, Nature Biotechnology. vol. 16, pp. 258-261, Mar. 1998.
International Searching Authority, International Search Report—International Application No. PCT/EP2009/052509, dated Jun. 3, 2009, together with the Written Opinion of the International Searching Authority, 17 pages.
The International Bureau of WIPO, International Preliminary Report on Patentability, Application No. PCT/EP2009/052509, dated Nov. 2, 2010, 8 pages.
Holler et al., "In vitro evolution of a T cell receptor with high affinity for peptide/MHC," *Proc. Natl. Acad. Sci. USA*, vol. 97, No. 10, pp. 5387-5392 (May 2000).

(56) References Cited

OTHER PUBLICATIONS

Kieke et al., "Selection of functional T cell receptor mutants from a yeast surface-display library," *Proc. Natl. Acad. Sci. USA*, vol. 96, No. 10, pp. 5651-5656 (May 1999).
Li et al. "Directed evoluation of human T-cell receptors with picomolar affinities by phage display," *Nat. Biotechnol.*, vol. 23, No. 3, pp. 349-354 (Mar. 2005).
Shusta et al., "Directed evolution of a stable scaffold for T-cell receptor engineering," *Nat. Biotechnol.*, vol. 18, No. 7, pp. 754-759 (Jul. 2000).
Weber et al., "Class II-restricted T cell receptor engineered in vitro for higher affinity retains peptide specificity and function," *Proc. Natl. Acad. Sci. USA*, vol. 102, No. 52, pp. 19033-19038 (Dec. 2005).
Canadian Intellectual Property Office, Official Action—Application No. 2,721,614, dated Mar. 16, 2015 (3 pages).
State Intellectual Property Office of People's Republic of China, Initial Search Report—Application No. 200780032991.X (2 pages).
Archana Shanker Anand and Anand, Response to First Examination Report —Application No. 4657/DELNP/2007, dated Jan. 17, 2014 (8 pages).
Japanese Patent Office, Office Action (Notice of Reasons for Rejection)—Application No. 2013-246485, dated Mar. 3, 2015 (2 pages).

Fig. 3 (SEQ ID No. 1): crystal structure of an IgG1 Fc fragment

```
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVDKS RWQQGNVFSC SVMHEALHNH YTQKSLSLSP GK           232
```

Fig. 4 (SEQ ID No. 2): human IgG including randomized amino acid modifications

```
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELXXXQVSL TCLVKGFYPS DIAVEWESNG QPENNYKTTP   180
PVLDSDGSFF LYSKLTVXXX XXXXXRWXXG NVFSCSVMHE ALHNHYTQKS LSLSPGK      237
```

Fig. 5 (SEQ ID No. 11): amino acid sequence of FcabRGD4L

```
EPKSCDKTHT CPPCPAPELL GGPSVFLFPP KPKDTLMISR TPEVTCVVVD VSHEDPEVKF    60
NWYVDGVEVH NAKTKPREEQ YNSTYRVVSV LTVLHQDWLN GKEYKCKVSN KALPAPIEKT   120
ISKAKGQPRE PQVYTLPPSR DELTKNQVSL TCLVKGFYPS DIAVEWESNG QPENNYKTTP   180
PVLDSDGSFF LYSKLTVGCR GDCLSRWQQG NVFSCSVMHE ALHNHYTQKS LSLSPGKESG   240
GSAAAEQKLI SEEDLNGAAT VESCLAKPHT ENSFTNVWKD DKTLDRYANY EGCLWNATGV   300
VVCTGDETQC YGTWVPIGLA IPENEGGGSE GGGSEGGGSE GGGTKPPEYG DTPIPGYTYI   360
NPLDGTYPPG TEQNPANPNP SLEESQPLNT FMFQNNRFRN RQGALTVYTG TVTQGTDPVK   420
TYYQYTPVSS KAMYDAYWNG KFRDCAFHSG FNEDPFVCEY QGQSSDLPQP PVNAGGGSGG   480
GSGGGSEGGG SEGGGSEGGG SEGGGSGGGS GSGDFDYEKM ANANKGAMTE NADENALQSD   540
AKGKLDSVAT DYGAAIDGFI GDVSGLANGN GATGDFAGSN SQMAQVGDGD NSPLMNNFRQ   600
YLPSLPQSVE CRPYVFGAGK PYEFSIDCDK INLFRGVFAF LLYVATFMYV FSTFANILRN   660
KS                                                                  662
```

Fig. 6A (SEQ ID No. 12): vector pHENFcabRGD4

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
```

Fig. 6B (SEQ ID No. 12 cont'd.)

```
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt aagcttgcat gcaaattcta tttcaaggag acagtcataa   2280
tgaaatacct attgcctacg gcagccgctg gattgttatt actcgcggcc cagccggcca   2340
tggccgagcc caaatcttgt gacaaaactc acacatgccc accgtgccca gcacctgaac   2400
tcctgggggg accgtcagtc ttcctcttcc ccccaaaacc caaggacacc ctcatgatct   2460
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtgggtt   2940
gccgcggtga ttgtctgagc aggtggcagc aggggaacgt cttctcatgc tccgtgatgc   3000
atgaggctct gcacaaccac tacacgcaga agagcctctc cctgtctccg ggtaaagcgg   3060
ccgcagaaca aaaactcatc tcagaagagg atctgaatgg ggccgcatag actgttgaaa   3120
gttgtttagc aaaacctcat acagaaaatt catttactaa cgtctggaaa gacgacaaaa   3180
ctttagatcg ttacgctaac tatgagggct gtctgtggaa tgctacaggc gttgtggttt   3240
gtactggtga cgaaactcag tgttacggta catgggttcc tattgggctt gctatccctg   3300
aaaatgaggg tggtggctct gagggtggcg gttctgaggg tggcggttct gagggtggcg   3360
gtactaaacc tcctgagtac ggtgatacac ctattccggg ctatacttat atcaaccctc   3420
tcgacggcac ttatccgcct ggtactgagc aaaaccccgc taatcctaat ccttctcttg   3480
aggagtctca gcctcttaat actttcatgt ttcagaataa taggttccga aataggcagg   3540
gtgcattaac tgtttatacg ggcactgtta ctcaaggcac tgaccccgtt aaaacttatt   3600
accagtacac tcctgtatca tcaaaagcca tgtatgacgc ttactggaac ggtaaattca   3660
gagactgcgc tttccattct ggctttaatg aggatccatt cgtttgtgaa tatcaaggcc   3720
aatcgtctga cctgcctcaa cctcctgtca atgctggcgg cggctctggt ggtggttctg   3780
gtggcggctc tgagggtggc ggctctgagg gtggcggttc tgagggtggc ggctctgagg   3840
gtggcggttc cggtggcggc tccggttccg gtgattttga ttatgaaaaa atggcaaacg   3900
ctaataaggg ggctatgacc gaaaatgccg atgaaaacgc gctacagtct gacgctaaag   3960
gcaaacttga ttctgtcgct actgattacg gtgctgctat cgatggtttc attggtgacg   4020
tttccggcct tgctaatggt aatggtgcta ctggtgattt tgctggctct aattcccaaa   4080
tggctcaagt cggtgacggt gataattcac ctttaatgaa taatttccgt caatatttac   4140
cttctttgcc tcagtcggtt gaatgtcgcc cttatgtctt tggcgctggt aaaccatatg   4200
aattttctat tgattgtgac aaaataaact tattccgtgg tgtctttgcg tttcttttat   4260
atgttgccac ctttatgtat gtattttcga cgtttgctaa catactgcat aaggagtctt   4320
aataagaatt cactggccgt cgttttacaa cgtcgtgact gggaaaaccc tggcgttacc   4380
caacttaatc gccttgcagc acatccccct ttcgccagct ggcgtaatag cgaagaggcc   4440
cgcaccgatc gcccttccca acagttgcgc agcctgaatg gcgaatggcg cctgatgcgg   4500
tattttctcc ttacgcatct gtgcggtatt tcacaccgca cgtcaaagca accatagtac   4560
gcgccctgta gcggcgcatt aagcgcggcg ggtgtggtgg ttacgcgcag cgtgaccgct   4620
acacttgcca gcgccctagc gcccgctcct ttcgctttct tcccttcctt tctcgccacg   4680
ttcgccggct ttccccgtca agctctaaat cgggggctcc ctttagggtt ccgatttagt   4740
gctttacggc acctcgaccc caaaaaactt gatttgggtg atggttcacg tagtgggcca   4800
tcgccctgat agacggtttt tcgccctttg acgttggagt ccacgttctt taatagtgga   4860
ctcttgttcc aaactggaac aacactcaac cctatctcgg gctattcttt tgatttataa   4920
gggattttgc cgatttcggc ctattggtta aaaaatgagc tgatttaaca aaaatttaac   4980
gcgaatttta acaaaatatt aacgtttaca attttatggt gcactctcag tacaatctgc   5040
tctgatgccg catagttaag ccagccccga cacccgccaa cacccgctga cgcgccctga   5100
cgggcttgtc tgctcccggc atccgcttac agacaagctg tgaccgtctc cgggagctgc   5160
atgtgtcaga ggttttcacc gtcatcaccg aaacgcgcga                         5200
```

Fig. 7A (SEQ ID No. 14): vector pHENF cabRGD4L

```
gacgaaaggg cctcgtgata cgcctatttt tataggttaa tgtcatgata ataatggttt      60
cttagacgtc aggtggcact tttcggggaa atgtgcgcgg aacccctatt tgtttatttt     120
tctaaataca ttcaaatatg tatccgctca tgagacaata accctgataa atgcttcaat     180
aatattgaaa aaggaagagt atgagtattc aacatttccg tgtcgccctt attccctttt     240
ttgcggcatt ttgccttcct gtttttgctc acccagaaac gctggtgaaa gtaaaagatg     300
ctgaagatca gttgggtgca cgagtgggtt acatcgaact ggatctcaac agcggtaaga     360
tccttgagag ttttcgcccc gaagaacgtt ttccaatgat gagcactttt aaagttctgc     420
tatgtggcgc ggtattatcc cgtattgacg ccgggcaaga gcaactcggt cgccgcatac     480
actattctca gaatgacttg gttgagtact caccagtcac agaaaagcat cttacggatg     540
gcatgacagt aagagaatta tgcagtgctg ccataaccat gagtgataac actgcggcca     600
acttacttct gacaacgatc ggaggaccga aggagctaac cgcttttttg cacaacatgg     660
gggatcatgt aactcgcctt gatcgttggg aaccggagct gaatgaagcc ataccaaacg     720
acgagcgtga caccacgatg cctgtagcaa tggcaacaac gttgcgcaaa ctattaactg     780
gcgaactact tactctagct tcccggcaac aattaataga ctggatggag gcggataaag     840
ttgcaggacc acttctgcgc tcggcccttc cggctggctg gtttattgct gataaatctg     900
gagccggtga gcgtgggtct cgcggtatca ttgcagcact ggggccagat ggtaagccct     960
cccgtatcgt agttatctac acgacgggga gtcaggcaac tatggatgaa cgaaatagac    1020
agatcgctga gataggtgcc tcactgatta agcattggta actgtcagac caagtttact    1080
catatatact ttagattgat ttaaaacttc atttttaatt taaaaggatc taggtgaaga    1140
tcctttttga taatctcatg accaaaatcc cttaacgtga gttttcgttc cactgagcgt    1200
cagaccccgt agaaaagatc aaaggatctt cttgagatcc tttttttctg cgcgtaatct    1260
gctgcttgca aacaaaaaaa ccaccgctac cagcggtggt ttgtttgccg gatcaagagc    1320
taccaactct ttttccgaag gtaactggct tcagcagagc gcagatacca aatactgtcc    1380
ttctagtgta gccgtagtta ggccaccact tcaagaactc tgtagcaccg cctacatacc    1440
tcgctctgct aatcctgtta ccagtggctg ctgccagtgg cgataagtcg tgtcttaccg    1500
ggttggactc aagacgatag ttaccggata aggcgcagcg gtcgggctga acggggggtt    1560
cgtgcacaca gcccagcttg gagcgaacga cctacaccga actgagatac ctacagcgtg    1620
agcattgaga aagcgccacg cttcccgaag ggagaaaggc ggacaggtat ccggtaagcg    1680
gcagggtcgg aacaggagag cgcacgaggg agcttccagg gggaaacgcc tggtatcttt    1740
atagtcctgt cgggtttcgc cacctctgac ttgagcgtcg atttttgtga tgctcgtcag    1800
gggggcggag cctatggaaa aacgccagca acgcggcctt tttacggttc ctggcctttt    1860
gctggccttt tgctcacatg ttctttcctg cgttatcccc tgattctgtg gataaccgta    1920
ttaccgcctt tgagtgagct gataccgctc gccgcagccg aacgaccgag cgcagcgagt    1980
cagtgagcga ggaagcggaa gagcgcccaa tacgcaaacc gcctctcccc gcgcgttggc    2040
cgattcatta atgcagctgg cacgacaggt ttcccgactg gaaagcgggc agtgagcgca    2100
acgcaattaa tgtgagttag ctcactcatt aggcacccca ggctttacac tttatgcttc    2160
cggctcgtat gttgtgtgga attgtgagcg gataacaatt tcacacagga aacagctatg    2220
accatgatta cgccaagctt aagcttgcat gcaaattcta tttcaaggag acagtcataa    2280
tgaaatacct attgcctacg gcagccgctg gattgttatt actcgcggcc cagccggcca    2340
tggccgaggc caaatcttgt gacaaaactc acacatgccc accgtgccca gcacctgaac    2400
tcctgggggg accgtcagtc ttcctcttcc ccccaaaacc caaggacacc ctcatgatct    2460
cccggacccc tgaggtcaca tgcgtggtgg tggacgtgag ccacgaagac cctgaggtca    2520
agttcaactg gtacgtggac ggcgtggagg tgcataatgc caagacaaag ccgcgggagg    2580
agcagtacaa cagcacgtac cgtgtggtca gcgtcctcac cgtcctgcac caggactggc    2640
tgaatggcaa ggagtacaag tgcaaggtct ccaacaaagc cctcccagcc cccatcgaga    2700
aaaccatctc caaagccaaa gggcagcccc gagaaccaca ggtgtacacc ctgcccccat    2760
cccgggatga gctgaccaag aaccaggtca gcctgacctg cctggtcaaa ggcttctatc    2820
ccagcgacat cgccgtggag tgggagagca atgggcagcc ggagaacaac tacaagacca    2880
cgcctcccgt gctggactcc gacggctcct tcttcctcta cagcaagctt accgtggggt    2940
gcccgggtga ttgtctgagc aggtggcagc aggggaacgt cttctcatgc tccgtgatgc    3000
atgaggctct gcacaaccac tacacgcaga agagcctctc cctgtctccg ggtaaggagg    3060
gtggtggctc tgcggccgca gaacaaaaac tcatctcaga agaggatctg aatggggccg    3120
catagactgt tgaaagttgt ttagcaaaac ctcatacaga aaattcattt actaacgtct    3180
ggaaagacga caaaacttta gatcgttacg ctaactatga gggctgtctg tggaatgcta    3240
caggcgttgt ggtttgtact ggtgacgaaa ctcagtgtta cggtacatgg gttcctattg    3300
ggcttgctat ccctgaaaat gagggtggtg gctctgaggg tggcggttct gagggtggcg    3360
gttctgaggg tggcggtact aaacctcctg agtacggtga tacacctatt ccgggctata    3420
cttatatcaa ccctctcgac ggcacttatc cgcctggtac tgagcaaaac cccgctaatc    3480
ctaatccttc tcttgaggag tctcagcctc ttaatacttt catgtttcag aataataggt    3540
tccgaaatag gcaggggtca ttaactgttt atacgggcac tgttactcaa ggcactgacc    3600
ccgttaaaac ttattaccag tacactcctg tatcatcaaa agccatgtat gacgcttact    3660
```

Fig. 7B (SEQ ID No. 14 cont'd.)

```
ggaacggtaa attcagagac tgcgctttcc attctggctt taatgaggat ccattcgttt    3720
gtgaatatca aggccaatcg tctgacctgc ctcaacctcc tgtcaatgct ggcggcggct    3780
ctggtggtgg ttctggtggc ggctctgagg gtggcggctc tgagggtggc ggttctgagg    3840
gtggcggctc tgagggtggc ggttccggtg gcggctccgg ttccggtgat tttgattatg    3900
aaaaaatggc aaacgctaat aagggggcta tgaccgaaaa tgccgatgaa aacgcgctac    3960
agtctgacgc taaaggcaaa cttgattctg tcgctactga ttacggtgct gctatcgatg    4020
gtttcattgg tgacgtttcc ggccttgcta atggtaatgg tgctactggt gattttgctg    4080
gctctaattc ccaaatggct caagtcggtg acggtgataa ttcaccttta atgaataatt    4140
tccgtcaata tttaccttct ttgcctcagt cggttgaatg tcgcccttat gtctttggcg    4200
ctggtaaacc atatgaattt tctattgatt gtgacaaaat aaacttattc cgtggtgtct    4260
ttgcgtttct tttatatgtt gccaccttta tgtatgtatt ttcgacgttt gctaacatac    4320
tgcataagga gtcttaataa gaattcactg gccgtcgttt tacaacgtcg tgactgggaa    4380
aaccctggcg ttacccaact taatcgcctt gcagcacatc cccctttcgc cagctggcgt    4440
aatagcgaag aggcccgcac cgatcgccct tcccaacagt tgcgcagcct gaatggcgaa    4500
tggcgcctga tgcggtattt tctccttacg catctgtgcg gtatttcaca ccgcacgtca    4560
aagcaaccat agtacgcgcc ctgtagcggc gcattaagcg cggcgggtgt ggtggttacg    4620
cgcagcgtga ccgctacact tgccagcgcc ctagcgcccg ctcctttcgc tttcttccct    4680
tcctttctcg ccacgttcgc cggctttccc cgtcaagctc taaatcgggg gctcccttta    4740
gggttccgat ttagtgcttt acggcacctc gaccccaaaa aacttgattt gggtgatggt    4800
tcacgtagtg ggccatcgcc ctgatagacg gtttttcgcc ctttgacgtt ggagtccacg    4860
ttctttaata gtggactctt gttccaaact ggaacaacac tcaaccctat ctcgggctat    4920
tcttttgatt tataagggat tttgccgatt tcggcctatt ggttaaaaaa tgagctgatt    4980
taacaaaaat ttaacgcgaa ttttaacaaa atattaacgt ttacaatttt atggtgcact    5040
ctcagtacaa tctgctctga tgccgcatag ttaagccagc cccgacaccc gccaacaccc    5100
gctgacgcgc cctgacgggc ttgtctgctc ccggcatccg cttacagaca agctgtgacc    5160
gtctccggga gctgcatgtg tcagaggttt tcaccgtcat caccgaaacg cgcga         5215
```

Fig. 8A (SEQ ID No. 15): vector pYD1dX

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt tttagcacag gaactgacaa     600
ctatatgcga gcaaatcccc tcaccaactt tagaatcgac gccgtactct ttgtcaacga     660
ctactatttt ggccaacggg aaggcaatgc aaggagtttt tgaatattac aaatcagtaa     720
cgtttgtcag taattgcggt tctcacccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccagtg tggtggaatt ctgcagatat ccagcacagt     960
ggcggccgct cgatcgagtc tagagggccc ttcgaaggta agcctatccc taaccctctc    1020
ctcggtctcg attctacgcg taccggtcat catcaccatc accattgagt ttaaacccgc    1080
tgatctgata acaacagtgt agatgtaaca aaatcgactt tgttcccact gtacttttag    1140
ctcgtacaaa atacaatata cttttcattt ctccgtaaac aacatgtttt cccatgtaat    1200
atctttttct atttttcgtt ccgttaccaa ctttacacat actttatata gctattcact    1260
tctatacact aaaaaactaa gacaatttta attttgctgc ctgccatatt tcaatttgtt    1320
ataaattcct ataatttatc ctattagtag ctaaaaaaag atgaatgtga atcgaatcct    1380
aagagaattg ggcaagtgca caaacaatac ttaaataaat actactcagt aataacctat    1440
ttcttagcat ttttgacgaa atttgctatt ttgttagagt cttttacacc atttgtctcc    1500
acacctccgc ttacatcaac accaataacg ccatttaatc taagcgcatc accaacattt    1560
tctggcgtca gtccaccagc taacataaaa tgtaagctct cggggctctc ttgccttcca    1620
acccagtcag aaatcgagtt ccaatccaaa agttcacctg tcccacctgc ttctgaatca    1680
aacaagggaa taaacgaatg aggtttctgt gaagctgcac tgagtagtat gttgcagtct    1740
tttggaaata cgagtctttt aataactggc aaaccgagga actcttggta ttcttgccac    1800
gactcatctc cgtgcagttg gacgatatca atgccgtaat cattgaccag agccaaaaca    1860
```

Fig. 8B (SEQ ID No. 15 cont'd.)

```
tcctccttag gttgattacg aaacacgcca accaagtatt tcggagtgcc tgaactattt   1920
ttatatgctt ttacaagact tgaaattttc cttgcaataa ccgggtcaat tgttctcttt   1980
ctattgggca cacatataat acccagcaag tcagcatcgg aatctagagc acattctgcg   2040
gcctctgtgc tctgcaagcc gcaaactttc accaatggac cagaactacc tgtgaaatta   2100
ataacagaca tactccaagc tgcctttgtg tgcttaatca cgtatactca cgtgctcaat   2160
agtcaccaat gccctccctc ttggccctct cctttctttt ttcgaccgaa tttcttgaag   2220
gacgaaaggg cctcgtgata cgcctatttt tataggttaa tgtcatgata ataatggttt   2280
cttaggacgg atcgcttgcc tgtaacttac acgcgcctcg tatcttttaa tgatggaata   2340
atttgggaat ttactctgtg tttatttatt tttatgtttt gtatttggat tttagaaagt   2400
aaataaagaa ggtagaagag ttacggaatg aagaaaaaaa aataaacaaa ggtttaaaaa   2460
atttcaacaa aaagcgtact ttacatatat atttattaga caagaaaagc agattaaata   2520
gatatacatt cgattaacga taagtaaaat gtaaaatcac aggattttcg tgtgtggtct   2580
tctacacaga caagatgaaa caattcggca ttaatacctg agagcaggaa gagcaagata   2640
aaaggtagta tttgttggcg atccccctag agtcttttac atcttcggaa aacaaaaact   2700
attttttctt taatttcttt ttttactttc tatttttaat ttatatattt atattaaaaa   2760
atttaaatta taattatttt tatagcacgt gatgaaaagg acccaggtgg cacttttcgg   2820
ggaaatgtgc gcggaacccc tatttgttta tttttctaaa tacattcaaa tatgtatccg   2880
ctcatgagac aataaccctg ataaatgctt caataatatt gaaaaaggaa gagtatgagt   2940
attcaacatt tccgtgtcgc ccttattccc ttttttgcgg cattttgcct tcctgttttt   3000
gctcacccag aaacgctggt gaaagtaaaa gatgctgaag atcagttggg tgcacgagtg   3060
ggttacatcg aactggatct caacagcggt aagatccttg agagttttcg ccccgaagaa   3120
cgttttccaa tgatgagcac ttttaaagtt ctgctatgtg gcgcggtatt atcccgtgtt   3180
gacgccgggc aagagcaact cggtcgccgc atacactatt ctcagaatga cttggttgag   3240
tactcaccag tcacagaaaa gcatcttacg gatggcatga cagtaagaga attatgcagt   3300
gctgccataa ccatgagtga taacactgcg gccaacttac ttctgacaac gatcggagga   3360
ccgaaggagc taaccgcttt tttgcacaac atgggggatc atgtaactcg ccttgatcgt   3420
tgggaaccgg agctgaatga agccatacca aacgacgagc gtgacaccac gatgcctgta   3480
gcaatggcaa caacgttgcg caaactatta actggcgaac tacttactct agcttcccgg   3540
caacaattaa tagactggat ggaggcggat aaagttgcag gaccacttct gcgctcggcc   3600
cttccggctg gctggtttat tgctgataaa tctggagccg gtgagcgtgg gtctcgcggt   3660
atcattgcag cactggggcc agatggtaag ccctcccgta tcgtagttat ctacacgacg   3720
gggagtcagg caactatgga tgaacgaaat agacagatcg ctgagatagg tgcctcactg   3780
attaagcatt ggtaactgtc agaccaagtt tactcatata tactttagat tgatttaaaa   3840
cttcattttt aatttaaaag gatctaggtg aagatccttt ttgataatct catgaccaaa   3900
atcccttaac gtgagttttc gttccactga gcgtcagacc ccgtagaaaa gatcaaagga   3960
tcttcttgag atcctttttt tctgcgcgta atctgctgct tgcaaacaaa aaaaccaccg   4020
ctaccagcgg tggtttgttt gccggatcaa gagctaccaa ctctttttcc gaaggtaact   4080
ggcttcagca gagcgcagat accaaatact gtccttctag tgtagccgta gttaggccac   4140
cacttcaaga actctgtagc accgcctaca tacctcgctc tgctaatcct gttaccagtg   4200
gctgctgcca gtggcgataa gtcgtgtctt accgggttgg actcaagacg atagttaccg   4260
gataaggcgc agcggtcggg ctgaacgggg ggttcgtgca cacagcccag cttggagcga   4320
acgacctaca ccgaactgag atacctacag cgtgagctat gagaaagcgc cacgcttccc   4380
gaagggagaa aggcggacag gtatccggta agcggcaggg tcggaacagg agagcgcacg   4440
agggagcttc cagggggaaa cgcctggtat ctttatagtc ctgtcgggtt tcgccacctc   4500
tgacttgagc gtcgattttt gtgatgctcg tcaggggggc ggagcctatg gaaaaacgcc   4560
agcaacgcgg cctttttacg gttcctggcc ttttgctggc cttttgctca catgttcttt   4620
cctgcgttat cccctgattc tgtggataac cgtattaccg cctttgagtg agctgatacc   4680
gctcgccgca gccgaacgac cgagcgcagc gagtcagtga gcgaggaagc ggaagagcgc   4740
ccaatacgca aaccgcctct ccccgcgcgt tggccgattc attaatgcag ctggcacgac   4800
aggtttcccg actggaaagc gggcagtgag cgcaacgcaa ttaatgtgag ttacctcact   4860
cattaggcac cccaggcttt acactttatg cttccggctc gtatgttgtg tggaattgtg   4920
agcggataac aatttcacac aggaaacagc tatgaccatg attacgccaa gctcggaatt   4980
aaccctcact aaagggaaca aaagctggct agt                                5013
```

Fig. 9A (SEQ ID No. 16): vector pYD1dXFc

```
acggattaga agccgccgag cgggtgacag ccctccgaag gaagactctc ctccgtgcgt   60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
```

Fig. 9B (SEQ ID No. 16 cont'd.)

```
tcacagatct ataaatgcac aaactgcata accactttaa ctcatccttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt tttagcacag gaactgacaa     600
ctatatgcga gcaaatcccc tcaccaactt tagaatcgac gccgtactct ttgtcaacga     660
ctactatttt ggccaacggg aaggcaatgc aaggagtttt tgaatattac aaatcagtaa     720
cgtttgtcag taattgcggt tctcaccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccgcta gcaccaaggg cccatcggtc ttccccctgg     960
caccctcctc caagagcacc tctgggggca cagcggccct gggctgcctg gtcaaggact    1020
acttccccga accggtgacg gtgtcgtgga actcaggcgc cctgaccagc ggcgtgcaca    1080
ccttcccggc tgtcctacag tcctcaggac tctactccct cagcagcgtg gtgaccgtgc    1140
cctccagcag cttgggcacc cagacctaca tctgcaatgt gaatcacaag cccagcaata    1200
ccaaggtgga caagaaggtg gagcccaaga gcagcgacaa gacacacacg tgtcccccat    1260
gtcccgcccc tgagctgctg ggcggccctt ccgtgttcct gttccctccc aagcccaagg    1320
acaccctgat gatctcccgg acccctgagg tgacctgtgt ggtggtggac gtgagccacg    1380
aggaccccga ggtgaagttc aactggtacg tggacggcgt ggaggtgcac aacgccaaga    1440
ccaagcctag agaggagcag tacaacagca cctaccgcgt ggtgagcgtg ctgaccgtgc    1500
tgcaccagga ttggctgaat ggcaaggagt acaagtgcaa ggtgagcaac aaggccctgc    1560
ctgcccccat cgagaagacc atctccaagg ccaagggcca gcctcgagaa ccacaggtgt    1620
acaccctgcc cccatcccgg gatgagctga ccaagaacca ggtcagcctg acctgcctgg    1680
tcaaaggctt ctatcccagc gacatcgccg tggagtggga gagcaatggg cagccggaga    1740
acaactacaa gaccacgcct cccgtgctgg actccgacgg ctccttcttc ctctacagca    1800
agctcaccgt ggacaagagc aggtggcagc aggggaacgt cttctcatgc tccgtgatgc    1860
atgaggctct gcacaaccac tacacacaga agagcctctc cctgtctccg ggtaaatgag    1920
cggccgctcg atcgagtcta gagggccctt cgaaggtaag cctatcccta accctctcct    1980
cggtctcgat tctacgcgta ccggtcatca tcaccatcac cattgagttt aaacccgctg    2040
atctgataac aacagtgtag atgtaacaaa atcgactttg ttcccactgt acttttagct    2100
cgtacaaaat acaatatact tttcattttt ccgtaaacaa catgttttcc catgtaatat    2160
ccttttctat ttttcgttcc gttaccaact ttacacatac tttatatagc tattcacttc    2220
tatacactaa aaaactaaga caattttaat tttgctgcct gccatatttc aatttgttat    2280
aaattcctat aatttatcct attagtagct aaaaaaagat gaatgtgaat cgaatcctaa    2340
gagaattggg caagtgcaca aacaatactt aaataaatac tactcagtaa taacctattt    2400
cttagcattt ttgacgaaat ttgctatttt gttagagtct tttacaccat ttgtctccac    2460
acctccgctt acatcaacac caataacgcc atttaatcta agcgcatcac caacattttc    2520
tggcgtcagt ccaccagcta acataaaatg taagctctcg gggctctctt gccttccaac    2580
ccagtcagaa atcgagttcc aatccaaaag ttcacctgtc ccacctgctt ctgaatcaaa    2640
caagggaata aacgaatgag gtttctgtga agctgcactg agtagtatgt tgcagtcttt    2700
tggaaatacg agtcttttaa taactggcaa accgaggaac tcttggtatt cttgccacga    2760
ctcatctccg tgcagttgga cgatatcaat gccgtaatca ttgaccagag ccaaaacatc    2820
ctccttaggt tgattacgaa acacgccaac caagtatttc ggagtgcctg aactattttt    2880
atatgctttt acaagacttg aaattttcct tgcaataacc gggtcaattg ttctctttct    2940
attgggcaca catataatac ccagcaagtc agcatcggaa tctagagcac attctgcggc    3000
ctctgtgctc tgcaagccgc aaactttcac caatggacca gaactacctg tgaaattaat    3060
aacagacata ctccaagctg cctttgtgtg cttaatcacg tatactcacg tgctcaatag    3120
tcaccaatgc cctccctctt ggccctctcc ttttcttttt tcgaccgaat ttcttgaaga    3180
cgaaagggcc tcgtgatacg cctattttta taggttaatg tcatgataat aatggtttct    3240
taggacggat cgcttgcctg taacttacac gcgcctcgta tcttttaatg atggaataat    3300
ttgggaattt actctgtgtt tatttatttt tatgttttgt atttggattt tagaaagtaa    3360
ataaagaagg tagaagagtt acggaatgaa gaaaaaaaaa taaacaaagg tttaaaaaat    3420
ttcaacaaaa agcgtacttt acatatatat ttattagaca agaaaagcag attaaataga    3480
tatacattcg attaacgata agtaaaatgt aaaatcacag gattttcgtg tgtggtcttc    3540
tacacagaca agatgaaaca attcggcatt aatacctgag agcaggaaga gcaagataaa    3600
aggtagtatt tgttggcgat ccccctagag tcttttacat cttcggaaaa caaaaactat    3660
tttttcttta atttcttttt ttactttcta tttttaattt atatatttat attaaaaaat    3720
ttaaattata attattttta tagcacgtga tgaaaaggac ccaggtggca cttttcgggg    3780
aaatgtgcgc ggaaccccta tttgtttatt tttctaaata cattcaaata tgtatccgct    3840
catgagacaa taaccctgat aaatgcttca ataatattga aaaaggaaga gtatgagtat    3900
tcaacatttc cgtgtcgccc ttattccctt ttttgcggca ttttgccttc ctgtttttgc    3960
```

Fig. 9C(SEQ ID No. 16 con't.)

```
tcacccagaa acgctggtga aagtaaaaga tgctgaagat cagttgggtg cacgagtggg     4020
ttacatcgaa ctggatctca acagcggtaa gatccttgag agttttcgcc ccgaagaacg     4080
ttttccaatg atgagcactt ttaaagttct gctatgtggc gcggtattat cccgtgttga     4140
cgccgggcaa gagcaactcg gtcgccgcat acactattct cagaatgact tggttgagta     4200
ctcaccagtc acagaaaagc atcttacgga tggcatgaca gtaagagaat tatgcagtgc     4260
tgccataacc atgagtgata acactgcggc caacttactt ctgacaacga tcggaggacc     4320
gaaggagcta accgcttttt tgcacaacat gggggatcat gtaactcgcc ttgatcgttg     4380
ggaaccggag ctgaatgaag ccataccaaa cgacgagcgt gacaccacga tgcctgtagc     4440
aatggcaaca acgttgcgca aactattaac tggcgaacta cttactctag cttcccggca     4500
acaattaata gactggatgg aggcggataa agttgcagga ccacttctgc gctcggccct     4560
tccggctggc tggtttattg ctgataaatc tggagccggt gagcgtgggt ctcgcggtat     4620
cattgcagca ctggggccag atggtaagcc ctcccgtatc gtagttatct acacgacggg     4680
gagtcaggca actatggatg aacgaaatag acagatcgct gagataggtg cctcactgat     4740
taagcattgg taactgtcag accaagttta ctcatatata ctttagattg atttaaaact     4800
tcatttttaa tttaaaagga tctaggtgaa gatccttttt gataatctca tgaccaaaat     4860
cccttaacgt gagttttcgt tccactgagc gtcagacccc gtagaaaaga tcaaaggatc     4920
ttcttgagat cctttttttc tgcgcgtaat ctgctgcttg caaacaaaaa aaccaccgct     4980
accagcggtg gtttgtttgc cggatcaaga gctaccaact ctttttccga aggtaactgg     5040
cttcagcaga gcgcagatac caaatactgt ccttctagtg tagccgtagt taggccacca     5100
cttcaagaac tctgtagcac cgcctacata cctcgctctg ctaatcctgt taccagtggc     5160
tgctgccagt ggcgataagt cgtgtcttac cgggttggac tcaagacgat agttaccgga     5220
taaggcgcag cggtcgggct gaacgggggg ttcgtgcaca cagcccagct tggagcgaac     5280
gacctacacc gaactgagat acctacagcg tgagcattga gaaagcgcca cgcttcccga     5340
agggagaaag gcggacaggt atccggtaag cggcagggtc ggaacaggag agcgcacgag     5400
ggagcttcca gggggaaacg cctggtatct ttatagtcct gtcgggtttc gccacctctg     5460
acttgagcgt cgatttttgt gatgctcgtc aggggggcgg agcctatgga aaaacgccag     5520
caacgcggcc tttttacggt tcctggcctt ttgctggcct tttgctcaca tgttctttcc     5580
tgcgttatcc cctgattctg tggataaccg tattaccgcc tttgagtgag ctgataccgc     5640
tcgccgcagc cgaacgaccg agcgcagcga gtcagtgagc gaggaagcgg aagagcgccc     5700
aatacgcaaa ccgcctctcc ccgcgcgttg gccgattcat taatgcagct ggcacgacag     5760
gtttcccgac tggaaagcgg gcagtgagcg caacgcaatt aatgtgagtt agctcactca     5820
ttaggcaccc caggctttac actttatgct tccggctcgt atgttgtgtg gaattgtgag     5880
cggataacaa tttcacacag gaaacagcta tgaccatgat tacgccaagc tcggaattaa     5940
ccctcactaa agggaacaaa agctggctag t                                    5971
```

Fig. 10A (SEQ ID No. 17): pYD1CH12

```
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga      240
ttagtttttt agccttattt ctggggtaat taatcagcga agcgatgatt tttgatctat      300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat agggaatatt aagctaattc tacttcatac attttcaatt aagatgcagt      540
tacttcgctg tttttcaata ttttctgtta ttgcttcagt tttagcacag gaactgacaa      600
ctatatgcga gcaaatcccc tcaccaactt tagaatcgac gccgtactct ttgtcaacga      660
ctactatttt ggccaacggg aaggcaatgc aaggagtttt tgaatattac aaatcagtaa      720
cgtttgtcag taattgcggt tctcacccct caacaactag caaaggcagc cccataaaca      780
cacagtatgt ttttaagctt ctgcaggcta gtggtggtgg tggttctggt ggtggtggtt      840
ctggtggtgg tggttctgct agcatgactg gtggacagca aatgggtcgg gatctgtacg      900
acgatgacga taaggtacca ggatccgcta gcaccaaggg ccccagcgtg ttccctctgg      960
cccccagctc caagagcacc tccggcggca ccgccgccct gggctgcctg gtgaaggatt     1020
acttccccga gcccgtgacc gtgagctgga acagcggcgc cctgaccagc ggcgtgcaca     1080
ccttccccgc cgtgctgcag tccagcggcc tgtactccct gagcagcgtg gtgaccgtgc     1140
ccagcagcag cctgggcacc cagacctaca tctgcaatgt gaaccacaag cccagcaata     1200
ccaaggtgga taagaaggtg gagcccaaga gcagcgacaa gacacacacg tgtcccccat     1260
gtcccgcccc tgagctgctg ggcggccctt ccgtgttcct gttccctccc aagcccaagg     1320
acaccctgat gatctcccgg acccctgagg tgacctgtgt ggtggtggac gtgagccacg     1380
aggaccccga ggtgaagttc aactggtacg tggacggcgt ggaggtgcac aacgccaaga     1440
```

Fig. 10B (SEQ ID No. 17 cont'd.)

```
ccaagcctag agaggagcag tacaacagca cctaccgcgt ggtgagcgtg ctgaccgtgc 1500
tgcaccagga ttggctgaat ggcaaggagt acaagtgcaa ggtgagcaac aaggccctgc 1560
ctgcccccat cgagaagacc atctccaagg ccaagggcca gcctcgaggc cgctcgatcg 1620
agtctagagg gcccttcgaa ggtaagccta tccctaaccc tctcctcggt ctcgattcta 1680
cgcgtaccgg tcatcatcac catcaccatt gagtttaaac ccgctgatct gataacaaca 1740
gtgtagatgt aacaaaatcg actttgttcc cactgtactt ttagctcgta caaaatacaa 1800
tatacttttc atttctccgt aaacaacatg ttttcccatg taatatcctt ttctattttt 1860
cgttccgtta ccaactttac acatacttta tatagctatt cacttctata cactaaaaaa 1920
ctaagacaat tttaattttg ctgcctgcca tatttcaatt tgttataaat tcctataatt 1980
tatcctatta gtagctaaaa aaagatgaat gtgaatcgaa tcctaagaga attgggcaag 2040
tgcacaaaca atacttaaat aaatactact cagtaataac ctatttctta gcatttttga 2100
cgaaatttgc tattttgtta gagtctttta caccatttgt ctccacacct ccgcttacat 2160
caacaccaat aacgccattt aatctaagcg catcaccaac attttctggc gtcagtccac 2220
cagctaacat aaaatgtaag ctctcggggc tctcttgcct tccaacccag tcagaaatcg 2280
agttccaatc caaaagttca cctgtcccac ctgcttctga atcaaacaag ggaataaacg 2340
aatgaggttt ctgtgaagct gcactgagta gtatgttgca gtcttttgga aatacgagtc 2400
ttttaataac tggcaaaccg aggaactctt ggtattcttg ccacgactca tctccgtgca 2460
gttggacgat atcaatgccg taatcattga ccagagccaa aacatcctcc ttaggttgat 2520
tacgaaacac gccaaccaag tatttcggag tgcctgaact atttttatat gcttttacaa 2580
gacttgaaat tttccttgca ataaccgggt caattgttct ctttctattg ggcacacata 2640
taatacccag caagtcagca tcggaatcta gagcacattc tgcggcctct gtgctctgca 2700
agccgcaaac tttcaccaat ggaccagaac tacctgtgaa attaataaca gacatactcc 2760
aagctgcctt tgtgtgctta atcacgtata ctcacgtgct caatagtcac caatgccctc 2820
cctcttggcc ctctcctttt cttttttcga ccgaatttct tgaagacgaa agggcctcgt 2880
gatacgccta tttttatagg ttaatgtcat gataataatg gtttcttagg acggatcgct 2940
tgcctgtaac ttacacgcgc ctcgtatctt ttaatgatgg aataatttgg gaatttactc 3000
tgtgtttatt tatttttatg ttttgtattt ggattttaga aagtaaataa agaaggtaga 3060
agagttacgg aatgaagaaa aaaaaataaa caaaggttta aaaaatttca acaaaaagcg 3120
tactttacat atatatttat tagacaagaa aagcagatta aatagatata cattcgatta 3180
acgataagta aaatgtaaaa tcacaggatt ttcgtgtgtg gtcttctaca cagacaagat 3240
gaaacaattc ggcattaata cctgagagca ggaagagcaa gataaaaggt agtatttgtt 3300
ggcgatcccc ctagagtctt ttacatcttc ggaaaacaaa aactattttt tctttaattt 3360
ctttttttac tttctatttt taatttatat atttatatta aaaaatttaa attataatta 3420
tttttatagc acgtgatgaa aaggacccag gtggcacttt tcggggaaat gtgcgcggaa 3480
cccctatttg tttatttttc taaatacatt caaatatgta tccgctcatg agacaataac 3540
cctgataaat gcttcaataa tattgaaaaa ggaagagtat gagtattcaa catttccgtg 3600
tcgcccttat tccctttttt gcggcatttt gccttcctgt ttttgctcac ccagaaacgc 3660
tggtgaaagt aaaagatgct gaagatcagt tgggtgcacg agtgggttac atcgaactgg 3720
atctcaacag cggtaagatc cttgagagtt ttcgccccga agaacgtttt ccaatgatga 3780
gcacttttaa agttctgcta tgtggcgcgg tattatcccg tgttgacgcc gggcaagagc 3840
aactcggtcg ccgcatacac tattctcaga atgacttggt tgagtactca ccagtcacag 3900
aaaagcatct tacggatggc atgacagtaa gagaattatg cagtgctgcc ataaccatga 3960
gtgataacac tgcggccaac ttacttctga caacgatcgg aggaccgaag gagctaaccg 4020
cttttttgca caacatgggg gatcatgtaa ctcgccttga tcgttgggaa ccggagctga 4080
atgaagccat accaaacgac gagcgtgaca ccacgatgcc tgtagcaatg gcaacaacgt 4140
tgcgcaaact attaactggc gaactactta ctctagcttc ccggcaacaa ttaatagact 4200
ggatggaggc ggataaagtt gcaggaccac ttctgcgctc ggcccttccg gctggctggt 4260
ttattgctga taaatctgga gccggtgagc gtgggtctcg cggtatcatt gcagcactgg 4320
ggccagatgg taagccctcc cgtatcgtag ttatctacac gacggggagt caggcaacta 4380
tggatgaacg aaatagacag atcgctgaga taggtgcctc actgattaag cattggtaac 4440
tgtcagacca agtttactca tatatacttt agattgattt aaaacttcat ttttaattta 4500
aaaggatcta ggtgaagatc ctttttgata atctcatgac caaaatccct taacgtgagt 4560
tttcgttcca ctgagcgtca gaccccgtag aaaagatcaa aggatcttct tgagatcctt 4620
tttttctgcg cgtaatctgc tgcttgcaaa caaaaaaacc accgctacca gcggtggttt 4680
gtttgccgga tcaagagcta ccaactcttt ttccgaaggt aactggcttc agcagagcgc 4740
agataccaaa tactgtcctt ctagtgtagc cgtagttagg ccaccacttc aagaactctg 4800
tagcaccgcc tacatacctc gctctgctaa tcctgttacc agtggctgct gccagtggcg 4860
ataagtcgtg tcttaccggg ttggactcaa gacgatagtt accggataag gcgcagcggt 4920
cgggctgaac ggggggttcg tgcacacagc ccagcttgga gcgaacgacc tacaccgaac 4980
tgagatacct acagcgtgag cattgagaaa gcgccacgct tcccgaaggg agaaaggcgg 5040
acaggtatcc ggtaagcggc agggtcggaa caggagagcg cacgagggag cttccagggg 5100
```

Fig. 10C (SEQ ID No. 17 cont'd.)

```
ggaacgcctg gtatctttat agtcctgtcg ggtttcgcca cctctgactt gagcgtcgat     5160
ttttgtgatg ctcgtcaggg gggcggagcc tatggaaaaa cgccagcaac gcggcctttt     5220
tacggttcct ggccttttgc tggccttttg ctcacatgtt ctttcctgcg ttatcccctg     5280
attctgtgga taaccgtatt accgcctttg agtgagctga taccgctcgc cgcagccgaa     5340
cgaccgagcg cagcgagtca gtgagcgagg aagcggaaga gcgcccaata cgcaaaccgc     5400
ctctccccgc gcgttggccg attcattaat gcagctggca cgacaggttt cccgactgga     5460
aagcgggcag tgagcgcaac gcaattaatg tgagttacct cactcattag gcaccccagg     5520
ctttacactt tatgcttccg gctcgtatgt tgtgtggaat tgtgagcgga taacaatttc     5580
acacaggaaa cagctatgac catgattacg ccaagctcgg aattaaccct cactaaaggg     5640
aacaaaagct ggctagt                                                    5657
```

Fig. 11 (SEQ ID No. 18): Fcab01

```
ggcccagccg gccatggccg agcccaaatc ttgtgacaaa actcacacat gcccaccgtg       60
cccagcacct gaactcctgg ggggaccgtc agtcttcctc ttccccccaa aacccaagga      120
caccctcatg atctcccgga cccctgaggt cacatgcgtg gtggtggacg tgagccacga      180
agaccctgag gtcaagttca actggtacgt ggacggcgtg gaggtgcata atgccaagac      240
aaagccgcgg gaggagcagt acaacagcac gtaccgtgtg gtcagcgtcc tcaccgtcct      300
gcaccaggac tggctgaatg gcaaggagta caagtgcaag gtctccaaca aagccctccc      360
agcccccatc gagaaaacca tctccaaagc caaagggcag cctcgagaac cacaggtgta      420
caccctgccc ccatcccggg atgaactgnn bnnbnnbcag gtcagcctga cctgcctggt      480
caaaggcttc tatcccagcg acatcgccgt ggagtgggag agcaatgggc agccggagaa      540
caactacaag accacgcctc ccgtgctgga ctccgacggc tccttcttcc tctacagcaa      600
gctcaccgtg nnbnnbnnbn nbnnbnnbnn bnnbaggtgg nnbnnbggga acgtcttctc      660
atgctccgtg atgcatgagg ctctgcacaa ccactacacg cagaagagcc tctccctgtc      720
tccgggtaaa gcggccgc                                                    738
```

Fig. 12 (SEQ ID No. 19): Fcab02

```
ggcccagccg gccatggccg agcccaaatc ttgtgacaaa actcacacat gcccaccgtg       60
cccagcacct gaactcctgg ggggaccgtc agtcttcctc ttccccccaa aacccaagga      120
caccctcatg atctcccgga cccctgaggt cacatgcgtg gtggtggacg tgagccacga      180
agaccctgag gtcaagttca actggtacgt ggacggcgtg gaggtgcata atgccaagac      240
aaagccgcgg gaggagcagt acaacagcac gtaccgtgtg gtcagcgtcc tcaccgtcct      300
gcaccaggac tggctgaatg gcaaggagta caagtgcaag gtctccaaca aagccctccc      360
agcccccatc gagaaaacca tctccaaagc caaagggcag cctcgagaac cacaggtgta      420
caccctgccc ccatcccggg atgagctgkm tkmtkmtcag gtgagcctga cctgcctggt      480
caaaggcttc tatcccagcg acatcgccgt ggagtgggag agcaatgggc agccggagaa      540
caactacaag accacgcctc ccgtgctgga ctccgacggc tccttcttcc tctacagcaa      600
gctcaccgtg kmtkmtkmtk mtkmtkmtkm tkmtaggtgg kmtkmtggga acgtcttctc      660
atgctccgtg atgcatgagg ctctgcacaa ccactacacg cagaagagcc tctccctgtc      720
tccgggtaaa gcggccgc                                                    738
```

Fig. 13 (SEQ ID No. 20): Fcab03

```
ggcccagccg gccatggccg agcccaaatc ttgtgacaaa actcacacat gcccaccgtg       60
cccagcacct gaactcctgg ggggaccgtc agtcttcctc ttccccccaa aacccaagga      120
caccctcatg atctcccgga cccctgaggt cacatgcgtg gtggtggacg tgagccacga      180
agaccctgag gtcaagttca actggtacgt ggacggcgtg gaggtgcata atgccaagac      240
aaagccgcgg gaggagcagt acaacagcac gtaccgtgtg gtcagcgtcc tcaccgtcct      300
gcaccaggac tggctgaatg gcaaggagta caagtgcaag gtctccaaca aagccctccc      360
agcccccatc gagaaaacca tctccaaagc caaagggcag cctcgagaac cacaggtgta      420
caccctgccc ccttcccggg atgagctgnn bnnbnnbcag gtcagcctga cctgcctggt      480
caaaggcttc tatcccagcg acatcgccgt ggagtgggag agcaatgggc agccggagaa      540
caactacaag accacgcctc ccgtgctgga ctccgacggc tccttcttcc tctacagcaa      600
gctcaccgtg ggttctnnbn nbnnbnnbnn bnnbnnbnnb agcggcaggt ggnnbnnbgg      660
gaacgtcttc tcatgctccg tgatgcatga ggctctgcac aaccactaca cgcagaagag      720
cctctccctg tctccgggta aagcggccgc                                       750
```

Fig. 14 (SEQ ID No. 21): Fcab04

```
ggcccagccg gccatggccg agcccaaatc ttgtgacaaa actcacacat gcccaccgtg    60
cccagcacct gaactcctgg ggggaccgtc agtcttcctc ttccccccaa aacccaagga   120
caccctcatg atctcccgga cccctgaggt cacatgcgtg gtggtggacg tgagccacga   180
agaccctgag gtcaagttca actggtacgt ggacggcgtg gaggtgcata atgccaagac   240
aaagccgcgg gaggagcagt acaacagcac gtaccgtgtg gtcagcgtcc tcaccgtcct   300
gcaccaggac tggctgaatg gcaaggagta caagtgcaag gtctccaaca aagccctccc   360
agcccccatc gagaaaacca tctccaaagc caaagggcag cctcgagaac cacaggtgta   420
caccctgccc ccatctcggg atgagctgkm tkmtkmtcag gtcagcctga cctgcctggt   480
caaaggcttc tatcccagcg acatcgccgt ggagtgggag agcaatgggc agccggagaa   540
caactacaag accacgcctc ccgtgctgga ctccgacggc tccttcttcc tctacagcaa   600
gctcaccgtg ggttctkmtk mtkmtkmtkm tkmtkmtkmt agcggcaggt ggkmtkmtgg   660
gaacgtcttc tcatgctccg tgatgcatga ggctctgcac aaccactaca cgcagaagag   720
cctctccctg tctccgggta aagcggccgc                                    750
```

Fig. 15 (SEQ ID No. 22): Fcab05

```
ggcccagccg gccatggccg agcccaaatc ttgtgacaaa actcacacat gcccaccgtg    60
cccagcacct gaactcctgg ggggaccgtc agtcttcctc ttccccccaa aacccaagga   120
caccctcatg atctcccgga cccctgaggt cacatgcgtg gtggtggacg tgagccacga   180
agaccctgag gtcaagttca actggtacgt ggacggcgtg gaggtgcata atgccaagac   240
aaagccgcgg gaggagcagt acaacagcac gtaccgtgtg gtcagcgtcc tcaccgtcct   300
gcaccaggac tggctgaatg gcaaggagta caagtgcaag gtctccaaca aagccctccc   360
agcccccatc gagaaaacca tctccaaagc caaagggcag cctcgagaac cacaggtgta   420
caccctgccc ccatcccgtg atgagkmtnn bnnbnnbkmt gtcagcctga cctgcctggt   480
caaaggcttc tatcccagcg acatcgccgt ggagtgggag agcaatgggc agccggagaa   540
caactacaag accacgcctc ccgtgctgga ctccgacggc tccttcttcc tctacagcaa   600
gctcaccgtg nnbnnbnnbn nbnnbnnbnn bnnbaggtgg nnbnnbggga acgtcttctc   660
atgctccgtg atgcatgagg ctctgcacaa ccactacacg cagaagagcc tctccctgtc   720
tccgggtaaa gcggccgc                                                 738
```

Fig. 16 (SEQ ID No. 23): Fcab06

```
ggcccagccg gccatggccg agcccaaatc ttgtgacaaa actcacacat gcccaccgtg    60
cccagcacct gaactcctgg ggggaccgtc agtcttcctc ttccccccaa aacccaagga   120
caccctcatg atctcccgga cccctgaggt cacatgcgtg gtggtggacg tgagccacga   180
agaccctgag gtcaagttca actggtacgt ggacggcgtg gaggtgcata atgccaagac   240
aaagccgcgg gaggagcagt acaacagcac gtaccgtgtg gtcagcgtcc tcaccgtcct   300
gcaccaggac tggctgaatg gcaaggagta caagtgcaag gtctccaaca aagccctccc   360
agcccccatc gagaaaacca tctccaaagc caaagggcag cctcgagaac cacaggtgta   420
caccctgccc ccatcccggg acgagkmtkm tkmtkmtkmt gtcagcctga cctgcctggt   480
caaaggcttc tatcccagcg acatcgccgt ggagtgggag agcaatgggc agccggagaa   540
caactacaag accacgcctc ccgtgctgga ctccgacggc tccttcttcc tctacagcaa   600
gctcaccgtg kmtkmtkmtk mtkmtkmtkm tkmtaggtgg kmtkmtggga acgtcttctc   660
atgctccgtg atgcatgagg ctctgcacaa ccactacacg cagaagagcc tctccctgtc   720
tccgggtaaa gcggccgc                                                 738
```

Fig. 17A (SEQ ID No.72): vector pYD1

```
acggattaga agccgccgag cgggtgacag ccctccgaag gaagactctc ctccgtgcgt    60
cctcgtcttc accggtcgcg ttcctgaaac gcagatgtgc ctcgcgccgc actgctccga   120
acaataaaga ttctacaata ctagctttta tggttatgaa gaggaaaaat tggcagtaac   180
ctggccccac aaaccttcaa atgaacgaat caaattaaca accataggat gataatgcga   240
ttagtttttt agccttattt ctggggtaat taatcagcga agcgatgatt tttgatctat   300
taacagatat ataaatgcaa aaactgcata accactttaa ctaatacttt caacattttc   360
ggtttgtatt acttcttatt caaatgtaat aaaagtatca acaaaaaatt gttaatatac   420
ctctatactt taacgtcaag gagaaaaaac cccggatcgg actactagca gctgtaatac   480
gactcactat agggaatatt aagctaattc tacttcatac attttcaatt aagatgcagt   540
tacttcgctg tttttcaata ttttctgtta ttgcttcagt tttagcacag gaactgacaa   600
```

Fig. 17B (SEQ ID No.72 cont'd.)

```
ctatatgcga gcaaatcccc tcaccaactt tagaatcgac gccgtactct ttgtcaacga      660
ctactatttt ggccaacggg aaggcaatgc aaggagtttt tgaatattac aaatcagtaa      720
cgtttgtcag taattgcggt tctcacccct caacaactag caaaggcagc cccataaaca      780
cacagtatgt ttttaagctt ctgcaggcta gtggtggtgg tggttctggt ggtggtggtt      840
ctggtggtgg tggttctgct agcatgactg gtggacagca aatgggtcgg gatctgtacg      900
acgatgacga taaggtacca ggatccagtg tggtggaatt ctgcagatat ccagcacagt      960
ggcggccgct cgagtctaga gggcccttcg aaggtaagcc tatccctaac cctctcctcg     1020
gtctcgattc tacgcgtacc ggtcatcatc accatcacca ttgagtttaa acccgctgat     1080
ctgataacaa cagtgtagat gtaacaaaat cgactttgtt cccactgtac ttttagctcg     1140
tacaaaatac aatatacttt tcatttctcc gtaaacaaca tgttttccca tgtaatatcc     1200
ttttctattt ttcgttccgt taccaacttt acacatactt tatatagcta ttcacttcta     1260
tacactaaaa aactaagaca attttaattt tgctgcctgc catatttcaa tttgttataa     1320
attcctataa tttatcctat tagtagctaa aaaaagatga atgtgaatcg aatcctaaga     1380
gaattgggca agtgcacaaa caatacttaa ataaatacta ctcagtaata acctatttct     1440
tagcattttt gacgaaattt gctattttgt tagagtcttt tacaccattt gtctccacac     1500
ctccgcttac atcaacacca ataacgccat ttaatctaag cgcatcacca acattttctg     1560
gcgtcagtcc accagctaac ataaaatgta agctctcggg gctctcttgc cttccaaccc     1620
agtcagaaat cgagttccaa tccaaaagtt cacctgtccc acctgcttct gaatcaaaca     1680
agggaataaa cgaatgaggt ttctgtgaag ctgcactgag tagtatgttg cagtcttttg     1740
gaaatacgag tcttttaata actggcaaac cgaggaactc ttggtattct tgccacgact     1800
catctccgtg cagttggacg atatcaatgc cgtaatcatt gaccagagcc aaaacatcct     1860
ccttaggttg attacgaaac acgccaacca agtatttcgg agtgcctgaa ctatttttat     1920
atgcttttac aagacttgaa attttccttg caataaccgg gtcaattgtt ctctttctat     1980
tgggcacaca tataataccc agcaagtcag catcggaatc tagagcacat tctgcggcct     2040
ctgtgctctg caagccgcaa actttcacca atggaccaga actacctgtg aaattaataa     2100
cagacatact ccaagctgcc tttgtgtgct taatcacgta tactcacgtg ctcaatagtc     2160
accaatgccc tccctcttgg ccctctcctt ttcttttttc gaccgaattt cttgaagacg     2220
aaagggcctc gtgatacgcc tatttttata ggttaatgtc atgataataa tggtttctta     2280
ggacggatcg cttgcctgta acttacacgc gcctcgtatc ttttaatgat ggaataattt     2340
gggaatttac tctgtgttta tttattttta tgttttgtat ttggatttta gaaagtaaat     2400
aaagaaagta gaagagttac ggaatgaaga aaaaaaaata aacaaaggtt taaaaaattt     2460
caacaaaaag cgtactttac atatatattt attagacaag aaaagcagat taaatagata     2520
tacattcgat taacgataag taaaatgtaa aatcacagga ttttcgtgtg tggtcttcta     2580
cacagacaag atgaaacaat tcggcattaa tacctgagag caggaagagc aagataaaag     2640
gtagtatttg ttggcgatcc ccctagagtc ttttacatct tcggaaaaca aaaactattt     2700
tttctttaat ttcttttttt actttctatt tttaatttat atatttatat taaaaaattt     2760
aaattataat tatttttata gcacgtgatg aaaaggaccc aggtggcact tttcggggaa     2820
atgtgcgcgg aacccctatt tgtttatttt tctaaataca ttcaaatatg tatccgctca     2880
tgagacaata accctgataa atgcttcaat aatattgaaa aaggaagagt atgagtattc     2940
aacatttccg tgtcgccctt attccctttt ttgcggcatt ttgccttcct gtttttgctc     3000
acccagaaac gctggtgaaa gtaaaagatg ctgaagatca gttgggtgca cgagtgggtt     3060
acatcgaact ggatctcaac agcggtaaga tccttgagag ttttcgcccc gaagaacgtt     3120
ttccaatgat gagcactttt aaagttctgc tatgtggcgc ggtattatcc cgtgttgacg     3180
ccgggcaaga gcaactcggt cgccgcatac actattctca gaatgacttg gttgagtact     3240
caccagtcac agaaaagcat cttacggatg gcatgacagt aagagaatta tgcagtgctg     3300
ccataaccat gagtgataac actgcggcca acttacttct gacaacgatc ggaggaccga     3360
aggagctaac cgcttttttg cacaacatgg gggatcatgt aactcgcctt gatcgttggg     3420
aaccggagct gaatgaagcc ataccaaacg acgagcgtga caccacgatg cctgtagcaa     3480
tggcaacaac gttgcgcaaa ctattaactg gcgaactact tactctagct tcccggcaac     3540
aattaataga ctggatggag gcggataaag ttgcaggacc acttctgcgc tcggcccttc     3600
cggctggctg gtttattgct gataaatctg gagccggtga gcgtgggtct cgcggtatca     3660
ttgcagcact ggggccagat ggtaagccct cccgtatcgt agttatctac acgacgggga     3720
gtcaggcaac tatggatgaa cgaaatagac agatcgctga gataggtgcc tcactgatta     3780
agcattggta actgtcagac caagtttact catatatact ttagattgat ttaaaacttc     3840
atttttaatt taaaaggatc taggtgaaga tcctttttga taatctcatg accaaaatcc     3900
cttaacgtga gttttcgttc cactgagcgt cagaccccgt agaaaagatc aaaggatctt     3960
cttgagatcc tttttttctg cgcgtaatct gctgcttgca aacaaaaaaa ccaccgctac     4020
cagcggtggt ttgtttgccg gatcaagagc taccaactct ttttccgaag gtaactggct     4080
tcagcagagc gcagatacca aatactgtcc ttctagtgta gccgtagtta ggccaccact     4140
tcaagaactc tgtagcaccg cctacatacc tcgctctgct aatcctgtta ccagtggctg     4200
ctgccagtgg cgataagtcg tgtcttaccg ggttggactc aagacgatag ttaccggata     4260
```

Fig. 17C (SEQ ID No. 72 cont'd.)

aggcgcagcg gtcgggctga acggggggtt cgtgcacaca gcccagcttg gagcgaacga 4320
cctacaccga actgagatac ctacagcgtg agcattgaga aagcgccacg cttcccgaag 4380
ggagaaaggc ggacaggtat ccggtaagcg gcagggtcgg aacaggagag cgcacgaggg 4440
agcttccagg gggaaacgcc tggtatcttt atagtcctgt cgggtttcgc cacctctgac 4500
ttgagcgtcg atttttgtga tgctcgtcag gggggcggag cctatggaaa aacgccagca 4560
acgcggcctt tttacggttc ctggcctttt gctggccttt tgctcacatg ttctttcctg 4620
cgttatcccc tgattctgtg gataaccgta ttaccgcctt tgagtgagct gataccgctc 4680
gccgcagccg aacgaccgag cgcagcgagt cagtgagcga ggaagcggaa gagcgcccaa 4740
tacgcaaacc gcctctcccc gcgcgttggc cgattcatta atgcagctgg cacgacaggt 4800
ttcccgactg gaaagcgggc agtgagcgca acgcaattaa tgtgagttac ctcactcatt 4860
aggcacccca ggctttacac tttatgcttc cggctcctat gttgtgtgga attgtgagcg 4920
gataacaatt tcacacagga aacagctatg accatgatta cgccaagctc ggaattaacc 4980
ctcactaaag ggaacaaaag ctggctagt 5009

Fig. 18A (SEQ ID No.73): modified vector pYD1Nhe acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgcttcagt gctagcacag gaactgacaa 600
ctatatgcga gcaaatcccc tcaccaactt tagaatcgac gccgtactct ttgtcaacga 660
ctactatttt ggccaacggg aaggcaatgc aaggagtttt tgaatattac aaatcagtaa 720
cgtttgtcag taattgcggt tctcacccct caacaactag caaaggcagc cccataaaca 780
cacagtatgt ttttaagctt ctgcaggcta gtggtggtgg tggttctggt ggtggtggtt 840
ctggtggtgg tggttctgct agcatgactg gtggacagca aatgggtcgg gatctgtacg 900
acgatgacga taaggtacca ggatccagtg tggtggaatt ctgcagatat ccagcacagt 960
ggcggccgct cgagtctaga gggcccttcg aaggtaagcc tatccctaac cctctcctcg 1020
gtctcgattc tacgcgtacc ggtcatcatc accatcacca ttgagtttaa acccgctgat 1080
ctgataacaa cagtgtagat gtaacaaaat cgactttgtt cccactgtac ttttagctcg 1140
tacaaaatac aatatacttt tcatttctcc gtaaacaaca tgttttccca tgtaatatcc 1200
ttttctattt ttcgttccgt taccaacttt acacatactt tatatagcta ttcacttcta 1260
tacactaaaa aactaagaca attttaattt tgctgcctgc catatttcaa tttgttataa 1320
attcctataa tttatcctat tagtagctaa aaaaagatga atgtgaatcg aatcctaaga 1380
gaattgggca agtgcacaaa caatacttaa ataaatacta ctcagtaata acctatttct 1440
tagcattttt gacgaaattt gctattttgt tagagtcttt tacaccattt gtctccacac 1500
ctccgcttac atcaacacca ataacgccat ttaatctaag cgcatcacca acattttctg 1560
gcgtcagtcc accagctaac ataaaatgta agctctcggg gctctcttgc cttccaaccc 1620
agtcagaaat cgagttccaa tccaaaagtt cacctgtccc acctgcttct gaatcaaaca 1680
agggaataaa cgaatgaggt ttctgtgaag ctgcactgag tagtatgttg cagtcttttg 1740
gaaatacgag tcttttaata actggcaaac cgaggaactc ttggtattct tgccacgact 1800
catctccgtg cagttggacg atatcaatgc cgtaatcatt gaccagagcc aaaacatcct 1860
ccttaggttg attacgaaac acgccaacca agtatttcgg agtgcctgaa ctatttttat 1920
atgcttttac aagacttgaa attttccttg caataaccgg gtcaattgtt ctctttctat 1980
tgggcacaca tataataccc agcaagtcag catcggaatc tagagcacat tctgcggcct 2040
ctgtgctctg caagccgcaa actttcacca atggaccaga actacctgtg aaattaataa 2100
cagacatact ccaagctgcc tttgtgtgct taatcacgta tactcacgtg ctcaatagtc 2160
accaatgccc tccctcttgg ccctctcctt ttcttttttc gaccgaattt cttgaagacg 2220
aaagggcctc gtgatacgcc tatttttata ggttaatgtc atgataataa tggtttctta 2280
ggacggatcg cttgcctgta acttacacgc gcctcgtatc ttttaatgat ggaataattt 2340
gggaatttac tctgtgttta tttattttta tgttttgtat ttggatttta gaaagtaaat 2400
aaagaaggta gaagagttac ggaatgaaga aaaaaaaata aacaaaggtt taaaaaattt 2460
caacaaaaag cgtactttac atatatattt attagacaag aaaagcagat taaatagata 2520
tacattcgat taacgataag taaaatgtaa aatcacagga ttttcgtgtg tggtcttcta 2580
cacagacaag atgaaacaat tcggcattaa tacctgagag caggaagagc aagataaaag 2640
gtagtatttg ttggcgatcc ccctagagtc ttttacatct tcggaaaaca aaaactattt 2700

Fig. 18B (SEQ ID No.73 cont'd.)

```
tttctttaat ttcttttttt actttctatt tttaatttat atatttatat taaaaaattt    2760
aaattataat tatttttata gcacgtgatg aaaaggaccc aggtggcact tttcggggaa    2820
atgtgcgcgg aacccctatt tgtttatttt tctaaataca ttcaaatatg tatccgctca    2880
tgagacaata accctgataa atgcttcaat aatattgaaa aaggaagagt atgagtattc    2940
aacatttccg tgtcgccctt attccctttt ttgcggcatt ttgccttcct gtttttgctc    3000
acccagaaac gctggtgaaa gtaaaagatg ctgaagatca gttgggtgca cgagtgggtt    3060
acatcgaact ggatctcaac agcggtaaga tccttgagag ttttcgcccc gaagaacgtt    3120
ttccaatgat gagcactttt aaagttctgc tatgtggcgc ggtattatcc cgtgttgacg    3180
ccgggcaaga gcaactcggt cgccgcatac actattctca gaatgacttg gttgagtact    3240
caccagtcac agaaaagcat cttacggatg gcatgacagt aagagaatta tgcagtgctg    3300
ccataaccat gagtgataac actgcggcca acttacttct gacaacgatc ggaggaccga    3360
aggagctaac cgcttttttg cacaacatgg gggatcatgt aactcgcctt gatcgttggg    3420
aaccggagct gaatgaagcc ataccaaacg acgagcgtga caccacgatg cctgtagcaa    3480
tggcaacaac gttgcgcaaa ctattaactg gcgaactact tactctagct tcccggcaac    3540
aattaataga ctggatggag gcggataaag ttgcaggacc acttctgcgc tcggcccttc    3600
cggctggctg gtttattgct gataaatctg gagccggtga gcgtgggtct cgcggtatca    3660
ttgcagcact ggggccagat ggtaagccct cccgtatcgt agttatctac acgacgggga    3720
gtcaggcaac tatggatgaa cgaaatagac agatcgctga gataggtgcc tcactgatta    3780
agcattggta actgtcagac caagtttact catatatact ttagattgat ttaaaacttc    3840
atttttaatt taaaaggatc taggtgaaga tcctttttga taatctcatg accaaaatcc    3900
cttaacgtga gttttcgttc cactgagcgt cagaccccgt agaaaagatc aaaggatctt    3960
cttgagatcc tttttttctg cgcgtaatct gctgcttgca aacaaaaaaa ccaccgctac    4020
cagcggtggt ttgtttgccg gatcaagagc taccaactct ttttccgaag gtaactggct    4080
tcagcagagc gcagatacca aatactgtcc ttctagtgta gccgtagtta ggccaccact    4140
tcaagaactc tgtagcaccg cctacatacc tcgctctgct aatcctgtta ccagtggctg    4200
ctgccagtgg cgataagtcg tgtcttaccg ggttggactc aagacgatag ttaccggata    4260
aggcgcagcg gtcgggctga acggggggtt cgtgcacaca gcccagcttg gagcgaacga    4320
cctacaccga actgagatac ctacagcgtg agctatgaga aagcgccacg cttcccgaag    4380
ggagaaaggc ggacaggtat ccggtaagcg gcagggtcgg aacaggagag cgcacgaggg    4440
agcttccagg gggaaacgcc tggtatcttt atagtcctgt cgggtttcgc cacctctgac    4500
ttgagcgtcg atttttgtga tgctcgtcag gggggcggag cctatggaaa aacgccagca    4560
acgcggcctt tttacggttc ctggcctttt gctggccttt tgctcacatg ttctttcctg    4620
cgttatcccc tgattctgtg gataaccgta ttaccgcctt tgagtgagct gataccgctc    4680
gccgcagccg aacgaccgag cgcagcgagt cagtgagcga ggaagcggaa gagcgcccaa    4740
tacgcaaacc gcctctcccc gcgcgttggc cgattcatta atgcagctgg cacgacaggt    4800
ttcccgactg gaaagcgggc agtgagcgca acgcaattaa tgtgagttac ctcactcatt    4860
aggcacccca ggctttacac tttatgcttc cggctcgtat gttgtgtgga attgtgagcg    4920
gataacaatt tcacacagga aacagctatg accatgatta cgccaagctc ggaattaacc    4980
ctcactaaag ggaacaaaag ctggctagt                                      5009
```

Fig. 19A (SEQ ID No.74): vector pYD1lnk

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt gctagcagct ggggccatgg     600
ttactgattg gcgcgccgga tccttcagac tctgcagaat tcggccgcgt acttaattaa     660
gtttaaaccc gctgatctga taacaacagt gtagatgtaa caaaatcgac tttgttccca     720
ctgtactttt agctcgtaca aaatacaata tacttttcat ttctccgtaa acaacatgtt     780
ttcccatgta atatcctttt ctatttttcg ttccgttacc aactttacac atactttata     840
tagctattca cttctataca ctaaaaaact aagacaattt taattttgct gcctgccata     900
tttcaatttg ttataaattc ctataattta tcctattagt agctaaaaaa agatgaatgt     960
gaatcgaatc ctaagagaat tgggcaagtg cacaaacaat acttaaataa atactactca    1020
gtaataacct atttcttagc atttttgacg aaatttgcta ttttgttaga gtcttttaca    1080
ccatttgtct ccacacctcc gcttacatca acaccaataa cgccatttaa tctaagcgca    1140
```

Fig. 19B (SEQ ID No. 74 cont'd.)

```
tcaccaacat tttctggcgt cagtccacca gctaacataa aatgtaagct ctcggggctc   1200
tcttgccttc caacccagtc agaaatcgag ttccaatcca aaagttcacc tgtcccacct   1260
gcttctgaat caaacaaggg aataaacgaa tgaggtttct gtgaagctgc actgagtagt   1320
atgttgcagt cttttggaaa tacgagtctt ttaataactg gcaaaccgag gaactcttgg   1380
tattcttgcc acgactcatc tccgtgcagt tggacgatat caatgccgta atcattgacc   1440
agagccaaaa catcctcctt aggttgatta cgaaacacgc caaccaagta tttcggagtg   1500
cctgaactat ttttatatgc ttttacaaga cttgaaattt tccttgcaat aaccgggtca   1560
attgttctct ttctattggg cacacatata atacccagca agtcagcatc ggaatctaga   1620
gcacattctg cggcctctgt gctctgcaag ccgcaaactt tcaccaatgg accagaacta   1680
cctgtgaaat taataacaga catactccaa gctgcctttg tgtgcttaat cacgtatact   1740
cacgtgctca atagtcacca atgccctccc tcttggccct ctcctttctt tttttcgacc   1800
gaatttcttg aagacgaaag ggcctcgtga tacgcctatt tttataggtt aatgtcatga   1860
taataatggt ttcttaggac ggatcgcttg cctgtaactt acacgcgcct cgtatctttt   1920
aatgatggaa taatttggga atttactctg tgtttattta tttttatgtt ttgtatttgg   1980
attttagaaa gtaaataaag aaggtagaag agttacggaa tgaagaaaaa aaaataaaca   2040
aaggtttaaa aaatttcaac aaaaagcgta ctttacatat atatttatta gacaagaaaa   2100
gcagattaaa tagatataca ttcgattaac gataagtaaa atgtaaaatc acaggatttt   2160
cgtgtgtggt cttctacaca gacaagatga aacaattcgg cattaatacc tgagagcagg   2220
aagagcaaga taaaaggtag tatttgttgg cgatcccct agagtctttt acatcttcgg   2280
aaaacaaaaa ctattttttc tttaatttct ttttttactt tctattttta atttatatat   2340
ttatattaaa aaatttaaat tataattatt tttatagcac gtgatgaaaa ggacccaggt   2400
ggcacttttc ggggaaatgt gcgcggaacc cctatttgtt tatttttcta aatacattca   2460
aatatgtatc cgctcatgag acaataaccc tgataaatgc ttcaataata ttgaaaaagg   2520
aagagtatga gtattcaaca tttccgtgtc gcccttattc ccttttttgc ggcattttgc   2580
cttcctgttt ttgctcaccc agaaacgctg gtgaaagtaa aagatgctga agatcagttg   2640
ggtgcacgag tgggttacat cgaactggat ctcaacagcg gtaagatcct tgagagtttt   2700
cgccccgaag aacgttttcc aatgatgagc acttttaaag ttctgctatg tggcgcggta   2760
ttatcccgtg ttgacgccgg gcaagagcaa ctcggtcgcc gcatacacta ttctcagaat   2820
gacttggttg agtactcacc agtcacagaa aagcatctta cggatggcat gacagtaaga   2880
gaattatgca gtgctgccat aaccatgagt gataacactg cggccaactt acttctgaca   2940
acgatcggag gaccgaagga gctaaccgct tttttgcaca acatggggga tcatgtaact   3000
cgccttgatc gttgggaacc ggagctgaat gaagccatac caaacgacga gcgtgacacc   3060
acgatgcctg tagcaatggc aacaacgttg cgcaaactat taactggcga actacttact   3120
ctagcttccc ggcaacaatt aatagactgg atggaggcgg ataaagttgc aggaccactt   3180
ctgcgctcgg cccttccggc tggctggttt attgctgata aatctggagc cggtgagcgt   3240
gggtctcgcg gtatcattgc agcactgggg ccagatggta agccctcccg tatcgtagtt   3300
atctacacga cggggagtca ggcaactatg gatgaacgaa atagacagat cgctgagata   3360
ggtgcctcac tgattaagca ttggtaactg tcagaccaag tttactcata tatactttag   3420
attgatttaa aacttcattt ttaatttaaa aggatctagg tgaagatcct ttttgataat   3480
ctcatgacca aaatccctta acgtgagttt tcgttccact gagcgtcaga ccccgtagaa   3540
aagatcaaag gatcttcttg agatcctttt tttctgcgcg taatctgctg cttgcaaaca   3600
aaaaaaccac cgctaccagc ggtggtttgt ttgccggatc aagagctacc aactcttttt   3660
ccgaaggtaa ctggcttcag cagagcgcag ataccaaata ctgtccttct agtgtagccg   3720
tagttaggcc accacttcaa gaactctgta gcaccgccta catacctcgc tctgctaatc   3780
ctgttaccag tggctgctgc cagtggcgat aagtcgtgtc ttaccgggtt ggactcaaga   3840
cgatagttac cggataaggc gcagcggtcg ggctgaacgg ggggttcgtg cacacagccc   3900
agcttggagc gaacgaccta caccgaactg agatacctac agcgtgagca ttgagaaagc   3960
gccacgcttc ccgaagggag aaaggcggac aggtatccgg taagcggcag ggtcggaaca   4020
ggagagcgca cgagggagct tccaggggga aacgcctggt atctttatag tcctgtcggg   4080
tttcgccacc tctgacttga gcgtcgattt ttgtgatgct cgtcaggggg gcggagccta   4140
tggaaaaacg ccagcaacgc ggccttttta cggttcctgg ccttttgctg gccttttgct   4200
cacatgttct ttcctgcgtt atcccctgat tctgtggata accgtattac cgcctttgag   4260
tgagctgata ccgctcgccg cagccgaacg accgagcgca gcgagtcagt gagcgaggaa   4320
gcggaagagc gcccaatacg caaaccgcct ctccccgcgc gttggccgat tcattaatgc   4380
agctggcacg acaggtttcc cgactggaaa gcgggcagtg agcgcaacgc aattaatgtg   4440
agttacctca ctcattaggc accccaggct ttacacttta tgcttccggc tcctatgttg   4500
tgtggaattg tgagcggata acaatttcac acaggaaaca gctatgacca tgattacgcc   4560
aagctcggaa ttaaccctca ctaaagggaa caaaagctgg ctagt                   4605
```

Fig. 20A (SEQ ID No. 75): vector pYD1mata

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt gctagccgct ggggccatgg    600
ttactgattg gcgcgccgga tccgatgtaa caaaatcgac tttgttccca ctgtactttt    660
agctcgtaca aaatacaata tacttttcat ttctccgtaa acaacatgtt ttcccatgta    720
atatcctttt ctatttttcg ttccgttacc aactttacac atactttata tagctattca    780
cttctataca ctaaaaaact aagacaattt taattttgct gcctgccata tttcaatttg    840
ttataaattc ctataattta tcctattagt agctaaaaaa agatgaatgt gaatcgaatc    900
ctaagagaat tgctgcagaa ttcggccgcg tacttaatta agtttaaacc cgctgatctg    960
ataacaacag tgtagatgta acaaaatcga ctttgttccc actgtacttt tagctcgtac   1020
aaaatacaat atacttttca tttctccgta aacaacatgt tttcccatgt aatatccttt   1080
tctatttttc gttccgttac caactttaca catactttat atagctattc acttctatac   1140
actaaaaaac taagacaatt ttaattttgc tgcctgccat atttcaattt gttataaatt   1200
cctataattt atcctattag tagctaaaaa aagatgaatg tgaatcgaat cctaagagaa   1260
ttgggcaagt gcacaaacaa tacttaaata aatactactc agtaataacc tatttcttag   1320
catttttgac gaaatttgct attttgttag agtcttttac accatttgtc tccacacctc   1380
cgcttacatc aacaccaata acgccattta atctaagcgc atcaccaaca ttttctggcg   1440
tcagtccacc agctaacata aaatgtaagc tctcggggct ctcttgcctt ccaacccagt   1500
cagaaatcga gttccaatcc aaaagttcac ctgtcccacc tgcttctgaa tcaaacaagg   1560
gaataaacga atgaggtttc tgtgaagctg cactgagtag tatgttgcag tcttttggaa   1620
atacgagtct tttaataact ggcaaaccga ggaactcttg gtattcttgc cacgactcat   1680
ctccgtgcag ttggacgata tcaatgccgt aatcattgac cagagccaaa acatcctcct   1740
taggttgatt acgaaacacg ccaaccaagt atttcggagt gcctgaacta tttttatatg   1800
cttttacaag acttgaaatt ttccttgcaa taaccgggtc aattgttctc tttctattgg   1860
gcacacatat aatacccagc aagtcagcat cggaatctag agcacattct gcggcctctg   1920
tgctctgcaa gccgcaaact ttcaccaatg gaccagaact acctgtgaaa ttaataacag   1980
acatactcca agctgccttt gtgtgcttaa tcacgtatac tcacgtgctc aatagtcacc   2040
aatgccctcc ctcttggccc tctccttttc ttttttcgac cgaatttctt gaagacgaaa   2100
gggcctcgtg atacgcctat ttttataggt taatgtcatg ataataatgg tttcttagga   2160
cggatcgctt gcctgtaact tacacgcgcc tcgtatcttt taatgatgga ataatttggg   2220
aatttactct gtgtttattt atttttatgt tttgtatttg gattttagaa agtaaataaa   2280
gaaggtagaa gagttacgga atgaagaaaa aaaaataaac aaaggtttaa aaaatttcaa   2340
caaaaagcgt actttacata tatatttatt agacaagaaa agcagattaa atagatatac   2400
attcgattaa cgataagtaa aatgtaaaat cacaggattt tcgtgtgtgg tcttctacac   2460
agacaagatg aaacaattcg gcattaatac ctgagagcag gaagagcaag ataaaaggta   2520
gtatttgttg gcgatccccc tagagtcttt tacatcttcg gaaaacaaaa actatttttt   2580
ctttaatttc tttttttact ttctattttt aatttatata tttatattaa aaaatttaaa   2640
ttataattat ttttatagca cgtgatgaaa aggacccagg tggcactttt cggggaaatg   2700
tgcgcggaac ccctatttgt ttatttttct aaatacattc aaatatgtat ccgctcatga   2760
gacaataacc ctgataaatg cttcaataat attgaaaaag gaagagtatg agtattcaac   2820
atttccgtgt cgcccttatt cccttttttg cggcattttg ccttcctgtt tttgctcacc   2880
cagaaacgct ggtgaaagta aaagatgctg aagatcagtt gggtgcacga gtgggttaca   2940
tcgaactgga tctcaacagc ggtaagatcc ttgagagttt tcgccccgaa gaacgttttc   3000
caatgatgag cacttttaaa gttctgctat gtggcgcggt attatcccgt gttgacgccg   3060
ggcaagagca actcggtcgc cgcatacact attctcagaa tgacttggtt gagtactcac   3120
cagtcacaga aaagcatctt acggatggca tgacagtaag agaattatgc agtgctgcca   3180
taaccatgag tgataacact gcggccaact tacttctgac aacgatcgga ggaccgaagg   3240
agctaaccgc ttttttgcac aacatggggg atcatgtaac tcgccttgat cgttgggaac   3300
cggagctgaa tgaagccata ccaaacgacg agcgtgacac cacgatgcct gtagcaatgg   3360
caacaacgtt gcgcaaacta ttaactggcg aactacttac tctagcttcc cggcaacaat   3420
taatagactg gatggaggcg gataaagttg caggaccact tctgcgctcg gcccttccgg   3480
ctggctggtt tattgctgat aaatctggag ccggtgagcg tgggtctcgc ggtatcattg   3540
cagcactggg gccagatggt aagccctccc gtatcgtagt tatctacacg acggggagtc   3600
aggcaactat ggatgaacga aatagacaga tcgctgagat aggtgcctca ctgattaagc   3660
```

Fig. 20B (SEQ ID No. 75 cont'd.)

attggtaact gtcagaccaa gtttactcat atatacttta gattgattta aaacttcatt 3720
tttaatttaa aaggatctag gtgaagatcc tttttgataa tctcatgacc aaaatccctt 3780
aacgtgagtt ttcgttccac tgagcgtcag accccgtaga aaagatcaaa ggatcttctt 3840
gagatccttt ttttctgcgc gtaatctgct gcttgcaaac aaaaaaacca ccgctaccag 3900
cggtggtttg tttgccggat caagagctac caactctttt tccgaaggta actggcttca 3960
gcagagcgca gataccaaat actgtccttc tagtgtagcc gtagttaggc caccacttca 4020
agaactctgt agcaccgcct acatacctcg ctctgctaat cctgttacca gtggctgctg 4080
ccagtggcga taagtcgtgt cttaccgggt tggactcaag acgatagtta ccggataagg 4140
cgcagcggtc gggctgaacg gggggttcgt gcacacagcc cagcttggag cgaacgacct 4200
acaccgaact gagataccta cagcgtgagc attgagaaag cgccacgctt cccgaaggga 4260
gaaaggcgga caggtatccg gtaagcggca gggtcggaac aggagagcgc acgagggagc 4320
ttccaggggg aaacgcctgg tatctttata gtcctgtcgg gtttcgccac ctctgacttg 4380
agcgtcgatt tttgtgatgc tcgtcagggg ggcggagcct atggaaaaac gccagcaacg 4440
cggccttttt acggttcctg gccttttgct ggccttttgc tcacatgttc tttcctgcgt 4500
tatcccctga ttctgtggat aaccgtatta ccgcctttga gtgagctgat accgctcgcc 4560
gcagccgaac gaccgagcgc agcgagtcag tgagcgagga agcggaagag cgcccaatac 4620
gcaaaccgcc tctccccgcg cgttggccga ttcattaatg cagctggcac gacaggtttc 4680
ccgactggaa agcgggcagt gagcgcaacg caattaatgt gagttacctc actcattagg 4740
caccccaggc tttacacttt atgcttccgg ctcgtatgtt gtgtggaatt gtgagcggat 4800
aacaatttca cacaggaaac agctatgacc atgattacgc caagctcgga attaaccctc 4860
actaaaggga acaaaagctg gctagt 4886

Fig. 21A (SEQ ID NO.76): vector pYD1gal acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgcttcagt gctagccgct ggggccatgg 600
ttactgattg gcgcgccgga tccgatgtaa caaaatcgac tttgttccca ctgtactttt 660
agctcgtaca aaatacaata tacttttcat ttctccgtaa acaacatgtt ttcccatgta 720
atatcctttt ctatttttcg ttccgttacc aactttacac atactttata tagctattca 780
cttctataca ctaaaaaact aagacaattt taattttgct gcctgccata tttcaatttg 840
ttataaattc ctataattta tcctattagt agctaaaaaa agatgaatgt gaatcgaatc 900
ctaagagaat tgctgcagaa ttcacggatt agaagccgcc gagcgggtga cagccctccg 960
aaggaagact ctcctccgtg cgtcctcgtc ttcaccggtc gcgttcctga aacgcagatg 1020
tgcctcgcgc cgcactgctc cgaacaataa agattctaca atactagctt ttatggttat 1080
gaagaggaaa aattggcagt aacctggccc cacaaacctt caaatgaacg aatcaaatta 1140
acaaccatag gatgataatg cgattagttt tttagcctta tttctggggt aattaatcag 1200
cgaagcgatg atttttgatc tattaacaga tatataaatg caaaaactgc ataaccactt 1260
taactaatac tttcaacatt ttcggtttgt attacttctt attcaaatgt aataaaagta 1320
tcaacaaaaa attgttaata tacctctata ctttaacgtc aaggagaaaa aaccccggat 1380
cggactacta gcagctgtaa tacgactcac tatagggaat attaagctaa ttctacttca 1440
tacattttca attaagatgc agttacttcg ctgtttttca atattttctg ttattgcttc 1500
agttttagca caggaactga caactatatg cgagcaaatc ccctcaccaa ctttagaatc 1560
gacgccgtac tctttgtcaa cgactactat tttggccaac gggaaggcaa tgcaaggagt 1620
ttttgaatat tacaaatcag taacgtttgt cagtaattgc ggttctcacc cctcaacaac 1680
tagcaaaggc agccccataa acacacagta tgtttttaag cttctgcagg ctagtggtgg 1740
tggtggttct ggtggtggtg gttctggtgg tggtggttct gctagcatga ctggtggaca 1800
gcaaggccta attctgatgc ggccgcacat catcaccatc accattgatt aattaagttt 1860
aaacccgctg atctgataac aacagtgtag atgtaacaaa atcgactttg ttcccactgt 1920
acttttagct cgtacaaaat acaatatact tttcatttct ccgtaaacaa catgttttcc 1980
catgtaatat ccttttctat ttttcgttcc gttaccaact ttacacatac tttatatagc 2040
tattcacttc tatacactaa aaaactaaga caattttaat tttgctgcct gccatatttc 2100
aatttgttat aaattcctat aatttatcct attagtagct aaaaaaagat gaatgtgaat 2160
cgaatcctaa gagaattggg caagtgcaca aacaatactt aaataaatac tactcagtaa 2220

Fig. 21B (SEQ ID No.76 cont'd.)

```
taacctattt cttagcattt ttgacgaaat ttgctatttt gttagagtct tttacaccat   2280
ttgtctccac acctccgctt acatcaacac caataacgcc atttaatcta agcgcatcac   2340
caacattttc tggcgtcagt ccaccagcta acataaaatg taagctctcg gggctctctt   2400
gccttccaac ccagtcagaa atcgagttcc aatccaaaag ttcacctgtc ccacctgctt   2460
ctgaatcaaa caagggaata aacgaatgag gtttctgtga agctgcactg agtagtatgt   2520
tgcagtcttt tggaaatacg agtcttttaa taactggcaa accgaggaac tcttggtatt   2580
cttgccacga ctcatctccg tgcagttgga cgatatcaat gccgtaatca ttgaccagag   2640
ccaaaacatc ctccttaggt tgattacgaa acacgccaac caagtatttc ggagtgcctg   2700
aactattttt atatgctttt acaagacttg aaattttcct tgcaataacc gggtcaattg   2760
ttctctttct attgggcaca catataatac ccagcaagtc agcatcggaa tctagagcac   2820
attctgcggc ctctgtgctc tgcaagccgc aaactttcac caatggacca gaactacctg   2880
tgaaattaat aacagacata ctccaagctg cctttgtgtg cttaatcacg tatactcacg   2940
tgctcaatag tcaccaatgc cctccctctt ggccctctcc ttttcttttt tcgaccgaat   3000
ttcttgaaga cgaaagggcc tcgtgatacg cctattttta taggttaatg tcatgataat   3060
aatggtttct taggacggat cgcttgcctg taacttacac gcgcctcgta tcttttaatg   3120
atggaataat ttgggaattt actctgtgtt tatttatttt tatgttttgt atttggattt   3180
tagaaagtaa ataaagaagg tagaagagtt acggaatgaa gaaaaaaaaa taaacaaagg   3240
tttaaaaaat ttcaacaaaa agcgtacttt acatatatat ttattagaca agaaaagcag   3300
attaaataga tatacattcg attaacgata agtaaaatgt aaaatcacag gattttcgtg   3360
tgtggtcttc tacacagaca agatgaaaca attcggcatt aatacctgag agcaggaaga   3420
gcaagataaa aggtagtatt tgttggcgat ccccctagag tcttttacat cttcggaaaa   3480
caaaaactat tttttcttta atttcttttt ttactttcta tttttaattt atatatttat   3540
attaaaaaat ttaaattata attattttta tagcacgtga tgaaaaggac ccaggtggca   3600
cttttcgggg aaatgtgcgc ggaaccccta tttgtttatt tttctaaata cattcaaata   3660
tgtatccgct catgagacaa taaccctgat aaatgcttca ataatattga aaaaggaaga   3720
gtatgagtat tcaacatttc cgtgtcgccc ttattccctt ttttgcggca ttttgccttc   3780
ctgtttttgc tcacccagaa acgctggtga aagtaaaaga tgctgaagat cagttgggtg   3840
cacgagtggg ttacatcgaa ctggatctca acagcggtaa gatccttgag agttttcgcc   3900
ccgaagaacg ttttccaatg atgagcactt ttaaagttct gctatgtggc gcggtattat   3960
cccgtgttga cgccgggcaa gagcaactcg gtcgccgcat acactattct cagaatgact   4020
tggttgagta ctcaccagtc acagaaaagc atcttacgga tggcatgaca gtaagagaat   4080
tatgcagtgc tgccataacc atgagtgata acactgcggc caacttactt ctgacaacga   4140
tcggaggacc gaaggagcta accgcttttt tgcacaacat gggggatcat gtaactcgcc   4200
ttgatcgttg ggaaccggag ctgaatgaag ccataccaaa cgacgagcgt gacaccacga   4260
tgcctgtagc aatggcaaca acgttgcgca aactattaac tggcgaacta cttactctag   4320
cttcccggca acaattaata gactggatgg aggcggataa agttgcagga ccacttctgc   4380
gctcggccct tccggctggc tggtttattg ctgataaatc tggagccggt gagcgtgggt   4440
ctcgcggtat cattgcagca ctggggccag atggtaagcc ctcccgtatc gtagttatct   4500
acacgacggg cagtcaggca actatggatg aacgaaatag acagatcgct gagataggtg   4560
cctcactgat taagcattgg taactgtcag accaagttta ctcatatata ctttagattg   4620
atttaaaact tcatttttaa tttaaaagga tctaggtgaa gatccttttt gataatctca   4680
tgaccaaaat cccttaacgt gagttttcgt tccactgagc gtcagacccc gtagaaaaga   4740
tcaaaggatc ttcttgagat cctttttttc tgcgcgtaat ctgctgcttg caaacaaaaa   4800
aaccaccgct accagcggtg gtttgtttgc cggatcaaga gctaccaact ctttttccga   4860
aggtaactgg cttcagcaga gcgcagatac caaatactgt ccttctagtg tagccgtagt   4920
taggccacca cttcaagaac tctgtagcac cgcctacata cctcgctctg ctaatcctgt   4980
taccagtggc tgctgccagt ggcgataagt cgtgtcttac cgggttggac tcaagacgat   5040
agttaccgga taaggcgcag cggtcgggct gaacgggggg ttcgtgcaca cagcccagct   5100
tggagcgaac gacctacacc gaactgagat acctacagcg tgagcattga gaaagcgcca   5160
cgcttcccga agggagaaag gcggacaggt atccggtaag cggcagggtc ggaacaggag   5220
agcgcacgag ggagcttcca gggggaaacg cctggtatct ttatagtcct gtcgggtttc   5280
gccacctctg acttgagcgt cgatttttgt gatgctcgtc aggggggcgg agcctatgga   5340
aaaacgccag caacgcggcc tttttacggt tcctggcctt ttgctggcct tttgctcaca   5400
tgttctttcc tgcgttatcc cctgattctg tggataaccg tattaccgcc tttgagtgag   5460
ctgataccgc tcgccgcagc cgaacgaccg agcgcagcga gtcagtgagc gaggaagcgg   5520
aagagcgccc aatacgcaaa ccgcctctcc ccgcgcgttg gccgattcat taatgcagct   5580
ggcacgacag gtttcccgac tggaaagcgg gcagtgagcg caacgcaatt aatgtgagtt   5640
acctcactca ttaggcaccc caggctttac actttatgct tccggctcgt atgttgtgtg   5700
gaattgtgag cggataacaa tttcacacag gaaacagcta tgaccatgat tacgccaagc   5760
tcggaattaa ccctcactaa agggaacaaa agctggctag t                       5801
```

Fig. 22 (SEQ ID No.77): 4D5H ggccagcaag gccaagaggt tcaactagtg gagtctggcg gtggcctggt gcagccaggg 60
ggctcactcc gtttgtcctg tgcagcttct ggcttcaaca ttaaagacac ctatatacac 120
tgggtgcgtc aggccccggg taagggcctg gaatgggttg caaggattta tcctacgaat 180
ggttatacta gatatgccga tagcgtcaag ggccgtttca ctataagcgc agacacatcc 240
aaaaacacag cctacctgca gatgaacagc ctgcgtgctg aggacactgc cgtctattat 300
tgttctagat ggggagggga cggcttctat gctatggact actggggtca aggaaccctg 360
gtcaccgtct cctcggctag caccaagggc cccagcgtgt tccctctggc ccccagctcc 420
aagagcacct ccggcggcac cgccgccctg ggctgcctgg tgaaggatta cttcccagag 480
cccgtgaccg tgagctggaa cagcggcgcc ctgaccagcg gcgtgcacac cttccccgcc 540
gtgctgcagt ccagcggcct gtactccctg agcagcgtgg tgaccgtgcc cagcagcagc 600
ctgggcaccc agacctacat ctgcaatgtg aaccacaagc ccagcaatac caaggtggat 660
aagaaggtgg agcccaagag ctgcgcggcc gc 692

Fig. 23 (SEQ ID No.78): 4D5L ccatggcgga tatccagatg acccagtccc cgagctccct gtccgcctct gtgggcgata 60
gggtcaccat cacctgccgt gccagtcagg atgtgaatac tgctgtagcc tggtatcaac 120
agaaaccagg aaaagctccg aaactactga tttactcggc atccttcctc tactctggag 180
tcccttctcg cttctctgga tccagatctg ggacggattt cactctgacc atcagcagtc 240
tgcagccgga agacttcgca acttattact gtcagcaaca ttatactact cctcccacgt 300
tcggacaggg taccaaggtg gagatcaaac gtacggtggc ggcgccatct gtcttcatct 360
tcccgccatc tgatgagcag cttaagtctg gaactgcctc tgttgtgtgc ctgctgaata 420
acttctatcc cagagaggcc aaagtacagt ggaaggtgga taacgccctc caatcgggta 480
actcccagga gagtgtcaca gagcaggaca gcaaggacag cacctacagc ctcagcagca 540
ccctgacgct gagcaaagca gactacgaga aacacaaagt ctacgcctgc gaagtcaccc 600
atcagggcct gagctcgccc gtcacaaaga gcttcaacag gggagagtgt tgaggcgcgc 660
c 661

Fig. 24A (SEQ ID No.79): vector pYD4D5hc acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgcttcagt gctagccgct ggggccatgg 600
ttactgattg gcgcgccgga tccgatgtaa caaaatcgac tttgttccca ctgtactttt 660
agctcgtaca aaatacaata tacttttcat ttctccgtaa acaacatgtt ttcccatgta 720
atatcctttt ctatttttcg ttccgttacc aactttacac atactttata tagctattca 780
cttctataca ctaaaaaact aagacaattt taattttgct gcctgccata tttcaatttg 840
ttataaattc ctataattta tcctattagt agctaaaaaa agatgaatgt gaatcgaatc 900
ctaagagaat tgctgcagaa ttcacggatt agaagccgcc gagcgggtga cagccctccg 960
aaggaagact ctcctccgtg cgtcctcgtc ttcaccggtc gcgttcctga aacgcagatg 1020
tgcctcgcgc cgcactgctc cgaacaataa agattctaca atactagctt ttatggttat 1080
gaagaggaaa aattggcagt aacctggccc cacaaacctt caaatgaacg aatcaaatta 1140
acaaccatag gatgataatg cgattagttt tttagcctta tttctggggt aattaatcag 1200
cgaagcgatg atttttgatc tattaacaga tatataaatg caaaaactgc ataaccactt 1260
taactaatac tttcaacatt ttcggtttgt attacttctt attcaaatgt aataaaagta 1320
tcaacaaaaa attgttaata tacctctata ctttaacgtc aaggagaaaa aaccccggat 1380
cggactacta gcagctgtaa tacgactcac tatagggaat attaagctaa ttctacttca 1440
tacattttca attaagatgc agttacttcg ctgtttttca atattttctg ttattgcttc 1500
agttttagca caggaactga caactatatg cgagcaaatc ccctcaccaa ctttagaatc 1560
gacgccgtac tctttgtcaa cgactactat tttggccaac gggaaggcaa tgcaaggagt 1620
ttttgaatat tacaaatcag taacgtttgt cagtaattgc ggttctcacc cctcaacaac 1680

Fig. 24B (SEQ ID No.79 cont'd.)

```
tagcaaaggc agccccataa acacacagta tgtttttaag ctttctgcagg ctagtggtgg    1740
tggtggttct ggtggtggtg gttctggtgg tggtggttct gctagcatga ctggtggcca    1800
gcaaggccaa ggttctgagg ttcaactagt ggagtctggc ggtggcctgg tgcagccagg    1860
gggctcactc cgtttgtcct gtgcagcttc tggcttcaac attaaagaca cctatataca    1920
ctgggtgcgt caggccccgg gtaagggcct ggaatgggtt gcaaggattt atcctacgaa    1980
tggttatact agatatgccg atagcgtcaa gggccgtttc actataagcg cagacacatc    2040
caaaaacaca gcctacctgc agatgaacag cctgcgtgct gaggacactg ccgtctatta    2100
ttgttctaga tggggagggg acggcttcta tgctatggac tactggggtc aaggaaccct    2160
ggtcaccgtc tcctcggcta gcaccaaggg cccagcgtg ttccctctgg ccccaagctc    2220
caagagcacc tcgggcggca ccgccgccct gggctgcctg gtgaaggatt acttcccaga    2280
gcccgtgacc gtgagctgga acagcggcgc cctgaccagc ggcgtgcaca cctttcccgc    2340
cgtgctgcag tccagcggcc tgtactccct gagcagcgtg gtgaccgtgc ccagcagcag    2400
cctgggcacc cagacctaca tctgcaatgt gaaccacaag cccagcaata ccaaggtgga    2460
taagaaggtg gagcccaaga gctgcgcggc cgcacatcat caccatcacc attgattaat    2520
taagtttaaa cccgctgatc tgataacaac agtgtagatg taacaaaatc gactttgttc    2580
ccactgtact tttagctcgt acaaaataca atatactttt catttctccg taaacaacat    2640
gttttcccat gtaatatcct tttctatttt tcgttccgtt accaacttta cacatacttt    2700
atatagctat tcacttctat acactaaaaa actaagacaa ttttaatttt gctgcctgcc    2760
atatttcaat ttgttataaa ttccttataat ttatcctatt agtagctaaa aaaagatgaa    2820
tgtgaatcga atcctaagag aattgggcaa gtgcacaaac aatacttaaa taaatactac    2880
tcagtaataa cctatttctt agcatttttg acgaaatttg ctattttgtt agagtctttt    2940
acaccatttg tctccacacc tccgcttaca tcaacaccaa taacgccatt taatctaagc    3000
gcatcaccaa cattttctgg cgtcagtcca ccagctaaca taaaatgtaa gctctcgggg    3060
ctctcttgcc ttccaaccca gtcagaaatc gagttccaat ccaaaagttc acctgtccca    3120
cctgcttctg aatcaaacaa gggaataaac gaatgaggtt tctgtgaagc tgcactgagt    3180
agtatgttgc agtcttttgg aaatacgagt cttttaataa ctggcaaacc gaggaactct    3240
tggtattctt gccacgactc atctccgtgc agttggacga tatcaatgcc gtaatcattg    3300
accagagcca aaacatcctc cttaggttga ttacgaaaca cgccaaccaa gtatttcgga    3360
gtgcctgaac tatttttata tgcttttaca agacttgaaa ttttccttgc aataaccggg    3420
tcaattgttc tctttctatt gggcacacat ataataccca gcaagtcagc atcggaatct    3480
agagcacatt ctgcggcctc tgtgctctgc aagccgcaaa ctttcaccaa tggaccagaa    3540
ctacctgtga aattaataac agacatactc caagctgcct ttgtgtgctt aatcacgtat    3600
actcacgtgc tcaatagtca ccaatgccct ccctcttggc cctctccttt tctttttttcg    3660
accgaatttc ttgaagacga aagggcctcg tgatacgcct atttttatag gttaatgtca    3720
tgataataat ggtttcttag gacggatcgc ttgcctgtaa cttacacgcg cctcgtatct    3780
tttaatgatg gaataatttg ggaatttact ctgtgtttat ttattttat gttttgtatt    3840
tggattttag aaagtaaata aagaaggtag aagagttacg gaatgaagaa aaaaaaataa    3900
acaaaggttt aaaaaatttc aacaaaaagc gtactttaca tatatattta ttagacaaga    3960
aaagcagatt aaatagatat acattcgatt aacgataagt aaaatgtaaa atcacaggat    4020
tttcgtgtgt ggtcttctac acagacaaga tgaaacaatt cggcattaat acctgagagc    4080
aggaagagca agataaaagg tagtatttgt tggcgatccc cctagagtct tttacatctt    4140
cggaaaacaa aaactatttt ttctttaatt tcttttttta ctttctattt ttaatttata    4200
tatttatatt aaaaaattta aattataatt atttttatag cacgtgatga aaaggaccca    4260
ggtggcactt ttcggggaaa tgtgcgcgga acccctattt gtttattttt ctaaatacat    4320
tcaaatatgt atccgctcat gagacaataa ccctgataaa tgcttcaata atattgaaaa    4380
aggaagagta tgagtattca acatttccgt gtcgccctta ttcccttttt tgcggcattt    4440
tgccttcctg tttttgctca cccagaaacg ctggtgaaag taaaagatgc tgaagatcag    4500
ttgggtgcac gagtgggtta catcgaactg gatctcaaca gcggtaagat ccttgagagt    4560
tttcgccccg aagaacgttt tccaatgatg agcactttta aagttctgct atgtggcgcg    4620
gtattatccc gtgttgacgc cgggcaagag caactcggtc gccgcataca ctattctcag    4680
aatgacttgg ttgagtactc accagtcaca gaaaagcatc ttacggatgg catgacagta    4740
agagaattat gcagtgctgc cataaccatg agtgataaca ctgcggccaa cttacttctg    4800
acaacgatcg gaggaccgaa ggagctaacc gcttttttgc acaacatggg ggatcatgta    4860
actcgccttg atcgttggga accggagctg aatgaagcca taccaaacga cgagcgtgac    4920
accacgatgc ctgtagcaat ggcaacaacg ttgcgcaaac tattaactgg cgaactactt    4980
actctagctt cccggcaaca attaatagac tggatggagg cggataaagt tgcaggacca    5040
cttctgcgct cggcccttcc ggctggctgg tttattgctg ataaatctgg agccggtgag    5100
cgtgggtctc gcggtatcat tgcagcactg gggccagatg gtaagccctc ccgtatcgta    5160
gttatctaca cgacggggag tcaggcaact atggatgaac gaaatagaca gatcgctgag    5220
ataggtgcct cactgattaa gcattggtaa ctgtcagacc aagtttactc atatatactt    5280
tagattgatt taaaacttca tttttaattt aaaaggatct aggtgaagat cctttttgat    5340
```

Fig. 24C (SEQ ID No.79 cont'd.)

```
aatctcatga ccaaaatccc ttaacgtgag ttttcgttcc actgagcgtc agaccccgta     5400
gaaaagatca aaggatcttc ttgagatcct ttttttctgc gcgtaatctg ctgcttgcaa     5460
acaaaaaaac caccgctacc agcggtggtt tgtttgccgg atcaagagct accaactctt     5520
tttccgaagg taactggctt cagcagagcg cagataccaa atactgtcct tctagtgtag     5580
ccgtagttag gccaccactt caagaactct gtagcaccgc ctacatacct cgctctgcta     5640
atcctgttac cagtggctgc tgccagtggc gataagtcgt gtcttaccgg gttggactca     5700
agacgatagt taccggataa ggcgcagcgg tcgggctgaa cggggggttc gtgcacacag     5760
cccagcttgg agcgaacgac ctacaccgaa ctgagatacc tacagcgtga gcattgagaa     5820
agcgccacgc ttcccgaagg gagaaaggcg gacaggtatc cggtaagcgg cagggtcgga     5880
acaggagagc gcacgaggga gcttccaggg ggaaacgcct ggtatcttta tagtcctgtc     5940
gggtttcgcc acctctgact tgagcgtcga tttttgtgat gctcgtcagg ggggcggagc     6000
ctatggaaaa acgccagcaa cgcggccttt ttacggttcc tggccttttg ctggcctttt     6060
gctcacatgt tctttcctgc gttatcccct gattctgtgg ataaccgtat taccgccttt     6120
gagtgagctg ataccgctcg ccgcagccga acgaccgagc gcagcgagtc agtgagcgag     6180
gaagcggaag agcgcccaat acgcaaaccg cctctccccg cgcgttggcc gattcattaa     6240
tgcagctggc acgacaggtt tcccgactgg aaagcgggca gtgagcgcaa cgcaattaat     6300
gtgagttacc tcactcatta ggcaccccag gctttacact ttatgcttcc ggctcgtatg     6360
ttgtgtggaa ttgtgagcgg ataacaattt cacacaggaa acagctatga ccatgattac     6420
gccaagctcg gaattaaccc tcactaaagg gaacaaaagc tggctagt                 6468
```

Fig 25 (SEQ ID No. 80): 4D5hp

```
EVQLVESGGG LVQPGGSLRL SCAASGFNIK DTYIHWVRQA PGKGLEWVAR IYPTNGYTRY      60
ADSVKGRFTI SADTSKNTAY LQMNSLRAED TAVYYCSRWG GDGFYAMDYW GQGTLVTVSS     120
ASTKGPSVFP LAPSSKSTSG GTAALGCLVK DYFPEPVTVS WNSGALTSGV HTFPAVLQSS     180
GLYSLSSVVT VPSSSLGTQT YICNVNHKPS NTKVDKKVEP KSC                       223
```

Fig. 26A (SEQ ID No. 81): vector pYD4D5hl

```
acggattaga agccgccgag cgggtgacag ccctccgaag gaagactctc ctccgtgcgt       60
cctcgtcttc accggtcgcg ttcctgaaac gcagatgtgc ctcgcgccgc actgctccga      120
acaataaaga ttctacaata ctagctttta tggttatgaa gaggaaaaat tggcagtaac      180
ctggccccac aaaccttcaa atgaacgaat caaattaaca accataggat gataatgcga      240
ttagtttttt agccttattt ctggggtaat taatcagcga agcgatgatt tttgatctat      300
taacagatat ataaatgcaa aaactgcata accactttaa ctaatacttt caacattttc      360
ggtttgtatt acttcttatt caaatgtaat aaaagtatca acaaaaaatt gttaatatac      420
ctctatactt taacgtcaag gagaaaaaac cccggatcgg actactagca gctgtaatac      480
gactcactat agggaatatt aagctaattc tacttcatac attttcaatt aagatgcagt      540
tacttcgctg tttttcaata ttttctgtta ttgcttcagt gctagccgct ggggccatgg      600
cggatatcca gatgacccag tccccgagct ccctgtccgc ctctgtgggc gatagggtca      660
ccatcacctg ccgtgccagt caggatgtga atactgctgt agcctggtat caacagaaac      720
caggaaaagc tccgaaacta ctgatttact cggcatcctt cctctactct ggagtccctt      780
ctcgcttctc tggatccaga tctgggacgg atttcactct gaccatcagc agtctgcagc      840
cggaagactt cgcaacttat tactgtcagc aacattatac tactcctccc acgttcggac      900
agggtaccaa ggtggagatc aaacgtacgg tggctgcacc atctgtcttc atcttcccgc      960
catctgatga gcagcttaag tctggaactg cctctgttgt gtgcctgctg aataacttct     1020
atcccagaga ggccaaagta cagtggaagg tggataacgc cctccaatcg ggtaactccc     1080
aggagagtgt cacagagcag gacagcaagg acagcaccta cagcctcagc agcaccctga     1140
cgctgagcaa agcagactac gagaaacaca aagtctacgc ctgcgaagtc acccatcagg     1200
gcctgagctc gcccgtcaca aagagcttca acaggggaga gtgttgaggc gcgccggatc     1260
cgatgtaaca aaatcgactt tgttcccact gtacttttag ctcgtacaaa atacaatata     1320
cttttcattt ctccgtaaac aacatgtttt cccatgtaat atccttttct atttttcgtt     1380
ccgttaccaa ctttacacat actttatata gctattcact tctatacact aaaaaactaa     1440
gacaatttta attttgctgc ctgccatatt tcaatttgtt ataaattcct ataatttatc     1500
ctattagtag ctaaaaaaag atgaatgtga atcgaatcct aagagaattg ctgcagaatt     1560
cacggattag aagccgccga gcgggtgaca gccctccgaa ggaagactct cctccgtgcg     1620
tcctcgtctt caccggtcgc gttcctgaaa cgcagatgtg cctcgcgccg cactgctccg     1680
aacaataaag attctacaat actagctttt atggttatga agaggaaaaa ttggcagtaa     1740
cctggcccca caaaccttca aatgaacgaa tcaaattaac aaccatagga tgataatgcg     1800
attagttttt tagccttatt tctggggtaa ttaatcagcg aagcgatgat ttttgatcta     1860
```

Fig. 26B (SEQ ID No. 81 cont'd.)

```
ttaacagata tataaatgca aaaactgcat aacoacttta actaatactt tcaacatttt 1920
cggtttgtat tacttattat tcaaatgtaa taaaagtatc aacaaaaaat tgttaatata 1980
cctctatact ttaacgtcaa ggagaaaaaa ccccggatcg gactactagc agctgtaata 2040
cgactcacta tagggaatat taagctaatt ctacttcata catttcaat taagatgcag 2100
ttacttcgct gttttttcaat atttctgtt attgcttcag ttttagcaca ggaactgaca 2160
actatatgcg agcaaatccc ctcaccaact ttagaatcga cgccgtactc tttgtcaacg 2220
actactattt tggccaacgg gaaggcaatg caaggagttt ttgaatatta caaatcagta 2280
acgtttgtca gtaattgcgg ttctcacccc tcaacaacta gcaaaggcag ccccataaac 2340
acacagtatg ttttaagct tctgcaggct agtggtggtg gtggttctgg tggtggtggt 2400
tctggtggtg gtggttctgc tagcatgact ggtggccagc aaggccaaga ggttcaacta 2460
gtggagtctg gcggtggcct ggtgcagcca ggggctcac tccgtttgtc ctgtgcagct 2520
tctggcttca acattaaaga cacctatata cactgggtgc gtcaggcccc gggtaagggc 2580
ctggaatggg ttgcaaggat ttatcctacg aatggttata ctagatatgc cgatagcgtc 2640
aagggccgtt tcactataag cgcagacaca tccaaaaaca cagcctacct gcagatgaac 2700
agcctgcgtg ctgaggacac tgccgtctat tattgttcta gatgggagg ggacggcttc 2760
tatgctatgg actactgggg tcaaggaacc ctggtcaccg tctcctcggc tagcaccaag 2820
ggcccatcgg tcttccccct ggcaccctcc tccaagagca cctctgggg cacagcggcc 2880
ctgggctgcc tggtcaagga ctacttcccc gaaccggtga cggtgtcgtg gaactcaggc 2940
gccctgacca gcggcgtgca caccttcccg gctgtcctac agtcctcagg actctactcc 3000
ctcagcagcg tggtgaccgt gccctccagc agcttgggca cccagaccta catctgcaac 3060
gtgaatcaca agcccagcaa caccaaggtg gacaagaaag ttgagcccaa gagctgcgcg 3120
gccgcacatc atcaccatca ccattgatta attaagttta aacccgctga tctgataaca 3180
acagtgtaga tgtaacaaaa tcgactttgt tcccactgta cttttagctc gtacaaaata 3240
caatatactt ttcatttctc cgtaaacaac atgttttccc atgtaatatc cttttctatt 3300
tttcgttccg ttaccaactt tacacatact ttatatagct attcacttct atacactaaa 3360
aaactaagac aattttaatt ttgctgcctg ccatatttca atttgttata aattcctata 3420
atttatccta ttagtagcta aaaaaagatg aatgtgaatc gaatcctaag agaattgggc 3480
aagtgcacaa acaatactta aataaatact actcagtaat aacctatttc ttagcatttt 3540
tgacgaaatt tgctattttg ttagagtctt ttacaccatt tgtctccaca cctccgctta 3600
catcaacacc aataacgcca tttaatctaa gcgcatcacc aacatttctt ggcgtcagtc 3660
caccagctaa cataaaatgt aagctctcgg ggctctcttg ccttccaacc cagtcagaaa 3720
tcgagttcca atccaaaagt tcacctgtcc cacctgcttc tgaatcaaac aagggaataa 3780
acgaatgagg tttctgtgaa gctgcactga gtagtatgtt gcagtctttt ggaaatacga 3840
gtcttttaat aactggcaaa ccgaggaact cttggtattc ttgccacgac tcatctccgt 3900
gcagttggac gatatcaatg ccgtaatcat tgaccagagc caaaacatcc tccttaggtt 3960
gattacgaaa cacgccaacc aagtatttcg gagtgcctga actattttta tatgctttta 4020
caagacttga aattttcctt gcaataaccg ggtcaattgt tctctttcta ttgggcacac 4080
atataatacc cagcaagtca gcatcggaat ctagagcaca ttctgcggcc tctgtgctct 4140
gcaagccgca aactttcacc aatggaccag aactacctgt gaaattaata acagacatac 4200
tccaagctgc ctttgtgtgc ttaatcacgt atactcacgt gctcaatagt caccaatgcc 4260
ctccctcttg gccctctcct tttctttttt cgaccgaatt tcttgaagac gaaagggcct 4320
cgtgatacgc ctatttttat aggttaatgt catgataata atggtttctt aggacggatc 4380
gcttgcctgt aacttacacg cgcctcgtat cttttaatga tggaataatt tgggaattta 4440
ctctgtgttt atttattttt atgttttgta tttggatttt agaaagtaaa taaagaaggt 4500
agaagagtta cggaatgaag aaaaaaaaat aaacaaaggt ttaaaaaatt tcaacaaaaa 4560
gcgtacttta catatatatt tattagacaa gaaaagcaga ttaaatagat atacattcga 4620
ttaacgataa gtaaaatgta aaatcacagg attttcgtgt gtggtcttct acacagacaa 4680
gatgaaacaa ttcggcatta atacctgaga gcaggaagag caagataaaa ggtagtattt 4740
gttggcgatc cccctagagt cttttacatc ttcggaaaac aaaaactatt ttttctttaa 4800
tttctttttt tactttctat ttttaattta tatatttata ttaaaaaatt taaattataa 4860
ttatttttat agcacgtgat gaaaaggacc caggtggcac ttttcgggga aatgtgcgcg 4920
gaacccctat ttgtttattt ttctaaatac attcaaatat gtatccgctc atgagacaat 4980
aaccctgata aatgcttcaa taatattgaa aaaggaagag tatgagtatt caacatttcc 5040
gtgtcgccct tattcccttt tttgcggcat tttgccttcc tgtttttgct cacccagaaa 5100
cgctggtgaa agtaaaagat gctgaagatc agttgggtgc acgagtgggt tacatcgaac 5160
tggatctcaa cagcggtaag atccttgaga gttttcgccc cgaagaacgt tttccaatga 5220
tgagcacttt taaagttctg ctatgtggcg cggtattatc ccgtgttgac gccgggcaag 5280
agcaactcgg tcgccgcata cactattctc agaatgactt ggttgagtac tcaccagtca 5340
cagaaaagca tcttacggat ggcatgacag taagagaatt atgcagtgct gccataacca 5400
tgagtgataa cactgcggcc aacttacttc tgacaacgat cggaggaccg aaggagctaa 5460
ccgctttttt gcacaacatg ggggatcatg taactcgcct tgatcgttgg gaaccggagc 5520
```

Fig. 26C (SEQ ID No. 81 cont'd.)

```
tgaatgaagc cataccaaac gacgagcgtg acaccacgat gcctgtagca atggcaacaa    5580
cgttgcgcaa actattaact ggcgaactac ttactctagc ttcccggcaa caattaatag    5640
actggatgga ggcggataaa gttgcaggac cacttctgcg ctcggccctt ccggctggct    5700
ggtttattgc tgataaatct ggagccggtg agcgtgggtc tcgcggtatc attgcagcac    5760
tggggccaga tggtaagccc tcccgtatcg tagttatcta cacgacgggg agtcaggcaa    5820
ctatggatga acgaaataga cagatcgctg agataggtgc ctcactgatt aagcattggt    5880
aactgtcaga ccaagtttac tcatatatac tttagattga tttaaaactt catttttaat    5940
ttaaaaggat ctaggtgaag atcctttttg ataatctcat gaccaaaatc ccttaacgtg    6000
agttttcgtt ccactgagcg tcagaccccg tagaaaagat caaaggatct tcttgagatc    6060
ctttttttct gcgcgtaatc tgctgcttgc aaacaaaaaa accaccgcta ccagcggtgg    6120
tttgtttgcc ggatcaagag ctaccaactc tttttccgaa ggtaactggc ttcagcagag    6180
cgcagatacc aaatactgtc cttctagtgt agccgtagtt aggccaccac ttcaagaact    6240
ctgtagcacc gcctacatac ctcgctctgc taatcctgtt accagtggct gctgccagtg    6300
gcgataagtc gtgtcttacc gggttggact caagacgata gttaccggat aaggcgcagc    6360
ggtcgggctg aacggggggt tcgtgcacac agcccagctt ggagcgaacg acctacaccg    6420
aactgagata cctacagcgt gagcattgag aaagcgccac gcttcccgaa gggagaaagg    6480
cggacaggta tccggtaagc ggcagggtcg gaacaggaga gcgcacgagg gagcttccag    6540
ggggaaacgc ctggtatctt tatagtcctg tcgggtttcg ccacctctga cttgagcgtc    6600
gatttttgtg atgctcgtca ggggggcgga gcctatggaa aaacgccagc aacgcggcct    6660
ttttacggtt cctggccttt tgctggcctt ttgctcacat gttctttcct gcgttatccc    6720
ctgattctgt ggataaccgt attaccgcct ttgagtgagc tgataccgct cgccgcagcc    6780
gaacgaccga gcgcagcgag tcagtgagcg aggaagcgga agagcgccca atacgcaaac    6840
cgcctctccc cgcgcgttgg ccgattcatt aatgcagctg gcacgacagg tttcccgact    6900
ggaaagcggg cagtgagcgc aacgcaatta atgtgagtta cctcactcat taggcacccc    6960
aggctttaca ctttatgctt ccggctccta tgttgtgtgg aattgtgagc ggataacaat    7020
ttcacacagg aaacagctat gaccatgatt acgccaagct cggaattaac cctcactaaa    7080
gggaacaaaa gctggctagt                                                7100
```

Fig. 27 (SEQ ID No. 82): 4D5lp

```
DIQMTQSPSS LSASVGDRVT ITCRASQDVN TAVAWYQQKP GKAPKLLIYS ASFLYSGVPS     60
RFSGSRSGTD FTLTISSLQP EDFATYYCQQ HYTTPPTFGQ GTKVEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214
```

Fig. 28A (SEQ ID No. 427): plasmid pYD1dX dCH1dCH3 Fcab wt

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt tttagcacag gaactgacaa     600
ctatatgcga gcaaatcccc tcaccaactt tagaatcgac gccgtactct ttgtcaacga     660
ctactatttt ggccaacggg aaggcaatgc aaggagtttt tgaatattac aaatcagtaa     720
cgtttgtcag taattgcggt tctcacccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccgagc ccaagagcag cgacaagaca cacacgtgtc     960
ccccatgtcc cgcccctgag ctgctgggcg gccctcccgt gttcctgttc cctcccaagc    1020
ccaaggacac cctgatgatc tcccggaccc ctgaggtgac ctgtgtggtg gtggacgtga    1080
gccacgagga ccccgaggtg aagttcaact ggtacgtgga cggcgtggag gtgcacaacg    1140
ccaagaccaa gcccagagag gagcagtaca acagcaccta ccgcgtggtg agcgtgctga    1200
ccgtgctgca ccaggattgg ctgaatggca aggagtacaa gtgcaaggtg agcaacaagg    1260
ccctgcctgc ccccatcgag aagaccatct ccaaggccaa gggccagcct cgagaaggta    1320
agcctatccc taaccctctc ctcggtctcg attctacgcg taccggtcat catcaccatc    1380
```

Figure 28B:
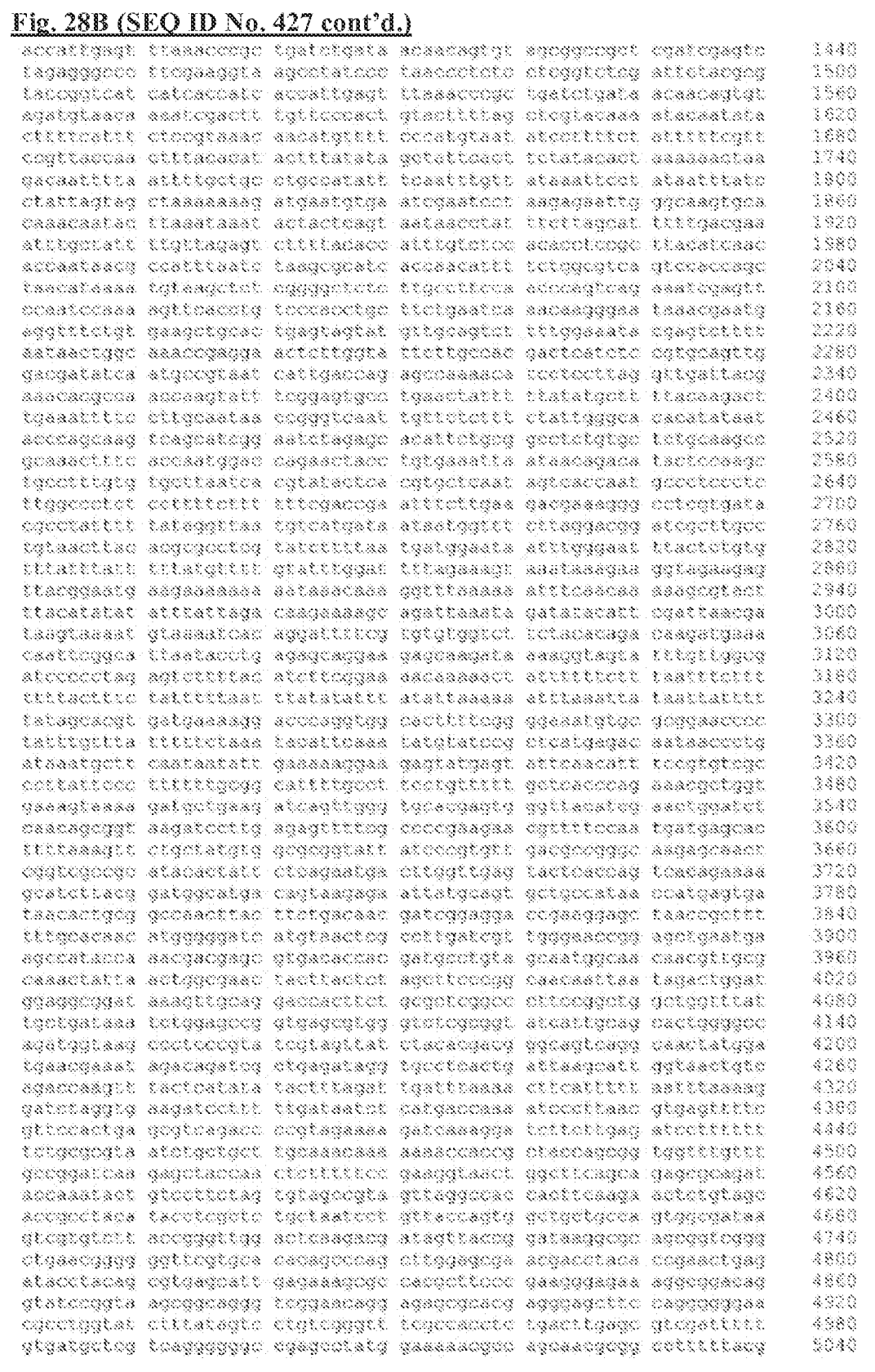

Fig. 28B (SEQ ID No. 427 cont'd.)

```
accattgagt ttaaacccgc tgatctgata acaacagtgt agcggccgct cgatcgagtc
tagagggccc ttcgaaggta agcctatccc taaccctctc ctcggtctcg attctacgcg
taccggtcat catcaccatc accattgagt ttaaacccgc tgatctgata acaacagtgt
agatgtaaca aaatcgactt tgttcccact gtacttttag ctcgtacaaa atacaatata
cttttcattt ctccgtaaac aacatgtttt cccatgtaat atccttttct atttttcgtt
ccgttaccaa ctttacacat actttatata gctattcact tctatacact aaaaaactaa
gacaatttta attttgctgc ctgccatatt tcaatttgtt ataaattcct ataatttatc
ctattagtag ctaaaaaaag atgaatgtga atcgaatcct aagagaattg ggcaagtgca
caaacaatac ttaaataaat actactcagt aataacctat ttcttagcat ttttgacgaa
atttgctatt ttgttagagt cttttacacc atttgtctcc acacctccgc ttacatcaac
accaataacg ccatttaatc taagcgcatc accaacattt tctggcgtca gtccaccagc
taacataaaa tgtaagctct cggggctctc ttgccttcca acccagtcag aaatcgagtt
ccaatccaaa agttcacctg tcccacctgc ttctgaatca aacaagggaa taaacgaatg
aggtttctgt gaagctgcac tgagtagtat gttgcagtct tttggaaata cgagtctttt
aataactggc aaaccgagga actcttggta ttcttgccac gactcatctc cgtgcagttg
gacgatatca atgccgtaat cattgaccag agccaaaaca tcctccttag gttgattacg
aaacacgcca accaagtatt tcggagtgcc tgaactattt ttatatgctt ttacaagact
tgaaattttc cttgcaataa ccgggtcaat tgttctcttt ctattgggca cacatataat
acccagcaag tcagcatcgg aatctagagc acattctgcg gcctctgtgc tctgcaagcc
gcaaactttc accaatggac cagaactacc tgtgaaatta ataacagaca tactccaagc
tgcctttgtg tgcttaatca cgtatactca cgtgctcaat agtcaccaat gccctccctc
ttggccctct ccttttcttt tttcgaccga atttcttgaa gacgaaaggg cctcgtgata
cgcctatttt tataggttaa tgtcatgata ataatggttt cttaggacgg atcgcttgcc
tgtaacttac acgcgcctcg tatcttttaa tgatggaata atttgggaat ttactctgtg
tttatttatt tttatgtttt gtatttggat tttagaaagt aaataaagaa ggtagaagag
ttacggaatg aagaaaaaaa aataaacaaa ggtttaaaaa atttcaacaa aaagcgtact
ttacatatat atttattaga caagaaaagc agattaaata gatatacatt cgattaacga
taagtaaaat gtaaaatcac aggattttcg tgtgtggtct tctacacaga caagatgaaa
caattcggca ttaatacctg agagcaggaa gagcaagata aaaggtagta tttgttggcg
atccccctag agtcttttac atcttcggaa aacaaaaact attttttctt taatttcttt
ttttactttc tatttttaat ttatatattt atattaaaaa atttaaatta taattatttt
tatagcacgt gatgaaaagg acccaggtgg cacttttcgg ggaaatgtgc gcggaacccc
tatttgttta tttttctaaa tacattcaaa tatgtatccg ctcatgagac aataaccctg
ataaatgctt caataatatt gaaaaaggaa gagtatgagt attcaacatt tccgtgtcgc
ccttattccc ttttttgcgg cattttgcct tcctgttttt gctcacccag aaacgctggt
gaaagtaaaa gatgctgaag atcagttggg tgcacgagtg ggttacatcg aactggatct
caacagcggt aagatccttg agagttttcg ccccgaagaa cgttttccaa tgatgagcac
ttttaaagtt ctgctatgtg gcgcggtatt atcccgtgtt gacgccgggc aagagcaact
cggtcgccgc atacactatt ctcagaatga cttggttgag tactcaccag tcacagaaaa
gcatcttacg gatggcatga cagtaagaga attatgcagt gctgccataa ccatgagtga
taacactgcg gccaacttac ttctgacaac gatcggagga ccgaaggagc taaccgcttt
tttgcacaac atgggggatc atgtaactcg ccttgatcgt tgggaaccgg agctgaatga
agccatacca aacgacgagc gtgacaccac gatgcctgta gcaatggcaa caacgttgcg
caaactatta actggcgaac tacttactct agcttcccgg caacaattaa tagactggat
ggaggcggat aaagttgcag gaccacttct gcgctcggcc cttccggctg gctggtttat
tgctgataaa tctggagccg gtgagcgtgg gtctcgcggt atcattgcag cactggggcc
agatggtaag ccctcccgta tcgtagttat ctacacgacg gggagtcagg caactatgga
tgaacgaaat agacagatcg ctgagatagg tgcctcactg attaagcatt ggtaactgtc
agaccaagtt tactcatata tactttagat tgatttaaaa cttcattttt aatttaaaag
gatctaggtg aagatccttt ttgataatct catgaccaaa atcccttaac gtgagttttc
gttccactga gcgtcagacc ccgtagaaaa gatcaaagga tcttcttgag atcctttttt
tctgcgcgta atctgctgct tgcaaacaaa aaaaccaccg ctaccagcgg tggtttgttt
gccggatcaa gagctaccaa ctctttttcc gaaggtaact ggcttcagca gagcgcagat
accaaatact gtccttctag tgtagccgta gttaggccac cacttcaaga actctgtagc
accgcctaca tacctcgctc tgctaatcct gttaccagtg gctgctgcca gtggcgataa
gtcgtgtctt accgggttgg actcaagacg atagttaccg gataaggcgc agcggtcggg
ctgaacgggg ggttcgtgca cacagcccag cttggagcga acgacctaca ccgaactgag
atacctacag cgtgagcatt gagaaagcgc cacgcttccc gaagggagaa aggcggacag
gtatccggta agcggcaggg tcggaacagg agagcgcacg agggagcttc caggggggaa
cgcctggtat ctttatagtc ctgtcgggtt tcgccacctc tgacttgagc gtcgattttt
gtgatgctcg tcaggggggc ggagcctatg gaaaaacgcc agcaacgcgg cctttttacg
```

Fig. 28C (SEQ ID No. 427 cont'd.)

```
gttcctggcc ttttgctggc cttttgctca catgttcttt cctgcgttat cccctgattc    5100
tgtggataac cgtattaccg cctttgagtg agctgatacc gctcgccgca gccgaacgac    5160
cgagcgcagc gagtcagtga gcgaggaagc ggaagagcgc ccaatacgca aaccgcctct    5220
ccccgcgcgt tggccgattc attaatgcag ctggcacgac aggtttcccg actggaaagc    5280
gggcagtgag cgcaacgcaa ttaatgtgag ttacctcact cattaggcac cccaggcttt    5340
acactttatg cttccggctc ctatgttgtg tggaattgtg agcggataac aatttcacac    5400
aggaaacagc tatgaccatg attacgccaa gctcggaatt aaccctcact aaagggaaca    5460
aaagctggct agt                                                       5473
```

Fig. 29A (SEQ ID No. 428): PYD1dx xCH1 Fcab wt

```
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttaagt tttagcacag gaactgacaa     600
ctatatgcga gcaaatcccc tcaccaactt tagaatcgac gccgtactct ttgtcaacga     660
ctactatttt ggccaacggg aaggcaatgc aaggagtttt tgaatattac aaatcagtaa     720
cgtttgtcag taattgcggt tctcacccct caacaactag caaaggcagc cccataaaca     780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccgagc ccaagagcag cgacaagaca cacacgtgtc     960
ccccatgtcc cgcccctgag ctgctgggcg gccctcccgt gttcctgttc cctcccaagc    1020
ccaaggacac cctgatgatc tcccggaccc ctgaggtgac ctgtgtggtg gtggacgtga    1080
gccacgagga ccccgaggtg aagttcaact ggtacgtgga cggcgtggag gtgcacaacg    1140
ccaagaccaa gcctagagag gagcagtaca acagcaccta ccgggtggtg agcgtgctga    1200
ccgtgctgca ccaggattgg ctgaatggca aggagtacaa gtgcaaggtg agcaacaagg    1260
ccctgcctgc ccccatcgag aagaccatct ccaaggccaa gggccagcct cgagaaccac    1320
aggtgtacac cctgccccca tcccgggatg agctgaccaa gaaccaggtc agcctgacct    1380
gcctggtcaa aggcttctat cccagcgaca tcgccgtgga gtgggagagc aatgggcagc    1440
cggagaacaa ctacaagacc acgcctcccg tgctggactc cgacggctcc ttcttcctct    1500
acagcaagct caccgtggac aagagcaggt ggcagcaggg gaacgtcttc tcatgctccg    1560
tgatgcatga ggctctgcac aaccactaca cacagaagag cctctccctg tctccgggta    1620
aatgagcggc cgctcgatcg agtctagagg gcccttcgaa ggtaagccta tccctaaccc    1680
tctcctcggt ctcgattcta cgcgtaccgg tcatcatcac catcaccatt gagtttaaac    1740
ccgctgatct gataacaaca gtgtagatgt aacaaaatcg actttgttcc cactgtactt    1800
ttagctcgta caaaatacaa tatacttttc atttctccgt aaacaacatg ttttcccatg    1860
taatatcctt ttctattttt cgttccgtta ccaactttac acatacttta tatagctatt    1920
cacttctata cactaaaaaa ctaagacaat tttaattttg ctgcctgcca tatttcaatt    1980
tgttataaat tcctataatt tatcctatta gtagctaaaa aaagatgaat gtgaatcgaa    2040
tcctaagaga attgggcaag tgcacaaaca atacttaaat aaatactact cagtaataac    2100
ctatttctta gcatttttga cgaaatttgc tattttgtta gagtctttta caccatttgt    2160
ctccacacct ccgcttacat caacaccaat aacgccattt aatctaagcg catcaccaac    2220
attttctggc gtcagtccac cagctaacat aaaatgtaag ctctcggggc tctcttgcct    2280
tccaacccag tcagaaatcg agttccaatc caaaagttca cctgtcccac ctgcttctga    2340
atcaaacaag ggaataaacg aatgaggttt ctgtgaagct gcactgagta gtatgttgca    2400
gtcttttgga aatacgagtc ttttaataac tggcaaaccg aggaactctt ggtattcttg    2460
ccacgactca tctccgtgca gttggacgat atcaatgccg taatcattga ccagagccaa    2520
aacatcctcc ttaggttgat tacgaaacac gccaaccaag tatttcggag tgcctgaact    2580
atttttatat gcttttacaa gacttgaaat tttccttgca ataaccgggt caattgttct    2640
ctttctattg ggcacacata taatacccag caagtcagca tcggaatcta gagcacattc    2700
tgcggcctct gtgctctgca agccgcaaac tttcaccaat ggaccagaac tacctgtgaa    2760
attaataaca gacatactcc aagctgcctt tgtgtgctta atcacgtata ctcacgtgct    2820
caatagtcac caatgccctc cctcttggcc ctctcctttt cttttttcga ccgaatttct    2880
tgaagacgaa agggcctcgt gatacgccta tttttatagg ttaatgtcat gataataatg    2940
gtttcttagg acggatcgct tgcctgtaac ttacacgcgc ctcgtatctt ttaatgatgg    3000
```

Fig. 29B (SEQ ID No. 428 cont'd.)

```
aataatttgg gaatttactc tgtgtttatt tatttttatg ttttgtattt ggattttaga   3060
aagtaaataa agaaggtaga agagttacgg aatgaagaaa aaaaaataaa caaaggttta   3120
aaaaatttca acaaaaagcg tactttacat atatatttat tagacaagaa aagcagatta   3180
aatagatata cattcgatta acgataagta aaatgtaaaa tcacaggatt ttcgtgtgtg   3240
gtcttctaca cagacaagat gaaacaattc ggcattaata cctgagagca ggaagagcaa   3300
gataaaaggt agtatttgtt ggcgatcccc ctagagtctt ttacatcttc ggaaaacaaa   3360
aactattttt tctttaattt ctttttttac tttctatttt taatttatat atttatatta   3420
aaaaatttaa attataatta tttttatagc acgtgatgaa aaggacccag gtggcacttt   3480
tcggggaaat gtgcgcggaa cccctatttg tttatttttc taaatacatt caaatatgta   3540
tccgctcatg agacaataac cctgataaat gcttcaataa tattgaaaaa ggaagagtat   3600
gagtattcaa catttccgtg tcgcccttat tccctttttt gcggcatttt gccttcctgt   3660
ttttgctcac ccagaaacgc tggtgaaagt aaaagatgct gaagatcagt tgggtgcacg   3720
agtgggttac atcgaactgg atctcaacag cggtaagatc cttgagagtt ttcgccccga   3780
agaacgtttt ccaatgatga gcacttttaa agttctgcta tgtggcgcgg tattatcccg   3840
tgttgacgcc gggcaagagc aactcggtcg ccgcatacac tattctcaga atgacttggt   3900
tgagtactca ccagtcacag aaaagcatct tacggatggc atgacagtaa gagaattatg   3960
cagtgctgcc ataaccatga gtgataacac tgcggccaac ttacttctga caacgatcgg   4020
aggaccgaag gagctaaccg cttttttgca caacatgggg gatcatgtaa ctcgccttga   4080
tcgttgggaa ccggagctga atgaagccat accaaacgac gagcgtgaca ccacgatgcc   4140
tgtagcaatg gcaacaacgt tgcgcaaact attaactggc gaactactta ctctagcttc   4200
ccggcaacaa ttaatagact ggatggaggc ggataaagtt gcaggaccac ttctgcgctc   4260
ggcccttccg gctggctggt ttattgctga taaatctgga gccggtgagc gtgggtctcg   4320
cggtatcatt gcagcactgg ggccagatgg taagccctcc cgtatcgtag ttatctacac   4380
gacggggagt caggcaacta tggatgaacg aaatagacag atcgctgaga taggtgcctc   4440
actgattaag cattggtaac tgtcagacca agtttactca tatatacttt agattgattt   4500
aaaacttcat ttttaattta aaaggatcta ggtgaagatc ctttttgata atctcatgac   4560
caaaatccct taacgtgagt tttcgttcca ctgagcgtca gaccccgtag aaaagatcaa   4620
aggatcttct tgagatcctt tttttctgcg cgtaatctgc tgcttgcaaa caaaaaaacc   4680
accgctacca gcggtggttt gtttgccgga tcaagagcta ccaactcttt ttccgaaggt   4740
aactggcttc agcagagcgc agataccaaa tactgtcctt ctagtgtagc cgtagttagg   4800
ccaccacttc aagaactctg tagcaccgcc tacatacctc gctctgctaa tcctgttacc   4860
agtggctgct gccagtggcg ataagtcgtg tcttaccggg ttggactcaa gacgatagtt   4920
accggataag gcgcagcggt cgggctgaac ggggggttcg tgcacacagc ccagcttgga   4980
gcgaacgacc tacaccgaac tgagatacct acagcgtgag cattgagaaa gcgccacgct   5040
tcccgaaggg agaaaggcgg acaggtatcc ggtaagcggc agggtcggaa caggagagcg   5100
cacgagggag cttccagggg gaaacgcctg gtatctttat agtcctgtcg ggtttcgcca   5160
cctctgactt gagcgtcgat ttttgtgatg ctcgtcaggg gggcggagcc tatggaaaaa   5220
cgccagcaac gcggcctttt tacggttcct ggccttttgc tggccttttg ctcacatgtt   5280
ctttcctgcg ttatcccctg attctgtgga taaccgtatt accgcctttg agtgagctga   5340
taccgctcgc cgcagccgaa cgaccgagcg cagcgagtca gtgagcgagg aagcggaaga   5400
gcgcccaata cgcaaaccgc ctctccccgc gcgttggccg attcattaat gcagctggca   5460
cgacaggttt cccgactgga aagcgggcag tgagcgcaac gcaattaatg tgagttagct   5520
cactcattag gcaccccagg ctttacactt tatgcttccg gctcgtatgt tgtgtggaat   5580
tgtgagcgga taacaatttc acacaggaaa cagctatgac catgattacg ccaagctcgg   5640
aattaaccct cactaaaggg aacaaaagct ggctagt                            5677
```

CYTOTOXIC IMMUNOGLOBULIN

This application is a continuation of U.S. application Ser. No. 14/470,425, filed Aug. 27, 2014, which is a continuation of U.S. application Ser. No. 12/990,119, filed Oct. 28, 2010, now U.S. Pat. No. 8,859,738, issued Oct. 14, 2014, which is a U.S. national phase entry of International Patent Application No. PCT/EP2009/052509, filed on Mar. 3, 2009, which claims the benefit of European Patent Application No. 08450068.5, filed May 2, 2008, the entirety of each of which is hereby incorporated by reference.

The invention relates to a cytotoxic immunoglobulin.

Monoclonal antibodies have been widely used as therapeutic binding agents. The basic antibody structure will be explained here using as example an intact IgGI immunoglobulin.

Two identical heavy (H) and two identical light (L) chains combine to form the Y-shaped antibody molecule. The heavy chains each have four domains. The amino terminal variable domains (VH) are at the tips of the Y. These are followed by three constant domains: CH1, CH2, and the carboxy-terminal CH3, at the base of the Y's stem. A short stretch, the switch, connects the heavy chain variable and constant regions. The hinge connects CH2 and CH3 (the Fc fragment) to the remainder of the antibody (the Fab fragments). One Fc and two identical Fab fragments can be produced by proteolytic cleavage of the hinge in an intact antibody molecule. The light chains are constructed of two domains, variable (VL) and constant (CL), separated by a switch.

Disulfide bonds in the hinge region connect the two heavy chains. The light chains are coupled to the heavy chains by additional disulfide bonds. Asn-linked carbohydrate moieties are attached at different positions in constant domains depending on the class of immunoglobulin. For IgGI two disulfide bonds in the hinge region, between Cys235 and Cys238 pairs, unite the two heavy chains. The light chains are coupled to the heavy chains by two additional disulfide bonds, between Cys229s in the CH1 domains and Cys214s in the CL domains. Carbohydrate moieties are attached to Asn306 of each CH2, generating a pronounced bulge in the stem of the Y.

These features have profound functional consequences. The variable regions of both the heavy and light chains (VH) and (VL) lie at the "tips" of the Y, where they are positioned to react with antigen. This tip of the molecule is the side on which the N-terminus of the amino acid sequence is located. The stem of the Y projects in a way to efficiently mediate effector functions such as the activation of complement and interaction with Fc receptors, or ADCC and ADCP. Its CH2 and CH3 domains bulge to facilitate interaction with effector proteins. The C-terminus of the amino acid sequence is located on the opposite side of the tip, which can be termed "bottom" of the Y.

Two types of light chain, termed lambda (λ) and kappa (K), are found in antibodies. A given immunoglobulin either has K chains or λ chains, never one of each.

No functional difference has been found between antibodies having λ or K light chains. Each domain in an antibody molecule has a similar structure of two beta sheets packed tightly against each other in a compressed antiparallel beta barrel. This conserved structure is termed the immunoglobulin fold. The immunoglobulin fold of constant domains contains a 3-stranded sheet packed against a 4-stranded sheet. The fold is stabilized by hydrogen bonding between the beta strands of each sheet, by hydrophobic bonding between residues of opposite sheets in the interior, and by a disulfide bond between the sheets. The 3-stranded sheet comprises strands C, F, and G, and the 4-stranded sheet has strands A, B, E, and D. The letters A through G denote the sequential positions of the beta strands along the amino acid sequence of the immunoglobulin fold.

The fold of variable domains has 9 beta strands arranged in two sheets of 4 and 5 strands. The 5-stranded sheet is structurally homologous to the 3-stranded sheet of constant domains, but contains the extra strands C and C". The remainder of the strands (A, B, C, D, E, F, G) have the same topology and similar structure as their counterparts in constant domain immunoglobulin folds. A disulfide bond links strands B and F in opposite sheets, as in constant domains.

The variable domains of both light and heavy immunoglobulin chains contain three hypervariable loops, or complementarity-determining regions (CDRs). The three CDRs of a V domain (CDR1, CDR2, CDR3) cluster at one end of the beta barrel. The CDRs are loops that connect beta strands B-C, C'-C", and F-G of the immunoglobulin fold. The residues in the CDRs vary from one immunoglobulin molecule to the next, imparting antigen specificity to each antibody.

The VL and VH domains at the tips of antibody molecules are closely packed such that the 6 CDRs (3 on each domain) cooperate in constructing a surface (or cavity) for antigen-specific binding. The natural antigen binding site of an antibody thus is composed of the loops which connect strands B-C, C'-C", and F-G of the light chain variable domain and strands B-C, C'-C", and F-G of the heavy chain variable domain.

The loops which are not CDR-loops in a native immunoglobulin, or not part of the antigen-binding pocket as determined by the CDR loops and optionally adjacent loops within the CDR loop region, do not have antigen binding or epitope binding specificity, but contribute to the correct folding of the entire immunoglobulin molecule and/or its effector or other functions and are therefore called structural loops for the purpose of this invention.

Prior art documents show that the immunoglobulin-like scaffold has been employed so far for the purpose of manipulating the existing antigen binding site, thereby introducing novel binding properties. In most cases the CDR regions have been engineered for antigen binding, in other words, in the case of the immunoglobulin fold, only the natural antigen binding site has been modified in order to change its binding affinity or specificity. A vast body of literature exists which describes different formats of such manipulated immunoglobulins, frequently expressed in the form of single-chain Fv fragments (scFv) or Fab fragments, either displayed on the surface of phage particles or solubly expressed in various prokaryotic or eukaryotic expression systems.

WO06/072620A1 describes a method of engineering an immunoglobulin which comprises a modification in a structural loop region to obtain new antigen binding sites. This method is broadly applicable to immunoglobulins and may be used to produce a library of immunoglobulins targeting a variety of antigens. A CH3 library has been shown to be useful for selecting specific binders to an antigen.

WO08/003103A2 describes the panning of a CH3, CH1 or CL library on a synthetic peptide, representing a mimotope of the CD20 antigen.

Various immunoglobulin libraries have been proposed in the art to obtain specific immunoglobulin binders. The prior art refers to monomeric monovalent display of binding domains, in general. WO9209690A2 describes phagemid particles displaying a single copy of a fusion protein on the surface of the particle. Thereby it was described to obtain high affinity binders from a library of phagemid particles, also called bacteriophages. Replicable expression vectors comprising genes encoding a binding polypeptide and a phage coat protein are provided so to form a gene fusion encoding a fusion protein, which is a chimeric protein of a phagemid particle, the phage coat protein and the binding polypeptide.

U.S. Pat. No. 5,223,409 generally describes the method of fusing a gene encoding a protein of interest to the N-terminal domain of the gene III coat protein of the filamentous phage M13. The gene fusion is mutated to form a library of structurally related fusion proteins that are expressed in low quantity on the surface of a phagemid particle. Biological selection and screening is employed to identify novel ligands useful as drug candidates.

However, there are some limitations in using such "fusion phage" or monovalent phage display and respective single fusion proteins. Many biologicals naturally occur in oligomeric form. For the purpose of the present invention oligomeric means dimeric, trimeric or even higher polymeric forms, up to 24 monomers.

The fusion phages according to the prior art are described to display monomeric fusion proteins, mainly because it was believed that binders of highest affinity could only be selected from a library if single fusion proteins are displayed by the phagemid particles. Native proteins are however often assembled as a dimer or even at a higher degree of oligomerization. To obtain dimeric display with a single fusion protein, some techniques have been developed that involve conditional stop codons located between the coat protein and the binding polypeptide (Dall'Acqua et al. The Journal of Immunology, 2002, 169: 5171-5180). Thereby soluble monomers of the polypeptides in addition to those fused to the phage are expressed, thus enabling the formation of a dimer. However, such stop codons requires propagation in specific suppressor host cells that may translate a stop codon in an amino acid, to provide an appropriate amount of fusion proteins in addition to the soluble binding polypeptides.

Prior art fusion proteins involve in some cases linker sequences to display larger binding polypeptides. Linker sequences of up to 24 amino acids are usually employed for standard purposes of displaying variable domains of an antibody. See for example, the display vector pCOMB3× (Hybrid. Hybridomics. 2003 April; 22(2):97-108. Development of functional human monoclonal single-chain variable fragment antibody against HIV-1 from human cervical B cells. Berry J D, Rutherford J, Silverman G J, Kaul R, ENa M, Gobuty S, Fuller R, Plummer F A, Barbas C F.)

Immunoglobulins based on full length IgGI have been widely used for treating patients suffering from solid tumors, in particular those overexpressing a receptor of the erbB class. Among those receptors are EGFR (Her1), Her2, Her2neu, Her3 and Her4.

Herceptin (trastuzumab, humAb4D5) is a product based on a monoclonal antibody for use in breast cancer therapy. Herceptin antibody is specific for the 4D5 epitope of the HER2 extracellular domain of her2neu (also called c-erbB-2 or MAC117).

"HER2 extracellular domain" or "HER2 ECD" refers to a domain of HER2 that is outside of a cell, either anchored to a cell membrane, or in circulation, including fragments thereof. The extracellular domain of HER2 may comprise four domains: "Domain I" (amino acid residues from about 1-195, "Domain II" (amino acid residues from about 196-319), "Domain III" (amino acid residues from about 320-488), and "Domain IV" (amino acid residues from about 489-630) (residue numbering without signal peptide).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2. The 4D5 epitope of HER2 encompasses any one or more residues in the region from about residue 529 to about residue 625, inclusive of the HER2 ECD, residue numbering including signal peptide.

The EGFR is a large (1,186 residues), monomeric glycoprotein with a single transmembrane region and a cytoplasmic tyrosine kinase domain flanked by noncatalytic regulatory regions. Sequence analyses have shown that the ectodomain (residues 1-621) contains four sub-domains, here termed L1, CR1, L2 and CR2, where L and CR are acronyms for large and Cys-rich respectively. The L1 and L2 domains have also been referred to as domains I and III, respectively. The CR domains have been previously referred to as domains II and IV, or as S1.1-S1.3 and S2.1-S2.3 where S is an abbreviation for small.

MAbs to the external domain of the EGFR have been developed that disrupt ligand binding to the receptor and subsequent signal transduction. Three EGFR-specific blocking antibodies have been characterized in greater detail in vitro and are presently used in clinical studies; these are mAbC225 (ERBITUX/cetuximab), mAb425 (EMD72000) and the human mAb ABX-EGF. C225 (Cetuximab/Erbitux) is FDA approved for metastatic colorectal cancer and mAb425 (EMD59000) whose humanized version (EMD72000) is currently in phase II clinical trials for various solid tumors expressing EGFr. C225 binds to distinct epitopes on the extracellular domain of EGFr. Independent binding of both antibodies to the wild type receptor and to the mutant receptor (EGFrVIII) which is prominently expressed in tumor cells, has been shown. Cetuximab interacts exclusively with domain III of the extracellular region of EGFR (sEGFR), particularly occluding the ligand binding region on this domain and sterically preventing the receptor from dimerization.

The spontaneously occurring mutant EGF receptor was first shown in glioblastoma. Known as EGFRvIII, this molecule represents a deletion of exons 2 through 7 in the extracellular domain of the EGF receptor. This removes 273 amino acids and creates a novel glycine at the fusion junction. The EGFRvIII (variously called de2-7 EGFR or deltaEGFR) has an in-frame deletion of the extracellular domain and is found in numerous types of human tumors.

WO9720858A1 relates to anti-Her2 antibodies which induce apoptosis in Her2 expressing cells. Therefore the monoclonal antibodies (mAbs), which bind to Her2, are generated by immunizing mice with purified soluble Her2.

WO06087637A2 relates to antibodies that recognise Her2/neu and exert an antiproliferative effect on Her2/neu expressing cells. This document describes an isolated antibody or a fragment, variant or derivative thereof, in particular the human Fab fragment, and the scFv fragment, capable of specifically binding to Her2neu, however, without cytotoxic activity.

Some prior art disclosures relate to antibody formats with a potential to inhibit tumor growth, in the absence of cytotoxic activities, such as ADCC.

Rovers et al (Cancer Immunol. Immunother. (2007) 56:303-317 describe anti-EGFR nanobodies with a potential to inhibit tumour cell growth.

WO03/075840A2 discloses antibodies that bind to KDR with an affinity comparable to or higher than human VEGF and that neutralizes activation of KDR, among them monovalent Fabs that neutralizes the activation of KDR, thus inhibiting angiogenesis and tumor growth. Other immunoglobulin fragments have been proposed for human therapy.

Patent application WO06036834A2 describes a biologically active peptide incorporated as an internal sequence into a loop region of an Fc domain; the specification concerns a molecule of which the internal peptide sequence may be added by insertion or replacement of amino acids in the previously existing Fc domain. An exemplary peptide is targeting p185HER2/neu.

Peptides targeting Her2/neu have been described by Park et al Nat. Biotechnol. (2000) 18(2):194-8. Though peptide binding affinities usually are in the lower range with a kD of greater than $10^{-6}$ M, the described exocyclic anti-HER2/neu peptide mimic exerted an unusually high affinity (KD=300 nM).

WO01/01748A2 describes peptide compounds that bind to human erbB2 gene product with low binding affinities. An exemplary peptide-Fc fusion protein directed to erbB2 was tested in a competition binding assays, with a low quantity of the same type of peptides used as competitors, resulting in a low IC50 value that would, however, not be indicative for a Kd or EC50 value, as determined in a saturation assay.

It is the object of present invention to provide improved immunoglobulin products binding to cell surfaces.

The object is solved by the subject matter as claimed.

SUMMARY OF THE INVENTION

According to the invention there is provided a cytotoxic modular antibody with a molecular weight of up to 60 kD, which is specifically binding to a cell surface target with a binding affinity of $Kd<10^{-8}$ M, preferably in the nanomolar range or lower. The high affinity modular antibody according to the invention is thus small sized with the advantage of easy penetration through a cell layer or tumor, to effect cell lysis or cell death at the site where the target is overexpressed. Alternatively, the modular antibody according to the invention preferably has an $IC50<10^{-8}$ M, as determined in a saturation binding assay.

The modular antibody according to the invention preferably exerts at least one of ADCC, ADCP, CDC or apoptotic activity.

The cytotoxic activity of the modular antibody according to the invention is preferably determined by its effector functions, as measured by at least one of ADCC, ADCP and CDC activity.

A preferred modular antibody according to the invention is an oligomer of modular antibody domains, in particular an oligomer of immunoglobulin domains, or a fragment of a full length immunoglobulin. The preferred antibody is a dimer selected from the group consisting of dimers of VHA/L, CH1/CL, CH2/CH2, CH3/CH3, Fc and Fab, or single chains thereof.

The modular antibody according to the invention preferably contains a binding site having a randomized antibody sequence and/or at least one binding site within a structural loop region, which is always understood to potentially include a terminal domain sequence that could be contributing to antigen binding. The site of the randomized antibody sequence may be within the CDR region or the structural loop region. Thus, binding to a target or a functional ligand, such as an effector molecule, which is in preferred cases also a scaffold ligand, is possible even through an immunoglobulin without CDR region, or at a site besides a CDR region.

According to a preferred embodiment, the cell surface target binding site is located within the CDR region, and the binding site with specificity to a functional ligand or a scaffold ligand is within the structural loop region.

According to an alternatively preferred embodiment, the binding site with specificity to a functional ligand or a scaffold ligand is within the CDR loop region and the cell surface target binding site located in a structural loop region.

The preferred modular antibody according to the invention has specific binding properties to bind a target, which is a receptor of the erbB class, such as selected from the group consisting of EGFR, Her2, Her2neu, HER3 and HER4. Preferred modular antibodies according to the invention are provided for treating patients suffering from a solid tumor, which tumor expresses a receptor of the erbB class.

Those anti-Her2 modular antibodies are particularly preferred that contain an amino acid sequence within the EF loop of a structural loop region, which sequence is selected from the group consisting of SEQ. ID. Numbers as listed in Table 4 and 5, which are optionally contained in an EF and/or AB and/or CD loop.

Though there was a long term need for highly effective, but small sized antibodies, it was the first time possible to obtain such modular antibody according to the invention, using a library of modular antibody domains, in particular a library of an oligomer of modular antibody domains binding to an effector ligand. Selected members of such a library have both properties, the target binding and the effector ligand binding, as a prerequisite for biological cytotoxicity or cytolysis. It is further preferred that the format of a modular antibody scaffold is not changed by producing variants and libraries of such scaffold, thus library members would still maintain the functional format as determined by binding to a scaffold ligand.

According to the invention there is further provided a method of producing a modular antibody according to claim 1, which comprises the steps of:

a. providing a library of an oligomer of modular antibody domains,
b. contacting said library with said target in the presence of an effector ligand,
c. selecting a library member having both properties,
   (i) target binding affinity of $Kd<10^{-8}$ M or $IC50<10^{-8}$ M, and
   (ii) cytotoxic activity, and
d. manufacturing a preparation of the modular antibody.

The preferred selection methods provide for the simultaneous binding of both, the target and the effector ligand, which is advantageous for the effective cytolysis. Simultaneous binding is preferably determined in a cell-based assay with two-dimensional differentiation, e.g. in a FACS system.

Preferably, the library members contain a randomized antibody sequence, wherein the site of mutagenesis optionally is within the CDR region or aside from the CDR region, preferably within the structural loop region, potentially including a terminal sequence.

The library as used in the method according to the invention is preferably produced according to a design that provides for mutagenesis aside from binding sites interacting with the effector ligand. Thus, a high quality library is preferably used, as determined by quality control measures employing assays of effector molecule binding or scaffold ligand binding.

The preferred method according to the invention further comprises the step of affinity maturation to increase the binding affinity to the cell surface target. This affinity maturation is preferably performed through mutagenesis of a selected immunoglobulin that has a determined binding specificity to bind the target, not cross-reacting with control proteins, however, having still a medium or low affinity. Preferably a library member that has a binding affinity with an IC50 or $Kd<10^{-6}$ M is further mutagenized to provide an affinity matured binder or a pool of such binders, i.e. a library of affinity matured binders with higher affinity with an IC50 or Kd<$10^{-7}$ M, preferably with an IC50 or Kd<$10^{-8}$ M, or even in the nanomolar or lower range. In this case, it is preferred the modular antibody according to the invention is still functional with regard to its cytotoxic effect.

According to a preferred embodiment there is provided a method of preparing a modular antibody according to the invention, for treating a patient suffering from a solid tumor, which tumor expresses a receptor of the erbB class.

The modular antibody according to the invention is preferably used for treating a patient suffering from a solid tumor, which tumor expresses a receptor of the erbB class.

FIGURES

FIG. 1:

Schematic presentation of the PCRs used for production of the fragments used for assembly of the library Fcab01. PCR primers are indicated by arrows with their respective 5'-3' orientation, and vertical lines indicate the approximate positions of the introduced restriction sites which were used for assembly of the mutated gene. The restriction sites are contained on the primers for ligations of the PCR fragments.

FIG. 2:

Amino acid sequence and secondary structure of a CH3 domain (IMGT numbering) where SEQ ID NO:440 reflects the linear sequence of the residues identified in the folded sequence. The randomization scheme is provided for the libraries Fcab01 to Fcab06. Randomized positions in the AB and EF loop are marked with a circle. X stands for all 20 amino acids, z only for Ala, Asp, Ser, Tyr.

FIG. 3:

crystal structure of an IgGI Fc fragment (amino acid sequence)

FIG. 4:

human IgG including randomized amino acid modifications (amino acid sequence)

FIG. 5:

amino acid sequence of FcabRGD4L (amino acid sequence)

FIGS. 6A and 6B:

vector pHENFcabRGD4 (nucleotide sequence)

FIGS. 7A and 7B:

vector pHENFcabRGD4L (nucleotide sequence)

FIGS. 8A and 8B (SEQ ID No.15):

vector pYDIdX (nucleotide sequence)

FIGS. 9A and 9B and 9C (SEQ ID No.16):

vector pYDIdXFc (nucleotide sequence)

FIGS. 10A and 10B and 10C (SEQ ID No.17):

pYD1 CH12 (nucleotide sequence)

FIG. 11 (SEQ ID No.18):

Fcab01 (nucleotide sequence)

FIG. 12 (SEQ ID No.19):

Fcab02 (nucleotide sequence)

FIG. 13 (SEQ ID No.20):

Fcab03 (nucleotide sequence)

FIG. 14 (SEQ ID No.21):

Fcab04 (nucleotide sequence)

FIG. 15 (SEQ ID No.22):

Fcab05 (nucleotide sequence)

FIG. 16 (SEQ ID No.23):

Fcab06 (nucleotide sequence)

FIGS. 17A and 17B and 17C (SEQ ID No.72):

vector pYD 1 (nucleotide sequence)

FIGS. 18A and 18B (SEQ ID No.73):

modified vector pYD1Nhe (nucleotide sequence)

FIGS. 19A and 19B (SEQ ID No.74):

vector pYD1Ink (nucleotide sequence)

FIGS. 20A and 20B (SEQ ID No.75):

vector pYDI mata (nucleotide sequence)

FIGS. 21A and 21B (SEQ ID No.76):

vector pYDIgal (nucleotide sequence)

FIG. 22 (SEQ ID No.77):

4D5H (nucleotide sequence)

FIG. 23 (SEQ ID No.78):

4D5L (nucleotide sequence)

FIGS. 24A and 24B and 24C (SEQ ID No.79):

vector pYD4D5hc (nucleotide sequence)

FIG. 25 (SEQ ID No.80):

4D5hp (amino acid sequence)

FIGS. 26A and 26B and 26C (SEQ ID No.81):

vector pYD4D5h1 (nucleotide sequence)

FIG. 27 (SEQ ID No.82):

4D5lp (amino acid sequence)

FIGS. 28A and 28B and 28C (SEQ ID No.427):

plasmid pYD1dX_dCH1dCH3_Fcab_wt (nucleotide sequence)

FIGS. 29A and 29B (SEQ ID No.428):

pYD1_dX_dCH1_Fcab_wt (nucleotide sequence)

DETAILED DESCRIPTION OF THE INVENTION

Definitions

Specific terms as used throughout the specification have the following meaning.

The term "immunoglobulin" as used according to the present invention is defined as polypeptides or proteins that may exhibit mono- or bi- or multi-specific, or mono-, bi- or multivalent binding properties, preferably at least two, more preferred at least three specific binding sites for epitopes of e.g. antigens, effector molecules or proteins either of pathogen origin or of human structure, like self-antigens including cell-associated or serum proteins. The term immunoglobulin as used according to the invention also includes functional fragments of an antibody, such as Fc, Fab, scFv, single chain dimers of CH1/CL domains, Fv, dimers like VH/VL, CH1/CL, CH2/CH2, CH3/CH3, or other derivatives or combinations of the immunoglobulins, like single chains of pairs of immunoglobulin domains. The definition further includes domains of the heavy and light chains of the variable region (such as dAb, Fd, V1, Vk, Vh, VHH) and the constant region or individual domains of an intact antibody such as CH1, CH2, CH3, CH4, Cl and Ck, as well as mini-domains consisting of at least two beta-strands of an immunoglobulin domain connected by a structural loop.

"Modular antibodies" as used according to the invention are defined as antigen-binding molecules, like human antibodies, composed of at least one polypeptide module or protein domain, preferably in the natural form. The term "modular antibodies" includes antigen-binding molecules that are either immunoglobulins, immunoglobulin-like proteins, or other proteins exhibiting modular formats and antigen-binding properties similar to immunoglobulins or antibodies, which can be used as antigen-binding scaffolds, preferably based on human proteins.

The term "immunoglobulin-like molecule" as used according to the invention refers to any antigen-binding protein, in particular to a human protein, which has a domain structure that can be built in a modular way. Immunoglobulin-like molecules as preferably used for the present invention are T-cell receptors (TCR) or soluble parts thereof, fibronectin, transferrin, CTLA-4, single-chain antigen receptors, e.g. those related to T-cell receptors and antibodies, antibody mimetics, adnectins, anticalins, phylomers, repeat proteins such as ankyrin repeats, avimers, Versabodies™, scorpio toxin based molecules, and other non-antibody protein scaffolds with antigen binding properties.

Ankyrin repeat (AR), armadillo repeat (ARM), leucine-rich repeat (LRR) and tetrathcopeptide repeat (TPR) proteins are the most prominent members of the protein class of repeat proteins. Repeat proteins are composed of homologous structural units (repeats) that stack to form elongated domains. The binding interaction is usually mediated by several adjacent repeats, leading to large target interaction surfaces.

Avimers contain A-domains as strings of multiple domains in several cell-surface receptors. Domains of this family bind naturally over 100 different known targets, including small molecules, proteins and viruses. Truncation analysis has shown that a target is typically contacted by multiple A-domains with each domain binding independently to a unique epitope. The avidity generated by combining multiple binding domains is a powerful approach to increase affinity and specificity, which these receptors have exploited during evolution.

Anticalins are engineered human proteins derived from the lipocalin scaffold with prescribed binding properties typical for humanized antibodies. Lipocalins comprise 160-180 amino acids and form conical beta-barrel proteins with a ligand-binding pocket surrounded by four loops. Small hydrophobic compounds are the natural ligands of lipocalins, and different lipocalin variants with new compound specificities (also termed 'anticalins') could be isolated after randomizing residues in this binding pocket.

Single chain antigen receptors contain a single variable domain and are 20% smaller than camelid single domain antibodies. Phylomers are peptides derived from biodiverse natural protein fragments.

It is understood that the term "modular antibody", "immunoglobulin", "immunoglobulin-like proteins" includes a derivative thereof as well. A derivative is any combination of one or more modular antibodies of the invention and or a fusion protein in which any domain or minidomain of the modular antibody of the invention may be fused at any position of one or more other proteins (such as other modular antibodies, immunoglobulins, ligands, scaffold proteins, enzymes, toxins and the like). A derivative of the modular antibody of the invention may also be obtained by association or binding to other substances by various chemical techniques such as covalent coupling, electrostatic interaction, di-sulphide bonding etc. The other substances bound to the immunoglobulins may be lipids, carbohydrates, nucleic acids, organic and inorganic molecules or any combination thereof (e.g. PEG, prodrugs or drugs). A derivative would also comprise an antibody with the same amino acid sequence but made completely or partly from non-natural or chemically modified amino acids. The term derivative also includes fragments and functional equivalents. The preferred derivatives still are functional with regard to both, target binding and cytotoxic activity.

A "structural loop" or "non-CDR-loop" according to the present invention is to be understood in the following manner: modular antibodies, immunoglobulins or immunoglobulin-like substances are made of domains with a so called immunoglobulin fold. In essence, antiparallel beta sheets are connected by loops to form a compressed antiparallel beta barrel. In the variable region, some of the loops of the domains contribute essentially to the specificity of the antibody, i.e. the binding to an antigen by the natural binding site of an antibody. These loops are called CDR-loops. The CDR loops are located within the CDR loop region, which may in some cases also include part of the variable framework region (called "VFR"), which is adjacent to the CDR loops. It is known that some loops of the VFR may contribute to the antigen binding pocket of an antibody, which generally is mainly determined by the CDR loops. Thus, those VFR loops are considered as part of the CDR loop region, and would not be appropriately used for engineering new antigen binding sites. Loops aside from the antigen-binding pocket or CDR loop region are usually called structural loops or non-CDR-loops. Contrary to the VFR within the CDR loop region or located proximal to the CDR loops, other loops of the VFR of variable domains would be considered structural loops and particularly suitable for use according to the invention. Those are preferably the structural loops of the VFR located opposite to the CDR loop region, or at the C-terminal side of a variable immunoglobulin domain. Constant domains have structural loops within a structural loop region, e.g. either at the C-terminal side of an antibody domain or at an N-terminal side, even within a side chain of an antibody domain. Constant domains are also called part of the framework region.

The term "antigen" or "target" as used according to the present invention shall in particular include all antigens and target molecules capable of being recognised by a binding site of a modular antibody. Specifically preferred antigens as targeted by the molecule according to the invention are those antigens or molecules, which have already been proven to be or are capable of being immunologically or therapeutically relevant, especially those, for which a clinical efficacy has been tested.

The term "target" or "antigen" as used herein shall in particular comprise molecules selected from the group consisting of allergens, tumor associated antigens, self antigens including cell surface receptors, enzymes, Fc-receptors, FcRn, HSA, IgG, interleukins or cytokines, proteins of the complement system, transport proteins, serum molecules, bacterial antigens, fungal antigens, protozoan antigen and viral antigens, also molecules responsible for transmissible spongiform encephalitis (TSE), such as prions, infective or not, and markers or molecules that relate to inflammatory conditions, such as pro-inflammatory factors, multiple sclerosis or alzheimer disease, or else haptens.

The term "cell surface antigens" shall include all antigens capable of being recognised by an antibody structure on the surface of a cell, and fragments of such molecules. Preferred cell surface antigens are those antigens, which have already been proven to be or which are capable of being immunologically or therapeutically relevant, especially those, for which a preclinical or clinical efficacy has been tested. Those cell surface molecules are specifically relevant for the purpose of the present invention, which mediate cell killing activity. Upon binding of the immunoglobulin according to the invention to preferably at least two of those cell surface molecules the immune system provides for cytolysis or cell death, thus a potent means for attacking human cells may be provided.

The antigen is either recognized as a whole target molecule or as a fragment of such molecule, especially substructures of targets, generally referred to as epitopes. Substructures of antigens are generally referred to as "epitopes" (e.g. B-cell epitopes, T-cell epitopes), as long as they are immunologically relevant, i.e. are also recognisable by natural or monoclonal antibodies. The term "epitope" as used herein according to the present invention shall in particular refer to a molecular structure which may completely make up a specific binding partner or be part of a specific binding partner to a binding site of modular antibody or an immunoglobulin of the present invention. The term epitope may also refer to haptens. Chemically, an epitope may either be composed of a carbohydrate, a peptide, a fatty acid, an organic, biochemical or inorganic substance or derivatives thereof and any combinations thereof. If an epitope is a polypeptide, it will usually include at least 3 amino acids, preferably 8 to 50 amino acids, and more preferably between about 10-20 amino acids in the peptide. There is no critical upper limit to the length of the peptide, which could comprise nearly the full length of a polypeptide sequence of a protein. Epitopes can be either linear or conformational epitopes. A linear epitope is comprised of a single segment of a primary sequence of a polypeptide chain. Linear epitopes can be contiguous or overlapping. Conformational epitopes are comprised of amino acids brought together by folding of the polypeptide to form a tertiary structure and the amino acids are not necessarily adjacent to one another in the linear sequence. Specifically, epitopes are at least part of diagnostically relevant molecules, i.e. the absence or presence of an epitope in a sample is qualitatively or quantitatively correlated to either a disease or to the health status of a patient or to a process status in manufacturing or to environmental and food status. Epitopes may also be at least part of therapeutically relevant molecules, i.e. molecules which can be targeted by the specific binding domain which changes the course of the disease.

As used herein, the term "specifically binds" or "specific binding" refers to a binding reaction which is determinative of the cognate ligand of interest in a heterogeneous population of molecules. Thus, under designated conditions (e.g. immunoassay conditions), the modular antibody binds to its particular target and does not bind in a significant amount to other molecules present in a sample. The specific binding means that binding is selective in terms of target identity, high, medium or low binding affinity or avidity, as selected. Selective binding is usually achieved if the binding constant or binding dynamics is at least 10 fold different, preferably the difference is at least 100 fold, and more preferred a least 1000 fold.

The term "expression system" refers to nucleic acid molecules containing a desired coding sequence and control sequences in operable linkage, so that hosts transformed or transfected with these sequences are capable of producing the encoded proteins. In order to effect transformation, the expression system may be included on a vector; however, the relevant DNA may then also be integrated into the host chromosome. Alternatively, an expression system can be used for in vitro transcription/translation.

All numbering of the amino acid sequences of the immunoglobulins is according to the IMGT numbering scheme (IMGT, the international ImMunoGeneTics, Lefranc et al., 1999, Nucleic Acids Res. 27: 209-212).

For the purposes of this invention, the term "binding agent" or "ligand" refers to a member of a binding pair, in particular binding polypeptides having the potential of serving as a binding domain for a binding partner. Examples of binding partners include pairs of binding agents with functional interactions, such as receptor binding to ligands, antibody binding to antigen or receptors, a drug binding to a target, and enzyme binding to a substrate The term "fusion protein" or "chimeric fusion protein" as used for the purpose of the invention shall mean the molecule composed of a genetic package, at least part of an outer surface structure, such as a coat protein, optionally a linker sequence, and a binding agent. The fusion protein is encoded by a vector with the gene of the binding agent and information to display a copy of the binding agent at the surface of the genetic package.

The term "cytotoxic" or "cytotoxic activity" as used for the purpose of the invention shall refer to any specific molecule directed against cellular antigens that, when bound to the antigen, activates the complement pathway or activates killer cells, resulting in cell lysis or triggers apoptosis. In particular it is referred to the activity on effector cells resulting in activation of cytotoxic T-cells or cells which mediate antibody-dependent cell cytotoxicity (ADCC), complement dependent cytotoxicity (CDC) and/or cellular phagocytosis (ADCP). It is further referred to an apoptotic effect, thus triggering programmed cell death (PCD). Modular antibodies according to the invention thus kill antibody-coated target cells, optionally either by binding to Fc receptors of effector cells or by inducing programmed cell death.

"Scaffold" shall mean a temporary framework either natural or artificial used to support the molecular structure of a polypeptide in the construction of variants or a repertoire of the polypeptide. It is usually a modular system of polypeptide domains that maintains the tertiary structure or the function of the parent molecule. Exemplary scaffolds are modular antibodies, which may be mutagenized to produce variants within said scaffold, to obtain a library.

The term "scaffold ligand" as used for the purpose of the invention shall mean a ligand that binds to a scaffold or the backbone of modular antibodies, thus determining the molecular structure or primary function and specificity of said modular antibody. In preferred cases the scaffold ligand is a functional ligand, mediating a biological function upon binding, like an effector ligand. In an alternative embodiment the scaffold ligand is a functional ligand, which is a specific target bound by the CDR region or structural loop region. The same scaffold ligand can bind many variants of a modular antibody regardless of their target specificities. In general, the presence of scaffold ligand binding site indicates that the variant is expressed and folded correctly. Thus, binding of the scaffold ligand to its binding site provides a method for preselecting, coselecting, characterization and screening of functional polypeptides functional polypeptides from a repertoire of polypeptides. Designing variants of modular antibodies that keep the binding property to a scaffold ligand avoids the preparation of variants that are non-functional, for example as a result of the introduction of mutations, folding mutants or expression mutants which would be or are incapable of binding to substantially any target or effector ligand. Such non-functional mutants sometimes are generated by the normal randomisation and variation procedures employed in the construction of polypeptide repertoires. Providing functional mutants that bind to a scaffold ligand permits the person skilled in the art to prepare a library of modular antibodies which is enriched in functional, well folded and highly expressed library members. For example, the scaffold can be a parent Fab and at least 20%, preferably at least 30%, more preferred at least 40% of the parent Fab variants are binding to the CDR-target of said parent Fab.

The term "effector ligand" as used for the purpose of the invention shall mean a ligand mediating effector functions, like an effector molecule. Exemplary effector ligands are Fc receptors or Fc receptor-like molecules interfering with immunoglobulins. An Fc receptor is a protein found on the surface of certain cells—including natural killer cells, macrophages, neutrophils, and mast cells—that contribute to the protective functions of the immune system. Its name is derived from its binding specificity for a part of an antibody known as the Fc (Fragment, crystallizable) region. Fc receptors bind to antibodies that are attached to infected cells or invading pathogens. Their activity stimulates phagocytic or cytotoxic cells to destroy microbes, or infected cells by antibody-mediated cellular phagocytosis (ADCP) or antibody-dependent cell-mediated cytotoxicity (ADCC). There are several different types of Fc receptors, which are classified based on the type of antibody that they recognize; for example those that bind the most common class of antibody, IgG, are called Fc-gamma receptors (FcγR), those that bind IgA are called Fc-alpha receptors (FcαR) and those that bind IgE are called Fc-epsilon receptors (FcϵR). Equivalent to an effector ligand and thus incorporated into the definition is any surrogate ligand that recognizes the same or similar binding site within the modular antibody, such as Protein A.

All FcγRs belong to the immunoglobulin superfamily and are the most important Fc receptors for inducing phagocytosis of opsonized (coated) microbes. This family includes several members; for example FcγRI (CD64), FcγRIIA (CD32a), FcγRIIB (CD32b), FcγRIIIA (CD16a), FcγRIIIB (CD16b); that differ in their antibody affinities due to their different molecular structure. For instance, FcγRI binds to IgG more strongly than FcγRII and FcγRIII, and has an extracellular portion composed of three immunoglobulin (Ig)-like domains, one more domain than FcγRII and FcγRIII. These properties allow activation of FcγRI by a sole IgG molecule (or monomer), while the latter two Fcγ receptors must bind multiple IgG molecules within an immune complex to be activated.

Another FcR is expressed on multiple cell types and is similar in structure to MHC class I. This receptor also binds IgG and is involved in preservation of this antibody. However, since this Fc receptor is also involved in transferring IgG from a mother either via the placenta to her fetus or in milk to her suckling infant, it is called the neonatal Fc receptor (FcRn). Recently this receptor has been implicated in being involved in homeostasis of IgG serum levels.

Antibody-Dependent Cell-Mediated Cytotoxicity (ADCC) is a mechanism of cell-mediated immunity whereby an effector cell of the immune system actively lyses a target cell that has been bound by specific antibodies. It is one of the mechanisms through which antibodies, as part of the humoral immune response, can act to limit and contain infection. Classical ADCC is mediated by natural killer (NK) cells; monocytes and eosinophils can also mediate ADCC. For example Eosinophils can kill certain parasitic worms known as helminths through ADCC. ADCC is part of the adaptive immune response due to its dependence on a prior antibody response.

The term "foreign" in the context of amino acids shall mean the newly introduced amino acids being naturally occurring, but foreign to the site of modification, or substitutes of naturally occurring amino acids. "Foreign" with reference to an antigen binding sites means that the antigen binding site is not naturally formed by the specific binding region of the agent, and a foreign binding partner, but not the natural binding partner of the agent, is bound by the newly engineered binding site.

The term "variable binding region" sometimes called "CDR region" as used herein refers to molecules with varying structures capable of binding interactions with antigens. Those molecules can be used as such or integrated within a larger protein, thus forming a specific region of such protein with binding function. The varying structures can be derived from natural repertoires of binding proteins such as immunoglobulins or phylomers or synthetic diversity, including repeat-proteins, avimers and anticalins. The varying structures can as well be produced by randomization techniques, in particular those described herein. These include mutagenized CDR or non-CDR regions, loop regions of immunoglobulin variable domains or constant domains.

Modified binding agents with different modifications at specific sites are referred to as "variants". Variants of a scaffold are preferably grouped to form libraries of binding agents, which can be used for selecting members of the library with predetermined functions. In accordance therewith, an antibody sequence is preferably randomized, e.g. through mutagenesis methods. According to a preferred embodiment a loop region of a binding agent, such as the parent antibody sequence comprising positions within one or more loops or at a terminal site, potentially contributing to a binding site, is preferably mutated or modified to produce libraries, preferably by random, semi-random or, in particular, by site-directed random mutagenesis methods, in particular to delete, exchange or introduce randomly generated inserts into loops or a loop region, preferably into the CDR loop region or structural loop region, which may include terminal sequences, that are located at one of the termini of an antibody domain or substructure.

Alternatively preferred is the use of combinatorial approaches. Any of the known mutagenesis methods may be employed, among them cassette mutagenesis. These methods may be used to make amino acid modifications at desired positions of the immunoglobulin of the present invention. In some cases positions are chosen randomly, e.g. with either any of the possible amino acids or a selection of preferred amino acids to randomize loop sequences, or amino acid changes are made using simplistic rules. For example all residues may be mutated preferably to specific amino acids, such as alanine, referred to as amino acid or alanine scanning Such methods may be coupled with more sophisticated engineering approaches that employ selection methods to screen higher levels of sequence diversity.

The cytotoxic modular antibody according to the invention with a molecular weight of less than 60 kD or up to 60 kD has a small size as compared to full length antibodies. The preferred size is up to 55 kD. Modular antibody single domains usually have a molecular size of 10-15 kD, thus a molecule based on, or consisting of 4 modular antibody domains would have a molecular size of 40-60 kD, depending on the glycosylation or any additional conjugation of pharmacologically active substances, like toxins or peptides.

The preferred format is an oligomer, composed of modular antibody domains, preferably up to 4 domains, more preferred 3 domains, and even more preferred based on 2 domains, which oligomer preferably comprises a heterodimer, such as Fab, or a homodimer, such as Fc. Formats based on the combination of 5 modular antibody domains or more are commonly thought not to exert the specific advantages of small sized antibody fragments, which are ease of expression in various expression systems and tissue penetration.

It is feasible to provide the preferred modular antibody of the invention as a single domain antibody. However, antibody domains tend to dimerize upon expression, either as a homodimer, like an Fc, or a heterodimer, like an Fab. The dimeric structure is thus considered advantageous to provide a stable molecule. The preferred dimers of immunoglobulin domains are selected from the group consisting of single domain dimers, like VHA/L, CH1/CL (kappa or lambda), CH2/CH2 and CH3/CH3. Dimers or oligomers of modular antibody domains can also be provided as single chain or two chain molecules, in particular those linking the C-terminus of one domain to the N-terminus of another.

Binding partners are agents that specifically bind to one another, usually through non-covalent interactions. Examples of binding partners include pairs of binding agents with functional interactions, such as receptor binding to ligands, antibody binding to antigen, a drug binding to a target, and enzyme binding to a substrate. Binding partners have found use in many therapeutic, diagnostic, analytical and industrial applications. Most prominent binding pairs are antibodies or immunoglobulins, fragments or derivatives thereof. In most cases the binding of such binding agents is required to mediate a biological effect or a function, a "functional interaction".

According to a specific embodiment of the present invention the cytotoxic modular antibody is a binding agent, which is an immunoglobulin of human or murine origin, and may be employed for various purposes, in particular in pharmaceutical compositions. Of course, the modified immunoglobulin may also be a humanized or chimeric immunoglobulin. The binding agent, which is a human immunoglobulin, is preferably selected or derived from the group consisting of IgA1, IgA2, IgD, IgE, IgG1, lgG2, lgG3, lgG4 and IgM. The murine immunoglobulin binding agent is preferably selected or derived from the group consisting of IgA, IgD, IgE, IgGI, lgG2A, lgG2B, lgG2C, lgG3 and IgM.

Such a binding agent comprises preferably a heavy and/or light chain or a part thereof. A modified immunoglobulin according to the invention may comprise a heavy and/or light chain, at least one variable and/or constant domain, or a part thereof including a minidomain.

A constant domain is an immunoglobulin fold unit of the constant part of an immunoglobulin molecule, also referred to as a domain of the constant region (e.g. CH1, CH2, CH3, CH4, Ck, Cl).

A variable domain is an immunoglobulin fold unit of the variable part of an immunoglobulin, also referred to as a domain of the variable region (e.g. Vh, Vk, Vl, Vd)

An exemplary modular antibody according to the invention consists of a constant domain selected from the group consisting of CH1, CH2, CH3, CH4, Igk-C, Igl-C, combinations, derivatives or a part thereof including a mini-domain, with at least one loop region, and is characterised in that said at least one loop region comprises at least one amino acid modification forming at least one modified loop region, wherein said at least one modified loop region binds specifically to at least one epitope of an antigen.

Another modular antibody according to the invention can consist of a variable domain of a heavy or light chain, combinations, derivatives or a part thereof including a minidomain, with at least one loop region, and is characterised in that said at least one loop region comprises at least one amino acid modification forming at least one modified loop region, wherein said at least one modified loop region binds specifically to at least one epitope of an antigen.

The modular antibody according to the present invention may comprise one or more domains (e.g. at least two, three, four, five, six, ten domains). If more than one domain is present in the modular antibody these domains may be of the same type or of varying types (e.g. CH1-CH1-CH2, CH3-CH3, $(CH2)_2$-$(CH3)_2$, with or without the hinge region). Of course also the order of the single domains may be of any kind (e.g. CH1-CH3-CH2, CH4-CH1-CH3-CH2).

The invention preferably refers to part of antibodies, such as parts of IgG, IgA, IgM, IgD, IgE and the like. The modular antibodies of the invention may also be a functional antibody fragment such as Fab, Fab2, scFv, Fv, Fc, Fcab™, an antigen-binding Fc, or parts thereof, or other derivatives or combinations of the immunoglobulins such as minibodies, domains of the heavy and light chains of the variable region (such as dAb, Fd, VL, including Vlambda and Vkappa, VH, VHH) as well as mini-domains consisting of two beta-strands of an immunoglobulin domain connected by at least two structural loops, as isolated domains or in the context of naturally associated molecules. A particular embodiment of the present invention refers to the Fc fragment of an antibody molecule, either as antigen-binding Fc fragment (Fcab™) through modifications of the amino acid sequence or as conjugates or fusions to receptors, peptides or other antigen-binding modules, such as scFv.

The modular antibodies can be used as isolated polypeptides or as combination molecules, e.g. through recombination, fusion or conjugation techniques, with other peptides or polypeptides. The peptides are preferably homologous to immunoglobulin domain sequences, and are preferably at least 5 amino acids long, more preferably at least 10 or even at least 50 or 100 amino acids long, and constitute at least partially the loop region of the immunoglobulin domain. The preferred binding characteristics relate to predefined epitope binding, affinity and avidity.

The modular antibody according to the invention is possibly further combined with one or more modified modular antibodies or with unmodified modular antibodies, or parts thereof, to obtain a combination modular antibody. Combinations are preferably obtained by recombination techniques, but also by binding through adsorption, electrostatic interactions or the like, or else through conjugation or chemical binding with or without a linker. The preferred linker sequence is either a natural linker sequence or functionally suitable artificial sequence.

In general the modular antibody according to the invention may be used as a building block to molecularly combine other modular antibodies or biologically active substances or molecules. It is preferred to molecularly combine at least one antibody binding to the specific partner via the variable or non-variable sequences, like structural loops, with at least one other binding molecule which can be an antibody, antibody fragment, a soluble receptor, a ligand or another antibody domain, or a binding moiety thereof. Other combinations refer to proteinaceous molecules, nucleic acids, lipids, organic molecules and carbohydrates.

The engineered molecules according to the present invention will be useful as stand-alone molecules, as well as fusion proteins or derivatives, most typically fused before or after modification in such a way as to be part of larger structures, e.g. of complete antibody molecules, or parts thereof. Immunoglobulins or fusion proteins as produced according to the invention thus also comprise Fc fragments, Fab fragments, Fv fragments, single chain antibodies, in particular single-chain Fv fragments, bi- or multispecific scFv, diabodies, unibodies, multibodies, multivalent or multimers of immunoglobulin domains and others. It will be possible to use the engineered proteins to produce molecules which are monospecific, bispecific, trispecific, and may even carry more specificities. By the invention it is be possible to control and preselect the valency of binding at the same time according to the requirements of the planned use of such molecules.

According to the present invention, the modular antibody optionally exerts one or more binding regions to antigens, including the binding site binding specifically to the cell surface target and the binding sites mediating effector function. Antigen binding sites to one or more antigens may be presented by the CDR-region or any other natural receptor binding structure, or be introduced into a structural loop region of an antibody domain, either of a variable or constant domain structure. The antigens as used for testing the binding properties of the binding sites may be naturally occurring molecules or chemically synthesized molecules or recombinant molecules, either in solution or in suspension, e.g. located on or in particles such as solid phases, on or in cells or on viral surfaces. It is preferred that the binding of an immunoglobulin to an antigen is determined when the antigen is still adhered or bound to molecules and structures in the natural context. Thereby it is possible to identify and obtain those modified immunoglobulins that are best suitable for the purpose of diagnostic or therapeutic use.

Modular antibody or immunoglobulin domains may be modified according to the present invention (as used herein the terms immunoglobulin and antibody are interchangeable) which modifications are preferably effected in immunoglobulin domains or parts thereof that are either terminal sequences, preferably a C-terminal sequence, and/or part of a loop region, which contains a loop, either a CDR-loop or a non-CDR loop, structural loops being the preferred sites of modifications or mutagenesis. According to a specific embodiment the structural loop region also includes a terminal sequence, which contributes to antigen binding. In some cases it is preferable to use a defined modified structural loop or a structural loop region, or parts thereof, as isolated molecules for binding or combination purposes.

It is particularly preferred that the modular antibody according to the invention is binding to said cell surface target through at least part of a structural loop and/or CDR loop.

In an alternate embodiment it is preferred that the modular antibody according to the invention is binding to said effector ligand, or a surrogate ligand for such an effector ligand, like protein A, through at least part of a structural loop and/or CDR loop, thus mediating the effector function.

In a preferred embodiment the binding agent is binding with its native or modified binding structure or newly formed binding site, specifically to at least two such epitopes that are identical or differ from each other, either of the same antigen or of different antigens.

In a preferred domain structure of a binding agent it is preferred to modify or randomize the modular antibody within at least one loop region or terminal region, resulting in a substitution, deletion and/or insertion of one or more nucleotides or amino acids, preferably a point mutation, or even the exchange of whole loops, more preferred the change of at least 2, 3, 4, 5, 6, 7, 8, 9, 10, 11, 12, 13, 14 or 15, up to 30 amino acids. Thereby the modified sequence comprises amino acids not included in the conserved regions of the loops, the newly introduced amino acids being naturally occurring, but foreign to the site of modification, or substitutes of naturally occurring amino acids.

However, the maximum number of amino acids inserted into a loop region of a binding agent preferably may not exceed the number of 30, preferably 25, more preferably 20 amino acids at a maximum. The substitution and the insertion of the amino acids occurs preferably randomly or semi-randomly using all possible amino acids or a selection of preferred amino acids for randomization purposes, by methods known in the art and as disclosed in the present patent application.

The site of modification may be at a specific single loop or a loop region, in particular a structural loop or a structural loop region. A loop region usually is composed of at least two, preferably at least 3 or at least 4 loops that are adjacent to each other, and which may contribute to the binding of an antigen through forming an antigen binding site or antigen binding pocket. It is preferred that the one or more sites of modification are located within the area of 10 amino acids, more preferably within 20, 30, 40, 50, 60, 70, 80, 90 up to 100 amino acids, in particular within a structural region to form a surface or pocket where the antigen can sterically access the loop regions.

In this regard the preferred modifications are engineered in the loop regions of CH1, CH2, CH3 and CH4, in particular in the range of amino acids 7 to 21, amino acids 25 to 39, amino acids 41 to 81, amino acids 83 to 85, amino acids 89 to 103 and amino acids 106 to 117, or within the terminal sequences, preferably within 6 amino acids from the C- or N-terminus of the antibody domain.

In another preferred embodiment a modification in the structural loop region comprising amino acids 92 to 98 is combined with a modification in the structural loop region comprising amino acids 8 to 20.

The above identified amino acid regions of the respective immunoglobulins comprise loop regions to be modified. Preferably, a modification in the structural loop region comprising amino acids 92 to 98 is combined with a modification in one or more of the other structural loops.

In a preferred embodiment a modification in the structural loop region comprising amino acids 92 to 98 is combined with a modification in the structural loop region comprising amino acids 41 to 45.2.

Most preferably each of the structural loops comprising amino acids 92 to 98, amino acids 41 to 45.2 and amino acids 8 to 20 contain at least one amino acid modification.

In another preferred embodiment each of the structural loops comprising amino acids 92 to 98, amino acids 41 to 45.2, and amino acids 8 to 20 contain at least one amino acid modification.

According to another preferred embodiment the amino acid residues in the area of positions 15 to 17, 29 to 34, 41 to 45.2, 84 to 85, 92 to 100, and/or 108 to 115 of CH3 are modified.

The preferred modifications of Igk-C and IgI-C of human origin are engineered in the loop regions in the area of amino acids 8 to 20, amino acids 26 to 36, amino acids 41 to 82, amino acids 83 to 88, amino acids 92 to 100, amino acids 107 to 124 and amino acids 123 to 126, or within the terminal sequences, preferably within 6 amino acids from the C- or N-terminus of the antibody domain.

The preferred modifications of loop regions of Igk-C and IgI-C of murine origin are engineered at sites in the area of amino acids 8 to 20, amino acids 26 to 36, amino acids 43 to 79, amino acids 83 to 85, amino acids 90 to 101, amino acids 108 to 116 and amino acids 122 to 126.

Another preferred immunoglobulin preferably used as a therapeutic according to the invention consists of a variable domain of a heavy or light chain, or a part thereof including a minidomain, with at least one loop region, preferably a structural loop region, and is characterised in that said at least one loop region comprises at least one amino acid modification forming at least one modified loop region, wherein said at least one modified loop region forms a relevant binding site as described above.

According to a specific embodiment the immunoglobulin preferably used according to the invention may contain a modification within the variable domain, which is selected from the group of VH, Vkappa, Vlambda, VHH and combinations thereof. More specifically, they comprise at least one modification within amino acids 7 to 22, amino acids 39 to 55, amino acids 66 to 79, amino acids 77 to 89 or amino acids 89 to 104, where the numbering of the amino acid position of the domains is that of the IMGT, or within the terminal sequences, preferably within 6 amino acids from the C- or N-terminus of the antibody domain.

In a specific embodiment, the immunoglobulin preferably used according to the invention is characterised in that the loop regions of VH or Vkappa or Vlambda of human origin comprise at least one modification within amino acids 7 to 22, amino acids 43 to 51, amino acids 67 to 77, amino acids 77 to 88, and amino acids 89 to 104, most preferably amino acid positions 12 to 17, amino acid positions 45 to 50, amino acid positions 68 to 77, amino acids 79 to 88, and amino acid positions 92 to 99, where the numbering of the amino acid position of the domains is that of the IMGT.

The structural loop regions of the variable domain of the immunoglobulin of human origin, as possible selected for modification purposes are preferably located in the area of amino acids 8 to 20, amino acids 44 to 50, amino acids 67 to 76, amino acids 78 to 87, and amino acids 89 to 101, or within the terminal sequences, preferably within 6 amino acids from the C- or N-terminus of the antibody domain.

According to a preferred embodiment the structural loop regions of the variable domain of the immunoglobulin of murine origin as possible selected for modification purposes are preferably located in the area of amino acids 6 to 20, amino acids 43 to 52, amino acids 67 to 79, amino acids 79 to 87, and amino acids 91 to 100, or within the terminal sequences, preferably within 6 amino acids from the C- or N-terminus of the antibody domain.

The immunoglobulin preferably used as a therapeutic according to the invention may also be of camelid origin. Camel antibodies comprise only one heavy chain and have the same antigen affinity as normal antibodies consisting of light and heavy chains. Consequently camel antibodies are much smaller than, e.g., human antibodies, which allows them to penetrate dense tissues to reach the antigen, where larger proteins cannot. Moreover, the comparative simplicity, high affinity and specificity and the potential to reach and interact with active sites, camel's heavy chain antibodies present advantages over common antibodies in the design, production and application of clinically valuable compounds.

According to another preferred embodiment of the present invention the structural loop regions of a modular antibody or an immunoglobulins of camelid origin are modified, e.g. within a VHH, in the region of amino acids 7 to 19, amino acids 43 to 55, amino acids 68 to 76, amino acids 80 to 87 and amino acids 91 to 101, or within the terminal sequences, preferably within 6 amino acids from the C- or N-terminus of the antibody domain.

The preferred method of producing the modular antibody according to the invention refers to engineering a modular antibody that is binding specifically to at least one first epitope, which comprises modifications in each of at least two sites or loops within a structural loop region, and determining the specific binding of said structural loop region to at least one second epitope, wherein the unmodified structural loop region (non-CDR region) does not specifically bind to said at least one second epitope. Thus, an antibody or antigen-binding structure specific for a first antigen may be improved by adding another valency or specificity against a second antigen, which specificity may be identical, either targeting different epitopes or the same epitope, to increase valency or to obtain bi-, oligo- or multispecific molecules.

On the other hand it is preferred to make use of those modular antibodies that contain native structures interacting with effector molecules or immune cells, preferably to bind an effector ligand. Those native structures either remain unchanged or are modulated for an increased effector function. Binding sites for e.g. Fc receptors are described to be located in a CH2 and/or CH3 domain region, and may be mutagenized by well known techniques.

ADCC, antibody-dependent cell-mediated cytotoxicity, is the killing of antibody-coated target cells by cells with Fc receptors that recognize the constant region of the bound antibody. Most ADCC is mediated by NK cells that have the Fc receptor FcgammaRIII or CD16 on their surface. Typical assays employ target cells, like Ramos cells, incubated with serially diluted antibody prior to the addition of freshly isolated effector cells. The ADCC assay is then further incubated for several hours and % cytotoxicity detected. Usually the Target: Effector ratio is about 1:16, but may be 1:1 up to 1:50.

Complement-dependent cytotoxicity (CDC) is a mechanism of killing cells, in which antibody bound to the target cell surface fixes complement, which results in assembly of the membrane attack complex that punches holes in the target cell membrane resulting in subsequent cell lysis. The commonly used CDC assay follows the same procedure as for ADCC determination, however, with complement containing serum instead of effector cells.

The cytotoxic activity as determined by either of ADCC and CDC assay is proven for a modular antibody according to the invention, if there is a significant increase in the percentage of cytolysis as compared to a control. The cytotoxic activity related to ADCC or CDC is preferably measured as the absolute percentage increase, which is preferably higher than 5%, more preferably higher than 10%, even more preferred higher than 20%.

The antibody-dependent cellular phagocytosis, ADCP sometimes called ADPC, is usually investigated side by side with cytolysis of cultured human cells. Phagocytosis by phagocytes, usually human monocytes or monocyte-derived macrophages, as mediated by an antibody can be determined as follows. Purified monocytes may be cultured with cytokines to enhance expression of FcγRs or to induce differentiation into macrophages. ADCP and ADCC assays are then performed with target cells. Phagocytosis is determined as the percentage of positive cells measured by flow cytometry. The positive ADCP activity is proven with a significant uptake of the antibody-antigen complex by the phagocytes. The cytotoxic activity related to ADCP is preferably measured as the absolute percentage uptake of the antibody-antigen complex by the phagocytes, which is preferably higher than 5%, more preferably higher than 10%, even more preferred higher than 20%.

In a typical assay PBMC or monoycytes or monocyte derived macrophages are resuspended in RF2 medium (RPMI 1640 supplemented with 2% FCS) in 96-well plates at a concentration of $1\times10^5$ viable cells in 100 ml/well. Appropriate target cells, expressing the target antigen, e.g. Her2/neu antigen and SKBR3 cells, are stained with PKH2 green fluorescence dye. Subsequently $1\times10^4$ PKH2-labeled target cells and an Her2 specific (IgGI) antibody (or modular antibody) or mouse IgGI isotype control (or modular antibody control) are added to the well of PBMCs in different concentrations (e.g. 1-100 μg/ml) and incubated in a final volume of 200 ml at 37° C. for 24 h. Following the incubation, PBMCs or monocytes or monocyte derived macrophages and target cells are harvested with EDTA-PBS and transferred to 96-well V-bottomed plates. The plates are centrifuged and the supernatant is aspirated. Cells are counterstained with a 100-ml mixture of RPE-conjugated anti-CD11 b, anti-CD14, and human IgG, mixed and incubated for 60 min on ice. The cells are washed and fixed with 2% formaldehyde-PBS. Two-color flow cytometric analysis is performed with e.g. a FACS Calibur under optimal gating. PKH2-labeled target cells (green) are detected in the FL-1 channel (emission wavelength, 530 nm) and RPE-labeled PBMC or monoycytes or monocyte derived macrophages (red) are detected in the FL-2 channel (emission wavelength, 575 nm). Residual target cells are defined as cells that are $PKH2^+/RPE^-$ Dual-labeled cells ($PKH2^+/RPE^-$) are considered to represent phagocytosis of targets by PBMC or monoycytes or monocyte derived macrophages. Phagocytosis of target cells is calculated with the following equation: percent phagocytosis=100×[(percent dual positive)/(percent dual positive+percent residual targets)]. All tests are usually performed in duplicate or triplicate and the results are expressed as mean 6 SD.

The apoptotic activity is preferably measured using standard methods of determinating dying or dead cells. In order to measure necrosis and apoptosis, cytotoxicity assays can be employed. These assays are can be radioactive and nonradioactive assays that measure increases in plasma membrane permeability, since dying cells become leaky or colorimetric assays that measure reduction in the metabolic activity of mitochondria; mitochondria in dead cells cannot metabolize dyes, while mitochondria in live cells can.

One can also measure early indicators for apoptosis such as fragmentation of DNA in populations of cells or in individual cells, in which apoptotic DNA breaks into different length pieces, alterations in membrane asymmetry (Phosphatidylserine based and Annexin V based assays), measurement of activation of apoptotic caspases or measurement of release of cytochrome C and AIF into cytoplasm by mitochondria.

The preferred cytotoxic activity of the modular antibody according to the invention amounts to at least 20% of cytolysis as measured in a respective ex vivo cell lysis assay.

Preferably the cytotoxic activity of the modular antibody according to the invention is mediating cell lysis or cell killing in a cell-based assay with an EC50<$10^{-8}$ M, preferably in the nanomolar range or below.

The effector function of the modular antibody according to the invention preferably is a biological cytotoxic activity, which usually differs from any synthetic cytotoxic activity, e.g. as provided through a toxin that may be conjugated to an immunoglobulin structure. Toxins usually do not activate effector molecules and the biological defence mechanism. Thus, the preferred cytotoxic activity of the modular antibodies according to the invention is a biological cytotoxic activity, which usually is immunostimulatory, leading to effective cytolysis.

The cytotoxic activity further is differentiated from the simple cell inhibition effect, where a substance is inhibiting cell growth, e.g. by binding to the receptor of a growth factor, thus blocking the growth factor function, or by inhibiting angiogenesis. Cytotoxicity is essentially considered as an active attack to kill cells, thus leading to cell death or lysis, and thus considered as a highly efficient way to immediately reduce the number of malignant or infected cells. As compared to cytotoxicic compounds, cell growth inhibors do not immediately kill cells, but only reduce the cell growth and proliferation, thus are considered to be less active for therapeutic purposes.

The modular antibody according to the invention may specifically bind to any kind of binding molecules or structures, in particular to antigens, proteinaceous molecules, proteins, peptides, polypeptides, nucleic acids, glycans, carbohydrates, lipids, organic molecules, in particular small organic molecules, anorganic molecules, or combinations or fusions thereof, including PEG, prodrugs or drugs. The preferred modular antibody according to the invention may comprise at least two loops or loop regions whereby each of the loops or loop regions may specifically bind to different molecules or epitopes.

Preferably the target antigen is selected from cell surface antigens, including receptors, in particular from the group consisting of erbB receptor tyrosine kinases (such as EGFR, HER2, HER3 and HER4, in particular those epitopes of the extracellular domains of such receptors, e.g. the 4D5 epitope), molecules of the TNF-receptor superfamily, such as Apo-1 receptor, TNFR1, TNFR2, nerve growth factor receptor NGFR, CD40, T-cell surface molecules, T-cell receptors, T-cell antigen OX40, TACI-receptor, BCMA, Apo-3, DR4, DR5, DR6, decoy receptors, such as DcR1, DcR2, CAR1, HVEM, GITR, ZTNFR-5, NTR-1, TNFL1 but not limited to these molecules, B-cell surface antigens, such as CD10, CD19, CD20, CD21, CD22, antigens or markers of solid tumors or hematologic cancer cells, cells of lymphoma or leukaemia, other blood cells including blood platelets, but not limited to these molecules.

According to a further preferred embodiment the target antigen is selected from those antigens presented by cells, like epithelial cells, cells of solid tumors, infected cells, blood cells, antigen-presenting cells and mononuclear cells. Those target antigens expressed or overexpressed by cells are preferably targeted, which are selected from the group consisting of tumor associated antigens, in particular EpCAM, tumor-associated glycoprotein-72 (TAG-72), tumor-associated antigen CA 125, Prostate specific membrane antigen (PSMA), High molecular weight melanoma-associated antigen (HMW-MAA), tumor-associated antigen expressing Lewis Y related carbohydrate, Carcinoembryonic antigen (CEA), CEACAM5, HMFG PEM, mucin MUC1, MUC18 and cytokeratin tumor-associated antigen, bacterial antigens, viral antigens, allergens, allergy related molecules IgE, cKIT and Fc-epsilon-receptorI, IRp60, IL-5 receptor, CCR3, red blood cell receptor (CR1), human serum albumin, mouse serum albumin, rat serum albumin, Fc receptors, like neonatal Fc-gamma-receptor FcRn, Fc-gamma-receptors Fc-gamma R1, Fc-gamma-RII, Fc-gamma RIII, Fc-alpha-receptors, Fc-epsilon-receptors, fluorescein, lysozyme, toll-like receptor 9, erythropoietin, CD2, CD3, CD3E, CD4, CD11, CD11a, CD14, CD16, CD18, CD19, CD20, CD22, CD23, CD25, CD28, CD29, CD30, CD32, CD33 (p67 protein), CD38, CD40, CD40L, CD52, CD54, CD56, CD64, CD80, CD147, GD3, IL-1, IL-1R, IL-2, IL-2R, IL-4, IL-5, IL-6, IL-6R, IL-8, IL-12, IL-15, IL-17, IL-18, IL-23, LIF, OSM, interferon alpha, interferon beta, interferon gamma; TNF-alpha, TNF-beta2, TNFalpha, TNFalphabeta, TNF-R1, TNF-RII, FasL, CD27L, CD30L, 4-1 BBL, TRAIL, RANKL, TWEAK, APRIL, BAFF, LIGHT, VEG1, OX40L, TRAIL Receptor-1, A1 Adenosine Receptor, Lymphotoxin Beta Receptor, TACI, BAFF-R, EPO; LFA-3, ICAM-1, ICAM-3, integrin beta1, integrin beta2, integrin alpha4/beta7, integrin alpha2, integrin alpha3, integrin alpha4, integrin alphaδ, integrin alphaθ, integrin alphav, alphaVbeta3 integrin, FGFR-3, Keratinocyte Growth Factor, GM-CSF, M-CSF, RANKL, VLA-1, VLA-4, L-selectin, anti-Id, E-selectin, HLA, HLA-DR, CTLA-4, T cell receptor, B7-1, B7-2, VNRintegrin, TGFbeta1, TGF-beta2, eotaxin1, BLyS (B-lymphocyte Stimulator), complement C5, IgE, IgA, IgD, IgM, IgG, factor VII, CBL, NCA 90, EGFR (ErbB-1), Her2/neu (ErbB-2), Her3 (ErbB-3), Her4 (ErbB4), Tissue Factor, VEGF, VEGFR, endothelin receptor, VLA-4, carbohydrates such as blood group antigens and related carbohydrates, Galili-Glycosylation, Gastrin, Gastrin receptors, tumor associated carbohydrates, Hapten NP-cap or NIP-cap, T cell receptor alpha/beta, E-selectin, P-glycoprotein, MRP3, MRP5, glutathione-S-transferase pi (multi drug resistance proteins), alpha-granule membrane protein (GMP) 140, digoxin, placental alkaline phosphatase (PLAP) and testicular PLAP-like alkaline phosphatase, transferrin receptor, Heparanase I, human cardiac myosin, Glycoprotein llb/llla (GPIIb/llla), human cytomegalovirus (HCMV) gH envelope glycoprotein, HIV gp120, HCMV, respiratory syncytial virus RSV F, RSVF Fgp, VNRintegrin, Hep B gp120, CMV, gpllbllla, HIV IMB gp120 V3 loop, respiratory syncytial virus (RSV) Fgp, Herpes simplex virus (HSV) gD glycoprotein, HSV gB glycoprotein, HCMV gB envelope glycoprotein, *Clostridium perfringens* toxin and fragments thereof.

Preferred modular antibodies according to the invention are binding said target antigen with a high affinity, in particular with a high on and/or a low off rate, or a high avidity of binding. Usually a binder is considered a high affinity binder with a Kd<$10^{-9}$ M. Medium affinity binders with a Kd of less than $10^{-6}$ up to $10^{-9}$ M may be provided according to the invention as well, preferably in conjunction with an affinity maturation process.

Affinity maturation is the process by which antibodies with increased affinity for antigen are produced. With structural changes of an antibody, including amino acid mutagenesis or as a consequence of somatic mutation in immunoglobulin gene segments, variants of a binding site to an antigen are produced and selected for greater affinities. Affinity matured modular antibodies may exhibit a several logfold greater affinity than a parent antibody. Single parent antibodies may be subject to affinity maturation. Alternatively pools of modular antibodies with similar binding affinity to the target antigen may be considered as parent structures that are varied to obtain affinity matured single antibodies or affinity matured pools of such antibodies.

The preferred affinity maturated variant of a modular antibody according to the invention exhibits at least a 10 fold increase in affinity of binding, preferably at least a 100 fold increase. The affinity maturation may be employed in the course of the selection campaigns employing respective libraries of parent molecules, either with modular antibodies having medium binding affinity to obtain the modular antibody of the invention having the specific target binding property of a binding affinity Kd<$10^{-8}$ M and/or a potency of IC50<$10^{-8}$ M. Alternatively, the binding potency or affinity may be even more increased by affinity maturation of the modular antibody according to the invention to obtain the high values corresponding to a Kd or IC50 of less than $10^{-9}$ M, preferably less than $10^{-10}$ M or even less than $10^{-11}$ M, most preferred in the picomolar range.

The IC50, also called EC50 or 50% saturation concentration, is a measure for the binding potency of a modular antibody. It is the molar concentration of a binder, which produces 50% of the maximum possible binding at equilibrium or under saturation. The potency of a binder is usually defined by its IC50 (hereby understood as an EC50 value). This can be calculated for a given binder by determining the concentration of binder needed to elicit half saturation of the maximum binding. Elucidating an IC50 or EC50 value is useful for comparing the potency of antibodies or antibody variants with similar efficacies, in particular when determined in saturation binding assays, not in competition assays. In this case it is considered as the concentration, which determines the plasma concentration to obtain a half-maximal (50%) effect in vivo. The lower the IC50 or EC50, the greater the potency of the modular antibody, and the lower the concentration of the antibody that is required to inhibit the maximum biological response, like effector function or cytotoxic activity. Lower concentrations of antibodies may also be associated with fewer side effects.

The binding affinity of an antibody is usually characterized in terms of the concentration of the antibody, at which half of the antigen binding sites are occupied, known as the dissociation constant (Kd, or $K_0$).

Usually the affinity of an antibody correlates well with the IC50, when determined in a saturation binding assay. The affinity of an antagonist for its binding site ($K_1$) is understood as its ability to bind to a receptor, which determines the duration of binding and respective agonist activity. Measures to increase the affinity by affinity maturation usually also increase the potency of binding, resulting in the respective reduction of IC50 values in the same range of the Kd values.

The IC50 and Kd values may be determined using the saturation binding assays well-known in the art. Contrary to competition assays, the saturation binding assays provide a value independent on the concentration of a competitor, thus a comparable value, which may be indicative for the binding affinity in vivo.

The modular antibody according to the invention is preferably conjugated to a label or reporter molecule, selected from the group consisting of organic molecules, enzyme labels, radioactive labels, colored labels, fluorescent labels, chromogenic labels, luminescent labels, haptens, digoxigenin, biotin, metal complexes, metals, colloidal gold and mixtures thereof. Modified immunoglobulins conjugated to labels or reporter molecules may be used, for instance, in assay systems or diagnostic methods.

The modular antibody according to the invention may be conjugated to other molecules which allow the simple detection of said conjugate in, for instance, binding assays (e.g. ELISA) and binding studies.

In a preferred embodiment, antibody variants are screened using one or more cell-based or in vivo assays. For such assays, purified or unpurified modified immunoglobulins are typically added exogenously such that cells are exposed to individual immunoglobulins or pools of immunoglobulins belonging to a library. These assays are typically, but not always, based on the function of the immunoglobulin; that is, the ability of the antibody to bind to its target and mediate some biochemical event, for example effector function, ligand/receptor binding inhibition, apoptosis, and the like. Such assays often involve monitoring the response of cells to the antibody, for example cell survival, cell death, change in cellular morphology, or transcriptional activation such as cellular expression of a natural gene or reporter gene. For example, such assays may measure the ability of antibody variants to elicit ADCC, ADCP, CDC or apoptotic activity. For some assays additional cells or components, that is in addition to the target cells, may need to be added, for example example serum complement, or effector cells such as peripheral blood monocytes (PBMCs), NK cells, macrophages, and the like. Such additional cells may be from any organism, preferably humans, mice, rat, rabbit, and monkey. Modular antibodies may cause apoptosis of certain cell lines expressing the target, or they may mediate attack on target cells by immune cells which have been added to the assay. Methods for monitoring cell death or viability are known in the art, and include the use of dyes, immunochemical, cytochemical, and radioactive reagents. For example, caspase staining assays may enable apoptosis to be measured, and uptake or release of radioactive substrates or fluorescent dyes such as alamar blue may enable cell growth or activation to be monitored.

In a preferred embodiment, the DELFIART EuTDA-based cytotoxicity assay (Perkin Elmer, MA) may be used. Alternatively, dead or damaged target cells may be monitored by measuring the release of one or more natural intracellular components, for example lactate dehydrogenase.

Transcriptional activation may also serve as a method for assaying function in cell-based assays. In this case, response may be monitored by assaying for natural genes or immunoglobulins which may be upregulated, for example the release of certain interleukins may be measured, or alternatively readout may be via a reporter construct. Cell-based assays may also involve the measure of morphological changes of cells as a response to the presence of modular antibodies. Cell types for such assays may be prokaryotic or eukaryotic, and a variety of cell lines that are known in the art may be employed. Alternatively, cell-based screens are performed using cells that have been transformed or transfected with nucleic acids encoding the variants. That is, antibody variants are not added exogenously to the cells. For example, in one embodiment, the cell-based screen utilizes cell surface display. A fusion partner can be employed that enables display of modified immunoglobulins on the surface of cells (Witrrup, 2001, Curr Opin Biotechnol, 12:395-399).

In a preferred embodiment, the immunogenicity of the modular antibodies may be determined experimentally using one or more cell-based assays. In a preferred embodiment, ex vivo T-cell activation assays are used to experimentally quantitate immunogenicity. In this method, antigen presenting cells and naive T cells from matched donors are challenged with a peptide or whole antibody of interest one or more times. Then, T cell activation can be detected using a number of methods, for example by monitoring production of cytokines or measuring uptake of tritiated thymidine. In the most preferred embodiment, interferon gamma production is monitored using Elispot assays.

The biological properties of the modular antibody according to the invention may be characterized ex vivo in cell, tissue, and whole organism experiments. As is known in the art, drugs are often tested in vivo in animals, including but not limited to mice, rats, rabbits, dogs, cats, pigs, and monkeys, in order to measure a drug's efficacy for treatment against a disease or disease model, or to measure a drug's pharmacokinetics, pharmacodynamics, toxicity, and other properties. The animals may be referred to as disease models. Therapeutics are often tested in mice, including but not limited to nude mice, SCID mice, xenograft mice, and transgenic mice (including knockins and knockouts). Such experimentation may provide meaningful data for determination of the potential of the antibody to be used as a therapeutic with the appropriate half-life, effector function, apoptotic activity, cytotoxic or cytolytic activity. Any organism, preferably mammals, may be used for testing. For example because of their genetic similarity to humans, primates, monkeys can be suitable therapeutic models, and thus may be used to test the efficacy, toxicity, pharmacokinetics, pharmacodynamics, half-life, or other property of the modular antibody according to the invention. Tests of the substances in humans are ultimately required for approval as drugs, and thus of course these experiments are contemplated. Thus the modular antibodies of the present invention may be tested in humans to determine their therapeutic efficacy, toxicity, immunogenicity, pharmacokinetics, and/or other clinical properties. Especially those modular antibodies according to the invention that bind to single cell or a cellular complex through at least two binding motifs, preferably binding of at least three structures cross-linking target cells, would be considered effective in effector activity or preapoptotic or apoptotic activity upon cell targeting and cross-linking. Multivalent binding provides a relatively large association of binding partners, also called cross-linking, which is a prerequisite for apoptosis and cell death.

The modular antibody of the present invention may find use in a wide range of antibody products. In one embodiment the modular antibody of the present invention is used for therapy or prophylaxis, e.g. as an active or passive immunotherapy, for preparative, industrial or analytic use, as a diagnostic, an industrial compound or a research reagent, preferably a therapeutic. The modular antibody may find use in an antibody composition that is monoclonal or polyclonal. In a preferred embodiment, the modular antibodies of the present invention are used to capture or kill target cells that bear the target antigen, for example cancer cells. In an alternate embodiment, the modular antibodies of the present invention are used to block, antagonize, or agonize the target antigen, for example by antagonizing a cytokine or cytokine receptor.

In an alternately preferred embodiment, the modular antibodies of the present invention are used to block, antagonize, or agonize growth factors or growth factor receptors and thereby mediate killing the target cells that bear or need the target antigen.

In an alternately preferred embodiment, the modular antibodies of the present invention are used to block, antagonize, or agonize enzymes and substrate of enzymes.

In a preferred embodiment, a modular antibody is administered to a patient to treat a specific disorder. A "patient" for the purposes of the present invention includes both humans and other animals, preferably mammals and most preferably humans. By "specific disorder" herein is meant a disorder that may be ameliorated by the administration of a pharmaceutical composition comprising a modified immunoglobulin of the present invention.

In one embodiment, a modular antibody according to the present invention is the only therapeutically active agent administered to a patient. Alternatively, the modular antibody according the present invention is administered in combination with one or more other therapeutic agents, including but not limited to cytotoxic agents, chemotherapeutic agents, cytokines, growth inhibitory agents, anti-hormonal agents, kinase inhibitors, anti-angiogenic agents, cardioprotectants, or other therapeutic agents. The modular antibody may be administered concomitantly with one or more other therapeutic regimens. For example, a modular antibody of the present invention may be administered to the patient along with chemotherapy, radiation therapy, or both chemotherapy and radiation therapy. In one embodiment, the modular antibody of the present invention may be administered in conjunction with one or more antibodies, which may or may not comprise a modular antibody of the present invention. In accordance with another embodiment of the invention, the modular antibody of the present invention and one or more other anti-cancer therapies is employed to treat cancer cells ex vivo. It is contemplated that such ex vivo treatment may be useful in bone marrow transplantation and particularly, autologous bone marrow transplantation. It is of course contemplated that the antibodies of the invention can be employed in combination with still other therapeutic techniques such as surgery.

A variety of other therapeutic agents may find use for administration with the modular antibody of the present invention. In one embodiment, the modular antibody is administered with an anti-angiogenic agent, which is a compound that blocks, or interferes to some degree, the development of blood vessels. The anti-angiogenic factor may, for instance, be a small molecule or a protein, for example an antibody, Fc fusion molecule, or cytokine, that binds to a growth factor or growth factor receptor involved in promoting angiogenesis. The preferred anti-angiogenic factor herein is an antibody that binds to Vascular Endothelial Growth Factor (VEGF). In an alternate embodiment, the modular antibody is administered with a therapeutic agent that induces or enhances adaptive immune response, for example an antibody that targets CTLA-4. In an alternate embodiment, the modified immunoglobulin is administered with a tyrosine kinase inhibitor, which is a molecule that inhibits to some extent tyrosine kinase activity of a tyrosine kinase. In an alternate embodiment, the modular antibody of the present invention is administered with a cytokine. By "cytokine" as used herein is meant a generic term for proteins released by one cell population that act on another cell as intercellular mediators including chemokines.

Pharmaceutical compositions are contemplated wherein modular antibodies of the present invention and one or more therapeutically active agents are formulated. Stable formulations of the modular antibodies of the present invention are prepared for storage by mixing said immunoglobulin having the desired degree of purity with optional pharmaceutically acceptable carriers, excipients or stabilizers, in the form of lyophilized formulations or aqueous solutions. The formulations to be used for in vivo administration are preferably sterile. This is readily accomplished by filtration through sterile filtration membranes or other methods. The modular antibody and other therapeutically active agents disclosed herein may also be formulated as immuno liposomes, and/or entrapped in microcapsules.

Administration of the pharmaceutical composition comprising a modular antibody of the present invention, preferably in the form of a sterile aqueous solution, may be done in a variety of ways, including, but not limited to, orally, subcutaneously, intravenously, intranasally, intraotically, transdermally, mucosal, topically (e.g., gels, salves, lotions, creams, etc.), intraperitonear, intramuscularly, intrapulmonary (e.g., AERx™ inhalable technology commercially available from Aradigm, or Inhance™ pulmonary delivery system commercially available from Inhale Therapeutics), vaginally, parenterally, rectally, or intraocularly. A preferred method according to the invention refers to modular antibodies that are modified by a mutagenesis method to obtain a new binding site. The preferred mutagenesis refers to randomization techniques, where the amino acid sequence of a peptide or polypeptide is mutated in at least one position, thus a randomized sequence is obtained, which mediates antigen binding. For instance, specific antibody sequences are randomly modified to obtain a nucleic acid molecule coding for an immunoglobulin, immunoglobulin domain or a part thereof which comprises at least one nucleotide repeating unit, preferably within a structural loop coding region or within a terminal region, having the sequence 5'-NNS-3\ 5'-NNN-3\ 5'-NNB-3' or 5'-NNK-3'. In some embodiments the modified nucleic acid comprises nucleotide codons selected from the group of TMT, WMT, BMT, RMC, RMG, MRT, SRC, KMT, RST, YMT, MKC, RSA, RRC, NNK, NNN, NNS or any combination thereof (the coding is according to IUPAC).

The modification of the nucleic acid molecule may be performed by introducing synthetic oligonuleotides into a larger segment of nucleic acid or by de novo synthesis of a complete nucleic acid molecule. Synthesis of nucleic acid may be performed with tri-nucleotide building blocks which would reduce the number of nonsense sequence combinations if a subset of amino acids is to be encoded (e.g. Yanez et al. Nucleic Acids Res. (2004) 32:e158; Virnekas et al. Nucleic Acids Res. (1994) 22:5600-5607).

Another important aspect of the invention is that each potential binding domain remains physically associated with the particular DNA or RNA molecule which encodes it, and in addition, the fusion proteins oligomerize at the surface of a genetic package to present the binding polypeptide in the native and functional oligomeric structure. Once successful binding domains are identified, one may readily obtain the gene for expression, recombination or further engineering purposes. The form that this association takes is a "replicable genetic package", such as a virus, cell or spore which replicates and expresses the binding domain-encoding gene, and transports the binding domain to its outer surface. Another form is an in-vitro replicable genetic package such as ribosomes that link coding RNA with the translated protein. In ribosome display the genetic material is replicated by enzymatic amplification with polymerases.

Those cells or viruses or nucleic acid bearing the binding agents which recognize the target molecule are isolated and, if necessary, amplified. The genetic package preferably is M13 phage, and the protein includes the outer surface transport signal of the M13 gene III protein.

The preferred expression system for the fusion proteins is a non-suppressor host cell, which would be sensitive to a stop codon, such as an amber stop codon, and would thus stop translation thereafter. In the absence of such a stop codon such non-suppressor host cells, preferably *E. coli,* are preferably used. In the presence of such a stop codon supressor host cells would be used.

Preferably in the method of this invention the vector or plasmid of the genetic package is under tight control of the transcription regulatory element, and the culturing conditions are adjusted so that the amount or number of vector or phagemid particles displaying less than two copies of the fusion protein on the surface of the particle is less than about 20%. More preferably, the amount of vector or phagemid particles displaying less than two copies of the fusion protein is less than 10% the amount of particles displaying one or more copies of the fusion protein. Most preferably the amount is less than 1%.

The expression vector preferably used according to the invention is capable of expressing a binding polypeptide, and may be produced as follows: First a binding polypeptide gene library is synthesized by introducing a plurality of polynucleotides encoding different binding sequences. The plurality of polynucleotides may be synthesized in an appropriate amount to be joined in operable combination into a vector that can be propagated to express a fusion protein of said binding polypeptide. Alternatively the plurality of olynucleotides can also be amplified by polymerase chain reaction to obtain enough material for expression. However, this would only be advantageous if the binding polypeptide would be encoded by a large polynucleotide sequence, e.g. longer than 200 base pairs or sometimes longer than 300 base pairs. Thus, a diverse synthetic library is preferably formed, ready for selecting from said diverse library at least one expression vector capable of producing binding polypeptides having the desired preselected function and binding property, such as specificity.

The randomly modified nucleic acid molecule may comprise the above identified repeating units, which code for all known naturally occurring amino acids or a subset thereof. Those libraries that contain modified sequences wherein a specific subset of amino acids are used for modification purposes are called "focused" libraries. The member of such libraries have an increased probability of an amino acid of such a subset at the modified position, which is at least two times higher than usual, preferably at least 3 times or even at least 4 times higher. Such libraries have also a limited or lower number of library members, so that the number of actual library members reaches the number of theoretical library members. In some cases the number of library members of a focused library is not less than $10^3$ times the theoretical number, preferably not less than $10^2$ times, most preferably not less than 10 times.

Usually libraries according to the invention comprise at least 10 fusion proteins or potential binding agents or variants of scaffold proteins, preferably at least 100, more preferred at least 1000, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$, in cases of in vitro display methods, such as ribosomal display, even higher number are feasible.

Various alternatives are available for the manufacture of the gene encoding the randomized library. It is possible to produce the DNA by a completely synthetic approach, in which the sequence is divided into overlapping fragments which are subsequently prepared as synthetic oligonucleotides. These oligonucleotides are mixed together, and annealed to each other by first heating to ca. 100° C. and then slowly cooling down to ambient temperature. After this annealing step, the synthetically assembled gene can be either cloned directly, or it can be amplified by PCR prior to cloning. Alternatively, other methods for site directed mutagenesis can be employed for generation of the library insert, such as the Kunkel method (Kunkel T A. Rapid and efficient site-specific mutagenesis without phenotypic selection. Proc Natl Acad Sci USA. 1985 January; 82(2):488-92) or the Dpnl method (Weiner M P, Costa G L, Schoettlin W, Cline J, Mathur E, Bauer J C. Site-directed mutagenesis of double-stranded DNA by the polymerase chain reaction. Gene. 1994 Dec. 30; 151 (1-2):119-23.).

For various purposes, it may be advantageous to introduce silent mutations into the sequence encoding the library insert. For example, restriction sites can be introduced which facilitate cloning or modular exchange of parts of the sequence. Another example for the introduction of silent mutations is the ability to "mark" libraries, that means to give them a specific codon at a selected position, allowing them (or selected clones derived from them) e.g. to be recognized during subsequent steps, in which for example different libraries with different characteristics can be mixed together and used as a mixture in the panning procedure.

The invention also provides a method of producing an oligomer of modular antibody domains binding to a target comprising the steps of:

providing a library of oligomers of modular antibody domains produced according to the inventive method as described contacting said library with said target in the presence of a scaffold ligand, selecting a library member binding to said target in the presence of a scaffold ligand, and manufacturing a preparation of the functional oligomer.

The scaffold ligand can be selected from the group consisting of an effector molecule, FcRn, Protein A, Protein G, Protein L and CDR target. As an example, the effector molecule can be selected from the group consisting of CD64, CD32, CD16, Fc receptors.

The oligomers can be dimers selected from the group of VHA/VL, CH1/CL, CH2/CH2, CH3/CH3, Fc and Fab, or single chains thereof.

The method according to the invention can provide a library containing at least $10^2$ independent clones expressing functional oligomers of modular antibody domains or variants thereof. According to the invention it is also provided a pool of preselected independent clones, which is e.g. affinity maturated, which pool comprises preferably at least 10, more preferably at least 100, more preferably at least 1000, more preferably at least 10000, even more than 100000 independent clones. Those libraries, which contain the preselected pools, are preferred sources to select the high affinity modular antibodies according to the invention.

Libraries as used according to the invention preferably comprise at least $10^2$ library members, more preferred at least $10^3$, more preferred at least $10^4$, more preferred at least $10^5$, more preferred at least $10^6$ library members, more preferred at least $10^7$, more preferred at least $10^8$, more preferred at least $10^9$, more preferred at least $10^{10}$, more preferred at least $10^{11}$, up to $10^{12}$ members of a library, preferably derived from a parent molecule, which is a functional modular antibody as a scaffold containing at least one specific function or binding moiety, and derivatives thereof to engineer a new binding site apart from the original, functional binding region of said parent moiety.

Usually the libraries according to the invention further contain variants of the modular antibody, resulting from mutagenesis or randomization techniques. These variants include inactive or non-functional antibodies. Thus, it is preferred that any such libraries be screened with the appropriate assay for determining the functional effect. Preferred libraries, according to the invention, comprise at least $10^2$ variants of modular antibodies, more preferred at least 103, more preferred at least $10^4$, more preferred at least $10^5$, more preferred at least $10^6$, more preferred at least $10^7$, more preferred at least $10^8$, more preferred at least $10^9$, more preferred at least $10^{10}$, more preferred at least $10^{11}$, up to $10^{12}$ variants or higher to provide a highly diverse repertoire of antibodies for selecting the best suitable binders. Any such synthetic libraries may be generated using mutagenesis methods as disclosed herein.

Preferably the library is a yeast library and the yeast host cell exhibits at the surface of the cell the oligomers with the biological activity. The yeast host cell is preferably selected from the genera *Saccharomyces, Pichia, Hansenula, Schizisaccharomyces, Kluyveromyces, Yarrowia* and *Candida*. Most preferred, the host cell is *Saccharomyces cerevisiae.*

The invention further provides a high quality library containing at least $10^2$ independent clones of functional dimers of modular antibody domains or variants thereof, or the pools of optimized or preselected clones, e.g. the affinity matured clones, which pools are containing at least 10 independent clones that are binding to a target and to a scaffold ligand. The target can be a ligand binding to a parent molecule subject to amino acid variation. The parent molecule can be a functional oligomer, in particular a functional Fc or a functional Fab, or part thereof.

The library can contain functional dimers of modular antibody domains that are binding to a target and to a scaffold ligand, and at least 20%, preferably at least 30%, more preferred at least 40% of the functional dimers are binding to CD64. This is particularly preferred with a modular antibody that contains CH2 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to protein A. This is particularly preferred with a modular antibody that contains CH2 and CH3 domains, such as an Fc scaffold.

Alternatively, the library can contain functional dimers of modular antibody domains that are binding to a target and to a scaffold ligand, and at least 20%, preferably at least 30%, more preferred at least 40% of the functional dimers are binding to the same CDR target. This is particularly preferred with modular antibodies containing a variable region, such as an Fab scaffold with specificity to a single CDR target.

As is well-known in the art, there is a variety of display and selection technologies that may be used for the identification and isolation of proteins with certain binding characteristics and affinities, including, for example, display technologies such as cellular and non-cellular, in particular mobilized display systems. Among the cellular systems the phage display, virus display, yeast or other eukaryotic cell display, such as mammalian or insect cell display, may be used. Mobilized systems are relating to display systems in the soluble form, such as in vitro display systems, among them ribosome display, mRNA display or nucleic acid display.

Methods for production and screening of antibody variants are well-known in the art. General methods for antibody molecular biology, expression, purification, and screening are described in Antibody Engineering, edited by Duebel & Kontermann, Springer-Verlag, Heidelberg, 2001; and Hayhurst & Georgiou, 2001, Curr Opin Chem Biol 5:683-689; Maynard & Georgiou, 2000, Annu Rev Biomed Eng 2:339-76.

A library according to the invention may be designed as a dedicated library that contains at least 50% specific formats, preferably at least 60%, more preferred at least 70%, more preferred at least 80%, more preferred at least 90%, or those that mainly consist of specific antibody formats. Specific antibody formats are preferred, such that the preferred library according to the invention it is selected from the group consisting of a VH library, VHH library, Vkappa library, Vlambda library, Fab library, a CH1/CL library, an Fc library and a CH3 library. Libraries characterized by the content of composite molecules containing more than one antibody domains, such as an IgG library or Fc library are specially preferred. Other preferred libraries are those containing T-cell receptors, forming T-cell receptor libraries. Further preferred libraries are epitope libraries, wherein the fusion protein comprises a molecule with a variant of an epitope, also enabling the selection of competitive molecules having similar binding function, but different functionality. Exemplary is a TNFalpha library, wherein trimers of the TNFalpha fusion protein are displayed by a single genetic package.

The foregoing description will be more fully understood with reference to the following examples. Such examples are, however, merely representative of methods of practicing one or more embodiments of the present invention and should not be read as limiting the scope of invention.

EXAMPLES

Example 1

Construction of the Non-Focussed Fcab Library (Fcab0D and Phage Surface Display The crystal structure of an IgGI Fc fragment, which is published in the Brookhaven Database as entry 1 OQO.pdb was used to aid in the design of the Fcab library.

The sequence which was used as the basis for construction of the Fcab library is given in SEQ ID No.1 (FIG. 3). In this sequence, the first amino acid corresponds to GIu 216 of human IgGI (EU numbering; according to the IMGT database (imgt.cines.fr/textes/IMGTrepertoire/Proteins/protein/human/IGH/IGHC/Hu_IGHC allgenes.html; lookup 2007 06 25), it is the first residue of the human IgGI hinge region, which is given as: (E)PKSCDKTHTCPPCP) (SEQ ID NO:441) of the heavy constant chain hinge region of human IgGI.) The second-last residue of SEQ ID No.1 (FIG. 3) corresponds to GIy 446 of human IgGI (EU numbering; IMGT: residue number 129 of the CH3 domain of human IgG1).

After detailed analysis of the structure of loqo.pdb and by visual inspection of the residues forming the loops which connect the beta strands, it was decided to randomize residues 144, 145 and 146, which are part of the loop connecting beta strand A-B as well as 198,199, 200, 203 and 204, which are part of the loop connecting beta strand E-F of SEQ ID No.1 (FIG. 3). In addition to the mutated residues, 5 residues were inserted at residue number 198 of SEQ ID No.1 (FIG. 3). In SEQ ID No.2 (FIG. 4), the sequence of the library insert of library Fcab0I is given in which all randomized residue positions as well as the 5 inserted residues are designated with the letter X.

The engineered gene was produced by a series of PCR reactions using degenerate primers followed by ligation of the resulting PCR products. To facilitate ligation, some of the codons of the nucleotide sequence coding for SEQ ID No.1 (FIG. 3) were modified to produce restriction sites without changing the amino acid sequences (silent mutations). For insertion into the cloning vector pHEN1 (Nucleic Acids Res. 1991 Aug. 11; 19(15):4133-7. Multi-subunit proteins on the surface of filamentous phage: methodologies for displaying antibody (Fab) heavy and light chains. Hoogenboom H R, Griffiths A D, Johnson K S, Chiswell D J, Hudson P, Winter G.) in frame with the pelB secretion signal, the Ncol restriction site close to the 3' end of the pelB secretion signal was used. For the randomized residues, the codon NNS (IUPAC code, where S means nucleotides C and G) was chosen which encodes all 20 naturally occurring amino acids, but avoids 2 out of 3 stop codons. Other codons such as for example the NNB (B meaning nucleotides T, C and G) can also be used. The engineered sequence is given as a nucleotide sequence in SEQ ID No.3 (FIG. 5). This sequence also includes the restriction sites used for cloning into the phagmid display vector pHEN1, namely an Ncol site at the 5' end and a Notl site at the 3' end.

The sequences of the PCR primers used for assembly of the mutated CH3 domain are given in SEQ ID No.4 through SEQ ID No.9.

```
(PCR primer EPKSNCO)
                                        SEQ ID No. 4
ccatggccgagcccaaatcttgtgacaaaactc

(PCR primer CH3LSAC)
                                        SEQ ID No. 5
agtcgagctcgtcacgggatgggggcaggg

(PCR primer CH3CSAC)
                                        SEQ ID No. 6
gtacgagctcnnsnnsnnscaagtcagcctgacctgcctgg

(PCR primer CH3CHIN)
                                        SEQ ID No. 7
tgccaagcttgctgtagaggaagaaggagccg

(PCR primer CH3RHIN)
                                        SEQ ID No. 8
tgccaagcttaccgtgnnsnnsnnsaggtggnnsnnsgggaacgtcttct
catgctccg

(PCR primer CH3RNOT)
                                        SEQ ID No. 9
agttgcggccgctttacccggagacagggagag
```

FIG. 1 shows a schematic presentation of the PCR fragments generated for assembly of the mutated gene, and the primers used therefore.

cDNA of the heavy chain of the human monoclonal antibody 3D6 (Felgenhauer M, Kohl J, Rüker F. Nucleotide sequences of the cDNAs encoding the V-regions of H- and L-chains of a human mono-clonal antibody specific to HIV-1-gp41. Nucleic Acids Res. 1990 Aug. 25; 18(16):4927.) was used as template for the PCR reactions. The 3 PCR products were digested with Sacl and/or Hindlll respectively and ligated together. The ligation product was further digested with Ncol and Notl and ligated into the surface display phagmid vector pHEN1, which had previously been digested with Ncol and Notl. The ligation product was then transformed into *E. coli* by electroporation. A number of selected clones were controlled by restriction analysis and by DNA sequencing and were found to contain the insert as planned, including the correctly inserted randomized sequences. For the following steps of phage preparation, standard protocols were followed. Briefly, the ligation mixture was transformed into *E. coli* TG1 cells by electroporation. Subsequently, phage particles were rescued from *E. coli* TG1 cells with helper phage M13-KO7. Phage particles were then precipitated from culture supernatant with PEG/NaCI in two steps, dissolved in water and used for selection by panning or, alternatively, they were stored at minus 80° C.

Example 2

Construction of the Focused Fcab Library (Fcab02) and Phage Surface Display

As described in example 1, an Fcab library was prepared in which the randomized library positions are fully randomized, i.e. they are encoded by a codon such as NNS, NNB, NNK, NNN or others are used.

For clarity, the meaning of the letters such as N, B, S or K is defined by the IUPAC nucleotide ambiguity code, which is given in the following table:

TABLE 1

IUPAC nucleotide ambiguity code

| Symbol | Meaning | Nucleic Acid |
|---|---|---|
| A | A | Adenine |
| C | C | Cytosine |
| G | G | Guanine |
| T | T | Thymine |
| U | U | Uracil |
| M | A or C | |
| R | A or G | |
| W | A or T | |
| S | C or G | |
| Y | C or T | |
| K | G or T | |
| V | A or C or G | |
| H | A or C or T | |
| D | A or G or T | |
| B | C or G or T | |
| X | G or A or T or C | |
| N | G or A or T or C | |

Source: Nomenclature for incompletely specified bases in nucleic acid sequences: recommendations 1984. A Cornish-Bowden, Nucleic Acids Res. 1985 May 10; 13(9): 3021-3030.

These codons given above are designed such that all 20 amino acids are encoded by them. It may be preferable to choose subsets out of the possible amino acids. Examples can be found in the literature (Fellouse F A, Li B, Compaan D M, Peden A A, Hymowitz S G, Sidhu S S. Molecular recognition by a binary code. J Mol Biol. 2005 May 20; 348(5):1153-62. Epub 2005 Apr. 1; Fellouse F A, Wiesmann C, Sidhu S S. Synthetic antibodies from a four-amino-acid code: a dominant role for tyrosine in antigen recognition. Proc Natl Acad Sci USA. 2004 Aug. 24; 101 (34):12467-72. Epub 2004 Aug. 11). Focused libraries which for example allow for only 4 different amino acid types can be constructed e.g. by employing the codon KMT, which codes for the amino acids Ser, Tyr, Ala and Asp.

A focused Fcab library, designated Fcab02, has been constructed in the same way as described in example 1, except that the NNS codons were replaced by KMT codons.

Therefore, the letter “X” in SEQ ID No.2 (FIG. 4) now means “S, Y, A and D” (Ser, Tyr, Ala and Asp) in order to describe the focused library Fcab02

Example 3

Construction of a Phage Surface Display Library with Additional Amino Acid Residues Between the Library Insert (Binding Partner) and p3

In order to investigate accessibility of the potential binding site of the displayed protein a binding assay is performed: the phage suspension is reacted with anti-myc mAb 9E10-coated microplates (or immunotubes). After washing, the bound phages are detected with anti-M13-enzyme conjugate. As a control, helper phage—which does not display the protein fusion and the myc-tag is reacted with the plates. Other controls are reaction of phages with non-coated plates and reaction of phages with antiserum recognizing the p3-fusion partner of the phages.

Ideally, the anti-myc-reactivity of phages displaying the p3-fusion protein should give very clear ELISA readouts whereas helper phage reactions to anti-myc-mAb should not be above background (non-coated plates).—The structure of a CH3 dinner displayed at the surface of an M13 phage through binding to protein III as an anchor is such, that each CH3 is anchored to protein III using various linker length and compositions. Thus, the CH3 dinner is preferably displayed by two anchors.

Linker Optimization:

The linker between the protein to be displayed and the anchor protein of the genetic package (in case of filamentous phage e.g. p3, p8, pX, pIX, pVII) is especially important if the potential binding site of the displayed molecule is in spatial vicinity of the phage particle. In antibody libraries utilizing variable domains and antigen binding sites formed by CDR-loops and display of the library members as amino-terminal fusion to p3 the potential antigen binding site is directed away from the phage particle. Therefore, the linker structure between library members and the phage coat protein is not important. Engineering the bottom loops of immunoglobulin domains and performing phage display may however be an inefficient process and decreases yields of antigen binding clones or even preclude it. Varying the linker between a library member protein and its fusion partner on the surface can solve or may at least reduce this problem.

In order to select for optimal linker sequences (in terms of length and flexibility as well as stability) a library of linkers can be prepared in which the anchor protein at the surface of the genetic replicable package is fused to a known binding protein which is for sterical reasons notoriously difficult to select for.

This library of sequences can be varied in length and amino acid content.

Selection methods of the linker library for optimal linkers depend on the application but basically it should be for selecting all properties one wishes to have in a certain methodology. Enrichment against a difficult to select for antigen may yield linker sequences which allow library members a good access to the antigen. Incubation in protease solutions or under other harsh conditions or frequent passaging through host cells under proteolytic conditions (e.g. old microbial cultures) may be an appropriate selection for stable display linkers.

A library of linkers may be produced by any well known library technology. Synthetic linker sequence lengths may vary between 10-500 amino acids. Alternatively, linker can be complete proteins known to be of flexible nature.

Linker optimization Fcab0I:

As an example, library Fcab0I (as described in example 1) can be used. Originally, this library is cloned in the phagmid display vecor pHEN1, using NcoI and NotI restriction sites. When cloned in this manner, 18 amino acid residues are in between the C-terminal amino acid residue of the Fcab0I library insert and the N-terminal amino acid residue of phage M13 p3. The sequence of this junction region is given in SEQ ID No.10 SPGKAAAEQKLISEEDLNGAATVES—and is explained as follows: the first 4 residues, SPGK, (SEQ ID NO:442) are the 4 C-terminal residues of the Fcab0I library insert, followed by the amino acid sequence AAA, which is the amino acid residues encoded by the NotI restriction site, followed by the sequence EQKLISEEDL, (SEQ ID NO:443) which is the myc epitope, followed by NGAA, (SEQ ID NO:445) after which there is an amber stop codon, which is translated to Glutamine (Q) in amber suppressor strains of *E. coli* such as TG1. The C-terminal 4 residues of SEQ ID No.10, TVES, (SEQ ID NO:444) are the N-terminal 4 residues of phage M13 p3 as present in the vector pHEN1.

In order to construct a phage which displays an Fcab insert with an increased distance between the Fcab (the binding partner) and the body of the phage (the genetic package), 5 additional residues were inserted at the C-terminus of the Fcab insert FcabRGD4, directly upstream of the NotI cloning site, resulting in the clone FcabRGD4L. FcabRGD4 is an Fcab that has an integrin-binding RGD motif inserted in the EF-loop of the CH3 domain and which binds to ccvβ3-integπn in ELISA. As an increased-length linker sequence, the amino acid sequence EGGGS, which appears 8 times in the phage M13 p3 sequence was used. The resulting amino acid sequence of FcabRGD4L as expressed after cloning in pHEN1 is given in SEQ ID No.11 (FIG. 5). In SEQ ID No.11 (FIG. 5), amino acid residues 198-204 represent the RGD motif, amino acid residue 237 is the C-terminal residue of the Fcab insert, residues 238-242 represent the inserted linker sequence (which is the difference to unmodified pHEN1), which is followed by myc tag, amber stop codon and the p3 sequence.

For cloning of the construct, the FcabRGD4 sequence was amplified from pHENFcabRGD4 (SEQ ID No.12) using PCR primers EPKSNCO (SEQ ID No.4) and CH3rlink actagcggccgcagagccaccaccctccttacccggagacagggagag (SEQ ID No.13) and cloned via NcoI and NotI restriction sites into the vector pHEN1. The resulting vector, pHENFcabRGD4L (SEQ ID No.14/FIGS. 7A and 7B), has the additional linker sequence at nucleotide positions 3057-3071.

The two phagemid vectors, pHENFcabRGD4 and pHENFcabRGD4L were transformed into *E. coli* TG1. Subsequently, phage particles were rescued from *E. coli* TG1 cells with helper phage M13-K07. Phage particles were then precipitated from culture supernatant with PEG/NaCI in 2 steps, dissolved in water and used for ELISA. Phage ELISA was performed as follows:

The phage suspension is reacted with αvβ3-integrin-coated microplates (or immunotubes). After washing, the bound phages are detected with anti-M13-enzyme conjugate. As controls, helper phage—which does not display the protein fusion and the myc-tag is reacted with the plates as well as phage particles carrying wtFcab on their surface. Other controls are reaction of phages with non-coated plates and reaction of phages with antiserum recognizing the Fcab-fusion partner of the phages. Phage particles with the increased-length linker resulting from pHENFcabRGD4L react more readily with αvβ3-integhn than phage particles with the original linker as contained in pHENFcabRGD4, and therefore give a stronger signal in ELISA.

Phage selections can be performed in which phage particles with wtFcab are mixed with small amounts of phage particles carrying either FcabRGD4 or FcabRGD4L. After several (typically 3-5) rounds of panning, preferentially phages displaying FcabRGD4L are selected.

Example 4

Fcab™ Library Design

Figure 2:
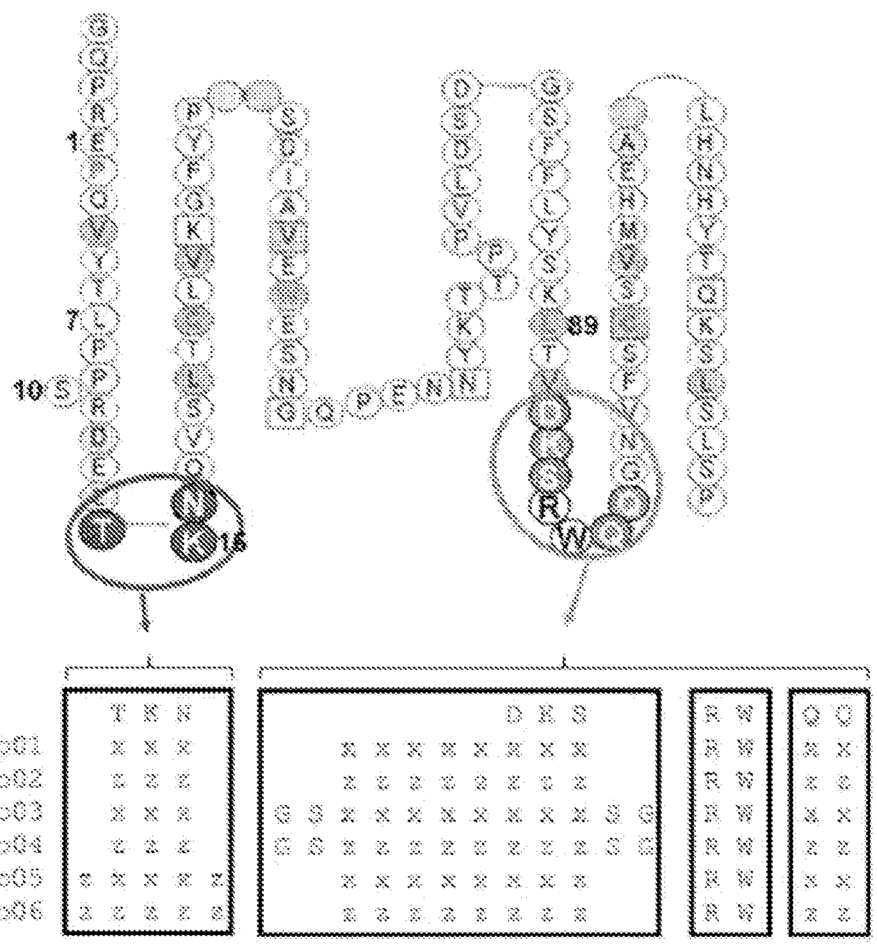

Design of Fcab Libraries (illustrated in FIG. 2): amino acid positions in nonCDR-loops of CH3 constant domains of antibodies are considered for randomization. Especially loops A-B, C-D and E-F are considered as they are on one side of the domain. Some of the design criteria for randomization at a certain position are described herein.

Amino acids frequently involved in antigen antibody interactions are described herein to be included in a focused library.

Libraries with restricted amino acid utilization have been shown to be sufficient to generate binders against virtually any antigen (Sidhu & Fellhouse, NATURE CHEMICAL BIOLOGY VOLUME 2 page 682ff.; Koide et al PNAS, volume 104 p 6632-6637). The advantage of such restricted (or focused) libraries is that they can be covered completely by current technologies. Ideally, the amino acid utilization reflects a natural amino acid utilization of ligand receptor binding. However, even libraries utilizing only 2 amino acids (Tyrosine and Serine) have been reported to yield good selection results (in terms of frequency of binders against different binders and in terms of affinity).

Loop Flexibility:

Certain loop structures may be required by the scaffold protein in order to keep the overall natural structure. Randomizing many amino acid positions in loops and even elongation of loops may be facilitated by building certain sequences either on one or on both sides of the randomized positions. These sequences may be flexible sequences in order to allow compensating for any tensions with certain library sequences in such a position.

TABLE 2

Exemplary Fcab ™ libraries, focused and non-focused

| | # of randomized positions | Theorectical diversty on amino acid level | Number of independent bacterial clones |
|---|---|---|---|
| Fcab01 | 13 | $8.2 \times 10^{18}$ | $0.6 \times 10^{9}$ |
| Fcab02 | 13, focused | $6.7 \times 10^{7}$ | $0.6 \times 10^{9}$ |
| Fcab03 | 13 | $8.2 \times 10^{18}$ | $1.0 \times 10^{9}$ |
| Fcab04 | 13, focused | $6.7 \times 10^{7}$ | $0.8 \times 10^{9}$ |
| Fcab05 | 15 | $1.3 \times 10^{18}$ | $0.8 \times 10^{9}$ |
| Fcab06 | 15, focused | $1.3 \times 10^{9}$ | $1.0 \times 10^{9}$ |

Fcab0I library is described in the examples above. The sequence space of the focused library designs Fcab02, Fcab04 and Fcab06 are covered by the actual bacterial library sizes of approximately 10e9. In contrast, the completely randomized libraries Fcab0I, Fcab03 and Fcab06 are actually grossly underrepresented.

Design of Loop Randomization in Yeast.

Similar to the examples mentioned above for Fcab library design and generation of the library in bacteria, yeast libraries were generated. As shown in Table 3, various combinations of modified AB loops, CD loops and EF loops were generated.

The AB loop modified in this example is ranging from amino acid 358 to 362 (wt sequence "LTKNQ"), the CD loop from amino acid 384 to 388 (wt sequence "NGQPE"), and the EF loop from 413 to 419 (wt sequence "DKSRWQQ").

As mentioned before, "X" stands for a complete randomization, and "Z" for a focused design. Amino acids, that were inserted and are not present on the wt Fc scaffold, are written between brackets in Table 3. For those libraries, where the loops were not modified, the one letter amino acid code of the respective wt sequence is mentioned in the table. As the number of theoretical combinations exceeds in most of these libraries the experimental number of clones, the number of independent yeast clones generated is shown in the last column.

TABLE 3

Exemplary Fcab ™ libraries, focused and non-focused, with AB loop, CD loop and EF loop mutations and insertions.

| Library name | theoretical size | AB loop | CD loop | EF loop | Independent clones |
|---|---|---|---|---|---|
| Fcab05 | $2.0 \times 10^{22}$ | ZXXXZ | NGQPE (SEQ ID NO: 447) | (XXXXX)X XXRWXX | $2.2 \times 10^{4}$ |
| Fcab05sABCD | $7.5 \times 10^{31}$ | XXXXX | XXXXX (XXXXX) | (XXXXX)X XXRWXX | $1.1 \times 10^{6}$ |
| Fcab05sCD | $6.8 \times 10^{29}$ | ZXXXZ | XXXXX | (XXXXX)X XXRWXX | $8.6 \times 10^{6}$ |
| Fcab05sAB | $1.3 \times 10^{24}$ | XXXXX | NGQPE (SEQ ID NO: 447) | (XXXXX)X XXRWXX | $5.3 \times 10^{7}$ |
| Fcab07 | $3.4 \times 10^{10}$ | LTKNQ (SEQ ID NO: 446) | NGQPE (SEQ ID NO: 447) | XXXXXXX | $5.3 \times 10^{7}$ |
| Fcab07AB | $1.2 \times 10^{18}$ | XXXXX | NGQPE (SEQ ID NO: 447) | XXXXXXX | $4.8 \times 10^{6}$ |
| Fcab07ABb | $1.2 \times 10^{18}$ | XXXXX | NGQPE (SEQ ID NO: 447) | XXXXXXX | $1.3 \times 10^{7}$ |
| Fcab07b | $3.4 \times 10^{10}$ | LTKNQ (SEQ ID NO: 446) | NGQPE (SEQ ID NO: 447) | XXXXXXX | $3.7 \times 10^{7}$ |
| Fcab07CD | $1.2 \times 10^{18}$ | LTKNQ (SEQ ID NO: 446) | XXXPE | XXXXXXX | $1.9 \times 10^{7}$ |
| Fcab07CDAB | $3.9 \times 10^{25}$ | XXXXX | XXXPE | XXXXXXX | $1.7 \times 10^{7}$ |
| Fcab08 | $3.4 \times 10^{7}$ | XXXXX | NGQPE (SEQ ID NO: 447) | DKSRWQQ (SEQ ID NO: 448) | $8.5 \times 10^{6}$ |
| Fcab08EF | $1.2 \times 10^{18}$ | XXXXX | NGQPE (SEQ ID NO: 447) | XXXXXXX | $2.2 \times 10^{7}$ |

Example 5

Cloning of Yeast Display Libraries by Homologous Recombination Vector pYD1 (Invitrogen) is used as the basic vector. The vector is modified as follows, in order to remove an XhoI site: pYD1 is cleaved with XhoI, treated with Klenow fragment of DNA polymerase and religated. The resulting sequence is given in pYDIdX (SEQ ID No.15/FIGS. 8A and 8B). pYDIdX contains a unique BamHI restriction site at position 921/925 and a unique NotI restriction site at position 963/967. It is opened with these two restriction enzymes. An insert encoding CH1-hinge-CH2-CH3 from human IgGI is prepared by PCR from cDNA encoding the heavy chain of a human IgGI monoclonal antibody. In this insert, a point mutation is introduced using standard procedures to mutate the C-terminal Cystein residue of the CH1 domain to a Serine. The insert is amplified using PCR primers that attached a BamHI and a Not restriction site to both ends respectively. These restriction sites are then used for cloning the insert into pYDIdX to yield the display vector pYDIdXFc (SEQ ID No.16/FIGS. 9A and 9B and 9C). The mutated codon at the C-terminus of the CH1 domain (Cys to Ser) is at positions 1233-1235 in the sequence pYDI DxFc. The stop codon of the insert is at position 1917/1919.

This vector is used as a positive control for the display of human CH1-hinge-CH2-CH3 on the surface of yeast and as a starting point for the construction of the vector pYD1 CH12 (see below).

Cloning of Libraries

Cloning of libraries in which mutations are introduced into structural loops of CH3 domains is performed in yeast by homologous recombination (gap repair). For this purpose, a recipient vector is prepared that lacks the CH3 domain: pYDIdXFc is cleaved with Xhol (position 1603/1607) and Notl (position 1921/1925), the large fragment is prepared by preparative gel electrophoresis, treated with Klenow fragment of DNA polymerase and re-ligated. This procedure reconstitutes a unique Xhol site (position 1603/1607) and yielded vector pYD1 CH12 (SEQ ID No.17/FIGS. 10A and 10B and 10C). pYD1 CH12 is subsequently cleaved with Xhol and is used as recipient vector for gap repair in yeast.

Alternatively, for the libraries listed in Table 3, a different recipient vector was constructed, which comprised only the hinge region, the CH1 and the CH2 domains, but was lacking the CH1 domain. In this vector, the CH1 domain was removed by cutting BamH1 (position:921/926) and Xhol (position: 1603/1608). Instead, we introduced a fragment produced by PCR that comprises the hinge region, the CH2 domain and the corresponding restriction enzyme sites. The resulting plasmid is pYD1_dX_dCH1_Fcab_wt (SEQ ID No.428/FIGS. 29A and 29B). In a further step we removed the CH3 domain of the latter plasmid digesting with Xhol (1309/1314) and Notl (1626/1633) and replaced it instead by two sequential tags: the V5 tag followed with the His6 tag, This sequence was obtained by PCR amplification from the pYD1 vector and cloned using Xhol and Notl restriction enzyme sites. The final plasmid, pYD1dX_dCH1dCH3_Fcab_wt (SEQ ID No.427/FIGS. 28A and 28B and 28C), was used as the library recipient vector. The pYD1dX_dCH1dCH3_Fcab_wt is coding for a human IgGI fragment starting from the hinge region and finishing at the beginning of CH3 domain. It contains a unique BamHI (921/926), Xhol (1309/1314) and Notl restriction site (1422/1429). The latter 2 are used for introducing the CH3 libraries by homologies recombination. The vector pYD1_dX_dCH1_Fcab_wt is used as a positive control for the display of human hinge-CH2-CH3 on the surface of yeast and pYD1dX_dCH1dCH3_Fcab_wt as a starting point for the construction of the libraries listed in Table 3.

As a source of insert for pYDIdXFc, Fcab libraries Fcab0I (SEQ ID No.18), Fcab02 (SEQ ID No.19), Fcab03 (SEQ ID No.20), Fcab04 (SEQ ID No.21), Fcab0δ (SEQ ID No.22) and Fcab06 (SEQ ID No.23) are used. These libraries are prepared by Standard DNA synthesis, and contain randomized residues as well as inserted residues in the AB loop (between residues 359 and 361 (EU numbering)) as well as in the EF loop (between residues 413 and 419 (EU numbering)) of the CH3 domain of human IgGI. From this synthetic DNA, the insert for gap repair in yeast is amplified by PCR using PCR primer pair

```
gapch35
                                          (SEQ ID No. 24)
caacaaggccctgcctgcccccatcgagaagaccatctccaaggccaagg
gccagcctcgagaaccacaggtgtacaccctgccc
and

gapfcs3
                                          (SEQ ID No. 25)
gagaccgaggagagggttagggataggcttaccttcgaagggccctctag
actcgatcgagcggccgctcatttacccggagacagggagagctc ttc.
```

100 μg of Xhol cleaved vector pYD1CH12 and 100 μg of insert are mixed and transformed in *Saccharomyces* strain EBY100 (Invitrogen) using the Lithium acetate procedure according to the following protocol, which is upscaled by a factor 100 to transform the required amount of cells and of DNA. Briefly, for a single transformation of 1 μg vector DNA and 1 μg insert DNA, 10 ml of YPD (2% peptone, 2% dextrose (D-glucose)) are inoculated with a yeast colony and shaken overnight at 30° C. The OD600 of the overnight culture is determined and the culture diluted to an OD600 of 0.4 in 50 ml of YPD and grown for an additional 2-4 hours. Cells are pelleted at 2500 rpm and resuspended in 40 ml 1× TE (10 mM Tris, pH 7.5, 1 mM EDTA). Cells are pelleted again at 2500 rpm and resuspended in 2 ml of 1 M LiAc/0.5× TE, followed by incubation at room temperature for 10 minutes. 1 μg vector DNA, 1 μg insert and 100 μg denatured sheared salmon sperm DNA (2 mg/ml) are mixed with 100 μl of the yeast suspension. 700 μl of 1 M LiAc/40% PEG-3350/1× TE are added and mixed with the yeast/DNA suspension, followed by incubation at 30° C. for 30 minutes. 88 μl DMSO are added, mixed and the mixture is incubated at 42° C. for 7 minutes, followed by centrifugation in a microcentrifuge for 10 seconds. The supernatant is then removed, the cell pellet is resuspended in 1 ml 1× TE and re-pelleted. The pellet is then resuspended in 50-100 μl TE and plated on minimal dextrose plates containing leucine (10 g/l yeast nitrogen base, 20 g/l dextrose, 0.1 g/l leucine, 15 g/l agar). After incubation of the plates at 30° C. for 2 to 4 days single colonies appeared that are subsequently harvested.

As a source of insert for the vector pYD1dX_dCH1dCH3, Fcab libraries listed in Table 3 are used. These libraries are prepared by standard DNA synthesis, and contain randomized residues as well as inserted residues in the AB loop, and the CD loop, as well as in the EF loop of the CH3 domain of human IgGI (see Table 3). From this synthetic DNA, the insert for gap repair in yeast is amplified by PCR using the oligos YCH3.25rec.back and YCH3.25rec.opt.for (primers used listed below). The basic transformation mix comprises 2 μg of Xhol-cleaved pYD1dX_dCH1dCH3_Fcab_wt and 1 μg of insert DNA, which are mixed and transformed in *Saccharomyces* strain EBY100 (Invitrogen) using the Lithium acetate procedure, which is upscaled by a factor 100 to get the required amount of transformants. Briefly, for a single transformation of 2 μg vector DNA and 1 μg insert DNA, 10 ml of YPD (2% peptone, 2% dextrose (D-glucose)) are inoculated with a yeast colony and shaken overnight at 30° C. The OD600 of the overnight culture is determined and the culture diluted to an OD600 of 0.3 in 50 ml of YPD and grown for an additional 6 hours or OD600 of 2.5. Cells are pelleted at 2500 rpm, washed twice: first, with 25 ml distilled water and then with 100 mM LiAc; and finally resuspended in 50 OuL 10 OmM LiAc. 2 μg vector DNA, 1 μg insert and 100 μg denatured sheared salmon sperm DNA (2 mg/ml) are mixed with 50 μl of the yeast in a solution containing PEG3500 (33% w/v) and 10 OmM LiAc in a final volume of 360 μL. After a good homogenization the yeasts are kept at 30° C. for 30 minutes and then at 42° C. for 45 minutes. The supernatant is then removed and the cell pellet is resuspended in YPD and the cells are allowed to recover for another 60-90 minutes at 30° C. The pellet is then incubated in selective media (plates and/or liquid, see below) at 30° C. for 2 days. The diversity of the library is determined by the number of single cells grown up to colonies on plates which have been prepared and inoculated immediately after the recovery period.

```
List of Primers:
a) CH3seqs/2 (SEQ ID No. 429): 5'-AAGGAGTACAAGTGCAAGG-3'

b) reverse primers:
CDmut_back (SEQ ID No. 430): 5'-GCT CTC CCA CTC CAC G-3'
EFmut_back (SEQ ID No. 431): 5'-CAC GGT GAG CTT GCT GTA GAG-3'
ABMUT5/2_back (SEQ ID No. 432): 5'-CTCATCCCGGGATGGG-3'
```

-continued

```
c) Forward primers (X = trinucleotide - synthesis for randomized
aminoacids)
CDmut5cod_for (SEQ ID No. 433):
5'-GTG GAG TGG GAG AGC X X X X X AAC AAC TAC AAG ACC ACG-3'
EFMUT7cod_for (SEQ ID No. 434):
5'-AGC AAG CTC ACC GTG X X X X X X X GGG AAC GTC TTC TCA TGC-3'
EFMUT3+2_for (SEQ ID No. 435):
5'-AGC AAG CTC ACC GTG X X X AGG TGG X X GGG AAC GTC TTC TCA TGC-
3'
ABMUT5 (wt)_for (SEQ ID No. 436):
5'-CCA TCC CGG GAT GAG X X X X X GTC AGC CTG ACC TGC CTG G-3'

d) CH3seqAS (SEQ ID No. 437):
5'-TAGAATCGAGACCGAGG-3'
e)YCH3.25rec.opt.for (SEQ ID No. 438):
5'-A CCA TCT CCA AGG CCA AGG-3'

f)Ych3.25rec.back (SEQ ID No. 439):
5'-AAG GGC CCT CTA GAC TCG-3'
```

Cultivation—Induction

The harvested yeast libraries (yFcab libaries) are inoculated in 10 ml SD-CAA medium (10 g/l yeast nitrogen base, 10 g/l casamino acids, and 20 g/l dextrose, 0.1 g/l leucine, 9.67 g/l NaH2PO4-2H2O and 10.19 g/l Na2HPO4-7H2O) and grown on a shaker at 250 rpm at 28° C. for 6-8 hours. The OD600 of the culture is determined, and the culture is diluted to an OD600 of 0.2, and grown under the same conditions until an OD600 of 1-2 is reached. Cells are harvested by centrifugation (3000 rpm/5 min/4° C.) and resuspended in induction medium SG/R-CAA (10 g/l yeast nitrogen base, 10 g/l casamino acids, and 20 g/l galactose, 10 g/l raffinose, 0.1 g/l leucine, 9.67 g/l NaH2PO4-2H2O and 10.19 g/l Na2HPO4-7H2O). Cultures are induced by incubation for 2 days on a shaker at 250 rpm at 20° C. and subsequently analysed and sorted. Alternatively, cultures were induced by incubation for 1 day on a shaker at 250 rpm at 37° C. and subsequently analysed and sorted.

Quality Control of yFcab Libraries yFcab libraries are tested for their expression level and quality of expressed Fcab's two days after induction with SD-CAA medium. The expression level is tested using a polyclonal anti human IgG-Fc antiserum (Sigma). For this purpose 0.5×10e6 library cells are diluted in 1 ml staining buffer (SB), which comprises of PBS with 2% BSA. Cells are pelleted and stained with 100 μl SB containing 1/2000 diluted anti human IgG-Fc-PE antiserum (Sigma) for 30 min on ice, washed twice with SB and subsequently analyzed in the FACS. In general 70%-80% of all cells in each library express Fcabs on their cell surface. To test correct folding of Fcabs, staining with Protein A is performed. Again 0.5×10e6 library cells are diluted in 1 ml staining buffer SB, cells are pelleted and stained with 100 μl SB containing 1 μg/ml Prot-A-FITC (Fluka) for 30' on ice, washed twice with SB and subsequently analyzed in the FACS. In general, the yFcab libraries as described above show >40% Prot A positive cells.

In order to test whether the Fcabs are expressed as dimers on the surface of the cells a staining with human CD64 is performed. 5×10e5 cells are pelleted and stained 30 min on ice with 50 μl SB containing 1 μg/ml CD64 (R&D Systemns). After a washing step, cells are resuspended in 50 μl SB containing 1 μg/ml Penta His Alexa Fluor 488 (QIAgen) and incubated another 30' on ice. The cells are washed and resuspended in 200 μl ice cold SB for FACS analysis. As control the cells are incubated with equivalent of the Penta His Alexa Fluor 488, without pre-incubation with CD64. After incubation the cells are washed once with ice cold SB and analysed in the FACS. In general, >50% of all cells in each library express dimeric Fcabs on their cell surface.

Biotinylation of Antigen (Her2)

Recombinant antigen e.g. Her2 (Bendermedsystems) was done with he EZ link system of Pierce according to the manufacturers instruction. In short, the antigen is dialyzed against PBS, diluted to 1 mg/ml in PBS and mixed with 10 mM sulfo-LC-LC-biotin (EZ link, Pierce), which was predisolved in water. The final ratio between antigen and biotin is 1:3 and the mixture is incubated at room temperature from 30'. Afterwards the mixture is "dialyzed" against PBS using Vivaspin MWCO3000 (Sartorius) columns (5×8', 4000 rpm). Finally the concentration of the biotinylated antigen (Her2) is tested by HPLC and aliquots are stored at −20° C.

The quality of the biotinylated antigen is tested by ELISA. First the plates are coated with an anti-Her2 antibody (e.g. Herceptin) at 10 μg/ml in PBS, 100 μl/well overnight at 4° C., after this the plate is washed 3× with washing buffer (WB) (PBS+0.05% Tween20) and blocked by blocking buffer (BB) (PBS+2% BSA) 1 h at room temperature. After 3× washing with WB, different concentrations of Her2-biotin are added in 100 μl/well BB for 1 h at room temperature, followed by 3× washing with WB. Finally the plate is incubated with 1:25000 streptavidin-HRP (GE healthcare) in BB for 1 h at room temperature and washed 3× with WB. Colour is developed by adding 100 μl/well of the substrate TMB (Sigma) after −10 minutes the reaction is stopped by adding 100 μl/well of 30% $H_2SO_4$. The results is analysed with an ELISA reader at 450-630 nm.

Example 6

Production of Antigen Specific (Her2) Fcabs

Selection of Antigen Specific (Her2) Fcabs using FACS

First Selection Round:

Two days before FACSorting a yeast library containing 2.5×10e 8 individual Fcab clones is induced with SG/R-CAA medium to express the Fcabs on their cell surface as described above. After two days, the amount of cells covering e.g. 10 times the library (=2.5×10e9) is incubated for 30' on ice with 500 nM biotinylated antigen (Her2) in 2 ml SB. Then the cells are washed once with cold SB and subsequently incubated for 30' on ice with streptavidin-PE (from R&D systems) diluted 1:100 in SB. The cells are washed twice with ice cold SB and diluted to an end concentration of 1×10e9 cells/ml. Control stainings with 5×10e6 cell/ml in 100 μl are made with streptavidin-PE only, in the absence of antigen. Both the complete library and the control stainings are analysed in e.g. a FACS ARIA from BD. To set the gates for sorting the control cells are used. First a FSC/SSC gate (G1) is set to identify healthy yeast cells, from G1 a FSC-width versus FSC-area plot is made and only non-aggregating cells are selected in a new gate (G2). Cells in G2 are subsequently analysed for reactivity with streptavidin-PE using FSC versus FL-2 (PE channel). G3 is set to include 0.1% of (false) positive cells. Subsequently, at least 5×10e8 stained cells (twice the library size ideally more) are analysed with the settings as indicated above and the cells in G3 are sorted into a tube containing 2-3 ml SD-CAA medium. Roughly 5×10e5 cells (Pool1) are harvested in the first round of selection and propagated for 1 to 2 days, after which the cells can be stored at −80° C. and aliquots can be induced to express the Fcabs as described above. After two more days the next selection round can take place.

Second Selection Round:

Pool1 selected in round 1 are induced to express the Fcab on their surface as described above. At least 5×10e6 cells (comprising multiple copies of Pool1) are incubated for 30' on ice with 500 nM biotinylated antigen (Her2) in 1 ml SB. Then the cells are washed once with cold SB and subsequently incubated for 30 min on ice with streptavidin-PE (from R&D systems) diluted 1 in 100 in SB together with 2 μg/ml Protein A-FITC (Fluka). Next the cells are washed twice with ice cold SB and diluted to an end concentration of about 2×10e6 cells/ml. In addition, control stainings are made in which 5×10e6 cells/ml of PooM in 100 μl cells are incubated with a mixture of Prot A and streptavidin-PE as indicated above, but without the incubation with the antigen (Her2). In addition, 5×10e5 cell in 100 μl of a yeast clone expressing Fcab wt non randomized Fc fragment) is stained with Prot A—FITC as described above in the absence of streptavidin-PE. Fcab-wt expressing cells are analysed in e.g. a FACS ARIA from BD to set gates for sorting. First a FSC/SSC gate (G1) is set to identify healthy yeast cells, from G1 a FSC-width versus FSC-area plot is made and only non aggregating cells are selected in new gate (G2). Cells in G2 are subsequently analysed for Protein A expression using FSC versus FL-1 (FITC). G3 is set to cover strong Prot A positive cells (50-60% of parent gate) and G4 is set to cover weak Prot A positive cells (20-30% of parent cells). G3+G4 will include roughly 70-80% of all cells in G2. Now the Pool cells stained for streptavidin-PE in the presence of Prot A-FITC are used to set the rest of the sorting gates. First G1 and G2 are checked with the Pool cells and if necessary adjusted. Pool cells will have lesser events in G3 and maybe also in G4 indicating that not all cells in PooM express Fcabs that are folded as the Fcab-wt. Using the control stained Pool cells a new gate is prepared both for G3 and G4. The new gates are set in a plot FSC and FL-2 (PE). Gate (G5) is prepared that includes 0.1% (false) streptavidin positive cells in G3 and the same is done for cells in G4 resulting in G6. In the next step at least 5×10e6 cells stained for Her2-biotin+streptavidin-PE and Prot A-FITC are sorted by the FACS-ARIA. Cells are collected from G5 (Pool2.1 and G6 (Pool2.2) in separate tubes containing 2-3 ml yeast culture medium. Between 10 and 1000 clones can be expected from both gates. Both new pools are propagated for 1 or 2 days and stored at −80° C. Cells from 2.1 and 2.2 may be either used for direct further sorting in a third round or they may be subjected, (preferably after mixing the two clone together again) to a round of additional randomization of the AB loop (affinity maturation) before they are further sorted in FACS.

Affinity Maturation for Selected Clones/Pools

For affinity maturation, diversity is introduced in selected clones or in pools of selected clones preferably in one loop only, here the AB loop. For this purpose, a PCR was made with a primer that contained degenerate codons at positions 359, 360 and 361 (EU numbering) (primer Abmut, gaaccacaggtgtacaccctgcccccatcccgg-gatgagctgnnbnnbnnbcaggtcagcctgacctgcc tggtcaaag, SEQ ID No.26), or alternatively with a primer that contained degenerate codons at positions 358, 359, 360,361 and 362 (EU numbering) (primer Abmut2LR, gaaccacaggtgtacaccct-gcccccatcccgggatgagnnbnnbnn-bnnbnnbgtcagcctgacctgcctggtca aag, SEQ ID No.27).

The second primer used in these PCRs is gapfcs3 in both cases. In order to create flanking sequences for efficient gap repair in yeast, the resulting PCR products were further amplified with the primer pair gapch35 and gapfsc3 and subsequently transformed in *Saccharomyces cerevisiae* strain EBY100 by Lithiumacetate transformation together with XhoI cleaved pYD1 CH12 as described above. As alternative primers for randomization of the described residues in the AB loop, primers such as Abmuti L (gaaccacaggtgtacaccctgc-ccccatcccgggatgagnnbnnbnnbnn-bcaggtcagcctgacctgcctggtca aag, SEQ ID No.28) or Abmuti R (gaaccacaggtgtacaccctgc-ccccatcccgggatgagctgnnbnnbnnbnnbgtcagcctgacctgcctggtca aag, SEQ ID No.29) were also used used. In an analogous manner, residues in the EF loop were randomized by total randomization.

Alternatively randomization was performed using spiked oligonucleotides as primers on the individual clone y-Her.C2.P4.2-9. In this case the oligos were designed similar to the before mentioned for complete randomization of the respective loops, however the randomized part contained 70% of the original base in the first and second position of the codon and 10% of each of the other 3 nucleotides. The third position was containing 70% of the original base and 30% of the base according to the NNK or NNS codon.

The Abmut primer resulted in 8000 new variants (Pool2.3) of each clone and the Abmut2LR primer lead to 3×10e6 new variants (Pool2.4) upon complete randomization. Therefore Pools 2.3 and 2.4 both resulted in new libraries of approximately 10e8 individual since the starting material (Pool2.1+2.2) already contained approximately 10-1000 clones.

Third Selection Round

Affinity matured pools 2.3 and 2.4 and if necessary Pool2.1 (only the Prot A positive cells are preferred) were induced to express Fcabs on their cell surface as described above and subsequently sorted as described for "Second selection round", with exception that the Pools 2.3 and 2.4 are much bigger and therefore staining volumes for the pools are equal to those of the library staining described in "First selection round". In the third selection round, only Her2 positive/Prot A positive cells were sorted. Pools derived from these selections contained typically >20% Her2/Prot A positive cells. If not then a fourth and fifth (or even more) round(s) of selection for Her2 together with or also without protein A were performed. For example, affinity maturation of the H242-9Q clone yielded an increase in the binding affinity from EC50=155 nM to 18.9 nM (H10-03-6 clone).

Clone Analyses:

Individual clones from pools containing Her2/Prot A cells (>20% is preferred) were prepared either by plating the pools on agar plates with SD-CAA medium or by spotting the singles cells (=clones) directly from the FACS ARIA onto the plates without generating a pool. Clones are allowed to grow and are transferred to liquid cultures and stored in −80° C.

Aliquots of the clones were subsequently induced to express Fcabs on their cell surface as described above and screened for a number of parameters in the FACS. These parameters were: a dose response range of the antigen used for selection (Her2) with and without the presence of Prot A-FITC, CD64 staining as described above. In addition using similar staining protocols a number of irrelevant biotinylated antigen was screened to identify non-cross reacting Fcabs.

It was observed that, after several rounds of selecting antigen (Her2)+Prot A positive cells, a large percentage of clones show >25% antigen (Her2) positivity when stained with 500 nM antigen (Her2) and >70% Prot A positivity when stained with 2 μg/ml Prot A-FITC. In most of the cases these clones also showed >50% CD64 binding. Thus this reflects the Prot A and CD64 staining levels of non-randomized Fc fragments (Fcab wt) expressed on yeast.

Clones selected as described above with characteristics as described above were produced as soluble molecules. This was done mainly by transient transfection but also by stable transfection of the Fcab DNA into new host cells. For this purpose the DNA from individual yeast clones was isolated using standard procedures. The relevant DNA coding for the complete CH3 domain or only the part of the CH3 domain that is randomized in the library was amplified by PCR and transferred into a new expression vector containing the missing part of the Fcab and a suitable promoter and one of more selection markers such as G418, that allows selection of transfected cells out of a pool of non transfected cells. The new vector was then transiently transfected into a new host cell such as HEK293 or CHO. The host cells were allowed to recover and were subsequently cultured for up to 10 days. The supernatant of the cultures which contain the soluble Fcab was used for further testing after purification over Prot A. Stable cell lines can also be made by standard procedures.

TABLE 4

Sequences of selected Her2 binding yeast clones from initial libraries, after pool expansion and after affinity maturation: with reference to numbering of SEQ ID No. 1 (FIG. 3) (CD loop: AA169ffNGQPE)

| Clone name | AB loop AA143ff | EF Loop AA198ff |
|---|---|---|
| Fcab wt | LTKNQ (SEQ ID No. 30) | ---DKSRWQQ |
| y-Her.C2-P3.1-1 | LDNSQ (SEQ ID No. 31) | IRSSVGSRRWWS (SEQ ID No. 51) |
| y-Her.C2-P3.1-3 | YEGSS (SEQ ID No. 32) | ARYSPRMLRWAH (SEQ ID No. 52) |
| y-Her.C2-P3.1-5 | YMSAD (SEQ ID No. 33) | SRRDSSLLRWAH (SEQ ID No. 53) |
| y-Her.C2-P3.1-6 | YRRGD (SEQ ID No. 34) | APGSKGYRRWAL (SEQ ID No. 54) |
| y-Her.C2-P3.1-8 | LMSRQ (SEQ ID No. 35) | DKPFWGTSRWSE (SEQ ID No. 55) |
| y-Her.C2-P3.1-16 | LHLAQ (SEQ ID No. 36) | SINDLINHRWPY (SEQ ID No. 56) |
| y-Her.C2-P3.1-18 | YLSKD (SEQ ID No. 37) | MWGSRDYWRWSH (SEQ ID No. 57) |
| y-Her.C2-P3.2-3 | YRSGS (SEQ ID No. 38) | NSGSAMMVRWAH (SEQ ID No. 58) |
| y-Her.C2-P3.2-9 | LRDGQ (SEQ ID No. 39) | QRSRLSRQRWWR (SEQ ID No. 59) |
| y-Her.C2-P4.2-3 | YSANT (SEQ ID No. 40) | ARYSPRMLRWAH (SEQ ID No. 60) |
| y-Her.C2-P4.2-4 | YASNT (SEQ ID No. 41) | ARYSPRMLRWAH (SEQ ID No. 60) |
| y-Her.C2-P4.2-5 | YSGGS (SEQ ID No. 42) | ARYSPRMLRWAH (SEQ ID No. 60) |
| y-Her.C2-P4.2-6 | YGRDS (SEQ ID No. 43) | ARYSPRMLRWAH (SEQ ID No. 60) |
| y-Her.C2-P4.2-8 | YAGGT (SEQ ID No. 44) | ARYSPRMLRWAH (SEQ ID No. 60) |
| y-Her.C2-P4.2-10 | YSSDS (SEQ ID No. 45) | ARYSPRMLRWAH (SEQ ID No. 60) |
| y-Her.C2-P4.2-12 | YHSGS (SEQ ID No. 46) | ARYSPRMLRWAH (SEQ ID No. 60) |
| y-Her.C2-P4.2-15 | YLTNS (SEQ ID No. 47) | ARYSPRMLRWAH (SEQ ID No. 60) |
| y-Her.C2-P4.2-18 | YGSEE (SEQ ID No. 48) | ARYSPRMLRWAH (SEQ ID No. 60) |
| y-Her.C2-P4.2-19 | YRSGE (SEQ ID No. 49) | ARYSPRMLRWAH (SEQ ID No. 60) |
| y-Her.C2-P4.2-20 | YGTDD (SEQ ID No. 50) | ARYSPRMLRWAH (SEQ ID No. 60) |
| y-Her.C2-P4.2-9 | YLHGD (SEQ ID No. 161) | ARYSPRMLRWAH (SEQ ID No. 60) |
| HAF1311A1 | YLHGD (SEQ ID No. 161) | VSRYSMTMWRWAH (SEQ ID No. 61) |
| HAF1311A10 | YLHGD (SEQ ID No. 161) | VSRYSRSMMRWAH (SEQ ID No. 62) |
| HAF1311A11 | YLHGD (SEQ ID No. 161) | VPRYSQMMWRWAH (SEQ ID No. 63) |

TABLE 4-continued

Sequences of selected Her2 binding yeast clones from initial libraries, after pool expansion and after affinity maturation: with reference to numbering of SEQ ID No. 1 (FIG. 3) (CD loop: AA169ffNGQPE)

| Clone name | AB loop AA143ff | EF Loop AA198ff |
|---|---|---|
| HAF1311A12 | YLHGD (SEQ ID No. 161) | ITRYSRQMLRWAH (SEQ ID No. 64) |
| HAF1311A2 | YLHGD (SEQ ID No. 161) | VPRYSALMWRWAH (SEQ ID No. 65) |
| HAF1311A3 | YLHGD (SEQ ID No. 161) | VARHSEAMWKWGH (SEQ ID No. 66) |
| HAF1311A4 | YLHGD (SEQ ID No. 161) | VGRYSQRMWRWAH (SEQ ID No. 67) |
| HAF1311A5 | YLHGD (SEQ ID No. 161) | VARYSPTMWRWAH (SEQ ID No. 68) |
| HAF1311A6 | YLHGD (SEQ ID No. 161) | VGRHSPTMWRWAH (SEQ ID No. 69) |
| HAF1311A7 | YLHGD (SEQ ID No. 161) | LGRWSPKMWRWAH (SEQ ID No. 70) |
| HAF1311A8 | YLHGD (SEQ ID No. 161) | VARWSPSMWRWAH (SEQ ID No. 71) |
| HAF1311A9 | YLHGD (SEQ ID No. 161) | VARNSPSMWRWAH (SEQ ID No. 83) |
| HAF1311B1 | YLHGD (SEQ ID No. 161) | VARWSPSMVRWAH (SEQ ID No. 84) |
| HAF1311B10 | YLHGD (SEQ ID No. 161) | VARKNMRKWRRTH (SEQ ID No. 85) |
| HAF1311B12 | YLHGD (SEQ ID No. 161) | VSRYSPTMWQWAH (SEQ ID No. 68) |
| HAF1311B2 | YLHGD (SEQ ID No. 161) | VARYSQTNWRWAH (SEQ ID No. 87) |
| HAF1311B3 | YLHGD (SEQ ID No. 161) | MPRFSPSMWRWAH (SEQ ID No. 88) |
| HAF1311B4 | YLHGD (SEQ ID No. 161) | VTRYSQSMWRWAH (SEQ ID No. 89) |
| HAF1311B5 | YLHGD (SEQ ID No. 161) | IERYSTRMWSWAH (SEQ ID No. 90) |
| HAF1311B6 | YLHGD (SEQ ID No. 161) | VARHSPEMWHWAH (SEQ ID No. 91) |
| HAF1311B7 | YLHGD (SEQ ID No. 161) | VARGSPSMWSWGH (SEQ ID No. 92) |
| HAF1311B8 | YLHGD (SEQ ID No. 161) | VARHSQTMWRWAH (SEQ ID No. 93) |
| HAF1311B9 | YLHGD (SEQ ID No. 161) | LARYSPGMWRWAH (SEQ ID No. 94) |
| HAF1311B1 | YLHGD (SEQ ID No. 161) | VPRFSPTMWKWAH (SEQ ID No. 95) |
| HAF1311C1 | YLHGD (SEQ ID No. 161) | VPRWSRTMLRWAH (SEQ ID No. 96) |
| HAF1311C10 | YLHGD (SEQ ID No. 161) | VPRWSRTMLRWAH (SEQ ID No. 97) |
| HAF1311C11 | YLHGD (SEQ ID No. 161) | VPRYSPRMWRWAH (SEQ ID No. 98) |
| HAF1311C2 | YLHGD (SEQ ID No. 161) | IARHSKSMWSWAH (SEQ ID No. 99) |
| HAF13112C3 | YLHGD (SEQ ID No. 161) | MPRWSKSLSGWAH (SEQ ID No. 100) |
| HAF1311C5 | YLHGD (SEQ ID No. 161) | VARYTPSMWRWAH (SEQ ID No. 101) |
| HAF1311C7 | YLHGD (SEQ ID No. 161) | VARNSLTMWRWAH (SEQ ID No. 102) |
| HAF1311C8 | YLHGD (SEQ ID No. 161) | VARYSPSMWKWAH (SEQ ID No. 103) |
| HAF1311C9 | YLHGD (SEQ ID No. 161) | VARFSPSMWRWAH (SEQ ID No. 104) |
| HAF1311D2 | YLHGD (SEQ ID No. 161) | LARWSPSLSRWAH (SEQ ID No. 105) |
| HAF1311D3 | YLHGD (SEQ ID No. 161) | VARYSPSMWRWAH (SEQ ID No. 106) |
| HAF1311D4 | YLHGD (SEQ ID No. 161) | VPRSSLTMWKWAH (SEQ ID No. 107) |
| HAF1311D5 | YLHGD (SEQ ID No. 161) | VPRHSTRMWKWAH (SEQ ID No. 108) |
| HAF1311D6 | YLHGD (SEQ ID No. 161) | VPRHSRRMWRWAH (SEQ ID No. 109) |
| HAF1311D7 | YLHGD (SEQ ID No. 161) | VTRYSPSMWRWAH (SEQ ID No. 110) |

TABLE 4-continued

Sequences of selected Her2 binding yeast clones from initial libraries, after pool expansion and after affinity maturation: with reference to numbering of SEQ ID No. 1 (FIG. 3) (CD loop: AA169ffNGQPE)

| Clone name | AB loop AA143ff | EF Loop AA198ff |
|---|---|---|
| HAF1311E10 | YLHGD (SEQ ID No. 161) | VPRHSRRMWRWAH (SEQ ID No. 109) |
| HAF1311E2 | YLHGD (SEQ ID No. 161) | MPRWSKSLSGWAH (SEQ ID No. 100) |
| HAF1311E3 | YLHGD (SEQ ID No. 161) | VTRHSSSMWRWAH (SEQ ID No. 111) |
| HAF1311E4 | YLHGD (SEQ ID No. 161) | VARYSRSMKKWAH (SEQ ID No. 112) |
| HAF1311E5 | YLHGD (SEQ ID No. 161) | VARGSTTMWRWAH (SEQ ID No. 113) |
| HAF1311E6 | YLHGD (SEQ ID No. 161) | VARSSPEMWRWAH (SEQ ID No. 114) |
| HAF1311E7 | YLHGD (SEQ ID No. 161) | VARYSTGMWNWAH (SEQ ID No. 115) |
| HAF1311E8 | YLHGD (SEQ ID No. 161) | VPRYSQRMWRWAH (SEQ ID No. 116) |
| HAF1311E9 | YLHGD (SEQ ID No. 161) | VPRNSPRMWRWAH (SEQ ID No. 117) |
| HAF1312F1 | YLHGD (SEQ ID No. 161) | LARWSPSMSRWAH (SEQ ID No. 118) |
| HAF1312G12 | YLHGD (SEQ ID No. 161) | LARWSPSMKSWAH (SEQ ID No. 119) |
| HAF1312F11 | YLHGD (SEQ ID No. 161) | LPRYSTKMKRWAH (SEQ ID No. 120) |
| HAF1312F7 | YLHGD (SEQ ID No. 161) | IPRWSQQMSRWAH (SEQ ID No. 121) |
| HAF1312F3 | YLHGD (SEQ ID No. 161) | VGRWTPSMWRWAH (SEQ ID No. 122) |
| HAF1312F5 | YLHGD (SEQ ID No. 161) | VGRWTPSMWRWAH (SEQ ID No. 123) |
| HAF1312G10 | YLHGD (SEQ ID No. 161) | VKRSSPSMWRWAH (SEQ ID No. 124) |
| HAF1312G2 | YLHGD (SEQ ID No. 161) | VARFSPSMWRWAH (SEQ ID No. 104) |
| HAF1312G1 | YLHGD (SEQ ID No. 161) | LARYSPGMWNWAH (SEQ ID No. 125) |
| HAF1312G9 | YLHGD (SEQ ID No. 161) | IARYSPNMWNWAH (SEQ ID No. 126) |
| HAF1312G8 | YLHGD (SEQ ID No. 161) | IARYSPSMWRWAH (SEQ ID No. 127) |
| HAF1312F12 | YLHGD (SEQ ID No. 161) | VARFSPSMLKWAH (SEQ ID No. 128) |
| HAF1312F2 | YLHGD (SEQ ID No. 161) | VARYSKSMLKWAH (SEQ ID No. 129) |
| HAF1312F10 | YLHGD (SEQ ID No. 161) | VARHSRTMWRWGH (SEQ ID No. 130) |
| HAF1312G7 | YLHGD (SEQ ID No. 161) | IARHSREMLRWAH (SEQ ID No. 131) |
| HAF1312F8 | YLHGD (SEQ ID No. 161) | VARYSSTMSRWAH (SEQ ID No. 132) |
| HAF1321A1 | YLHGD (SEQ ID No. 161) | VPRYSQRMWRWAH (SEQ ID No. 116) |
| HAF1321B11 | YLHGD (SEQ ID No. 161) | VPRYSQMMWRWAH (SEQ ID No. 63) |
| HAF1321A2 | YLHGD (SEQ ID No. 161) | VPRYSPRMWRWAH (SEQ ID No. 98) |
| HAF1321A10 | YLHGD (SEQ ID No. 161) | IPRWSQQMSRWAH (SEQ ID No. 122) |
| HAF1321A4 | YLHGD (SEQ ID No. 161) | VPRHSLKKLQRKH (SEQ ID No. 133) |
| HAF1321B10 | YLHGD (SEQ ID No. 161) | VARHSLSMWRWAH (SEQ ID No. 87) |
| HAF1321A5 | YLHGD (SEQ ID No. 161) | VARYSPSMWNWAH (SEQ ID No. 134) |
| HAF1321B1 | YLHGD (SEQ ID No. 161) | VARYSPTMWKWAH (SEQ ID No. 148) |
| HAF1321A11 | YLHGD (SEQ ID No. 161) | VARFSPSMWRWAH (SEQ ID No. 104) |
| HAF1321B5 | YLHGD (SEQ ID No. 161) | VSRFSPSMWRWAH (SEQ ID No. 149) |
| HAF1321B2 | YLHGD (SEQ ID No. 161) | VGRWTPSMWRWAH (SEQ ID No. 123) |

TABLE 4-continued

Sequences of selected Her2 binding yeast clones from initial libraries, after pool expansion and after affinity maturation: with reference to numbering of SEQ ID No. 1 (FIG. 3) (CD loop: AA169ffNGQPE)

| Clone name | AB loop AA143ff | EF Loop AA198ff |
|---|---|---|
| HAF1321B6 | YLHGD (SEQ ID No. 161) | IARYSPSMWRWAH (SEQ ID No. 127) |
| HAF1321B7 | YLHGD (SEQ ID No. 161) | IARYSPSMWRWAH (SEQ ID No. 127) |
| HAF1321B9 | YLHGD (SEQ ID No. 161) | IPRYTPSMWRWAH (SEQ ID No. 150) |
| HAF1322C10 | YLHGD (SEQ ID No. 161) | IPRWSQQMSRWAH (SEQ ID No. 122) |
| HAF1322C11 | YLHGD (SEQ ID No. 161) | VPRHSRRMWRWAH (SEQ ID No. 151) |
| HAF1322C7 | YLHGD (SEQ ID No. 161) | LPRHSRRMWRWAH (SEQ ID No. 152) |
| HAF1322C6 | YLHGD (SEQ ID No. 161) | LARWSPSMLRWAH (SEQ ID No. 153) |
| HAF1322C3 | YLHGD (SEQ ID No. 161) | VARHSLSMWRWAH (SEQ ID No. 87) |
| HAF1322C4 | YLHGD (SEQ ID No. 161) | VARHSPAMWRWAH (SEQ ID No. 154) |
| HAF1322C8 | YLHGD (SEQ ID No. 161) | VARSSPSMWRWAH (SEQ ID No. 147) |
| H10-03-6 | YLHGD (SEQ ID No. 161) | VPRHSARMWRWAH (SEQ ID No. 155) |
| H10-03-6R | YLYGD (SEQ ID No. 161) | VPRHSARMWRWAH (SEQ ID No. 155) |
| H10-03-6Y | YLYGD (SEQ ID No. 161) | VPRYSARMWRWAH (SEQ ID No. 156) |
| ABEFs0101 | YLYGD (SEQ ID No. 161) | VARYSPSMWRWGH (SEQ ID No. 135) |
| ABS0101G | YLSAD (SEQ ID No. 161) | VARYSPSMWRWAH (SEQ ID No. 106) |
| ABS0101P | YLSAD (SEQ ID No. 161) | VPRYSASMWRWGH (SEQ ID No. 136) |
| ABS0101PG | YLSAD (SEQ ID No. 161) | VPRYSASMWRWAH (SEQ ID No. 137) |
| EF3-1 | YLHGD (SEQ ID No. 161) | LPRYSPGMWRWAH (SEQ ID No. 138) |
| EF3-2 | YLHGD (SEQ ID No. 161) | VARYSPSMWNWAH (SEQ ID No. 134) |
| EF3-3 | YLHGD (SEQ ID No. 161) | VARYSPSMWRWGH (SEQ ID No. 135) |
| EF3-4 | YLHGD (SEQ ID No. 161) | IPRWSQQMSRWAH (SEQ ID No. 122) |
| EF3-6 | YLHGD (SEQ ID No. 161) | VARYSQTMSRWAH (SEQ ID No. 139) |
| EF3-7 | YLHGD (SEQ ID No. 161) | IARYSPSMWRWAH (SEQ ID No. 127) |
| EF3-8 | YLHGD (SEQ ID No. 161) | VAGYRPRRSGSSH (SEQ ID No. 140) |
| EF3-9 | YLHGD (SEQ ID No. 161) | LARHSANMKRWAH (SEQ ID No. 141) |
| EF3-13 | YLHGD (SEQ ID No. 161) | VARHSPSMWSWAH (SEQ ID No. 124) |
| EF3-14 | YLHGD (SEQ ID No. 161) | VARYTPSMWRWAH (SEQ ID No. 101) |
| EF3-15 | YLHGD (SEQ ID No. 161) | VARWSPSMFRWAH (SEQ ID No. 143) |
| EF3-16 | YLHGD (SEQ ID No. 161) | LARWSPSMFRWAH (SEQ ID No. 119) |
| EF3-17 | YLHGD (SEQ ID No. 161) | VARHSRTMWRWGH (SEQ ID No. 130) |
| EF3-18 | YLHGD (SEQ ID No. 161) | LARWSPSMSRWAH (SEQ ID No. 118) |
| EF3-20 | YLHGD (SEQ ID No. 161) | VARWSPSMLRWAH (SEQ ID No. 144) |
| EF10-01 | YLHGD (SEQ ID No. 161) | VARSSPTMWRWAH (SEQ ID No. 145) |
| EF10-02 | YLHGD (SEQ ID No. 161) | VARYSPSMWRWAH (SEQ ID No. 106) |
| EF10-03 | YLHGD (SEQ ID No. 161) | VARWSPSMMRWAH (SEQ ID No. 71) |
| EF10-04 | YLHGD (SEQ ID No. 161) | VTRWSPTMMRWAM (SEQ ID No. 146) |

TABLE 4-continued

Sequences of selected Her2 binding yeast clones from initial libraries, after pool expansion and after affinity maturation: with reference to numbering of SEQ ID No. 1 (FIG. 3) (CD loop: AA169ffNGQPE)

| Clone name | AB loop AA143ff | EF Loop AA198ff |
|---|---|---|
| EF10-07 | YLHGD (SEQ ID No. 161) | VARNSPSMWRWAH (SEQ ID No. 83) |
| EF10-08 | YLHGD (SEQ ID No. 161) | LARWSPSLSRWAH (SEQ ID No. 105) |
| EF10-09 | YLHGD (SEQ ID No. 161) | VARSSPSMWRWAH (SEQ ID No. 147) |
| EF10-10 | YLHGD (SEQ ID No. 161) | VARYSPRMWRWAH (SEQ ID No. 157) |
| EF10-13 | YLHGD (SEQ ID No. 161) | VARYSRKMSSWGH (SEQ ID No. 158) |
| EF10-14 | YLHGD (SEQ ID No. 161) | LASYSPSMWRWGH (SEQ ID No. 159) |
| EF10-15 | YLHGD (SEQ ID No. 161) | VARYSPTMKRWAH (SEQ ID No. 160) |

TABLE 5

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H542-M3C8 | LSLPC (SEQ ID No. 164) | ISGPE (SEQ ID No. 240) | PQTPPSQ (SEQ ID No. 340) |
| H541-M2D7 | REGGR (SEQ ID No. 165) | NGQPE (SEQ ID No. 241) | DKPFWGTSRWSR (SEQ ID No. 55) |
| H541-M2E11 | LTKNQ (SEQ ID No. 166) | DGRPE (SEQ ID No. 242) | DKPFWGTSRWSR (SEQ ID No. 55) |
| H541-M2D12 | TKSFY (SEQ ID No. 167) | NGQPE (SEQ ID No. 241) | PPSPPRT (SEQ ID No. 341) |
| H541-M2H10 | TKGL_ (SEQ ID No. 172) | NGQPE (SEQ ID No. 241) | PPSPPRT (SEQ ID No. 341) |
| H541-M2H8 | TLAFY (SEQ ID No. 167) | NGQPE (SEQ ID No. 241) | PPSPPRT (SEQ ID No. 341) |
| H542-M3A10 | WWLFG (SEQ ID No. 168) | NGQPE (SEQ ID No. 241) | PWVRWMQ (SEQ ID No. 342) |
| H542-M3F10 | IKKKK (SEQ ID No. 169) | NGQPE (SEQ ID No. 241) | SRARWRH (SEQ ID No. 343) |
| H542-M3D5 | KWNKK (SEQ ID No. 170) | NGQPE (SEQ ID No. 241) | SRSRWRG (SEQ ID No. 344) |
| H542-M4A4 | KKKKK (SEQ ID No. 171) | NGQPE (SEQ ID No. 241) | PRWKM (SEQ ID No. 345) |
| H542-M3G11 | YKTKD (SEQ ID No. 173) | NGQPE (SEQ ID No. 241) | KRYNPRMVRWAH (SEQ ID No. 346) |
| H542-M3D9 | KKKKK (SEQ ID No. 171) | NGQPE (SEQ ID No. 241) | PQSRWYN (SEQ ID No. 347) |
| H542-M3F7 | KKKKK (SEQ ID No. 171) | NGQPE (SEQ ID No. 241) | PWSRWRL (SEQ ID No. 348) |
| H542-M4B12 | RKEKK (SEQ ID No. 174) | NGQPE (SEQ ID No. 241) | PQKRWRS (SEQ ID No. 349) |
| H542-M3D11 | WWVGG (SEQ ID No. 176) | DAGPE (SEQ ID No. 243) | PWVRWMQ (SEQ ID No. 342) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H542-M3A4 | WWRGG (SEQ ID No. 176) | NGQPE (SEQ ID No. 241) | PWVRWLQ (SEQ ID No. 350) |
| H542-M3B8 | WWRGG (SEQ ID No. 177) | NGQPE (SEQ ID No. 241) | PWVRWMQ (SEQ ID No. 342) |
| H542-M3C4 | YGHKY (SEQ ID No. 178) | NKQNH (SEQ ID No. 244) | PQKRWRS (SEQ ID No. 349) |
| H542-M4D4 | TKKET (SEQ ID No. 179) | NGQPE (SEQ ID No. 241) | ELEGEEQ (SEQ ID No. 351) |
| H542-M3A7 | TGGNK (SEQ ID No. 166) | NMGPE (SEQ ID No. 245) | NRSRWQQ (SEQ ID No. 352) |
| H542-M3C12 | LTKNQ (SEQ ID No. 166) | NGQPE (SEQ ID No. 241) | KKKKLKQ (SEQ ID No. 353) |
| H542-MCE10 | LTKNQ (SEQ ID No. 180) | NGQPE (SEQ ID No. 241) | KKKQLKK (SEQ ID No. 354) |
| H542-M3E6 | LDGDQ (SEQ ID No. 181) | NGQPE (SEQ ID No. 241) | QQKKRKKKK (SEQ ID No. 355) |
| H542-M4E9 | FIPHN (SEQ ID No. 182) | DCGPE (SEQ ID No. 246) | PPPLCAP (SEQ ID No. 356) |
| H542-M4D8 | KKKGK (SEQ ID No. 166) | NGQPE (SEQ ID No. 241) | SLNRWKR (SEQ ID No. 357) |
| H542-M4H8 | KKKGK (SEQ ID No. 182) | NGQPE (SEQ ID No. 241) | SLNRWKR (SEQ ID No. 357) |
| H542-M4B11 | LTKNQ (SEQ ID No. 166) | NGQPE (SEQ ID No. 241) | KNKKKRK (SEQ ID No. 358) |
| H542-M4C10 | LTKNQ (SEQ ID No. 166) | MDGPE (SEQ ID No. 247) | KKKKIKK (SEQ ID No. 359) |
| H542-M4F11 | LTKNQ (SEQ ID No. 166) | NGQPE (SEQ ID No. 241) | KKKKMKK (SEQ ID No. 360) |
| H542-M4C8 | LTKNQ (SEQ ID No. 166) | NGQPE (SEQ ID No. 241) | KRKKLKK (SEQ ID No. 361) |
| H542-M4G2 | KNKKK (SEQ ID No. 183) | NGQPE (SEQ ID No. 241) | REREWRK (SEQ ID No. 362) |
| H542-M4C7 | TKKET (SEQ ID No. 178) | NGQPE (SEQ ID No. 241) | ELEGEEQ (SEQ ID No. 351) |
| H561G3M1B8 | KKKNN (SEQ ID No. 184) | YPEKH (SEQ ID No. 248) | DKSRWQQ (SEQ ID No. 363) |
| H542-M4D10 | TKKET (SEQ ID No. 178) | NGQPE (SEQ ID No. 241) | ELEGEEQ (SEQ ID No. 351) |
| H542-M4B3 | KKKKR (SEQ ID No. 185) | NGQPE (SEQ ID No. 241) | PLRLPPM (SEQ ID No. 364) |
| H542-M4A6 | YGHKY (SEQ ID No. 177) | NKQBH (SEQ ID No. 244) | PQKRWRS (SEQ ID No. 349) |
| H561G3M1C6 | LKKKT (SEQ ID No. 186) | NGQPE (SEQ ID No. 241) | PRSNWYGNRWRR (SEQ ID No. 365) |
| H542-M4C1 | KKKKK (SEQ ID No. 171) | NGQPE (SEQ ID No. 241) | PQSRWYN (SEQ ID No. 347) |
| H542-M4F4 | KKKKK (SEQ ID No. 171) | NGQPE (SEQ ID No. 241) | PWSRWRL (SEQ ID No. 348) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H561G3M1E1 | TKGRW (SEQ ID No. 187) | NGAPQ (SEQ ID No. 249) | SRARWRH (SEQ ID No. 343) |
| H542-M4F6 | LSLPC (SEQ ID No. 164) | ISGPE (SEQ ID No. 240) | PQTPPSQ (SEQ ID No. 340) |
| H561G3M1A1 | KKKKK (SEQ ID No. 171) | NGQPE (SEQ ID No. 241) | TPGNLAL (SEQ ID No. 366) |
| H561G3M1A10 | KKKKN (SEQ ID No. 188) | NGQPE (SEQ ID No. 241) | SREDFRA (SEQ ID No. 367) |
| H561G3M1A9 | KHAET (SEQ ID No. 189) | NGQPE (SEQ ID No. 241) | LVSISVG (SEQ ID No. 368) |
| H561G3M1B10 | -KKKK (SEQ ID No. 190) | DYGPM (SEQ ID No. 250) | PSRRWRE (SEQ ID No. 369) |
| H561G3M1G4 | FFTYW (SEQ ID No. 191) | NGQPE (SEQ ID No. 241) | DRRRWTA (SEQ ID No. 370) |
| H561G3M1B9 | EGKRK (SEQ ID No. 192) | NGQPE (SEQ ID No. 241) | SRARWRH (SEQ ID No. 343) |
| H561G3M1C1 | RHGGW (SEQ ID No. 193) | NGQPE (SEQ ID No. 241) | DLQDKKY (SEQ ID No. 371) |
| H561G3M1C2 | KKKKK (SEQ ID No. 171) | NGQPE (SEQ ID No. 241) | ISVPPDE (SEQ ID No. 372) |
| H561G3M1H8 | -KSGY (SEQ ID No. 194) | RKKKW (SEQ ID No. 251) | SRARWRH (SEQ ID No. 343) |
| H561G3M1C8 | AKEGG (SEQ ID No. 195) | NGQPE (SEQ ID No. 241) | TGPDITV (SEQ ID No. 373) |
| H561G3M1D1 | KYWMA (SEQ ID No. 196) | NGQPE (SEQ ID No. 241) | IVLSGFR (SEQ ID No. 374) |
| H561G3M1D5 | KKKNK (SEQ ID No. 188) | DAGPE (SEQ ID No. 243) | MGIHNIN (SEQ ID No. 375) |
| H564G11M2F4 | LTKNQ (SEQ ID No. 166) | NGQPE (SEQ ID No. 241) | MKQDEMA (SEQ ID No. 376) |
| H561G3M1E2 | FFTYW (SEQ ID No. 191) | NGQPE (SEQ ID No. 241) | DRRRWTA (SEQ ID No. 370) |
| H561G3M1E6 | KKKKK (SEQ ID No. 171) | NGQPE (SEQ ID No. 241) | PQWRLQW (SEQ ID No. 377) |
| H561G3M1E7 | KKKNK (SEQ ID No. 188) | NGQPE (SEQ ID No. 241) | HRRLVAR (SEQ ID No. 378) |
| H561G3M1F10 | QLRNK (SEQ ID No. 197) | NGQPE (SEQ ID No. 241) | KQNLRRK (SEQ ID No. 379) |
| H561G3M1F2 | QRGRM (SEQ ID No. 198) | KGGRE (SEQ ID No. 252) | SRARWRH (SEQ ID No. 343) |
| H561G3M1G1 | QRGRM (SEQ ID No. 198) | KGGRE (SEQ ID No. 252) | SRARWRH (SEQ ID No. 343) |
| H564G11M2F12 | KNHNT (SEQ ID No. 199) | NGQPE (SEQ ID No. 241) | SRSRLHGNRWRR (SEQ ID No. 380) |
| H561G3M1H3 | KKKKK (SEQ ID No. 171) | GNWQP (SEQ ID No. 253) | NRERWRR (SEQ ID No. 381) |
| H561G3M1H7 | MSENE (SEQ ID No. 200) | NGQPE (SEQ ID No. 241) | TWVRWMQ (SEQ ID No. 382) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H564G11M2G2 | KKKNK (SEQ ID No. 188) | TTGPY (SEQ ID No. 254) | PWSRWRL (SEQ ID No. 348) |
| H564G11M2A10 | KKKNK (SEQ ID No. 188) | NGQPE (SEQ ID No. 241) | PHWQWKW (SEQ ID No. 383) |
| H564G11M2A4 | YGHKY (SEQ ID No. 177) | DMNQP (SEQ ID No. 255) | SKKKLRK (SEQ ID No. 384) |
| H564G11M2A5 | YGHKY (SEQ ID No. 177) | KWPMF (SEQ ID No. 256) | PWKELEK (SEQ ID No. 385) |
| H564G11M22A9 | WWMDY (SEQ ID No. 201) | NGQPE (SEQ ID No. 241) | KEKKLKK (SEQ ID No. 361) |
| H564G11M2B1 | YGHKY (SEQ ID No. 177) | HDQRH (SEQ ID No. 257) | TQKRWRS (SEQ ID No. 386) |
| H564G11M2B12 | MKKNK (SEQ ID No. 202) | LGMYM (SEQ ID No. 258) | PQKRWRS (SEQ ID No. 349) |
| H564G11M2B3 | YGHKY (SEQ ID No. 177) | NKMFT (SEQ ID No. 259) | NRKHLRA (SEQ ID No. 387) |
| H564G11M2B4 | EYFRH (SEQ ID No. 203) | NGQPE (SEQ ID No. 241) | TRRRWTR (SEQ ID No. 388) |
| H564G11M2B5 | KKKNK (SEQ ID No. 188) | NGQPE (SEQ ID No. 241) | DHRRINR (SEQ ID No. 389) |
| H564G11M2B7 | FDMRD (SEQ ID No. 204) | NGQPE (SEQ ID No. 241) | KRKKLKK (SEQ ID No. 361) |
| H564G11M2C1 | MKKPY (SEQ ID No. 205) | LGYPE (SEQ ID No. 260) | KKKKYHK (SEQ ID No. 390) |
| H564G11M2C11 | KKKNN (SEQ ID No. 184) | HGYQL (SEQ ID No. 261) | PWVRWMQ (SEQ ID No. 345) |
| H564G11M2C3 | YGHKY (SEQ ID No. 177) | NVFIE (SEQ ID No. 262) | QKKKLKK (SEQ ID No. 391) |
| H564G11M2C7 | FEMPY (SEQ ID No. 206) | NGQPE (SEQ ID No. 241) | KRKKLKK (SEQ ID No. 361) |
| H564G11M2C9 | YGHKY (SEQ ID No. 177) | NRGWH (SEQ ID No. 263) | PQKKLRK (SEQ ID No. 392) |
| H564G11M2D1 | KKKNH (SEQ ID No. 207) | PFTLK (SEQ ID No. 264) | DKRGIRK (SEQ ID No. 393) |
| H564G11M2D10 | FFTYW (SEQ ID No. 191) | NGQPE (SEQ ID No. 241) | DRRRWTA (SEQ ID No. 370) |
| H564G11M2D4 | -KKKK (SEQ ID No. 190) | DYGPM (SEQ ID No. 250) | PSRRWRE (SEQ ID No. 369) |
| H564G11M2D9 | YGHKY (SEQ ID No. 177) | STTRV (SEQ ID No. 265) | PQKRWRS (SEQ ID No. 349) |
| H564G11M2E10 | KKKNH (SEQ ID No. 207) | WDQHQ (SEQ ID No. 266) | EKKRWKE (SEQ ID No. 394) |
| H564G11M2E11 | -KKKK (SEQ ID No. 190) | DYGPM (SEQ ID No. 250) | TSRRWRE (SEQ ID No. 395) |
| H564G11M2E3 | YGHKY (SEQ ID No. 177) | SGWMM (SEQ ID No. 267) | KKEKLRK (SEQ ID No. 396) |
| H564G11M2E8 | YGHKY (SEQ ID No. 177) | WRKMT (SEQ ID No. 268) | PQKRWRS (SEQ ID No. 349) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H564G11M2H10 | YGHKY (SEQ ID No. 177) | FPKKY (SEQ ID No. 269) | PQKRWRS (SEQ ID No. 349) |
| H564G11M2F2 | MWEPS (SEQ ID No. 208) | NGQPE (SEQ ID No. 241) | KKKKLKK (SEQ ID No. 397) |
| H564G11M2F5 | LRGST (SEQ ID No. 209) | SYYFV (SEQ ID No. 270) | KKKKIMK (SEQ ID No. 398) |
| H564G11M2F6 | KKKKK (SEQ ID No. 171) | IRGTS (SEQ ID No. 271) | DQTRWRR (SEQ ID No. 399) |
| H564G11M2F7 | DSYMI (SEQ ID No. 210) | NGQPE (SEQ ID No. 241) | TWVRWMQ (SEQ ID No. 382) |
| H564G11M2F9 | YGHKY (SEQ ID No. 177) | QVPGW (SEQ ID No. 272) | KKKEIKK (SEQ ID No. 400) |
| H564G11M2G4 | YGHKY (SEQ ID No. 177) | DLPYQ (SEQ ID No. 273) | KKNKLKK (SEQ ID No. 401) |
| H564G11M2G6 | YGHKY (SEQ ID No. 188) | PRSHW (SEQ ID No. 274) | PQKRWRS (SEQ ID No. 349) |
| H564G11M2G7 | KKKNK (SEQ ID No. 188) | LYGHA (SEQ ID No. 275) | NRERWRR (SEQ ID No. 381) |
| H564G11M2G9 | KKKNK (SEQ ID No. 188) | NGQPE (SEQ ID No. 241) | PWWQFRQ (SEQ ID No. 402) |
| H564G11M2H2 | YGHKY (SEQ ID No. 177) | APYVH (SEQ ID No. 279) | KKKEIKK (SEQ ID No. 400) |
| H564G11M2H3 | MEQHS (SEQ ID No. 211) | NGQPE (SEQ ID No. 241) | KRKKLKK (SEQ ID No. 361) |
| H564G11M2H4 | YGHKY (SEQ ID No. 177) | RTGQK (SEQ ID No. 277) | PQKRWRS (SEQ ID No. 349) |
| H564G11M2h8 | YGHKY (SEQ ID No. 177) | PTYWY (SEQ ID No. 278) | NRKHLRA (SEQ ID No. 387) |
| H564G11M2h9 | KKKKH (SEQ ID No. 212) | EGMEI (SEQ ID No. 279) | PSRRWRE (SEQ ID No. 369) |
| H565_G12C1 | LKKKT (SEQ ID No. 186) | NGQPE (SEQ ID No. 241) | PRSNWYGNRWRR (SEQ ID No. 365) |
| H565_G12D5 | KKKKK (SEQ ID No. 171) | PVVGA (SEQ ID No. 280) | DQSKLSSLRWKK (SEQ ID No. 403) |
| H565_G12E4 | KKKKK (SEQ ID No. 171) | PLMVD (SEQ ID No. 281) | DQSKLSSLRWKK (SEQ ID No. 403) |
| H565_G12A1 | KKKNH (SEQ ID No. 207) | KYGSQ (SEQ ID No. 282) | PQKRWRS (SEQ ID No. 349) |
| H565_G12C4 | KKKNH (SEQ ID No. 207) | RWNNQ (SEQ ID No. 283) | PQKRWRS (SEQ ID No. 349) |
| H565_G12F1 | KKKNH (SEQ ID No. 207) | VYKQD (SEQ ID No. 284) | PQKRWRS (SEQ ID No. 349) |
| H565_G12A10 | KKKNH (SEQ ID No. 207) | NQMKF (SEQ ID No. 285) | PQKRWRS (SEQ ID No. 349) |
| H565_G12A8 | KKKNH (SEQ ID No. 207) | NHQHT (SEQ ID No. 286) | PQKRWRS (SEQ ID No. 349) |
| H565_G12A4 | KKKNH (SEQ ID No. 207) | KRFVD (SEQ ID No. 287) | PNEKLKK (SEQ ID No. 404) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H565_G12B2 | KKKNH (SEQ ID No. 207) | HHEPL (SEQ ID No. 288) | PLSRWKR (SEQ ID No. 405) |
| H565_G12F4 | KKKNH (SEQ ID No. 207) | PKMPY (SEQ ID No. 289) | NRKHLRA (SEQ ID No. 387) |
| H565_G12H5 | KKKNH (SEQ ID No. 207) | PKDHE (SEQ ID No. 290) | ARSRWRK (SEQ ID No. 408) |
| H565_G12G6 | LTKNQ (SEQ ID No. 166) | AKGSI (SEQ ID No. 291) | PKKRLRR (SEQ ID No. 409) |
| H565_G12A5 | YGHKY (SEQ ID No. 177) | EDPEM (SEQ ID No. 292) | KNKKRKK (SEQ ID No. 410) |
| H565_G12E9 | YGHKY (SEQ ID No. 177) | EFDHQ (SEQ ID No. 293) | KNKKRKK (SEQ ID No. 410) |
| H565_G12F8 | YGHKY (SEQ ID No. 177) | NEKQD (SEQ ID No. 294) | NTKKLKK (SEQ ID No. 411) |
| H565_G12D2 | YGHKY (SEQ ID No. 177) | APHYY (SEQ ID No. 295) | NRKRIRK (SEQ ID No. 412) |
| H565_G12F7 | YGHKY (SEQ ID No. 177) | PQLHL (SEQ ID No. 296) | SRKRFRS (SEQ ID No. 413) |
| H565_G12G2 | YGHKY (SEQ ID No. 177) | NWRAE (SEQ ID No. 297) | ARSRWRK (SEQ ID No. 408) |
| H565_G12H11 | YGHKY (SEQ ID No. 177) | NNQYK (SEQ ID No. 298) | PFRRWVK (SEQ ID No. 414) |
| H565_G12A7 | YGHKY (SEQ ID No. 177) | -RSIH (SEQ ID No. 299) | PQKRWRS (SEQ ID No. 349) |
| H565_G12A9 | YGHKY (SEQ ID No. 177) | RDRIM (SEQ ID No. 300) | PQKRWRS (SEQ ID No. 349) |
| H565_G12B3 | YGHKY (SEQ ID No. 177) | YGKGH (SEQ ID No. 301) | PQKRWRS (SEQ ID No. 349) |
| H565_G12B5 | YGHKY (SEQ ID No. 177) | GKGGK (SEQ ID No. 302) | PQKRWRS (SEQ ID No. 349) |
| H565_G12E3 | YGHKY (SEQ ID No. 177) | RHIGK (SEQ ID No. 303) | PQKRWRS (SEQ ID No. 349) |
| H565_G12E12 | YGHKY (SEQ ID No. 177) | QYTYH (SEQ ID No. 304) | PQKRWRS (SEQ ID No. 349) |
| H565_G12B1 | YGHKY (SEQ ID No. 177) | LHSHV (SEQ ID No. 305) | PQKRWRS (SEQ ID No. 349) |
| H565_G12B11 | YGHKY (SEQ ID No. 177) | STTRV (SEQ ID No. 265) | PQKRWRS (SEQ ID No. 349) |
| H565_G12D1 | YGHKY (SEQ ID No. 177) | ARDKR (SEQ ID No. 306) | PQKRWRS (SEQ ID No. 349) |
| H565_G12E2 | YGHKY (SEQ ID No. 177) | EHKKT (SEQ ID No. 307) | PQKRWRS (SEQ ID No. 349) |
| H565_G12C5 | YGHKY (SEQ ID No. 177) | MDEVP (SEQ ID No. 308) | PQKRWRS (SEQ ID No. 349) |
| H565_G12C7 | -KKKK (SEQ ID No. 190) | QDWQR (SEQ ID No. 309) | PQKRWRS (SEQ ID No. 349) |
| H565_G12G1 | -KKKK (SEQ ID No. 190) | PSDRE (SEQ ID No. 310) | PQKRWRS (SEQ ID No. 349) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H565_G12G8 | NKKKK (SEQ ID No. 213) | QNTRW (SEQ ID No. 311) | PQKRWRS (SEQ ID No. 349) |
| H565_G12C9 | -KKKK (SEQ ID No. 190) | DEGLH (SEQ ID No. 312) | PQKRWRS (SEQ ID No. 349) |
| H565_G12A11 | IMNDW (SEQ ID No. 214) | NGQPE (SEQ ID No. 241) | KRKKLKK (SEQ ID No. 361) |
| H565_G12D10 | WTNGD (SEQ ID No. 215) | NGQPE (SEQ ID No. 241) | KRKKLKK (SEQ ID No. 361) |
| H565_G12F6 | WWHDM (SEQ ID No. 216) | NGQPE (SEQ ID No. 241) | KRKKLKK (SEQ ID No. 361) |
| H565_G12B4 | WENPH (SEQ ID No. 217) | NGQPE (SEQ ID No. 241) | KRKKLKK (SEQ ID No. 361) |
| H565_G12H2 | LYHEH (SEQ ID No. 218) | NGQPE (SEQ ID No. 241) | KRKKLKK (SEQ ID No. 361) |
| H565_G12H8 | GGDQH (SEQ ID No. 219) | NGQPE (SEQ ID No. 241) | KRKKLKK (SEQ ID No. 361) |
| H565_G12C12 | IYVPY (SEQ ID No. 220) | NGQPE (SEQ ID No. 241) | KRKKLKK (SEQ ID No. 361) |
| H565_G12G10 | FEMPY (SEQ ID No. 206) | NGQPE (SEQ ID No. 241) | KRKKLKK (SEQ ID No. 361) |
| H565_G12C2 | VVTSQ (SEQ ID No. 221) | NGQPE (SEQ ID No. 241) | KRKKLKK (SEQ ID No. 361) |
| H565_G12B6 | WWNSK (SEQ ID No. 222) | NGQPE (SEQ ID No. 241) | KKKQLKK (SEQ ID No. 354) |
| H565_G12A12 | MTGPG (SEQ ID No. 223) | NGQPE (SEQ ID No. 241) | KKKKIKK (SEQ ID No. 359) |
| H565_G12D7 | MWEPS (SEQ ID No. 208) | NGQPE (SEQ ID No. 241) | KKKKLKK (SEQ ID No. 397) |
| H565_G12F3 | DTYHD (SEQ ID No. 224) | NGQPE (SEQ ID No. 241) | KKKKLKK (SEQ ID No. 397) |
| H565_G12F5 | QDEKT (SEQ ID No. 225) | NGQPE (SEQ ID No. 241) | KKKKIKK (SEQ ID No. 359) |
| H565_G12B12 | GDHRI (SEQ ID No. 226) | NGQPE (SEQ ID No. 241) | KKKKLKQ (SEQ ID No. 353) |
| H565_G12D8 | RNSNS (SEQ ID No. 227) | NGQPE (SEQ ID No. 241) | KKKKLKQ (SEQ ID No. 353) |
| H565_G12D9 | RENTM (SEQ ID No. 228) | NGQPE (SEQ ID No. 241) | NKKKKKK (SEQ ID No. 415) |
| H565_G12 | VNDKM (SEQ ID No. 229) | NGQPW (SEQ ID No. 241) | SKKKLRK (SEQ ID No. 364) |
| H565_G12 | RKKDE (SEQ ID No. 230) | WPNME (SEQ ID No. 313) | KKKKLKK (SEQ ID No. 397) |
| H565_G12 | SNSGY (SEQ ID No. 231) | MDGPE (SEQ ID No. 247) | KKKKIKK (SEQ ID No. 359) |
| H565_G12 | FEYRH (SEQ ID No. 232) | NGQPW (SEQ ID No. 241) | PKKRLRR (SEQ ID No. 409) |
| H565_G12 | QRGRM (SEQ ID No. 198) | KGGRE (SEQ ID No. 252) | SRARWRH (SEQ ID No. 343) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H565_G12 | KKKKK (SEQ ID No. 171) | NGQPW (SEQ ID No. 241) | NGKRLHS (SEQ ID No. 416) |
| H565_G12 | KKKKK (SEQ ID No. 171) | NGQPW (SEQ ID No. 241) | PKWLWHQ (SEQ ID No. 417) |
| H565_G12 | KKKKK (SEQ ID No. 171) | NGQPW (SEQ ID No. 241) | PWWKHHV (SEQ ID No. 418) |
| H565_G12 | KKKKK (SEQ ID No. 171) | NGQPW (SEQ ID No. 241) | PNWKYQW (SEQ ID No. 419) |
| H565_G12 | KKKKK (SEQ ID No. 171) | NGQPW (SEQ ID No. 241) | PQRKVAP (SEQ ID No. 420) |
| H565_G12 | RKKKK (SEQ ID No. 223) | NGQPW (SEQ ID No. 241) | PWYKVLM (SEQ ID No. 421) |
| H565_G12 | KKKKK (SEQ ID No. 171) | NGQPW (SEQ ID No. 241) | DRKWWTF (SEQ ID No. 422) |
| H565_G12 | KKKKK (SEQ ID No. 171) | MTGRV (SEQ ID No. 314) | DRERWRR (SEQ ID No. 407) |
| H565_G12 | KKKKK (SEQ ID No. 171) | GKYNI (SEQ ID No. 315) | DRERWRR (SEQ ID No. 407) |
| H565_G12 | KKKKK (SEQ ID No. 171) | NAYLL (SEQ ID No. 316) | DRERWRR (SEQ ID No. 407) |
| H565_G12 | KKKKK (SEQ ID No. 171) | NGQPW (SEQ ID No. 241) | DRERWRR (SEQ ID No. 407) |
| H565_G12 | KKKKK (SEQ ID No. 171) | AQYNV (SEQ ID No. 317) | DRERWRR (SEQ ID No. 407) |
| H565_G12 | KKKKK (SEQ ID No. 171) | LYGHA (SEQ ID No. 275) | NRERWRR (SEQ ID No. 381) |
| H565_G12G58 | KKKKK (SEQ ID No. 171) | LYGHA (SEQ ID No. 275) | DRERWRR (SEQ ID No. 407) |
| H565_G12A6 | KKKKK (SEQ ID No. 171) | NQVMT (SEQ ID No. 318) | PSRRWRE (SEQ ID No. 368) |
| H565_G12E6 | KKKKK (SEQ ID No. 171) | VVHDT (SEQ ID No. 319) | PRHEWVM (SEQ ID No. 423) |
| H565_G12B10 | KKKKK (SEQ ID No. 171) | NIWHQ (SEQ ID No. 320) | DKSRWQQ (SEQ ID No. 363) |
| H565_G12H6 | KKKKK (SEQ ID No. 171) | QWGNM (SEQ ID No. 321) | DKSRWQQ (SEQ ID No. 363) |
| H565_G12D12 | KKKKK (SEQ ID No. 171) | MHVKS (SEQ ID No. 322) | PWSRWMQ (SEQ ID No. 424) |
| H565_G12B9 | -KKKK (SEQ ID No. 190) | EYTVV (SEQ ID No. 323) | PLSRWKR (SEQ ID No. 405) |
| H565_G12E11 | -KKKK (SEQ ID No. 190) | GPYQD (SEQ ID No. 324) | PLSRWKR (SEQ ID No. 405) |
| H565_G12F9 | KKKKK (SEQ ID No. 171) | QGVLE (SEQ ID No. 325) | TQNQIKK (SEQ ID No. 406) |
| H571A1 | KKKKK (SEQ ID No. 171) | LYGHA (SEQ ID No. 275) | DRERWRR (SEQ ID No. 407) |
| H571C10 | KKKKK (SEQ ID No. 171) | QQPGV (SEQ ID No. 326) | DRERWRR (SEQ ID No. 407) |

TABLE 5-continued

Sequences of selected Her2 binding yeast clones from initial libraries, after pool expansion and after affinity maturation: with reference to numbering of SEQ ID No. 1 (FIG. 3)

| Clone name | AB loop AA143ff | CD loop AA169ff | EFLoop AA198ff |
|---|---|---|---|
| H571E6 | KKKKK (SEQ ID No. 171) | NQVRG (SEQ ID No. 327) | DRERWRR (SEQ ID No. 407) |
| H571D10 | KKKKK (SEQ ID No. 171) | VPHVL (SEQ ID No. 328) | DRERWRR (SEQ ID No. 407) |
| H571D4 | KKKKK (SEQ ID No. 171) | DGRKQ (SEQ ID No. 329) | DRERWRR (SEQ ID No. 407) |
| H571C3 | KKKKK (SEQ ID No. 171) | NASFE (SEQ ID No. 330) | DRERWRR (SEQ ID No. 407) |
| H571A3 | LTKNQ (SEQ ID No. 166) | KKRVV (SEQ ID No. 331) | SRARWLH (SEQ ID No. 425) |
| H571D7 | YGHKY (SEQ ID No. 177) | KGIKK (SEQ ID No. 332) | SRARWLH (SEQ ID No. 425) |
| H571B1 | QRGRM (SEQ ID No. 198) | KGGRE (SEQ ID No. 252) | SRARWLH (SEQ ID No. 425) |
| H571B9 | TKGRW (SEQ ID No. 187) | NGAPQ (SEQ ID No. 249) | SRARWLH (SEQ ID No. 425) |
| H571E5 | EGKRK (SEQ ID No. 192) | NGQPE (SEQ ID No. 241) | SRARWLH (SEQ ID No. 425) |
| H571A5 | YGHKY (SEQ ID No. 177) | PMGMG (SEQ ID No. 333) | PKKRLRR (SEQ ID No. 409) |
| H571A9 | YGHKY (SEQ ID No. 177) | PMGKY (SEQ ID No. 334) | PQKRWRS (SEQ ID No. 349) |
| H571C9 | YGHKY (SEQ ID No. 177) | FPKKY (SEQ ID No. 269) | PQKRWRS (SEQ ID No. 349) |
| H571B3 | YGHKY (SEQ ID No. 177) | RHIGK (SEQ ID No. 303) | PQKRWRS (SEQ ID No. 349) |
| H571D9 | YGNSY (SEQ ID No. 234) | RGIAK (SEQ ID No. 335) | PQKRWRS (SEQ ID No. 349) |
| H571C2 | KKKNK (SEQ ID No. 188) | LWGGM (SEQ ID No. 336) | PQKRWRS (SEQ ID No. 349) |
| H571C5 | KKKNH (SEQ ID No. 207) | NAHYI (SEQ ID No. 337) | PQKRWRS (SEQ ID No. 349) |
| H571B11 | RNRKK (SEQ ID No. 235) | SGTRL (SEQ ID No. 338) | PSRRWRE (SEQ ID No. 369) |
| H571A6 | WDHGS (SEQ ID No. 236) | NGQPE (SEQ ID No. 241) | KKKKIKK (SEQ ID No. 359) |
| H571F3 | FAKRT (SEQ ID No. 237) | NGQPE (SEQ ID No. 241) | KKKKLKQ (SEQ ID No. 353) |
| H571E12 | SMDKV (SEQ ID No. 238) | NLGPE (SEQ ID No. 339) | DKSRWQQ (SEQ ID No. 363) |
| H571A7 | FFTYW (SEQ ID No. 191) | NGQPE (SEQ ID No. 241) | DRRRWTA (SEQ ID No. 370) |
| H571D12 | EYFRH (SEQ ID No. 203) | NGQPE (SEQ ID No. 241) | TRRRWTR (SEQ ID No. 388) |
| H571D6 | RHQDR (SEQ ID No. 239) | NGQPE (SEQ ID No. 241) | NRSRLHGNRWRR (SEQ ID No. 426) |
| H571A2 | LKKKT (SEQ ID No. 186) | NGQPE (SEQ ID No. 241) | PRSNWTGNRWRR (SEQ ID No. 365) |

Expression and Purification of Antigen Specific Clones in Mammalian Cells:

Clones selected as described above with characteristics as described above are cloned into a mammalian expression vector such as pCEP4 (Invitrogen). Highly purified plasmid DNA (Qiagen) is used to transiently transfect HEK293 freestyle cells with Freestyle™ MAX Reagent as recommended by the manufacturer (Invitrogen). On day 5 post transfection, cell supernatants are cleared from cell debris by centrifugation and filtration through a 0.2 μM Stericup filter (Millipore). Alternatively, HEK293 freestyle cells or CHO cells are transfected with expression plasmids containing genes for antibiotics resistance such as neomycin or puromycin. The transfected cells are cultivated in the presence of the antibiotics resulting in specific survival of cell clones which stably express the antibiotics resistance gene together with the antigen specific Fc fragment. Such stable transfectants consistently secrete the protein of interest over long time periods. The antigen specific Fcabs are purified from cell supernatants by Protein A immuno-affinity chromatography. Bound Fcabs are eluted from Protein A by washing the column with glycine buffer (pH=2.9-4.0), followed by dialysis against PBS (pH=6.8). The purity of the Fcabs is determined by non-reducing SDS-PAGE analysis and potential aggregates are detected by size-exclusion HPLC using a Zorbax GF250 column and PBS as running buffer.

Structural Characterization of Fcabs:

Binding to Fc receptors and Protein A was used to estimate the overall structural integrity of the purified Fcabs. Association with the neonatal Fc receptor (FcRn) was measured by adding 10 μg/ml Fcab to a Biacore CM5 chip coupled to 5000 response units (RU) of recombinant human FcRn at pH=6.0. The dissociation of Fcab from FcRn was tested at pH=7.4. These experiments demonstrated a pH dependent interaction of the Her-2 specific Fcabs with FcRn with binding characteristics very similar to wild type Fcab. Binding of Fcabs to the high affinity Fc receptor CD64 was measured using a Biacore CM5 chip coated with 3000 RU Protein A, followed by adding a 10 μg/ml Fcab solution. Finally, human soluble CD64 at 5 μg/ml was added. The resulting binding curves were indistinguishable from those obtained with wild type Fcab. Interaction of recombinant Fcabs (10 m/ml) with Protein A was also measured by SPR using a Protein A coated Biacore CM5 chip (3000 RU). Again, the affinities were comparable wild the ones obtained with wild type Fcab.

Antigen Specific Binding of Fcabs:

The potency and specificity of Her-2 specific Fcabs to bind to Her-2 was assessed by ELISA. Human soluble Her-2 (Bender Med Systems, Austria) was coated to plastic at 2 μg/ml. After washing and blocking unspecific binding sites, increasing concentrations of Fcabs were added. To detect Her-2 bound Fcabs, anti-Fc CH2 domain specific monoclonal antibodies which were conjugated to horse radish peroxidase (Serotec) were added. The results demonstrated that some Her-2 specific Fcabs could interact with its target in the low nanomolar range (Table 6). This interaction was specific since binding to other Her family members (HeM, Her3 and Her4) was >100 fold weaker as judged by ELISA. No binding to Her-2 unrelated antigens was detected.

TABLE 6

Binding affinities of Her-2 specific Fcabs in ELISA:

| Fcab clone | Her-2 ELISA $EC_{50}$ [nM] | SKBR3 cell binding $EC_{50}$ [nM] |
|---|---|---|
| y-Her.C2.P4.2-3 | 463 | nd |
| y-Her.C2.P4.2-4 | 370 | nd |
| H561G3M1G4 | 263 | nd |
| y-Her.C2.P4.2-19 | 93 | nd |
| ABEFs0101 | 16.1 | 5.2 |
| H10-03-6 | 4.8 | 10.3 |
| EF3-17 | 4.7 | 1.3 |
| y-Her.C2.P4.2-9 | 4.3 | nd |
| H10-03-6R | 2.6 | 11.1 |

nd = not done.

Antigen binding was also determined by SPR. Biacore CM5 chips were coated with different amounts of human soluble Her-2 followed by addition of increasing concentrations of Fcabs. The affinity ($K_0$) of the Fcabs was calculated from the resulting binding curves after fitting using the software BiaEval. In these experimental conditions, the Her-2 specific Fcabs H561 G3M1 G4 and H10-03-6 bound to Her-2 with $K_0$ values of 7.5 nM and 8.6 nM, respectively. Antigen binding was also assessed by FACS using the Her-2 overexpressing human breast cancer cell lines SKBR3 and Calu-3. $1\times10^5$ cells were incubated with increasing concentrations of Fcabs for 60 minutes on ice. Then, unbound antibodies were removed by centrifugation and washing. Cell bound Fcabs were detected by incubation with anti-human Fc specific antibodies conjugated to phycoerythrin (Sigma) for 60 minutes on ice. After washing the cells, the intensity of fluorescence on the cell surface was measured in a FACS Calibur instrument (Beckton Dickinson). All tested Her-2 specific Fcabs bound to SKBR3 and Calu-3 cells but only minimally to MDA-MB468 cells which do not express Her-2 confirming the weak antigen cross-reactivity seen in ELISA. The apparent affinities ($EC_5O$) Of Her-2 specific Fcabs on SKBR3 cells are listed in Table 6.

Effector Function of Antigen Specific Fcabs (ADCC):

In order to determine if Her-2 specific Fcabs mediate Fc effector functions, ADCC assays are performed. In these types of assays, antibodies are bound to target cells and mark them for apoptosis by virtue of binding to Fc receptors on effector cells, such as natural killer (NK) cells. SKBR3 cells (target cells) which are labelled with the fluorescent dye carboxy-fluorescein succinimidyl ester (CFSE) are incubated with increasing concentrations of Her-2 specific Fcabs for 20 minutes at 37° C. Untouched NK cells are isolated from human blood of healthy donors by negative depletion in a AutoMACS device using MACS magnetic beads according to the manufacturers instructions (Miltenyi Biotech). Purified NK cells are mixed with opsonized SKBR3 cells in a ratio of 5:1 and incubated for 4 hours at 37° C. Afterwards, the fluorescence dye 7-amino actinomycin (7-AAD) is added which specifically stains apoptotic cells. Apoptotic SKBR3 cells are enumerated in the FACS as 7-AAD/CSFE double positive cells. Her-2 specific Fcabs H10-03-6 and ABEFs0101 proved to be potent mediators of SKBR3 cell killing with $EC_5O$ values of 1.1 nM and 1.0 nM, respectively. The mechanism of apoptosis induction is dependent on the presence of NK-cells which demonstrates that Her-2 specific Fcabs possess ADCC functionality.

Example 7

Yeast Display of 4D5 Fab

For the display of a Fab fragment on yeast, the yeast display vector pYD1 (Invitrogen) (SEQ ID No.72/FIGS. 17A and 17B and 17C) is modified as follows:

A Nhel restriction site is introduced by site directed mutagenesis at position 581/586 to yield the modified vector pYDI Nhe (SEQ ID No.73/FIGS. 18A and 18B). This vector is restricted with Nhel and Pmel, to yield 3 fragments. The largest fragment is the remaining vector backbone, in which a synthetic oligonucleotide linker is inserted to yield the vector pYDI Ink (SEQ ID No. 74/FIGS. 19A and 19B). A cassette which includes the MATa transcription termination region is then amplified by PCR from the vector pYD1 and is cloned into pYDI Ink via BamHI and Pstl restriction and ligation. The resulting vector is pYDI mata (SEQ ID No.75/FIGS. 20A and 20B). A cassette that contains the GAL1 promotor, the gene coding for Aga2 and a synthetic linker with Notl and Sfil cloning sites is amplified by PCR from pYD1 and cloned in pYDI mata via EcoRI and Pad restriction to yield the vector pYDIgal (SEQ. ID No.76/FIGS. 21A and 21B).

As an example for a Fab to be displayed on yeast, the genes coding for VH-CH1 and VL-CL respectively of the antibody 4D5 (Herceptin) are made synthetically (sequences 4D5H (SEQ ID No.77/FIG. 22) and 4D5L (SEQ ID No.78/FIG. 23)).

4D5H is flanked by Sfil and Notl restriction sites, and cloned into the vector pYDIgal to yield the vector pYD4D5hc (SEQ ID No.79/FIGS. 24A and 24B and 24C). In this vector, the N-terminus of 4D5H is fused to the C-terminus of Aga2, and at the C-terminus of 4D5H, a hexahistidine tag is attached, followed by the stop codon. The amino acid sequence of VH-CH1 of 4D5 is given in 4D5hp (SEQ ID No.80/FIG. 25).

4D5L is flanked by Ncol and Ascl restriction sites, and cloned into the vector pYD4D5hc to yield the vector pYD4D5h1 (SEQ ID No.81/FIGS. 26A and 26B and 26C). 4D5L is preceded by an Aga2 secretion signal, and carries a stop codon after the C-terminal Cysteine residue of the CL domain. The amino acid sequence of VL-CL of 4D5 is given in 4D5lp (SEQ ID No.82/FIG. 27).

For display of the 4D5 Fab, the vector pYD4D5h1 is transformed into the yeast strain EBY100 (Invitrogen), transformants are selected on minimal medium without tryptophan, and expression of the recombinant protein is induced by growth on galactose containing medium according to standard protocols (Invitrogen).

Example 8

Construction of a Library with Randomized Residues in Structural Loops of the CL Domain of 4D5 Fab As first step in the yeast display library construction, the wildt e CL (C kappa) domain is cut out from the display vector pYD4D5h1 (SEQ ID No.81) with restriction enzymes BsiWI and Ascl. A synthetic gene encoding human C kappa domain flanked by BsiWI and Ascl sites (in the context according to pYD4D5hl) is prepared in which random mutations and insertions respectively are introduced in the AB and EF loops. In this particular example, insertions of 3, 4 or 5 NNB codons are made between amino acid positions 16 and 17 of the human C kappa domain, and residue positions 92, 93, 94, 95, 97, 98 and 99 are replaced by NNB codons. (IMGT numbering, see FIG. 2). An NNB codon contains all 4 nucleotides at positions 1 and 2, and C, G and T at position 3. NNB therefore encodes all 20 naturally encoded amino acids.

The library is prepared and selected following standard procedures.

As a scaffold ligand the CDR target Her2neu and 4D5 epitope is used. Those members of the library are selected for production of a cytotoxic modular antibody according to the invention, that have a binding site engineered into the CL domain, which is specifically binding to an effector molecule, such as an Fcgamma receptor. The resulting Fab is tested for (i) Her2neu binding with a Kd$<10^{-8}$ M and an IC50$<10^{-8}$ M, and (ii) effector function using a CDC and/or ADCC assay.

The invention claimed is:

1. An isolated protein that binds specifically to human Her2, wherein the isolated protein comprises two polypeptides, wherein each polypeptide comprises a human IgG1 heavy chain fragment comprising a CH2 domain and a CH3 domain, wherein the CH3 domain comprises an AB loop comprising the amino acid sequence of SEQ ID NO: 191, a CD loop comprising the amino acid sequence of SEQ ID NO: 241 and an EF loop comprising the amino acid sequence of SEQ ID NO: 370.

2. The isolated protein of claim 1, wherein the CH3 domain comprises the amino acid sequence of the CH3 domain in SEQ ID NO: 1 or SEQ ID NO: 440 exclusive of that of loops AB and EF.

3. The isolated protein of claim 1, wherein the CH2 domain comprises the amino acid sequence of the CH2 domain in SEQ ID NO: 1.

4. The isolated protein of claim 2, wherein the CH2 domain comprises the amino acid sequence of the CH2 domain in SEQ ID NO: 1.

5. The isolated protein of claim 1, wherein the human IgG1 heavy chain fragment comprises a hinge.

6. The isolated protein of claim 1, wherein the human IgG1 heavy chain fragment comprises the amino acid sequence SEQ ID NO: 1 exclusive of that of loops AB and EF.

7. The isolated protein of claim 1, wherein the two polypeptides are connected by a disulfide bond.

8. The isolated protein of claim 7, wherein the two polypeptides are connected by 2 disulfide bonds.

9. The isolated protein of claim 1, which binds to human Her2 with a binding affinity of $Kd<10^{-8}$ M.

10. The isolated protein of claim 1, which is cytotoxic.

11. The isolated protein of claim 10, which triggers at least one of antibody-dependent cellular cytotoxicity (ADCC), antibody-dependent cellular phagocytosis (ADCP), complement dependent cytotoxicity (CDC), or apoptotic activity.

12. The isolated protein of claim 1, having a molecular weight of up to 60 kD.

13. An isolated protein that specifically binds to human Her2, wherein the isolated protein comprises two polypeptides, wherein each polypeptide comprises a human IgG1 heavy chain fragment comprising a CH2 domain and a CH3 domain, wherein the CH3 domain comprises an AB loop comprising the amino acid sequence of SEQ ID NO: 191, a CD loop comprising the amino acid sequence of SEQ ID NO: 241 and an EF loop comprising the amino acid sequence of SEQ ID NO: 370; and wherein the isolated protein has a molecular weight of up to 60 kD, a binding affinity of $Kd<10^{-8}$ M and is cytotoxic.

14. A pharmaceutical composition comprising the isolated protein of claim 1 and a pharmaceutically acceptable carrier.

15. The isolated protein of claim 10, which triggers apoptotic activity.

16. The isolated protein of claim 13, wherein the CH3 domain comprises the amino acid sequence of the CH3 domain in SEQ ID NO: 1 or SEQ ID NO: 440, exclusive of that of loops AB and EF.

17. The isolated protein of claim 13, wherein the CH2 domain comprises the amino acid sequence of the CH2 domain in SEQ ID NO: 1.

18. The isolated protein of claim 16, wherein the CH2 domain comprises the amino acid sequence of the CH2 domain in SEQ ID NO: 1.

19. The isolated protein of claim 13, wherein the human IgG1 heavy chain fragment comprises a hinge.

20. The isolated protein of claim 13, wherein the two polypeptides are connected by a disulfide bond.

21. The isolated protein of claim 20, wherein the two polypeptides are connected by 2 disulfide bonds.

22. The isolated protein of claim 13, which triggers apoptotic activity.

23. The isolated protein of claim 13, wherein the polypeptides are connected by a disulfide bond, and wherein the CH2 domain comprises the amino acid sequence of the CH2 domain of SEQ ID NO: 1 and the CH3 domain comprises the amino acid sequence of the CH3 domain of SEQ ID NO: 1 or SEQ ID NO: 440 exclusive of that of loops AB and EF.

24. The isolated protein of claim 23, which triggers apoptotic activity.

25. The isolated protein of claim 23, wherein the AB loop consists of the amino acid sequence of SEQ ID NO: 191, the CD loop consists of the amino acid sequence of SEQ ID NO: 241 and the EF loop consists of the amino acid sequence of SEQ ID NO: 370.

26. The isolated protein of claim 25, which triggers apoptotic activity.

27. The isolated protein of claim 13, wherein the polypeptides are connected by 2 disulfide bonds, and wherein the CH2 domain comprises the amino acid sequence of the CH2 domain of SEQ ID NO: 1 and the CH3 domain comprises the amino acid sequence of the CH3 domain of SEQ ID NO: 1 or SEQ ID NO: 440 exclusive of that of loops AB and EF.

28. The isolated protein of claim 27, which triggers apoptotic activity.

29. The isolated protein of claim 27, wherein the AB loop consists of the amino acid sequence of SEQ ID NO: 191, the CD loop consists of the amino acid sequence of SEQ ID NO: 241 and the EF loop consists of the amino acid sequence of SEQ ID NO: 370.

30. The isolated protein of claim 29, which triggers apoptotic activity.

* * * * *

SEQUENCE LISTING

```
<160> NUMBER OF SEQ ID NOS: 448

<210> SEQ ID NO 1
<211> LENGTH: 232
<212> TYPE: PRT
<213> ORGANISM: human

<400> SEQUENCE: 1

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 2
<211> LENGTH: 237
<212> TYPE: PRT
<213> ORGANISM: artificial
<220> FEATURE:
<223> OTHER INFORMATION: human IgG including randomized amino acid
      modifications
<220> FEATURE:
<221> NAME/KEY: misc_feature
<222> LOCATION: (144)..(146)
<223> OTHER INFORMATION: Xaa can be any naturally occurring amino acid
<220> FEATURE:
<221> NAME/KEY: misc_feature
<222> LOCATION: (198)..(205)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid

<400> SEQUENCE: 2

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Xaa
    130                 135                 140

Xaa Xaa Gln Val Ser Leu Thr Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Xaa Xaa Xaa Xaa Xaa Xaa Xaa Xaa Arg Trp Xaa
        195                 200                 205

Xaa Gly Asn Val Phe Ser Cys Ser Val Met His Glu Ala Leu His Asn
    210                 215                 220

His Tyr Thr Gln Lys Ser Leu Ser Leu Ser Pro Gly Lys
225                 230                 235


<210> SEQ ID NO 3
<211> LENGTH: 728
<212> TYPE: DNA
<213> ORGANISM: artificial
<220> FEATURE:
<223> OTHER INFORMATION: DNA Sequence for Cloning of modified IgG
      (engineered sequence)
<220> FEATURE:
<221> NAME/KEY: misc_feature
<222> LOCATION: (438)..(439)
<223> OTHER INFORMATION: n is a, c, g, or t
<220> FEATURE:
<221> NAME/KEY: misc_feature
<222> LOCATION: (441)..(442)
<223> OTHER INFORMATION: n is a, c, g, or t
<220> FEATURE:
<221> NAME/KEY: misc_feature
<222> LOCATION: (444)..(445)
<223> OTHER INFORMATION: n is a, c, g, or t
<220> FEATURE:
<221> NAME/KEY: misc_feature
<222> LOCATION: (600)..(601)
<223> OTHER INFORMATION: n is a, c, g, or t
<220> FEATURE:
<221> NAME/KEY: misc_feature
<222> LOCATION: (603)..(604)
<223> OTHER INFORMATION: n is a, c, g, or t
<220> FEATURE:
<221> NAME/KEY: misc_feature
<222> LOCATION: (606)..(607)
<223> OTHER INFORMATION: n is a, c, g, or t
<220> FEATURE:
<221> NAME/KEY: misc_feature
<222> LOCATION: (609)..(610)
<223> OTHER INFORMATION: n is a, c, g, or t
<220> FEATURE:
<221> NAME/KEY: misc_feature
<222> LOCATION: (612)..(613)
<223> OTHER INFORMATION: n is a, c, g, or t
<220> FEATURE:
<221> NAME/KEY: misc_feature
<222> LOCATION: (615)..(616)
<223> OTHER INFORMATION: n is a, c, g, or t
<220> FEATURE:
<221> NAME/KEY: misc_feature
<222> LOCATION: (618)..(619)
<223> OTHER INFORMATION: n is a, c, g, or t
<220> FEATURE:
<221> NAME/KEY: misc_feature
<222> LOCATION: (621)..(622)
<223> OTHER INFORMATION: n is a, c, g, or t
<220> FEATURE:
<221> NAME/KEY: misc_feature
<222> LOCATION: (630)..(631)
<223> OTHER INFORMATION: n is a, c, g, or t
<220> FEATURE:
<221> NAME/KEY: misc_feature
<222> LOCATION: (633)..(634)
<223> OTHER INFORMATION: n is a, c, g, or t

<400> SEQUENCE: 3
```

```
ccatggccga gcccaaatct tgtgacaaaa ctcacacatg cccaccgtgc ccagcacctg     60

aactcctggg gggaccgtca gtcttcctct tcccccaaaa acccaaggac accctcatga    120

tctcccggac ccctgaggtc acatgcgtgg tggtggacgt gagccacgaa gaccctgagg    180

tcaagttcaa ctggtacgtg gacggcgtgg aggtgcataa tgccaagaca aagccgcggg    240

aggagcagta caacagcacg taccgtgtgg tcagcgtcct caccgtcctg caccaggact    300

ggctgaatgg caaggagtac aagtgcaagg tctccaacaa agccctccca gcccccatcg    360

agaaaaccat ctccaaagcc aaagggcagc ctcgagaacc acaggtgtac accctgcccc    420

catcccgtga cgagctcnns nnsnnscaag tcagcctgac ctgcctggtc aaaggcttct    480

atcccagcga catcgccgtg gagtgggaga gcaatgggca gccggagaac aactacaaga    540

ccacgcctcc cgtgctggac tccgacggct ccttcttcct ctacagcaag cttaccgtgn    600

nsnnsnnsnn snnsnnsnns nnsaggtggn nsnnsgggaa cgtcttctca tgctccgtga    660

tgcatgaggc tctgcacaac cactacacac agaagagcct ctccctgtct ccgggtaaag    720

cggccgca                                                             728
```

<210> SEQ ID NO 4
<211> LENGTH: 33
<212> TYPE: DNA
<213> ORGANISM: artificial
<220> FEATURE:
<223> OTHER INFORMATION: PCR primer EPKSNCO

<400> SEQUENCE: 4

```
ccatggccga gcccaaatct tgtgacaaaa ctc                                  33
```

<210> SEQ ID NO 5
<211> LENGTH: 30
<212> TYPE: DNA
<213> ORGANISM: artificial
<220> FEATURE:
<223> OTHER INFORMATION: PCR primer CH3LSAC

<400> SEQUENCE: 5

```
agtcgagctc gtcacgggat gggggcaggg                                      30
```

<210> SEQ ID NO 6
<211> LENGTH: 41
<212> TYPE: DNA
<213> ORGANISM: artificial
<220> FEATURE:
<223> OTHER INFORMATION: PCR primer CH3CSAC
<220> FEATURE:
<221> NAME/KEY: misc_feature
<222> LOCATION: (11)..(12)
<223> OTHER INFORMATION: n is a, c, g, or t
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 6

```
gtacgagctc nnsnnsnnsc aagtcagcct gacctgcctg g                         41
```

<210> SEQ ID NO 7
<211> LENGTH: 32
<212> TYPE: DNA
<213> ORGANISM: artificial

<220> FEATURE:
<223> OTHER INFORMATION: PCR primer CH3CHIN

<400> SEQUENCE: 7
tgccaagctt gctgtagagg aagaaggagc cg 32

<210> SEQ ID NO 8
<211> LENGTH: 59
<212> TYPE: DNA
<213> ORGANISM: artificial
<220> FEATURE:
<223> OTHER INFORMATION: PCR primer CH3RHIN
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t

<400> SEQUENCE: 8
tgccaagctt accgtgnnsn nsnnsaggtg gnnsnnsggg aacgtcttct catgctccg 59

<210> SEQ ID NO 9
<211> LENGTH: 33
<212> TYPE: DNA
<213> ORGANISM: artificial
<220> FEATURE:
<223> OTHER INFORMATION: PCR primer CH3RNOT

<400> SEQUENCE: 9
agttgcggcc gctttacccg gagacaggga gag 33

<210> SEQ ID NO 10
<211> LENGTH: 25
<212> TYPE: PRT
<213> ORGANISM: artificial
<220> FEATURE:
<223> OTHER INFORMATION: junction region

<400> SEQUENCE: 10

Ser Pro Gly Lys Ala Ala Ala Glu Gln Lys Leu Ile Ser Glu Glu Asp
1 5 10 15

Leu Asn Gly Ala Ala Thr Val Glu Ser
20 25

<210> SEQ ID NO 11
<211> LENGTH: 662
<212> TYPE: PRT
<213> ORGANISM: artificial
<220> FEATURE:
<223> OTHER INFORMATION: amino acid sequence of FcabRGD4L

<400> SEQUENCE: 11

Glu Pro Lys Ser Cys Asp Lys Thr His Thr Cys Pro Pro Cys Pro Ala
1 5 10 15

-continued

```
Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Gly Cys Arg Gly Asp Cys Leu Ser Arg Trp Gln
        195                 200                 205

Gln Gly Asn Val Phe Ser Cys Ser Val Met His Glu Ala Leu His Asn
    210                 215                 220

His Tyr Thr Gln Lys Ser Leu Ser Leu Ser Pro Gly Lys Glu Gly Gly
225                 230                 235                 240

Gly Ser Ala Ala Ala Glu Gln Lys Leu Ile Ser Glu Glu Asp Leu Asn
                245                 250                 255

Gly Ala Ala Thr Val Glu Ser Cys Leu Ala Lys Pro His Thr Glu Asn
            260                 265                 270

Ser Phe Thr Asn Val Trp Lys Asp Asp Lys Thr Leu Asp Arg Tyr Ala
        275                 280                 285

Asn Tyr Glu Gly Cys Leu Trp Asn Ala Thr Gly Val Val Val Cys Thr
    290                 295                 300

Gly Asp Glu Thr Gln Cys Tyr Gly Thr Trp Val Pro Ile Gly Leu Ala
305                 310                 315                 320

Ile Pro Glu Asn Glu Gly Gly Gly Ser Glu Gly Gly Gly Ser Glu Gly
                325                 330                 335

Gly Gly Ser Glu Gly Gly Gly Thr Lys Pro Pro Glu Tyr Gly Asp Thr
            340                 345                 350

Pro Ile Pro Gly Tyr Thr Tyr Ile Asn Pro Leu Asp Gly Thr Tyr Pro
        355                 360                 365

Pro Gly Thr Glu Gln Asn Pro Ala Asn Pro Asn Pro Ser Leu Glu Glu
    370                 375                 380

Ser Gln Pro Leu Asn Thr Phe Met Phe Gln Asn Asn Arg Phe Arg Asn
385                 390                 395                 400

Arg Gln Gly Ala Leu Thr Val Tyr Thr Gly Thr Val Thr Gln Gly Thr
                405                 410                 415

Asp Pro Val Lys Thr Tyr Tyr Gln Tyr Thr Pro Val Ser Ser Lys Ala
            420                 425                 430
```

```
Met Tyr Asp Ala Tyr Trp Asn Gly Lys Phe Arg Asp Cys Ala Phe His
        435                 440                 445

Ser Gly Phe Asn Glu Asp Pro Phe Val Cys Glu Tyr Gln Gly Gln Ser
    450                 455                 460

Ser Asp Leu Pro Gln Pro Pro Val Asn Ala Gly Gly Gly Ser Gly Gly
465                 470                 475                 480

Gly Ser Gly Gly Gly Ser Glu Gly Gly Gly Ser Glu Gly Gly Gly Ser
                485                 490                 495

Glu Gly Gly Gly Ser Glu Gly Gly Gly Ser Gly Gly Gly Ser Gly Ser
            500                 505                 510

Gly Asp Phe Asp Tyr Glu Lys Met Ala Asn Ala Asn Lys Gly Ala Met
        515                 520                 525

Thr Glu Asn Ala Asp Glu Asn Ala Leu Gln Ser Asp Ala Lys Gly Lys
    530                 535                 540

Leu Asp Ser Val Ala Thr Asp Tyr Gly Ala Ala Ile Asp Gly Phe Ile
545                 550                 555                 560

Gly Asp Val Ser Gly Leu Ala Asn Gly Asn Gly Ala Thr Gly Asp Phe
                565                 570                 575

Ala Gly Ser Asn Ser Gln Met Ala Gln Val Gly Asp Gly Asp Asn Ser
            580                 585                 590

Pro Leu Met Asn Asn Phe Arg Gln Tyr Leu Pro Ser Leu Pro Gln Ser
        595                 600                 605

Val Glu Cys Arg Pro Tyr Val Phe Gly Ala Gly Lys Pro Tyr Glu Phe
    610                 615                 620

Ser Ile Asp Cys Asp Lys Ile Asn Leu Phe Arg Gly Val Phe Ala Phe
625                 630                 635                 640

Leu Leu Tyr Val Ala Thr Phe Met Tyr Val Phe Ser Thr Phe Ala Asn
                645                 650                 655

Ile Leu His Lys Glu Ser
            660
```

<210> SEQ ID NO 12
<211> LENGTH: 5200
<212> TYPE: DNA
<213> ORGANISM: artificial
<220> FEATURE:
<223> OTHER INFORMATION: vector pHENFcabRGD4

<400> SEQUENCE: 12

```
gacgaaaggg cctcgtgata cgcctatttt tataggttaa tgtcatgata ataatggttt      60

cttagacgtc aggtggcact tttcggggaa atgtgcgcgg aacccctatt tgtttatttt     120

tctaaataca ttcaaatatg tatccgctca tgagacaata accctgataa atgcttcaat     180

aatattgaaa aaggaagagt atgagtattc aacatttccg tgtcgccctt attccctttt     240

ttgcggcatt ttgccttcct gtttttgctc acccagaaac gctggtgaaa gtaaaagatg     300

ctgaagatca gttgggtgca cgagtgggtt acatcgaact ggatctcaac agcggtaaga     360

tccttgagag ttttcgcccc gaagaacgtt ttccaatgat gagcactttt aaagttctgc     420

tatgtggcgc ggtattatcc cgtattgacg ccgggcaaga gcaactcggt cgccgcatac     480

actattctca gaatgacttg gttgagtact caccagtcac agaaaagcat cttacggatg     540

gcatgacagt aagagaatta tgcagtgctg ccataaccat gagtgataac actgcggcca     600

acttacttct gacaacgatc ggaggaccga aggagctaac cgcttttttg cacaacatgg     660

gggatcatgt aactcgcctt gatcgttggg aaccggagct gaatgaagcc ataccaaacg     720
```

```
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt aagcttgcat gcaaattcta tttcaaggag acagtcataa   2280
tgaaatacct attgcctacg gcagccgctg gattgttatt actcgcggcc cagccggcca   2340
tggccgagcc caaatcttgt gacaaaactc acacatgccc accgtgccca gcacctgaac   2400
tcctgggggg accgtcagtc ttcctcttcc ccccaaaacc caaggacacc ctcatgatct   2460
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtgggtt   2940
gccgcggtga ttgtctgagc aggtggcagc aggggaacgt cttctcatgc tccgtgatgc   3000
atgaggctct gcacaaccac tacacgcaga agagcctctc cctgtctccg ggtaaagcgg   3060
ccgcagaaca aaaactcatc tcagaagagg atctgaatgg ggccgcatag actgttgaaa   3120
```

```
gttgtttagc aaaacctcat acagaaaatt catttactaa cgtctggaaa gacgacaaaa   3180

ctttagatcg ttacgctaac tatgagggct gtctgtggaa tgctacaggc gttgtggttt   3240

gtactggtga cgaaactcag tgttacggta catgggttcc tattgggctt gctatccctg   3300

aaaatgaggg tggtggctct gagggtggcg gttctgaggg tggcggttct gagggtggcg   3360

gtactaaacc tcctgagtac ggtgatacac ctattccggg ctatacttat atcaaccctc   3420

tcgacggcac ttatccgcct ggtactgagc aaaaccccgc taatcctaat ccttctcttg   3480

aggagtctca gcctcttaat actttcatgt ttcagaataa taggttccga aataggcagg   3540

gtgcattaac tgtttatacg ggcactgtta ctcaaggcac tgaccccgtt aaaacttatt   3600

accagtacac tcctgtatca tcaaaagcca tgtatgacgc ttactggaac ggtaaattca   3660

gagactgcgc tttccattct ggctttaatg aggatccatt cgtttgtgaa tatcaaggcc   3720

aatcgtctga cctgcctcaa cctcctgtca atgctggcgg cggctctggt ggtggttctg   3780

gtggcggctc tgagggtggc ggctctgagg gtggcggttc tgagggtggc ggctctgagg   3840

gtggcggttc cggtggcggc tccggttccg gtgattttga ttatgaaaaa atggcaaacg   3900

ctaataaggg ggctatgacc gaaaatgccg atgaaaacgc gctacagtct gacgctaaag   3960

gcaaacttga ttctgtcgct actgattacg gtgctgctat cgatggtttc attggtgacg   4020

tttccggcct tgctaatggt aatggtgcta ctggtgattt tgctggctct aattcccaaa   4080

tggctcaagt cggtgacggt gataattcac ctttaatgaa taatttccgt caatatttac   4140

cttctttgcc tcagtcggtt gaatgtcgcc cttatgtctt tggcgctggt aaaccatatg   4200

aattttctat tgattgtgac aaaataaact tattccgtgg tgtctttgcg tttcttttat   4260

atgttgccac ctttatgtat gtattttcga cgtttgctaa catactgcat aaggagtctt   4320

aataagaatt cactggccgt cgttttacaa cgtcgtgact gggaaaaccc tggcgttacc   4380

caacttaatc gccttgcagc acatccccct ttcgccagct ggcgtaatag cgaagaggcc   4440

cgcaccgatc gcccttccca acagttgcgc agcctgaatg gcgaatggcg cctgatgcgg   4500

tattttctcc ttacgcatct gtgcggtatt tcacaccgca cgtcaaagca accatagtac   4560

gcgccctgta gcggcgcatt aagcgcggcg ggtgtggtgg ttacgcgcag cgtgaccgct   4620

acacttgcca gcgccctagc gcccgctcct ttcgctttct tcccttcctt tctcgccacg   4680

ttcgccggct ttccccgtca agctctaaat cgggggctcc ctttagggtt ccgatttagt   4740

gctttacggc acctcgaccc caaaaaactt gatttgggtg atggttcacg tagtgggcca   4800

tcgccctgat agacggtttt tcgccctttg acgttggagt ccacgttctt taatagtgga   4860

ctcttgttcc aaactggaac aacactcaac cctatctcgg gctattcttt tgatttataa   4920

gggattttgc cgatttcggc ctattggtta aaaaatgagc tgatttaaca aaaatttaac   4980

gcgaatttta acaaaatatt aacgtttaca attttatggt gcactctcag tacaatctgc   5040

tctgatgccg catagttaag ccagccccga cacccgccaa cacccgctga cgcgccctga   5100

cgggcttgtc tgctcccggc atccgcttac agacaagctg tgaccgtctc cgggagctgc   5160

atgtgtcaga ggttttcacc gtcatcaccg aaacgcgcga                         5200
```

<210> SEQ ID NO 13
<211> LENGTH: 48
<212> TYPE: DNA
<213> ORGANISM: artificial
<220> FEATURE:
<223> OTHER INFORMATION: CH3rlink

<400> SEQUENCE: 13

```
actagcggcc gcagagccac caccctcctt acccggagac agggagag                48
```

<210> SEQ ID NO 14
<211> LENGTH: 5215
<212> TYPE: DNA
<213> ORGANISM: artificial
<220> FEATURE:
<223> OTHER INFORMATION: vector pHENFcabRGD4L

<400> SEQUENCE: 14

```
gacgaaaggg cctcgtgata cgcctatttt tataggttaa tgtcatgata ataatggttt     60
cttagacgtc aggtggcact tttcggggaa atgtgcgcgg aacccctatt tgtttatttt    120
tctaaataca ttcaaatatg tatccgctca tgagacaata accctgataa atgcttcaat    180
aatattgaaa aaggaagagt atgagtattc aacatttccg tgtcgccctt attccctttt    240
ttgcggcatt ttgccttcct gtttttgctc acccagaaac gctggtgaaa gtaaaagatg    300
ctgaagatca gttgggtgca cgagtgggtt acatcgaact ggatctcaac agcggtaaga    360
tccttgagag ttttcgcccc gaagaacgtt ttccaatgat gagcactttt aaagttctgc    420
tatgtggcgc ggtattatcc cgtattgacg ccgggcaaga gcaactcggt cgccgcatac    480
actattctca gaatgacttg gttgagtact caccagtcac agaaaagcat cttacggatg    540
gcatgacagt aagagaatta tgcagtgctg ccataaccat gagtgataac actgcggcca    600
acttacttct gacaacgatc ggaggaccga aggagctaac cgcttttttg cacaacatgg    660
gggatcatgt aactcgcctt gatcgttggg aaccggagct gaatgaagcc ataccaaacg    720
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc atttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc tttttttctg cgcgtaatct   1260
gctgcttgca aacaaaaaaa ccaccgctac cagcggtggt ttgtttgccg gatcaagagc   1320
taccaactct ttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg gtcgggctga acggggggtt   1560
cgtgcacaca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg atttttgtga tgctcgtcag   1800
gggggcggag cctatggaaa aacgccagca acgcggcctt tttacggttc ctggcctttt   1860
gctggccttt tgctcacatg ttctttcctg cgttatcccc tgattctgtg gataaccgta   1920
ttaccgcctt tgagtgagct gataccgctc gccgcagccg aacgaccgag cgcagcgagt   1980
```

```
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt aagcttgcat gcaaattcta tttcaaggag acagtcataa   2280
tgaaatacct attgcctacg gcagccgctg gattgttatt actcgcggcc cagccggcca   2340
tggccgagcc caaatcttgt gacaaaactc acacatgccc accgtgccca gcacctgaac   2400
tcctgggggg accgtcagtc ttcctcttcc ccccaaaacc caaggacacc ctcatgatct   2460
cccggacccc tgaggtcaca tgcgtggtgg tggacgtgag ccacgaagac cctgaggtca   2520
agttcaactg gtacgtggac ggcgtggagg tgcataatgc caagacaaag ccgcgggagg   2580
agcagtacaa cagcacgtac cgtgtggtca gcgtcctcac cgtcctgcac caggactggc   2640
tgaatggcaa ggagtacaag tgcaaggtct ccaacaaagc cctcccagcc cccatcgaga   2700
aaaccatctc caaagccaaa gggcagcccc gagaaccaca ggtgtacacc ctgcccccat   2760
cccgggatga gctgaccaag aaccaggtca gcctgacctg cctggtcaaa ggcttctatc   2820
ccagcgacat cgccgtggag tgggagagca atgggcagcc ggagaacaac tacaagacca   2880
cgcctcccgt gctggactcc gacggctcct tcttcctcta cagcaagctt accgtgggtt   2940
gccgcggtga ttgtctgagc aggtggcagc aggggaacgt cttctcatgc tccgtgatgc   3000
atgaggctct gcacaaccac tacacgcaga agagcctctc cctgtctccg ggtaaggagg   3060
gtggtggctc tgcggccgca gaacaaaaac tcatctcaga agaggatctg aatggggccg   3120
catagactgt tgaaagttgt ttagcaaaac ctcatacaga aaattcattt actaacgtct   3180
ggaaagacga caaaacttta gatcgttacg ctaactatga gggctgtctg tggaatgcta   3240
caggcgttgt ggtttgtact ggtgacgaaa ctcagtgtta cggtacatgg gttcctattg   3300
ggcttgctat ccctgaaaat gagggtggtg gctctgaggg tggcggttct gagggtggcg   3360
gttctgaggg tggcggtact aaacctcctg agtacggtga tacacctatt ccgggctata   3420
cttatatcaa ccctctcgac ggcacttatc cgcctggtac tgagcaaaac cccgctaatc   3480
ctaatccttc tcttgaggag tctcagcctc ttaatacttt catgtttcag aataataggt   3540
tccgaaatag gcagggtgca ttaactgttt atacgggcac tgttactcaa ggcactgacc   3600
ccgttaaaac ttattaccag tacactcctg tatcatcaaa agccatgtat gacgcttact   3660
ggaacggtaa attcagagac tgcgctttcc attctggctt taatgaggat ccattcgttt   3720
gtgaatatca aggccaatcg tctgacctgc ctcaacctcc tgtcaatgct ggcggcggct   3780
ctggtggtgg ttctggtggc ggctctgagg gtggcggctc tgagggtggc ggttctgagg   3840
gtggcggctc tgagggtggc ggttccggtg gcggctccgg ttccggtgat tttgattatg   3900
aaaaaatggc aaacgctaat aagggggcta tgaccgaaaa tgccgatgaa aacgcgctac   3960
agtctgacgc taaaggcaaa cttgattctg tcgctactga ttacggtgct gctatcgatg   4020
gtttcattgg tgacgtttcc ggccttgcta atggtaatgg tgctactggt gattttgctg   4080
gctctaattc ccaaatggct caagtcggtg acggtgataa ttcaccttta atgaataatt   4140
tccgtcaata tttaccttct ttgcctcagt cggttgaatg tcgcccttat gtctttggcg   4200
ctggtaaacc atatgaattt tctattgatt gtgacaaaat aaacttattc cgtggtgtct   4260
ttgcgtttct tttatatgtt gccaccttta tgtatgtatt ttcgacgttt gctaacatac   4320
```

```
tgcataagga gtcttaataa gaattcactg gccgtcgttt tacaacgtcg tgactgggaa   4380

aaccctggcg ttacccaact taatcgcctt gcagcacatc ccccttttcgc cagctggcgt   4440

aatagcgaag aggcccgcac cgatcgccct tcccaacagt tgcgcagcct gaatggcgaa   4500

tggcgcctga tgcggtattt tctccttacg catctgtgcg gtatttcaca ccgcacgtca   4560

aagcaaccat agtacgcgcc ctgtagcggc gcattaagcg cggcgggtgt ggtggttacg   4620

cgcagcgtga ccgctacact tgccagcgcc ctagcgcccg ctcctttcgc tttcttccct   4680

tcctttctcg ccacgttcgc cggctttccc cgtcaagctc taaatcgggg gctcccttta   4740

gggttccgat ttagtgcttt acggcacctc gaccccaaaa aacttgattt gggtgatggt   4800

tcacgtagtg ggccatcgcc ctgatagacg gtttttcgcc ctttgacgtt ggagtccacg   4860

ttctttaata gtggactctt gttccaaact ggaacaacac tcaaccctat ctcgggctat   4920

tcttttgatt tataagggat tttgccgatt tcggcctatt ggttaaaaaa tgagctgatt   4980

taacaaaaat ttaacgcgaa ttttaacaaa atattaacgt ttacaatttt atggtgcact   5040

ctcagtacaa tctgctctga tgccgcatag ttaagccagc cccgacaccc gccaacaccc   5100

gctgacgcgc cctgacgggc ttgtctgctc ccggcatccg cttacagaca agctgtgacc   5160

gtctccggga gctgcatgtg tcagaggttt tcaccgtcat caccgaaacg cgcga        5215
```

```
<210> SEQ ID NO 15
<211> LENGTH: 5013
<212> TYPE: DNA
<213> ORGANISM: artificial
<220> FEATURE:
<223> OTHER INFORMATION: vector pYD1dX

<400> SEQUENCE: 15
```

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt tttagcacag gaactgacaa    600

ctatatgcga gcaaatcccc tcaccaactt tagaatcgac gccgtactct ttgtcaacga    660

ctactatttt ggccaacggg aaggcaatgc aaggagtttt tgaatattac aaatcagtaa    720

cgtttgtcag taattgcggt tctcacccct caacaactag caaaggcagc cccataaaca    780

cacagtatgt ttttaagctt ctgcaggcta gtggtggtgg tggttctggt ggtggtggtt    840

ctggtggtgg tggttctgct agcatgactg gtggacagca aatgggtcgg gatctgtacg    900

acgatgacga taaggtacca ggatccagtg tggtggaatt ctgcagatat ccagcacagt    960

ggcggccgct cgatcgagtc tagagggccc ttcgaaggta agcctatccc taaccctctc   1020

ctcggtctcg attctacgcg taccggtcat catcaccatc accattgagt ttaaacccgc   1080

tgatctgata acaacagtgt agatgtaaca aaatcgactt tgttcccact gtacttttag   1140

ctcgtacaaa atacaatata cttttcattt ctccgtaaac aacatgtttt cccatgtaat   1200
```

```
atccttttct atttttcgtt ccgttaccaa ctttacacat actttatata gctattcact   1260
tctatacact aaaaaactaa gacaatttta attttgctgc ctgccatatt tcaatttgtt   1320
ataaattcct ataatttatc ctattagtag ctaaaaaaag atgaatgtga atcgaatcct   1380
aagagaattg ggcaagtgca caaacaatac ttaaataaat actactcagt aataacctat   1440
ttcttagcat ttttgacgaa atttgctatt ttgttagagt cttttacacc atttgtctcc   1500
acacctccgc ttacatcaac accaataacg ccatttaatc taagcgcatc accaacattt   1560
tctggcgtca gtccaccagc taacataaaa tgtaagctct cggggctctc ttgccttcca   1620
acccagtcag aaatcgagtt ccaatccaaa agttcacctg tcccacctgc ttctgaatca   1680
aacaagggaa taaacgaatg aggtttctgt gaagctgcac tgagtagtat gttgcagtct   1740
tttggaaata cgagtctttt aataactggc aaaccgagga actcttggta ttcttgccac   1800
gactcatctc cgtgcagttg gacgatatca atgccgtaat cattgaccag agccaaaaca   1860
tcctccttag gttgattacg aaacacgcca accaagtatt tcggagtgcc tgaactattt   1920
ttatatgctt ttacaagact tgaaattttc cttgcaataa ccgggtcaat tgttctcttt   1980
ctattgggca cacatataat acccagcaag tcagcatcgg aatctagagc acattctgcg   2040
gcctctgtgc tctgcaagcc gcaaactttc accaatggac cagaactacc tgtgaaatta   2100
ataacagaca tactccaagc tgcctttgtg tgcttaatca cgtatactca cgtgctcaat   2160
agtcaccaat gccctccctc ttggccctct cctttcttt tttcgaccga atttcttgaa   2220
gacgaaaggg cctcgtgata cgcctatttt tataggttaa tgtcatgata ataatggttt   2280
cttaggacgg atcgcttgcc tgtaacttac acgcgcctcg tatcttttaa tgatggaata   2340
atttgggaat ttactctgtg tttatttatt tttatgtttt gtatttggat tttagaaagt   2400
aaataaagaa ggtagaagag ttacggaatg aagaaaaaaa aataaacaaa ggtttaaaaa   2460
atttcaacaa aaagcgtact ttacatatat atttattaga caagaaaagc agattaaata   2520
gatatacatt cgattaacga taagtaaaat gtaaaatcac aggattttcg tgtgtggtct   2580
tctacacaga caagatgaaa caattcggca ttaatacctg agagcaggaa gagcaagata   2640
aaaggtagta tttgttggcg atccccctag agtcttttac atcttcggaa aacaaaaact   2700
atttttttctt taatttcttt ttttactttc tatttttaat ttatatattt atattaaaaa   2760
atttaaatta taattatttt tatagcacgt gatgaaaagg acccaggtgg cacttttcgg   2820
ggaaatgtgc gcggaacccc tatttgttta tttttctaaa tacattcaaa tatgtatccg   2880
ctcatgagac aataaccctg ataaatgctt caataatatt gaaaaaggaa gagtatgagt   2940
attcaacatt tccgtgtcgc ccttattccc ttttttgcgg cattttgcct tcctgttttt   3000
gctcacccag aaacgctggt gaaagtaaaa gatgctgaag atcagttggg tgcacgagtg   3060
ggttacatcg aactggatct caacagcggt aagatccttg agagttttcg ccccgaagaa   3120
cgttttccaa tgatgagcac ttttaaagtt ctgctatgtg gcgcggtatt atcccgtgtt   3180
gacgccgggc aagagcaact cggtcgccgc atacactatt ctcagaatga cttggttgag   3240
tactcaccag tcacagaaaa gcatcttacg gatggcatga cagtaagaga attatgcagt   3300
gctgccataa ccatgagtga taacactgcg gccaacttac ttctgacaac gatcggagga   3360
ccgaaggagc taaccgcttt tttgcacaac atgggggatc atgtaactcg ccttgatcgt   3420
tgggaaccgg agctgaatga agccatacca aacgacgagc gtgacaccac gatgcctgta   3480
gcaatggcaa caacgttgcg caaactatta actggcgaac tacttactct agcttcccgg   3540
```

```
caacaattaa tagactggat ggaggcggat aaagttgcag gaccacttct gcgctcggcc   3600
cttccggctg gctggtttat tgctgataaa tctggagccg gtgagcgtgg gtctcgcggt   3660
atcattgcag cactggggcc agatggtaag ccctcccgta tcgtagttat ctacacgacg   3720
ggcagtcagg caactatgga tgaacgaaat agacagatcg ctgagatagg tgcctcactg   3780
attaagcatt ggtaactgtc agaccaagtt tactcatata tactttagat tgatttaaaa   3840
cttcattttt aatttaaaag gatctaggtg aagatccttt ttgataatct catgaccaaa   3900
atcccttaac gtgagttttc gttccactga gcgtcagacc ccgtagaaaa gatcaaagga   3960
tcttcttgag atcctttttt tctgcgcgta atctgctgct tgcaaacaaa aaaaccaccg   4020
ctaccagcgg tggtttgttt gccggatcaa gagctaccaa ctctttttcc gaaggtaact   4080
ggcttcagca gagcgcagat accaaatact gtccttctag tgtagccgta gttaggccac   4140
cacttcaaga actctgtagc accgcctaca tacctcgctc tgctaatcct gttaccagtg   4200
gctgctgcca gtggcgataa gtcgtgtctt accgggttgg actcaagacg atagttaccg   4260
gataaggcgc agcggtcggg ctgaacgggg ggttcgtgca cacagcccag cttggagcga   4320
acgacctaca ccgaactgag atacctacag cgtgagcatt gagaaagcgc cacgcttccc   4380
gaagggagaa aggcggacag gtatccggta agcggcaggg tcggaacagg agagcgcacg   4440
agggagcttc cagggggaaa cgcctggtat ctttatagtc ctgtcgggtt tcgccacctc   4500
tgacttgagc gtcgattttt gtgatgctcg tcaggggggc cgagcctatg gaaaaacgcc   4560
agcaacgcgg cctttttacg gttcctggcc ttttgctggc cttttgctca catgttcttt   4620
cctgcgttat cccctgattc tgtggataac cgtattaccg cctttgagtg agctgatacc   4680
gctcgccgca gccgaacgac cgagcgcagc gagtcagtga gcgaggaagc ggaagagcgc   4740
ccaatacgca aaccgcctct ccccgcgcgt tggccgattc attaatgcag ctggcacgac   4800
aggtttcccg actggaaagc gggcagtgag cgcaacgcaa ttaatgtgag ttacctcact   4860
cattaggcac cccaggcttt acactttatg cttccggctc ctatgttgtg tggaattgtg   4920
agcggataac aatttcacac aggaaacagc tatgaccatg attacgccaa gctcggaatt   4980
aaccctcact aaagggaaca aaagctggct agt                                5013
```

<210> SEQ ID NO 16
<211> LENGTH: 5971
<212> TYPE: DNA
<213> ORGANISM: artificial
<220> FEATURE:
<223> OTHER INFORMATION: vector pYD1dXFc

<400> SEQUENCE: 16

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt tttagcacag gaactgacaa    600
```

```
ctatatgcga gcaaatcccc tcaccaactt tagaatcgac gccgtactct ttgtcaacga    660
ctactatttt ggccaacggg aaggcaatgc aaggagtttt tgaatattac aaatcagtaa    720
cgtttgtcag taattgcggt tctcacccct caacaactag caaaggcagc cccataaaca    780
cacagtatgt ttttaagctt ctgcaggcta gtggtggtgg tggttctggt ggtggtggtt    840
ctggtggtgg tggttctgct agcatgactg gtggacagca aatgggtcgg gatctgtacg    900
acgatgacga taaggtacca ggatccgcta gcaccaaggg ccccagcgtg ttccctctgg    960
cccccagctc caagagcacc tccggcggca ccgccgccct gggctgcctg gtgaaggatt   1020
acttcccaga gcccgtgacc gtgagctgga acagcggcgc cctgaccagc ggcgtgcaca   1080
cctttcccgc cgtgctgcag tccagcggcc tgtactccct gagcagcgtg gtgaccgtgc   1140
ccagcagcag cctgggcacc cagacctaca tctgcaatgt gaaccacaag cccagcaata   1200
ccaaggtgga taagaaggtg gagcccaaga gcagcgacaa gacacacacg tgtcccccat   1260
gtcccgcccc tgagctgctg ggcggccctt ccgtgttcct gttccctccc aagccaaagg   1320
acaccctgat gatctcccgg acccctgagg tgacctgtgt ggtggtggac gtgagccacg   1380
aggacccaga ggtgaagttc aactggtacg tggacggcgt ggaggtgcac aacgccaaga   1440
ccaagcctag agaggagcag tacaacagca cctaccgcgt ggtgagcgtg ctgaccgtgc   1500
tgcaccagga ttggctgaat ggcaaggagt acaagtgcaa ggtgagcaac aaggccctgc   1560
ctgcccccat cgagaagacc atctccaagg ccaagggcca gcctcgagaa ccacaggtgt   1620
acaccctgcc cccatcccgg gatgagctga ccaagaacca ggtcagcctg acctgcctgg   1680
tcaaaggctt ctatcccagc gacatcgccg tggagtggga gagcaatggg cagccggaga   1740
acaactacaa gaccacgcct cccgtgctgg actccgacgg ctccttcttc ctctacagca   1800
agctcaccgt ggacaagagc aggtggcagc aggggaacgt cttctcatgc tccgtgatgc   1860
atgaggctct gcacaaccac tacacacaga agagcctctc cctgtctccg ggtaaatgag   1920
cggccgctcg atcgagtcta gagggccctt cgaaggtaag cctatcccta accctctcct   1980
cggtctcgat tctacgcgta ccggtcatca tcaccatcac cattgagttt aaacccgctg   2040
atctgataac aacagtgtag atgtaacaaa atcgactttg ttcccactgt acttttagct   2100
cgtacaaaat acaatatact ttcatttct ccgtaaacaa catgttttcc catgtaatat   2160
ccttttctat ttttcgttcc gttaccaact ttacacatac tttatatagc tattcacttc   2220
tatacactaa aaaactaaga caattttaat tttgctgcct gccatatttc aatttgttat   2280
aaattcctat aatttatcct attagtagct aaaaaaagat gaatgtgaat cgaatcctaa   2340
gagaattggg caagtgcaca aacaatactt aaataaatac tactcagtaa taacctattt   2400
cttagcattt ttgacgaaat ttgctatttt gttagagtct tttacaccat ttgtctccac   2460
acctccgctt acatcaacac caataacgcc atttaatcta agcgcatcac caacattttc   2520
tggcgtcagt ccaccagcta acataaaatg taagctctcg ggctctcttt gccttccaac   2580
ccagtcagaa atcgagttcc aatccaaaag ttcacctgtc ccacctgctt ctgaatcaaa   2640
caagggaata aacgaatgag gtttctgtga agctgcactg agtagtatgt tgcagtcttt   2700
tggaaatacg agtcttttaa taactggcaa accgaggaac tcttggtatt cttgccacga   2760
ctcatctccg tgcagttgga cgatatcaat gccgtaatca ttgaccagag ccaaaacatc   2820
ctccttaggt tgattacgaa acacgccaac caagtatttc ggagtgcctg aactattttt   2880
atatgctttt acaagacttg aaattttcct tgcaataacc gggtcaattg ttctctttct   2940
```

```
attgggcaca catataatac ccagcaagtc agcatcggaa tctagagcac attctgcggc   3000
ctctgtgctc tgcaagccgc aaactttcac caatggacca gaactacctg tgaaattaat   3060
aacagacata ctccaagctg cctttgtgtg cttaatcacg tatactcacg tgctcaatag   3120
tcaccaatgc cctccctctt ggccctctcc ttttcttttt tcgaccgaat ttcttgaaga   3180
cgaaagggcc tcgtgatacg cctattttta taggttaatg tcatgataat aatggtttct   3240
taggacggat cgcttgcctg taacttacac gcgcctcgta tcttttaatg atggaataat   3300
ttgggaattt actctgtgtt tatttatttt tatgttttgt atttggattt tagaaagtaa   3360
ataaagaagg tagaagagtt acggaatgaa gaaaaaaaaa taaacaaagg tttaaaaaat   3420
ttcaacaaaa agcgtacttt acatatatat ttattagaca agaaaagcag attaaataga   3480
tatacattcg attaacgata agtaaaatgt aaaatcacag gattttcgtg tgtggtcttc   3540
tacacagaca agatgaaaca attcggcatt aatacctgag agcaggaaga gcaagataaa   3600
aggtagtatt tgttggcgat cccccctagag tcttttacat cttcggaaaa caaaaactat   3660
tttttcttta atttcttttt ttactttcta tttttaattt atatatttat attaaaaaat   3720
ttaaattata attattttta tagcacgtga tgaaaaggac ccaggtggca cttttcgggg   3780
aaatgtgcgc ggaaccccta tttgtttatt tttctaaata cattcaaata tgtatccgct   3840
catgagacaa taaccctgat aaatgcttca ataatattga aaaaggaaga gtatgagtat   3900
tcaacatttc cgtgtcgccc ttattccctt ttttgcggca ttttgccttc ctgtttttgc   3960
tcacccagaa acgctggtga aagtaaaaga tgctgaagat cagttgggtg cacgagtggg   4020
ttacatcgaa ctggatctca acagcggtaa gatccttgag agttttcgcc ccgaagaacg   4080
ttttccaatg atgagcactt ttaaagttct gctatgtggc gcggtattat cccgtgttga   4140
cgccgggcaa gagcaactcg gtcgccgcat acactattct cagaatgact tggttgagta   4200
ctcaccagtc acagaaaagc atcttacgga tggcatgaca gtaagagaat tatgcagtgc   4260
tgccataacc atgagtgata acactgcggc caacttactt ctgacaacga tcggaggacc   4320
gaaggagcta accgcttttt tgcacaacat gggggatcat gtaactcgcc ttgatcgttg   4380
ggaaccggag ctgaatgaag ccataccaaa cgacgagcgt gacaccacga tgcctgtagc   4440
aatggcaaca acgttgcgca aactattaac tggcgaacta cttactctag cttcccggca   4500
acaattaata gactggatgg aggcggataa agttgcagga ccacttctgc gctcggccct   4560
tccggctggc tggtttattg ctgataaatc tggagccggt gagcgtgggt ctcgcggtat   4620
cattgcagca ctggggccag atggtaagcc ctcccgtatc gtagttatct acacgacggg   4680
cagtcaggca actatggatg aacgaaatag acagatcgct gagataggtg cctcactgat   4740
taagcattgg taactgtcag accaagttta ctcatatata ctttagattg atttaaaact   4800
tcatttttaa tttaaaagga tctaggtgaa gatccttttt gataatctca tgaccaaaat   4860
cccttaacgt gagttttcgt tccactgagc gtcagacccc gtagaaaaga tcaaaggatc   4920
ttcttgagat cctttttttc tgcgcgtaat ctgctgcttg caaacaaaaa aaccaccgct   4980
accagcggtg gtttgtttgc cggatcaaga gctaccaact ctttttccga aggtaactgg   5040
cttcagcaga gcgcagatac caaatactgt ccttctagtg tagccgtagt taggccacca   5100
cttcaagaac tctgtagcac cgcctacata cctcgctctg ctaatcctgt taccagtggc   5160
tgctgccagt ggcgataagt cgtgtcttac cgggttggac tcaagacgat agttaccgga   5220
taaggcgcag cggtcgggct gaacgggggg ttcgtgcaca cagcccagct tggagcgaac   5280
gacctacacc gaactgagat acctacagcg tgagcattga gaaagcgcca cgcttcccga   5340
```

```
agggagaaag gcggacaggt atccggtaag cggcagggtc ggaacaggag agcgcacgag   5400

ggagcttcca gggggaaacg cctggtatct ttatagtcct gtcgggtttc gccacctctg   5460

acttgagcgt cgatttttgt gatgctcgtc aggggggcgg agcctatgga aaaacgccag   5520

caacgcggcc tttttacggt tcctggcctt ttgctggcct tttgctcaca tgttctttcc   5580

tgcgttatcc cctgattctg tggataaccg tattaccgcc tttgagtgag ctgataccgc   5640

tcgccgcagc cgaacgaccg agcgcagcga gtcagtgagc gaggaagcgg aagagcgccc   5700

aatacgcaaa ccgcctctcc ccgcgcgttg gccgattcat taatgcagct ggcacgacag   5760

gtttcccgac tggaaagcgg gcagtgagcg caacgcaatt aatgtgagtt acctcactca   5820

ttaggcaccc caggctttac actttatgct tccggctcct atgttgtgtg gaattgtgag   5880

cggataacaa tttcacacag gaaacagcta tgaccatgat tacgccaagc tcggaattaa   5940

ccctcactaa agggaacaaa agctggctag t                                  5971
```

```
<210> SEQ ID NO 17
<211> LENGTH: 5657
<212> TYPE: DNA
<213> ORGANISM: artificial
<220> FEATURE:
<223> OTHER INFORMATION: pYD1CH12

<400> SEQUENCE: 17
```

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt tttagcacag gaactgacaa    600

ctatatgcga gcaaatcccc tcaccaactt tagaatcgac gccgtactct ttgtcaacga    660

ctactatttt ggccaacggg aaggcaatgc aaggagtttt tgaatattac aaatcagtaa    720

cgtttgtcag taattgcggt tctcacccct caacaactag caaaggcagc cccataaaca    780

cacagtatgt tttaagctt ctgcaggcta gtggtggtgg tggttctggt ggtggtggtt    840

ctggtggtgg tggttctgct agcatgactg gtggacagca aatgggtcgg gatctgtacg    900

acgatgacga taaggtacca ggatccgcta gcaccaaggg ccccagcgtg ttccctctgg    960

cccccagctc caagagcacc tccggcggca ccgccgccct gggctgcctg gtgaaggatt   1020

acttcccaga gcccgtgacc gtgagctgga acagcggcgc cctgaccagc ggcgtgcaca   1080

cctttcccgc cgtgctgcag tccagcggcc tgtactccct gagcagcgtg gtgaccgtgc   1140

ccagcagcag cctgggcacc cagacctaca tctgcaatgt gaaccacaag cccagcaata   1200

ccaaggtgga taagaaggtg gagcccaaga gcagcgacaa gacacacacg tgtcccccat   1260

gtcccgcccc tgagctgctg ggcggccctt ccgtgttcct gttccctccc aagccaaagg   1320

acaccctgat gatctcccgg acccctgagg tgacctgtgt ggtggtggac gtgagccacg   1380
```

```
aggacccaga ggtgaagttc aactggtacg tggacggcgt ggaggtgcac aacgccaaga   1440
ccaagcctag agaggagcag tacaacagca cctaccgcgt ggtgagcgtg ctgaccgtgc   1500
tgcaccagga ttggctgaat ggcaaggagt acaagtgcaa ggtgagcaac aaggccctgc   1560
ctgcccccat cgagaagacc atctccaagg ccaagggcca gcctcgaggc cgctcgatcg   1620
agtctagagg gcccttcgaa ggtaagccta tccctaaccc tctcctcggt ctcgattcta   1680
cgcgtaccgg tcatcatcac catcaccatt gagtttaaac ccgctgatct gataacaaca   1740
gtgtagatgt aacaaaatcg actttgttcc cactgtactt ttagctcgta caaaatacaa   1800
tatacttttc atttctccgt aaacaacatg ttttcccatg taatatcctt ttctattttt   1860
cgttccgtta ccaactttac acatacttta tatagctatt cacttctata cactaaaaaa   1920
ctaagacaat tttaattttg ctgcctgcca tatttcaatt tgttataaat tcctataatt   1980
tatcctatta gtagctaaaa aaagatgaat gtgaatcgaa tcctaagaga attgggcaag   2040
tgcacaaaca atacttaaat aaatactact cagtaataac ctatttctta gcatttttga   2100
cgaaatttgc tattttgtta gagtctttta caccatttgt ctccacacct ccgcttacat   2160
caacaccaat aacgccattt aatctaagcg catcaccaac attttctggc gtcagtccac   2220
cagctaacat aaaatgtaag ctctcggggc tctcttgcct tccaacccag tcagaaatcg   2280
agttccaatc caaaagttca cctgtcccac ctgcttctga atcaaacaag ggaataaacg   2340
aatgaggttt ctgtgaagct gcactgagta gtatgttgca gtcttttgga aatacgagtc   2400
ttttaataac tggcaaaccg aggaactctt ggtattcttg ccacgactca tctccgtgca   2460
gttggacgat atcaatgccg taatcattga ccagagccaa aacatcctcc ttaggttgat   2520
tacgaaacac gccaaccaag tatttcggag tgcctgaact atttttatat gcttttacaa   2580
gacttgaaat tttccttgca ataaccgggt caattgttct ctttctattg ggcacacata   2640
taatacccag caagtcagca tcggaatcta gagcacattc tgcggcctct gtgctctgca   2700
agccgcaaac tttcaccaat ggaccagaac tacctgtgaa attaataaca gacatactcc   2760
aagctgcctt tgtgtgctta atcacgtata ctcacgtgct caatagtcac caatgccctc   2820
cctcttggcc ctctcctttt cttttttcga ccgaatttct tgaagacgaa agggcctcgt   2880
gatacgccta tttttatagg ttaatgtcat gataataatg gtttcttagg acggatcgct   2940
tgcctgtaac ttacacgcgc ctcgtatctt ttaatgatgg aataatttgg gaatttactc   3000
tgtgtttatt tatttttatg ttttgtattt ggattttaga aagtaaataa agaaggtaga   3060
agagttacgg aatgaagaaa aaaaaataaa caaaggttta aaaaatttca acaaaaagcg   3120
tactttacat atatatttat tagacaagaa aagcagatta aatagatata cattcgatta   3180
acgataagta aaatgtaaaa tcacaggatt ttcgtgtgtg gtcttctaca cagacaagat   3240
gaaacaattc ggcattaata cctgagagca ggaagagcaa gataaaaggt agtatttgtt   3300
ggcgatcccc ctagagtctt ttacatcttc ggaaaacaaa aactattttt tctttaattt   3360
ctttttttac tttctatttt taatttatat atttatatta aaaaatttaa attataatta   3420
tttttatagc acgtgatgaa aaggacccag gtggcacttt tcggggaaat gtgcgcggaa   3480
cccctatttg tttatttttc taaatacatt caaatatgta tccgctcatg agacaataac   3540
cctgataaat gcttcaataa tattgaaaaa ggaagagtat gagtattcaa catttccgtg   3600
tcgcccttat tccctttttt gcggcatttt gccttcctgt ttttgctcac ccagaaacgc   3660
tggtgaaagt aaaagatgct gaagatcagt tgggtgcacg agtgggttac atcgaactgg   3720
atctcaacag cggtaagatc cttgagagtt ttcgccccga agaacgtttt ccaatgatga   3780
```

```
gcacttttaa agttctgcta tgtggcgcgg tattatcccg tgttgacgcc gggcaagagc   3840

aactcggtcg ccgcatacac tattctcaga atgacttggt tgagtactca ccagtcacag   3900

aaaagcatct tacggatggc atgacagtaa gagaattatg cagtgctgcc ataaccatga   3960

gtgataacac tgcggccaac ttacttctga caacgatcgg aggaccgaag gagctaaccg   4020

cttttttgca caacatgggg gatcatgtaa ctcgccttga tcgttgggaa ccggagctga   4080

atgaagccat accaaacgac gagcgtgaca ccacgatgcc tgtagcaatg gcaacaacgt   4140

tgcgcaaact attaactggc gaactactta ctctagcttc ccggcaacaa ttaatagact   4200

ggatggaggc ggataaagtt gcaggaccac ttctgcgctc ggcccttccg gctggctggt   4260

ttattgctga taaatctgga gccggtgagc gtgggtctcg cggtatcatt gcagcactgg   4320

ggccagatgg taagccctcc cgtatcgtag ttatctacac gacggggcagt caggcaacta   4380

tggatgaacg aaatagacag atcgctgaga taggtgcctc actgattaag cattggtaac   4440

tgtcagacca agtttactca tatatacttt agattgattt aaaacttcat ttttaattta   4500

aaaggatcta ggtgaagatc ctttttgata atctcatgac caaaatccct taacgtgagt   4560

tttcgttcca ctgagcgtca gaccccgtag aaaagatcaa aggatcttct tgagatcctt   4620

tttttctgcg cgtaatctgc tgcttgcaaa caaaaaaacc accgctacca gcggtggttt   4680

gtttgccgga tcaagagcta ccaactcttt ttccgaaggt aactggcttc agcagagcgc   4740

agataccaaa tactgtcctt ctagtgtagc cgtagttagg ccaccacttc aagaactctg   4800

tagcaccgcc tacatacctc gctctgctaa tcctgttacc agtggctgct gccagtggcg   4860

ataagtcgtg tcttaccggg ttggactcaa gacgatagtt accggataag gcgcagcggt   4920

cgggctgaac ggggggttcg tgcacacagc ccagcttgga gcgaacgacc tacaccgaac   4980

tgagatacct acagcgtgag cattgagaaa gcgccacgct tcccgaaggg agaaaggcgg   5040

acaggtatcc ggtaagcggc agggtcggaa caggagagcg cacgagggag cttccagggg   5100

ggaacgcctg gtatctttat agtcctgtcg ggtttcgcca cctctgactt gagcgtcgat   5160

ttttgtgatg ctcgtcaggg gggcgagcc tatggaaaaa cgccagcaac gcggcctttt   5220

tacggttcct ggccttttgc tggccttttg ctcacatgtt ctttcctgcg ttatcccctg   5280

attctgtgga taaccgtatt accgcctttg agtgagctga taccgctcgc cgcagccgaa   5340

cgaccgagcg cagcgagtca gtgagcgagg aagcggaaga gcgcccaata cgcaaaccgc   5400

ctctccccgc gcgttggccg attcattaat gcagctggca cgacaggttt cccgactgga   5460

aagcgggcag tgagcgcaac gcaattaatg tgagttacct cactcattag gcaccccagg   5520

ctttacactt tatgcttccg gctcctatgt tgtgtggaat tgtgagcgga taacaatttc   5580

acacaggaaa cagctatgac catgattacg ccaagctcgg aattaaccct cactaaaggg   5640

aacaaaagct ggctagt                                                  5657
```

<210> SEQ ID NO 18
<211> LENGTH: 738
<212> TYPE: DNA
<213> ORGANISM: artificial
<220> FEATURE:
<223> OTHER INFORMATION: Fcab01
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)

<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 18

```
ggcccagccg gccatggccg agcccaaatc ttgtgacaaa actcacacat gcccaccgtg     60

cccagcacct gaactcctgg ggggaccgtc agtcttcctc ttccccccaa aacccaagga    120

caccctcatg atctcccgga cccctgaggt cacatgcgtg gtggtggacg tgagccacga    180

agaccctgag gtcaagttca actggtacgt ggacggcgtg gaggtgcata atgccaagac    240

aaagccgcgg gaggagcagt acaacagcac gtaccgtgtg gtcagcgtcc tcaccgtcct    300

gcaccaggac tggctgaatg gcaaggagta caagtgcaag gtctccaaca aagccctccc    360

agcccccatc gagaaaacca tctccaaagc caaagggcag cctcgagaac cacaggtgta    420

caccctgccc ccatcccggg atgaactgnn bnnbnnbcag gtcagcctga cctgcctggt    480

caaaggcttc tatcccagcg acatcgccgt ggagtgggag agcaatgggc agccggagaa    540

caactacaag accacgcctc ccgtgctgga ctccgacggc tccttcttcc tctacagcaa    600

gctcaccgtg nnbnnbnnbn nbnnbnnbnn bnnbaggtgg nnbnnbggga acgtcttctc    660

atgctccgtg atgcatgagg ctctgcacaa ccactacacg cagaagagcc tctccctgtc    720

tccgggtaaa gcggccgc                                                  738
```

<210> SEQ ID NO 19
<211> LENGTH: 738
<212> TYPE: DNA
<213> ORGANISM: artificial

<220> FEATURE:
<223> OTHER INFORMATION: Fcab02

<400> SEQUENCE: 19

```
ggcccagccg gccatggccg agcccaaatc ttgtgacaaa actcacacat gcccaccgtg     60

cccagcacct gaactcctgg ggggaccgtc agtcttcctc ttccccccaa aacccaagga    120

caccctcatg atctcccgga cccctgaggt cacatgcgtg gtggtggacg tgagccacga    180

agaccctgag gtcaagttca actggtacgt ggacggcgtg gaggtgcata atgccaagac    240

aaagccgcgg gaggagcagt acaacagcac gtaccgtgtg gtcagcgtcc tcaccgtcct    300

gcaccaggac tggctgaatg gcaaggagta caagtgcaag gtctccaaca aagccctccc    360

agcccccatc gagaaaacca tctccaaagc caaagggcag cctcgagaac cacaggtgta    420

caccctgccc ccatcccggg atgagctgkm tkmtkmtcag gtgagcctga cctgcctggt    480

caaaggcttc tatcccagcg acatcgccgt ggagtgggag agcaatgggc agccggagaa    540

caactacaag accacgcctc ccgtgctgga ctccgacggc tccttcttcc tctacagcaa    600

gctcaccgtg kmtkmtkmtk mtkmtkmtkm tkmtaggtgg kmtkmtggga acgtcttctc    660

atgctccgtg atgcatgagg ctctgcacaa ccactacacg cagaagagcc tctccctgtc    720

tccgggtaaa gcggccgc                                                  738
```

<210> SEQ ID NO 20
<211> LENGTH: 750
<212> TYPE: DNA
<213> ORGANISM: artificial
<220> FEATURE:
<223> OTHER INFORMATION: Fcab03
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (635)..(636)
<223> OTHER INFORMATION: n is a, c, g, or t
<220> FEATURE:

<221> NAME/KEY: misc_feature
<222> LOCATION: (638)..(639)
<223> OTHER INFORMATION: n is a, c, g, or t
<220> FEATURE:
<221> NAME/KEY: misc_feature
<222> LOCATION: (653)..(654)
<223> OTHER INFORMATION: n is a, c, g, or t
<220> FEATURE:
<221> NAME/KEY: misc_feature
<222> LOCATION: (656)..(657)
<223> OTHER INFORMATION: n is a, c, g, or t

<400> SEQUENCE: 20

```
ggcccagccg gccatggccg agcccaaatc ttgtgacaaa actcacacat gcccaccgtg     60

cccagcacct gaactcctgg ggggaccgtc agtcttcctc ttccccccaa aacccaagga    120

caccctcatg atctcccgga cccctgaggt cacatgcgtg gtggtggacg tgagccacga    180

agaccctgag gtcaagttca actggtacgt ggacggcgtg gaggtgcata atgccaagac    240

aaagccgcgg gaggagcagt acaacagcac gtaccgtgtg gtcagcgtcc tcaccgtcct    300

gcaccaggac tggctgaatg gcaaggagta caagtgcaag gtctccaaca aagccctccc    360

agcccccatc gagaaaacca tctccaaagc caaagggcag cctcgagaac cacaggtgta    420

caccctgccc ccttcccggg atgagctgnn bnnbnnbcag gtcagcctga cctgcctggt    480

caaaggcttc tatcccagcg acatcgccgt ggagtgggag agcaatgggc agccggagaa    540

caactacaag accacgcctc ccgtgctgga ctccgacggc tccttcttcc tctacagcaa    600

gctcaccgtg ggttctnnbn nbnnbnnbnn bnnbnnbnnb agcggcaggt ggnnbnnbgg    660

gaacgtcttc tcatgctccg tgatgcatga ggctctgcac aaccactaca cgcagaagag    720

cctctccctg tctccgggta aagcggccgc                                     750
```

<210> SEQ ID NO 21
<211> LENGTH: 750
<212> TYPE: DNA
<213> ORGANISM: artificial
<220> FEATURE:
<223> OTHER INFORMATION: Fcab04

<400> SEQUENCE: 21

```
ggcccagccg gccatggccg agcccaaatc ttgtgacaaa actcacacat gcccaccgtg     60

cccagcacct gaactcctgg ggggaccgtc agtcttcctc ttccccccaa aacccaagga    120

caccctcatg atctcccgga cccctgaggt cacatgcgtg gtggtggacg tgagccacga    180

agaccctgag gtcaagttca actggtacgt ggacggcgtg gaggtgcata atgccaagac    240

aaagccgcgg gaggagcagt acaacagcac gtaccgtgtg gtcagcgtcc tcaccgtcct    300

gcaccaggac tggctgaatg gcaaggagta caagtgcaag gtctccaaca aagccctccc    360

agcccccatc gagaaaacca tctccaaagc caaagggcag cctcgagaac cacaggtgta    420

caccctgccc ccatctcggg atgagctgkm tkmtkmtcag gtcagcctga cctgcctggt    480

caaaggcttc tatcccagcg acatcgccgt ggagtgggag agcaatgggc agccggagaa    540

caactacaag accacgcctc ccgtgctgga ctccgacggc tccttcttcc tctacagcaa    600

gctcaccgtg ggttctkmtk mtkmtkmtkm tkmtkmtkmt agcggcaggt ggkmtkmtgg    660

gaacgtcttc tcatgctccg tgatgcatga ggctctgcac aaccactaca cgcagaagag    720

cctctccctg tctccgggta aagcggccgc                                     750
```

<210> SEQ ID NO 22
<211> LENGTH: 738

<212> TYPE: DNA
<213> ORGANISM: artificial
<220> FEATURE:
<223> OTHER INFORMATION: Fcab05
<220> FEATURE:
<221> NAME/KEY: misc_feature
<222> LOCATION: (449)..(450)
<223> OTHER INFORMATION: n is a, c, g, or t
<220> FEATURE:
<221> NAME/KEY: misc_feature
<222> LOCATION: (452)..(453)
<223> OTHER INFORMATION: n is a, c, g, or t
<220> FEATURE:
<221> NAME/KEY: misc_feature
<222> LOCATION: (455)..(456)
<223> OTHER INFORMATION: n is a, c, g, or t
<220> FEATURE:
<221> NAME/KEY: misc_feature
<222> LOCATION: (611)..(612)
<223> OTHER INFORMATION: n is a, c, g, or t
<220> FEATURE:
<221> NAME/KEY: misc_feature
<222> LOCATION: (614)..(615)
<223> OTHER INFORMATION: n is a, c, g, or t
<220> FEATURE:
<221> NAME/KEY: misc_feature
<222> LOCATION: (617)..(618)
<223> OTHER INFORMATION: n is a, c, g, or t
<220> FEATURE:
<221> NAME/KEY: misc_feature
<222> LOCATION: (620)..(621)
<223> OTHER INFORMATION: n is a, c, g, or t
<220> FEATURE:
<221> NAME/KEY: misc_feature
<222> LOCATION: (623)..(624)
<223> OTHER INFORMATION: n is a, c, g, or t
<220> FEATURE:
<221> NAME/KEY: misc_feature
<222> LOCATION: (626)..(627)
<223> OTHER INFORMATION: n is a, c, g, or t
<220> FEATURE:
<221> NAME/KEY: misc_feature
<222> LOCATION: (629)..(630)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (641)..(642)
<223> OTHER INFORMATION: n is a, c, g, or t
<220> FEATURE:
<221> NAME/KEY: misc_feature
<222> LOCATION: (644)..(645)
<223> OTHER INFORMATION: n is a, c, g, or t

<400> SEQUENCE: 22
ggcccagccg gccatggccg agcccaaatc ttgtgacaaa actcacacat gcccaccgtg 60
cccagcacct gaactcctgg ggggaccgtc agtcttcctc ttccccccaa aacccaagga 120
caccctcatg atctcccgga cccctgaggt cacatgcgtg gtggtggacg tgagccacga 180
agaccctgag gtcaagttca actggtacgt ggacggcgtg gaggtgcata atgccaagac 240
aaagccgcgg gaggagcagt acaacagcac gtaccgtgtg gtcagcgtcc tcaccgtcct 300
gcaccaggac tggctgaatg gcaaggagta caagtgcaag gtctccaaca aagccctccc 360
agcccccatc gagaaaacca tctccaaagc caaagggcag cctcgagaac cacaggtgta 420
caccctgccc ccatcccgtg atgagkmtnn bnnbnnbkmt gtcagcctga cctgcctggt 480
caaaggcttc tatcccagcg acatcgccgt ggagtgggag agcaatgggc agccggagaa 540
caactacaag accacgcctc ccgtgctgga ctccgacggc tccttcttcc tctacagcaa 600

```
gctcaccgtg nnbnnbnnbn nbnnbnnbnn bnnbaggtgg nnbnnbggga acgtcttctc    660

atgctccgtg atgcatgagg ctctgcacaa ccactacacg cagaagagcc tctccctgtc    720

tccgggtaaa gcggccgc                                                  738


<210> SEQ ID NO 23
<211> LENGTH: 738
<212> TYPE: DNA
<213> ORGANISM: artificial
<220> FEATURE:
<223> OTHER INFORMATION: Fcab06

<400> SEQUENCE: 23

ggcccagccg gccatggccg agcccaaatc ttgtgacaaa actcacacat gcccaccgtg     60

cccagcacct gaactcctgg ggggaccgtc agtcttcctc ttccccccaa aacccaagga    120

caccctcatg atctcccgga cccctgaggt cacatgcgtg gtggtggacg tgagccacga    180

agaccctgag gtcaagttca actggtacgt ggacggcgtg gaggtgcata atgccaagac    240

aaagccgcgg gaggagcagt acaacagcac gtaccgtgtg gtcagcgtcc tcaccgtcct    300

gcaccaggac tggctgaatg gcaaggagta caagtgcaag gtctccaaca aagccctccc    360

agcccccatc gagaaaacca tctccaaagc caaagggcag cctcgagaac cacaggtgta    420

caccctgccc ccatcccggg acgagkmtkm tkmtkmtkmt gtcagcctga cctgcctggt    480

caaaggcttc tatcccagcg acatcgccgt ggagtgggag agcaatgggc agccggagaa    540

caactacaag accacgcctc ccgtgctgga ctccgacggc tccttcttcc tctacagcaa    600

gctcaccgtg kmtkmtkmtk mtkmtkmtkm tkmtaggtgg kmtkmtggga acgtcttctc    660

atgctccgtg atgcatgagg ctctgcacaa ccactacacg cagaagagcc tctccctgtc    720

tccgggtaaa gcggccgc                                                  738


<210> SEQ ID NO 24
<211> LENGTH: 85
<212> TYPE: DNA
<213> ORGANISM: artificial
<220> FEATURE:
<223> OTHER INFORMATION: PCR primer gapch35

<400> SEQUENCE: 24

caacaaggcc ctgcctgccc ccatcgagaa gaccatctcc aaggccaagg gccagcctcg     60

agaaccacag gtgtacaccc tgccc                                           85


<210> SEQ ID NO 25
<211> LENGTH: 99
<212> TYPE: DNA
<213> ORGANISM: artificial
<220> FEATURE:
<223> OTHER INFORMATION: PCR primer gapfcs3

<400> SEQUENCE: 25

gagaccgagg agagggttag ggataggctt accttcgaag ggccctctag actcgatcga     60

gcggccgctc atttacccgg agacagggag aggctcttc                            99


<210> SEQ ID NO 26
<211> LENGTH: 79
<212> TYPE: DNA
<213> ORGANISM: artificial
<220> FEATURE:
<223> OTHER INFORMATION: primer Abmut
<220> FEATURE:
<221> NAME/KEY: misc_feature
```

<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 26
gaaccacagg tgtacaccct gcccccatcc cgggatgagc tgnnbnnbnn bcaggtcagc 60
ctgacctgcc tggtcaaag 79

<210> SEQ ID NO 27
<211> LENGTH: 79
<212> TYPE: DNA
<213> ORGANISM: artificial
<220> FEATURE:
<223> OTHER INFORMATION: primer Abmut2LR
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 27
gaaccacagg tgtacaccct gcccccatcc cgggatgagn nbnnbnnbnn bnnbgtcagc 60
ctgacctgcc tggtcaaag 79

<210> SEQ ID NO 28
<211> LENGTH: 79
<212> TYPE: DNA
<213> ORGANISM: artificial
<220> FEATURE:
<223> OTHER INFORMATION: primer Abmut1L
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 28
gaaccacagg tgtacaccct gcccccatcc cgggatgagn nbnnbnnbnn bcaggtcagc 60
ctgacctgcc tggtcaaag 79

<210> SEQ ID NO 29
<211> LENGTH: 79
<212> TYPE: DNA
<213> ORGANISM: artificial
<220> FEATURE:
<223> OTHER INFORMATION: primer Abmut1R
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 29
gaaccacagg tgtacaccct gcccccatcc cgggatgagc tgnnbnnbnn bnnbgtcagc 60
ctgacctgcc tggtcaaag 79

<210> SEQ ID NO 30
<211> LENGTH: 5
<212> TYPE: PRT
<213> ORGANISM: artificial
<220> FEATURE:
<223> OTHER INFORMATION: AB-loop sequence AA143ff

<400> SEQUENCE: 30

Leu Asp Asn Ser Gln
1 5

<210> SEQ ID NO 31
<211> LENGTH: 5
<212> TYPE: PRT
<213> ORGANISM: artificial
<220> FEATURE:
<223> OTHER INFORMATION: AB-loop sequence AA143ff

<400> SEQUENCE: 31

Tyr Glu Gly Ser Ser
1 5

<210> SEQ ID NO 32
<211> LENGTH: 5
<212> TYPE: PRT
<213> ORGANISM: artificial
<220> FEATURE:
<223> OTHER INFORMATION: AB-loop sequence AA143ff

<400> SEQUENCE: 32

Tyr Met Ser Ala Asp
1 5

<210> SEQ ID NO 33
<211> LENGTH: 5
<212> TYPE: PRT
<213> ORGANISM: artificial
<220> FEATURE:
<223> OTHER INFORMATION: AB-loop sequence AA143ff

<400> SEQUENCE: 33

Tyr Arg Arg Gly Asp
1 5

<210> SEQ ID NO 34
<211> LENGTH: 5
<212> TYPE: PRT
<213> ORGANISM: artificial
<220> FEATURE:
<223> OTHER INFORMATION: AB-loop sequence AA143ff

<400> SEQUENCE: 34

Leu Met Ser Arg Gln
1 5

<210> SEQ ID NO 35
<211> LENGTH: 5
<212> TYPE: PRT
<213> ORGANISM: artificial
<220> FEATURE:
<223> OTHER INFORMATION: AB-loop sequence AA143ff

<400> SEQUENCE: 35

Leu His Leu Ala Gln
1 5

<210> SEQ ID NO 36
<211> LENGTH: 5
<212> TYPE: PRT
<213> ORGANISM: artificial
<220> FEATURE:
<223> OTHER INFORMATION: AB-loop sequence AA143ff

<400> SEQUENCE: 36

Tyr Leu Ser Lys Asp
1 5

<210> SEQ ID NO 37
<211> LENGTH: 5
<212> TYPE: PRT
<213> ORGANISM: artificial
<220> FEATURE:
<223> OTHER INFORMATION: AB-loop sequence AA143ff

<400> SEQUENCE: 37

Tyr Arg Ser Gly Ser
1 5

<210> SEQ ID NO 38
<211> LENGTH: 5
<212> TYPE: PRT
<213> ORGANISM: artificial
<220> FEATURE:
<223> OTHER INFORMATION: AB-loop sequence AA143ff

<400> SEQUENCE: 38

Leu Arg Asp Gly Gln
1 5

<210> SEQ ID NO 39
<211> LENGTH: 5
<212> TYPE: PRT
<213> ORGANISM: artificial
<220> FEATURE:
<223> OTHER INFORMATION: AB-loop sequence AA143ff

<400> SEQUENCE: 39

```
Tyr Ser Ala Asn Thr
1               5


<210> SEQ ID NO 40
<211> LENGTH: 5
<212> TYPE: PRT
<213> ORGANISM: artificial
<220> FEATURE:
<223> OTHER INFORMATION: AB-loop sequence AA143ff

<400> SEQUENCE: 40

Tyr Ala Ser Asn Thr
1               5


<210> SEQ ID NO 41
<211> LENGTH: 5
<212> TYPE: PRT
<213> ORGANISM: artificial
<220> FEATURE:
<223> OTHER INFORMATION: AB-loop sequence AA143ff

<400> SEQUENCE: 41

Tyr Ser Asp Gly Asp
1               5


<210> SEQ ID NO 42
<211> LENGTH: 5
<212> TYPE: PRT
<213> ORGANISM: artificial
<220> FEATURE:
<223> OTHER INFORMATION: AB-loop sequence AA143ff

<400> SEQUENCE: 42

Tyr Ser Gly Gly Ser
1               5


<210> SEQ ID NO 43
<211> LENGTH: 5
<212> TYPE: PRT
<213> ORGANISM: artificial
<220> FEATURE:
<223> OTHER INFORMATION: AB-loop sequence AA143ff

<400> SEQUENCE: 43

Tyr Gly Arg Asp Ser
1               5


<210> SEQ ID NO 44
<211> LENGTH: 5
<212> TYPE: PRT
<213> ORGANISM: artificial
<220> FEATURE:
<223> OTHER INFORMATION: AB-loop sequence AA143ff

<400> SEQUENCE: 44

Tyr Ala Gly Gly Thr
1               5


<210> SEQ ID NO 45
<211> LENGTH: 5
<212> TYPE: PRT
<213> ORGANISM: artificial
<220> FEATURE:
<223> OTHER INFORMATION: AB-loop sequence AA143ff

<400> SEQUENCE: 45
```

Tyr Ser Ser Asp Ser
1 5

<210> SEQ ID NO 46
<211> LENGTH: 5
<212> TYPE: PRT
<213> ORGANISM: artificial
<220> FEATURE:
<223> OTHER INFORMATION: AB-loop sequence AA143ff

<400> SEQUENCE: 46

Tyr His Ser Gly Ser
1 5

<210> SEQ ID NO 47
<211> LENGTH: 5
<212> TYPE: PRT
<213> ORGANISM: artificial
<220> FEATURE:
<223> OTHER INFORMATION: AB-loop sequence AA143ff

<400> SEQUENCE: 47

Tyr Leu Thr Asn Ser
1 5

<210> SEQ ID NO 48
<211> LENGTH: 5
<212> TYPE: PRT
<213> ORGANISM: artificial
<220> FEATURE:
<223> OTHER INFORMATION: AB-loop sequence AA143ff

<400> SEQUENCE: 48

Tyr Gly Ser Glu Glu
1 5

<210> SEQ ID NO 49
<211> LENGTH: 5
<212> TYPE: PRT
<213> ORGANISM: artificial
<220> FEATURE:
<223> OTHER INFORMATION: AB-loop sequence AA143ff

<400> SEQUENCE: 49

Tyr Arg Ser Gly Glu
1 5

<210> SEQ ID NO 50
<211> LENGTH: 5
<212> TYPE: PRT
<213> ORGANISM: artificial
<220> FEATURE:
<223> OTHER INFORMATION: AB-loop sequence AA143ff

<400> SEQUENCE: 50

Tyr Gly Thr Asp Asp
1 5

<210> SEQ ID NO 51
<211> LENGTH: 12
<212> TYPE: PRT
<213> ORGANISM: artificial
<220> FEATURE:
<223> OTHER INFORMATION: EF-loop sequence AA198ff

<400> SEQUENCE: 51

Ile Arg Ser Ser Val Gly Ser Arg Arg Trp Trp Ser 1 5 10

<210> SEQ ID NO 52
<211> LENGTH: 12
<212> TYPE: PRT
<213> ORGANISM: artificial
<220> FEATURE:
<223> OTHER INFORMATION: EF-loop sequence AA198ff

<400> SEQUENCE: 52

Ala Arg Tyr Ser Pro Arg Met Leu Arg Trp Ala His
1 5 10

<210> SEQ ID NO 53
<211> LENGTH: 12
<212> TYPE: PRT
<213> ORGANISM: artificial
<220> FEATURE:
<223> OTHER INFORMATION: EF-loop sequence AA198ff

<400> SEQUENCE: 53

Ser Arg Arg Asp Ser Ser Leu Leu Arg Trp Ala His
1 5 10

<210> SEQ ID NO 54
<211> LENGTH: 12
<212> TYPE: PRT
<213> ORGANISM: artificial
<220> FEATURE:
<223> OTHER INFORMATION: EF-loop sequence AA198ff

<400> SEQUENCE: 54

Ala Pro Gly Ser Lys Gly Tyr Arg Arg Trp Ala Leu
1 5 10

<210> SEQ ID NO 55
<211> LENGTH: 12
<212> TYPE: PRT
<213> ORGANISM: artificial
<220> FEATURE:
<223> OTHER INFORMATION: EF-loop sequence AA198ff

<400> SEQUENCE: 55

Asp Lys Pro Phe Trp Gly Thr Ser Arg Trp Ser Arg
1 5 10

<210> SEQ ID NO 56
<211> LENGTH: 12
<212> TYPE: PRT
<213> ORGANISM: artificial
<220> FEATURE:
<223> OTHER INFORMATION: EF-loop sequence AA198ff

<400> SEQUENCE: 56

Ser Ile Asn Asp Leu Ile Asn His Arg Trp Pro Tyr
1 5 10

<210> SEQ ID NO 57
<211> LENGTH: 12
<212> TYPE: PRT
<213> ORGANISM: artificial
<220> FEATURE:
<223> OTHER INFORMATION: EF-loop sequence AA198ff

<400> SEQUENCE: 57

Met Trp Gly Ser Arg Asp Tyr Trp Arg Trp Ser His
1 5 10

<210> SEQ ID NO 58
<211> LENGTH: 12
<212> TYPE: PRT
<213> ORGANISM: artificial
<220> FEATURE:
<223> OTHER INFORMATION: EF-loop sequence AA198ff

<400> SEQUENCE: 58

Asn Ser Gly Ser Ala Met Met Val Arg Trp Ala His
1 5 10

<210> SEQ ID NO 59
<211> LENGTH: 12
<212> TYPE: PRT
<213> ORGANISM: artificial
<220> FEATURE:
<223> OTHER INFORMATION: EF-loop sequence AA198ff

<400> SEQUENCE: 59

Gln Arg Ser Arg Leu Ser Arg Gln Arg Trp Trp Arg
1 5 10

<210> SEQ ID NO 60
<211> LENGTH: 12
<212> TYPE: PRT
<213> ORGANISM: artificial
<220> FEATURE:
<223> OTHER INFORMATION: EF-loop sequence AA198ff

<400> SEQUENCE: 60

Ala Arg Tyr Ser Pro Arg Met Leu Arg Trp Ala His
1 5 10

<210> SEQ ID NO 61
<211> LENGTH: 13
<212> TYPE: PRT
<213> ORGANISM: artificial
<220> FEATURE:
<223> OTHER INFORMATION: EF-loop sequence AA198ff

<400> SEQUENCE: 61

Val Ser Arg Tyr Ser Met Thr Met Trp Arg Trp Ala His
1 5 10

<210> SEQ ID NO 62
<211> LENGTH: 13
<212> TYPE: PRT
<213> ORGANISM: artificial
<220> FEATURE:
<223> OTHER INFORMATION: EF-loop sequence AA198ff

<400> SEQUENCE: 62

Val Pro Arg Tyr Ser Arg Ser Met Met Arg Trp Ala His
1 5 10

<210> SEQ ID NO 63
<211> LENGTH: 13
<212> TYPE: PRT
<213> ORGANISM: artificial
<220> FEATURE:
<223> OTHER INFORMATION: EF-loop sequence AA198ff

<400> SEQUENCE: 63

Val Pro Arg Tyr Ser Gln Met Met Trp Arg Trp Ala His
1 5 10

<210> SEQ ID NO 64
<211> LENGTH: 13
<212> TYPE: PRT
<213> ORGANISM: artificial
<220> FEATURE:
<223> OTHER INFORMATION: EF-loop sequence AA198ff

<400> SEQUENCE: 64

Ile Thr Arg Tyr Ser Arg Gln Met Leu Arg Trp Ala His
1 5 10

<210> SEQ ID NO 65
<211> LENGTH: 13
<212> TYPE: PRT
<213> ORGANISM: artificial
<220> FEATURE:
<223> OTHER INFORMATION: EF-loop sequence AA198ff

<400> SEQUENCE: 65

Val Pro Arg Tyr Ser Ala Leu Met Trp Arg Trp Ala His
1 5 10

<210> SEQ ID NO 66
<211> LENGTH: 13
<212> TYPE: PRT
<213> ORGANISM: artificial
<220> FEATURE:
<223> OTHER INFORMATION: EF-loop sequence AA198ff

<400> SEQUENCE: 66

Val Ala Arg His Ser Glu Ala Met Trp Lys Trp Gly His
1 5 10

<210> SEQ ID NO 67
<211> LENGTH: 13
<212> TYPE: PRT
<213> ORGANISM: artificial
<220> FEATURE:
<223> OTHER INFORMATION: EF-loop sequence AA198ff

<400> SEQUENCE: 67

Val Gly Arg Tyr Ser Gln Arg Met Trp Arg Trp Ala His
1 5 10

<210> SEQ ID NO 68
<211> LENGTH: 13
<212> TYPE: PRT
<213> ORGANISM: artificial
<220> FEATURE:
<223> OTHER INFORMATION: EF-loop sequence AA198ff

<400> SEQUENCE: 68

Val Ala Arg Tyr Ser Pro Thr Met Trp Arg Trp Ala His
1 5 10

<210> SEQ ID NO 69
<211> LENGTH: 13
<212> TYPE: PRT
<213> ORGANISM: artificial
<220> FEATURE:
<223> OTHER INFORMATION: EF-loop sequence AA198ff

<400> SEQUENCE: 69

Val Gly Arg His Ser Pro Thr Met Trp Lys Trp Ala His
1 5 10

<210> SEQ ID NO 70
<211> LENGTH: 13
<212> TYPE: PRT
<213> ORGANISM: artificial
<220> FEATURE:
<223> OTHER INFORMATION: EF-loop sequence AA198ff

<400> SEQUENCE: 70

```
Leu Gly Arg Trp Ser Pro Lys Met Trp Arg Trp Ala His
1               5                   10
```

<210> SEQ ID NO 71
<211> LENGTH: 13
<212> TYPE: PRT
<213> ORGANISM: artificial
<220> FEATURE:
<223> OTHER INFORMATION: EF-loop sequence AA198ff

<400> SEQUENCE: 71

```
Val Ala Arg Trp Ser Pro Ser Met Met Arg Trp Ala His
1               5                   10
```

<210> SEQ ID NO 72
<211> LENGTH: 5009
<212> TYPE: DNA
<213> ORGANISM: artificial
<220> FEATURE:
<223> OTHER INFORMATION: vector pYD1

<400> SEQUENCE: 72

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt tttagcacag gaactgacaa    600

ctatatgcga gcaaatcccc tcaccaactt tagaatcgac gccgtactct ttgtcaacga    660

ctactatttt ggccaacggg aaggcaatgc aaggagtttt tgaatattac aaatcagtaa    720

cgtttgtcag taattgcggt tctcacccct caacaactag caaaggcagc cccataaaca    780

cacagtatgt ttttaagctt ctgcaggcta gtggtggtgg tggttctggt ggtggtggtt    840

ctggtggtgg tggttctgct agcatgactg gtggacagca aatgggtcgg gatctgtacg    900

acgatgacga taaggtacca ggatccagtg tggtggaatt ctgcagatat ccagcacagt    960

ggcggccgct cgagtctaga gggcccttcg aaggtaagcc tatccctaac cctctcctcg   1020

gtctcgattc tacgcgtacc ggtcatcatc accatcacca ttgagtttaa acccgctgat   1080

ctgataacaa cagtgtagat gtaacaaaat cgactttgtt cccactgtac ttttagctcg   1140

tacaaaatac aatatacttt tcatttctcc gtaaacaaca tgttttccca tgtaatatcc   1200

ttttctattt ttcgttccgt taccaacttt acacatactt tatatagcta ttcacttcta   1260

tacactaaaa aactaagaca attttaattt tgctgcctgc catatttcaa tttgttataa   1320
```

```
attcctataa tttatcctat tagtagctaa aaaaagatga atgtgaatcg aatcctaaga   1380
gaattgggca agtgcacaaa caatacttaa ataaatacta ctcagtaata acctatttct   1440
tagcattttt gacgaaattt gctattttgt tagagtcttt tacaccattt gtctccacac   1500
ctccgcttac atcaacacca ataacgccat ttaatctaag cgcatcacca acattttctg   1560
gcgtcagtcc accagctaac ataaaatgta agctctcggg gctctcttgc cttccaaccc   1620
agtcagaaat cgagttccaa tccaaaagtt cacctgtccc acctgcttct gaatcaaaca   1680
agggaataaa cgaatgaggt ttctgtgaag ctgcactgag tagtatgttg cagtcttttg   1740
gaaatacgag tcttttaata actggcaaac cgaggaactc ttggtattct tgccacgact   1800
catctccgtg cagttggacg atatcaatgc cgtaatcatt gaccagagcc aaaacatcct   1860
ccttaggttg attacgaaac acgccaacca agtatttcgg agtgcctgaa ctatttttat   1920
atgcttttac aagacttgaa attttccttg caataaccgg gtcaattgtt ctctttctat   1980
tgggcacaca tataataccc agcaagtcag catcggaatc tagagcacat tctgcggcct   2040
ctgtgctctg caagccgcaa actttcacca atggaccaga actacctgtg aaattaataa   2100
cagacatact ccaagctgcc tttgtgtgct taatcacgta tactcacgtg ctcaatagtc   2160
accaatgccc tccctcttgg ccctctcctt ttcttttttc gaccgaattt cttgaagacg   2220
aaagggcctc gtgatacgcc tatttttata ggttaatgtc atgataataa tggtttctta   2280
ggacggatcg cttgcctgta acttacacgc gcctcgtatc ttttaatgat ggaataattt   2340
gggaatttac tctgtgttta tttattttta tgttttgtat ttggatttta gaaagtaaat   2400
aaagaaggta gaagagttac ggaatgaaga aaaaaaaata aacaaaggtt taaaaaattt   2460
caacaaaaag cgtactttac atatatattt attagacaag aaaagcagat taaatagata   2520
tacattcgat taacgataag taaaatgtaa aatcacagga ttttcgtgtg tggtcttcta   2580
cacagacaag atgaaacaat tcggcattaa tacctgagag caggaagagc aagataaaag   2640
gtagtatttg ttggcgatcc ccctagagtc ttttacatct tcggaaaaca aaaactattt   2700
tttctttaat ttcttttttt actttctatt tttaatttat atatttatat taaaaaattt   2760
aaattataat tatttttata gcacgtgatg aaaaggaccc aggtggcact tttcggggaa   2820
atgtgcgcgg aacccctatt tgtttatttt tctaaataca ttcaaatatg tatccgctca   2880
tgagacaata accctgataa atgcttcaat aatattgaaa aaggaagagt atgagtattc   2940
aacatttccg tgtcgccctt attccctttt ttgcggcatt ttgccttcct gtttttgctc   3000
acccagaaac gctggtgaaa gtaaaagatg ctgaagatca gttgggtgca cgagtgggtt   3060
acatcgaact ggatctcaac agcggtaaga tccttgagag ttttcgcccc gaagaacgtt   3120
ttccaatgat gagcactttt aaagttctgc tatgtggcgc ggtattatcc cgtgttgacg   3180
ccgggcaaga gcaactcggt cgccgcatac actattctca gaatgacttg gttgagtact   3240
caccagtcac agaaaagcat cttacggatg gcatgacagt aagagaatta tgcagtgctg   3300
ccataaccat gagtgataac actgcggcca acttacttct gacaacgatc ggaggaccga   3360
aggagctaac cgcttttttg cacaacatgg gggatcatgt aactcgcctt gatcgttggg   3420
aaccggagct gaatgaagcc ataccaaacg acgagcgtga caccacgatg cctgtagcaa   3480
tggcaacaac gttgcgcaaa ctattaactg gcgaactact tactctagct tcccggcaac   3540
aattaataga ctggatggag gcggataaag ttgcaggacc acttctgcgc tcggcccttc   3600
cggctggctg gtttattgct gataaatctg gagccggtga gcgtgggtct cgcggtatca   3660
ttgcagcact ggggccagat ggtaagccct cccgtatcgt agttatctac acgacgggca   3720
```

```
gtcaggcaac tatggatgaa cgaaatagac agatcgctga gataggtgcc tcactgatta   3780

agcattggta actgtcagac caagtttact catatatact ttagattgat ttaaaacttc   3840

atttttaatt taaaaggatc taggtgaaga tcctttttga taatctcatg accaaaatcc   3900

cttaacgtga gttttcgttc cactgagcgt cagaccccgt agaaaagatc aaaggatctt   3960

cttgagatcc tttttttctg cgcgtaatct gctgcttgca aacaaaaaaa ccaccgctac   4020

cagcggtggt ttgtttgccg gatcaagagc taccaactct ttttccgaag gtaactggct   4080

tcagcagagc gcagatacca aatactgtcc ttctagtgta gccgtagtta ggccaccact   4140

tcaagaactc tgtagcaccg cctacatacc tcgctctgct aatcctgtta ccagtggctg   4200

ctgccagtgg cgataagtcg tgtcttaccg ggttggactc aagacgatag ttaccggata   4260

aggcgcagcg gtcgggctga acggggggtt cgtgcacaca gcccagcttg gagcgaacga   4320

cctacaccga actgagatac ctacagcgtg agcattgaga aagcgccacg cttcccgaag   4380

ggagaaaggc ggacaggtat ccggtaagcg gcagggtcgg aacaggagag cgcacgaggg   4440

agcttccagg gggaaacgcc tggtatcttt atagtcctgt cgggtttcgc cacctctgac   4500

ttgagcgtcg atttttgtga tgctcgtcag gggggcgag cctatggaaa aacgccagca   4560

acgcggcctt tttacggttc ctggcctttt gctggccttt tgctcacatg ttctttcctg   4620

cgttatcccc tgattctgtg gataaccgta ttaccgcctt tgagtgagct gataccgctc   4680

gccgcagccg aacgaccgag cgcagcgagt cagtgagcga ggaagcggaa gagcgcccaa   4740

tacgcaaacc gcctctcccc gcgcgttggc cgattcatta atgcagctgg cacgacaggt   4800

ttcccgactg gaaagcgggc agtgagcgca acgcaattaa tgtgagttac ctcactcatt   4860

aggcacccca ggctttacac tttatgcttc cggctcctat gttgtgtgga attgtgagcg   4920

gataacaatt tcacacagga aacagctatg accatgatta cgccaagctc ggaattaacc   4980

ctcactaaag ggaacaaaag ctggctagt                                      5009
```

<210> SEQ ID NO 73
<211> LENGTH: 5009
<212> TYPE: DNA
<213> ORGANISM: artificial
<220> FEATURE:
<223> OTHER INFORMATION: modified vector pYD1Nhe

<400> SEQUENCE: 73

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt gctagcacag gaactgacaa    600

ctatatgcga gcaaatcccc tcaccaactt tagaatcgac gccgtactct ttgtcaacga    660

ctactatttt ggccaacggg aaggcaatgc aaggagtttt tgaatattac aaatcagtaa    720
```

```
cgtttgtcag taattgcggt tctcacccct caacaactag caaaggcagc cccataaaca    780
cacagtatgt ttttaagctt ctgcaggcta gtggtggtgg tggttctggt ggtggtggtt    840
ctggtggtgg tggttctgct agcatgactg gtggacagca aatgggtcgg gatctgtacg    900
acgatgacga taaggtacca ggatccagtg tggtggaatt ctgcagatat ccagcacagt    960
ggcggccgct cgagtctaga gggcccttcg aaggtaagcc tatccctaac cctctcctcg   1020
gtctcgattc tacgcgtacc ggtcatcatc accatcacca ttgagtttaa acccgctgat   1080
ctgataacaa cagtgtagat gtaacaaaat cgactttgtt cccactgtac ttttagctcg   1140
tacaaaatac aatatacttt tcatttctcc gtaaacaaca tgttttccca tgtaatatcc   1200
ttttctattt ttcgttccgt taccaacttt acacatactt tatatagcta ttcacttcta   1260
tacactaaaa aactaagaca attttaattt tgctgcctgc catatttcaa tttgttataa   1320
attcctataa tttatcctat tagtagctaa aaaaagatga atgtgaatcg aatcctaaga   1380
gaattgggca agtgcacaaa caatacttaa ataaatacta ctcagtaata acctatttct   1440
tagcattttt gacgaaattt gctattttgt tagagtcttt tacaccattt gtctccacac   1500
ctccgcttac atcaacacca ataacgccat ttaatctaag cgcatcacca acattttctg   1560
gcgtcagtcc accagctaac ataaaatgta agctctcggg gctctcttgc cttccaaccc   1620
agtcagaaat cgagttccaa tccaaaagtt cacctgtccc acctgcttct gaatcaaaca   1680
agggaataaa cgaatgaggt ttctgtgaag ctgcactgag tagtatgttg cagtcttttg   1740
gaaatacgag tcttttaata actggcaaac cgaggaactc ttggtattct tgccacgact   1800
catctccgtg cagttggacg atatcaatgc cgtaatcatt gaccagagcc aaaacatcct   1860
ccttaggttg attacgaaac acgccaacca agtatttcgg agtgcctgaa ctatttttat   1920
atgcttttac aagacttgaa attttccttg caataaccgg gtcaattgtt ctctttctat   1980
tgggcacaca tataataccc agcaagtcag catcggaatc tagagcacat tctgcggcct   2040
ctgtgctctg caagccgcaa actttcacca atggaccaga actacctgtg aaattaataa   2100
cagacatact ccaagctgcc tttgtgtgct taatcacgta tactcacgtg ctcaatagtc   2160
accaatgccc tccctcttgg ccctctcctt ttcttttttc gaccgaattt cttgaagacg   2220
aaagggcctc gtgatacgcc tatttttata ggttaatgtc atgataataa tggtttctta   2280
ggacggatcg cttgcctgta acttacacgc gcctcgtatc ttttaatgat ggaataattt   2340
gggaatttac tctgtgttta tttattttta tgttttgtat ttggatttta gaaagtaaat   2400
aaagaaggta gaagagttac ggaatgaaga aaaaaaaata aacaaaggtt taaaaaattt   2460
caacaaaaag cgtactttac atatatattt attagacaag aaaagcagat taaatagata   2520
tacattcgat taacgataag taaaatgtaa aatcacagga ttttcgtgtg tggtcttcta   2580
cacagacaag atgaaacaat tcggcattaa tacctgagag caggaagagc aagataaaag   2640
gtagtatttg ttggcgatcc ccctagagtc ttttacatct tcggaaaaca aaaactattt   2700
tttctttaat ttcttttttt actttctatt tttaatttat atatttatat taaaaaattt   2760
aaattataat tatttttata gcacgtgatg aaaaggaccc aggtggcact tttcggggaa   2820
atgtgcgcgg aacccctatt tgtttatttt tctaaataca ttcaaatatg tatccgctca   2880
tgagacaata accctgataa atgcttcaat aatattgaaa aaggaagagt atgagtattc   2940
aacatttccg tgtcgccctt attccctttt ttgcggcatt ttgccttcct gtttttgctc   3000
acccagaaac gctggtgaaa gtaaaagatg ctgaagatca gttgggtgca cgagtgggtt   3060
acatcgaact ggatctcaac agcggtaaga tccttgagag ttttcgcccc gaagaacgtt   3120
```

```
ttccaatgat gagcactttt aaagttctgc tatgtggcgc ggtattatcc cgtgttgacg   3180

ccgggcaaga gcaactcggt cgccgcatac actattctca gaatgacttg gttgagtact   3240

caccagtcac agaaaagcat cttacggatg gcatgacagt aagagaatta tgcagtgctg   3300

ccataaccat gagtgataac actgcggcca acttacttct gacaacgatc ggaggaccga   3360

aggagctaac cgcttttttg cacaacatgg gggatcatgt aactcgcctt gatcgttggg   3420

aaccggagct gaatgaagcc ataccaaacg acgagcgtga caccacgatg cctgtagcaa   3480

tggcaacaac gttgcgcaaa ctattaactg gcgaactact tactctagct tcccggcaac   3540

aattaataga ctggatggag gcggataaag ttgcaggacc acttctgcgc tcggcccttc   3600

cggctggctg gtttattgct gataaatctg gagccggtga gcgtgggtct cgcggtatca   3660

ttgcagcact ggggccagat ggtaagccct cccgtatcgt agttatctac acgacgggca   3720

gtcaggcaac tatggatgaa cgaaatagac agatcgctga gataggtgcc tcactgatta   3780

agcattggta actgtcagac caagtttact catatatact ttagattgat ttaaaacttc   3840

atttttaatt taaaaggatc taggtgaaga tcctttttga taatctcatg accaaaatcc   3900

cttaacgtga gttttcgttc cactgagcgt cagaccccgt agaaaagatc aaaggatctt   3960

cttgagatcc tttttttctg cgcgtaatct gctgcttgca aacaaaaaaa ccaccgctac   4020

cagcggtggt ttgtttgccg gatcaagagc taccaactct ttttccgaag gtaactggct   4080

tcagcagagc gcagatacca aatactgtcc ttctagtgta gccgtagtta ggccaccact   4140

tcaagaactc tgtagcaccg cctacatacc tcgctctgct aatcctgtta ccagtggctg   4200

ctgccagtgg cgataagtcg tgtcttaccg ggttggactc aagacgatag ttaccggata   4260

aggcgcagcg gtcgggctga acggggggtt cgtgcacaca gcccagcttg gagcgaacga   4320

cctacaccga actgagatac ctacagcgtg agcattgaga aagcgccacg cttcccgaag   4380

ggagaaaggc ggacaggtat ccggtaagcg gcagggtcgg aacaggagag cgcacgaggg   4440

agcttccagg gggaaacgcc tggtatcttt atagtcctgt cgggtttcgc cacctctgac   4500

ttgagcgtcg atttttgtga tgctcgtcag gggggcggag cctatggaaa aacgccagca   4560

acgcggcctt tttacggttc ctggcctttt gctggccttt tgctcacatg ttctttcctg   4620

cgttatcccc tgattctgtg gataaccgta ttaccgcctt tgagtgagct gataccgctc   4680

gccgcagccg aacgaccgag cgcagcgagt cagtgagcga ggaagcggaa gagcgcccaa   4740

tacgcaaacc gcctctcccc gcgcgttggc cgattcatta atgcagctgg cacgacaggt   4800

ttcccgactg gaaagcgggc agtgagcgca acgcaattaa tgtgagttac ctcactcatt   4860

aggcacccca ggctttacac tttatgcttc cggctcctat gttgtgtgga attgtgagcg   4920

gataacaatt tcacacagga aacagctatg accatgatta cgccaagctc ggaattaacc   4980

ctcactaaag ggaacaaaag ctggctagt                                      5009
```

<210> SEQ ID NO 74
<211> LENGTH: 4605
<212> TYPE: DNA
<213> ORGANISM: artificial
<220> FEATURE:
<223> OTHER INFORMATION: vector pYD1lnk

<400> SEQUENCE: 74

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120
```

```
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt gctagccgct ggggccatgg    600
ttactgattg gcgcgccgga tccttcagac tctgcagaat tcggccgcgt acttaattaa    660
gtttaaaccc gctgatctga taacaacagt gtagatgtaa caaaatcgac tttgttccca    720
ctgtactttt agctcgtaca aaatacaata tacttttcat ttctccgtaa acaacatgtt    780
ttcccatgta atatcctttt ctatttttcg ttccgttacc aactttacac atactttata    840
tagctattca cttctataca ctaaaaaact aagacaattt taattttgct gcctgccata    900
tttcaatttg ttataaattc ctataattta tcctattagt agctaaaaaa agatgaatgt    960
gaatcgaatc ctaagagaat tggcaagtg cacaaacaat acttaaataa atactactca    1020
gtaataacct atttcttagc atttttgacg aaatttgcta ttttgttaga gtcttttaca   1080
ccatttgtct ccacacctcc gcttacatca acaccaataa cgccatttaa tctaagcgca   1140
tcaccaacat tttctggcgt cagtccacca gctaacataa aatgtaagct ctcggggctc   1200
tcttgccttc caacccagtc agaaatcgag ttccaatcca aaagttcacc tgtcccacct   1260
gcttctgaat caaacaaggg aataaacgaa tgaggtttct gtgaagctgc actgagtagt   1320
atgttgcagt cttttggaaa tacgagtctt ttaataactg gcaaaccgag gaactcttgg   1380
tattcttgcc acgactcatc tccgtgcagt tggacgatat caatgccgta atcattgacc   1440
agagccaaaa catcctcctt aggttgatta cgaaacacgc caaccaagta tttcggagtg   1500
cctgaactat ttttatatgc ttttacaaga cttgaaattt tccttgcaat aaccgggtca   1560
attgttctct ttctattggg cacacatata atacccagca agtcagcatc ggaatctaga   1620
gcacattctg cggcctctgt gctctgcaag ccgcaaactt tcaccaatgg accagaacta   1680
cctgtgaaat taataacaga catactccaa gctgcctttg tgtgcttaat cacgtatact   1740
cacgtgctca atagtcacca atgccctccc tcttggccct ctccttttct tttttcgacc   1800
gaatttcttg aagacgaaag ggcctcgtga tacgcctatt tttataggtt aatgtcatga   1860
taataatggt ttcttaggac ggatcgcttg cctgtaactt acacgcgcct cgtatctttt   1920
aatgatggaa taatttggga atttactctg tgtttattta tttttatgtt ttgtatttgg   1980
attttagaaa gtaaataaag aaggtagaag agttacggaa tgaagaaaaa aaaataaaca   2040
aaggtttaaa aaatttcaac aaaaagcgta ctttacatat atatttatta gacaagaaaa   2100
gcagattaaa tagatataca ttcgattaac gataagtaaa atgtaaaatc acaggatttt   2160
cgtgtgtggt cttctacaca gacaagatga aacaattcgg cattaatacc tgagagcagg   2220
aagagcaaga taaaaggtag tatttgttgg cgatccccct agagtctttt acatcttcgg   2280
aaaacaaaaa ctatttttc tttaatttct ttttttactt tctattttta atttatatat   2340
ttatattaaa aaatttaaat tataattatt tttatagcac gtgatgaaaa ggacccaggt   2400
ggcacttttc ggggaaatgt gcgcggaacc cctatttgtt tattttttcta aatacattca  2460
aatatgtatc cgctcatgag acaataaccc tgataaatgc ttcaataata ttgaaaaagg   2520
```

```
aagagtatga gtattcaaca tttccgtgtc gcccttattc ccttttttgc ggcattttgc   2580

cttcctgttt ttgctcaccc agaaacgctg gtgaaagtaa aagatgctga agatcagttg   2640

ggtgcacgag tgggttacat cgaactggat ctcaacagcg gtaagatcct tgagagtttt   2700

cgccccgaag aacgttttcc aatgatgagc acttttaaag ttctgctatg tggcgcggta   2760

ttatcccgtg ttgacgccgg gcaagagcaa ctcggtcgcc gcatacacta ttctcagaat   2820

gacttggttg agtactcacc agtcacagaa aagcatctta cggatggcat gacagtaaga   2880

gaattatgca gtgctgccat aaccatgagt gataacactg cggccaactt acttctgaca   2940

acgatcggag gaccgaagga gctaaccgct tttttgcaca acatggggga tcatgtaact   3000

cgccttgatc gttgggaacc ggagctgaat gaagccatac caaacgacga gcgtgacacc   3060

acgatgcctg tagcaatggc aacaacgttg cgcaaactat taactggcga actacttact   3120

ctagcttccc ggcaacaatt aatagactgg atggaggcgg ataaagttgc aggaccactt   3180

ctgcgctcgg cccttccggc tggctggttt attgctgata aatctggagc cggtgagcgt   3240

gggtctcgcg gtatcattgc agcactgggg ccagatggta agccctcccg tatcgtagtt   3300

atctacacga cgggcagtca ggcaactatg gatgaacgaa atagacagat cgctgagata   3360

ggtgcctcac tgattaagca ttggtaactg tcagaccaag tttactcata tatactttag   3420

attgatttaa aacttcattt ttaatttaaa aggatctagg tgaagatcct ttttgataat   3480

ctcatgacca aaatccctta acgtgagttt tcgttccact gagcgtcaga ccccgtagaa   3540

aagatcaaag gatcttcttg agatcctttt tttctgcgcg taatctgctg cttgcaaaca   3600

aaaaaaccac cgctaccagc ggtggtttgt ttgccggatc aagagctacc aactcttttt   3660

ccgaaggtaa ctggcttcag cagagcgcag ataccaaata ctgtccttct agtgtagccg   3720

tagttaggcc accacttcaa gaactctgta gcaccgccta catacctcgc tctgctaatc   3780

ctgttaccag tggctgctgc cagtggcgat aagtcgtgtc ttaccgggtt ggactcaaga   3840

cgatagttac cggataaggc gcagcggtcg ggctgaacgg ggggttcgtg cacacagccc   3900

agcttggagc gaacgaccta caccgaactg agatacctac agcgtgagca ttgagaaagc   3960

gccacgcttc ccgaagggag aaaggcggac aggtatccgg taagcggcag ggtcggaaca   4020

ggagagcgca cgagggagct tccaggggg aacgcctggt atctttatag tcctgtcggg   4080

tttcgccacc tctgacttga gcgtcgattt ttgtgatgct cgtcaggggg gccgagccta   4140

tggaaaaacg ccagcaacgc ggccttttta cggttcctgg ccttttgctg gccttttgct   4200

cacatgttct ttcctgcgtt atcccctgat tctgtggata accgtattac cgcctttgag   4260

tgagctgata ccgctcgccg cagccgaacg accgagcgca gcgagtcagt gagcgaggaa   4320

gcggaagagc gcccaatacg caaaccgcct ctccccgcgc gttggccgat tcattaatgc   4380

agctggcacg acaggtttcc cgactggaaa gcgggcagtg agcgcaacgc aattaatgtg   4440

agttacctca ctcattaggc accccaggct ttacacttta tgcttccggc tcctatgttg   4500

tgtggaattg tgagcggata acaatttcac acaggaaaca gctatgacca tgattacgcc   4560

aagctcggaa ttaaccctca ctaaagggaa caaaagctgg ctagt                   4605
```

<210> SEQ ID NO 75
<211> LENGTH: 4886
<212> TYPE: DNA
<213> ORGANISM: artificial
<220> FEATURE:
<223> OTHER INFORMATION: vector pYD1mata

<400> SEQUENCE: 75

```
acggattaga agccgccgag cgggtgacag ccctccgaag gaagactctc ctccgtgcgt     60
cctcgtcttc accggtcgcg ttcctgaaac gcagatgtgc ctcgcgccgc actgctccga    120
acaataaaga ttctacaata ctagctttta tggttatgaa gaggaaaaat tggcagtaac    180
ctggccccac aaaccttcaa atgaacgaat caaattaaca accataggat gataatgcga    240
ttagtttttt agccttattt ctggggtaat taatcagcga agcgatgatt tttgatctat    300
taacagatat ataaatgcaa aaactgcata accactttaa ctaatacttt caacattttc    360
ggtttgtatt acttcttatt caaatgtaat aaaagtatca acaaaaaatt gttaatatac    420
ctctatactt taacgtcaag gagaaaaaac cccggatcgg actactagca gctgtaatac    480
gactcactat agggaatatt aagctaattc tacttcatac attttcaatt aagatgcagt    540
tacttcgctg tttttcaata ttttctgtta ttgcttcagt gctagccgct ggggccatgg    600
ttactgattg gcgcgccgga tccgatgtaa caaaatcgac tttgttccca ctgtactttt    660
agctcgtaca aaatacaata tacttttcat ttctccgtaa acaacatgtt ttcccatgta    720
atatcctttt ctatttttcg ttccgttacc aactttacac atactttata tagctattca    780
cttctataca ctaaaaaact aagacaattt taattttgct gcctgccata tttcaatttg    840
ttataaattc ctataattta tcctattagt agctaaaaaa agatgaatgt gaatcgaatc    900
ctaagagaat tgctgcagaa ttcggccgcg tacttaatta agtttaaacc cgctgatctg    960
ataacaacag tgtagatgta acaaaatcga ctttgttccc actgtacttt tagctcgtac   1020
aaaatacaat atacttttca tttctccgta aacaacatgt tttcccatgt aatatccttt   1080
tctatttttc gttccgttac caactttaca catactttat atagctattc acttctatac   1140
actaaaaaac taagacaatt ttaattttgc tgcctgccat atttcaattt gttataaatt   1200
cctataattt atcctattag tagctaaaaa aagatgaatg tgaatcgaat cctaagagaa   1260
ttgggcaagt gcacaaacaa tacttaaata aatactactc agtaataacc tatttcttag   1320
catttttgac gaaatttgct attttgttag agtcttttac accatttgtc tccacacctc   1380
cgcttacatc aacaccaata acgccattta atctaagcgc atcaccaaca ttttctggcg   1440
tcagtccacc agctaacata aaatgtaagc tctcggggct ctcttgcctt ccaacccagt   1500
cagaaatcga gttccaatcc aaaagttcac ctgtcccacc tgcttctgaa tcaaacaagg   1560
gaataaacga atgaggtttc tgtgaagctg cactgagtag tatgttgcag tcttttggaa   1620
atacgagtct tttaataact ggcaaaccga ggaactcttg gtattcttgc cacgactcat   1680
ctccgtgcag ttggacgata tcaatgccgt aatcattgac cagagccaaa acatcctcct   1740
taggttgatt acgaaacacg ccaaccaagt atttcggagt gcctgaacta tttttatatg   1800
cttttacaag acttgaaatt ttccttgcaa taaccgggtc aattgttctc tttctattgg   1860
gcacacatat aatacccagc aagtcagcat cggaatctag agcacattct gcggcctctg   1920
tgctctgcaa gccgcaaact ttcaccaatg gaccagaact acctgtgaaa ttaataacag   1980
acatactcca agctgccttt gtgtgcttaa tcacgtatac tcacgtgctc aatagtcacc   2040
aatgccctcc ctcttggccc tctccttttc ttttttcgac cgaatttctt gaagacgaaa   2100
gggcctcgtg atacgcctat ttttataggt taatgtcatg ataataatgg tttcttagga   2160
cggatcgctt gcctgtaact tacacgcgcc tcgtatcttt taatgatgga ataatttggg   2220
aatttactct gtgtttattt atttttatgt tttgtatttg gattttagaa agtaaataaa   2280
gaaggtagaa gagttacgga atgaagaaaa aaaaataaac aaaggtttaa aaaatttcaa   2340
```

```
caaaaagcgt actttacata tatatttatt agacaagaaa agcagattaa atagatatac   2400
attcgattaa cgataagtaa aatgtaaaat cacaggattt tcgtgtgtgg tcttctacac   2460
agacaagatg aaacaattcg gcattaatac ctgagagcag gaagagcaag ataaaaggta   2520
gtatttgttg gcgatccccc tagagtcttt tacatcttcg gaaaacaaaa actatttttt   2580
ctttaatttc tttttttact ttctattttt aatttatata tttatattaa aaaatttaaa   2640
ttataattat ttttatagca cgtgatgaaa aggacccagg tggcactttt cggggaaatg   2700
tgcgcggaac ccctatttgt ttatttttct aaatacattc aaatatgtat ccgctcatga   2760
gacaataacc ctgataaatg cttcaataat attgaaaaag gaagagtatg agtattcaac   2820
atttccgtgt cgcccttatt cccttttttg cggcattttg ccttcctgtt tttgctcacc   2880
cagaaacgct ggtgaaagta aaagatgctg aagatcagtt gggtgcacga gtgggttaca   2940
tcgaactgga tctcaacagc ggtaagatcc ttgagagttt tcgccccgaa gaacgttttc   3000
caatgatgag cacttttaaa gttctgctat gtggcgcggt attatcccgt gttgacgccg   3060
ggcaagagca actcggtcgc cgcatacact attctcagaa tgacttggtt gagtactcac   3120
cagtcacaga aaagcatctt acggatggca tgacagtaag agaattatgc agtgctgcca   3180
taaccatgag tgataacact gcggccaact tacttctgac aacgatcgga ggaccgaagg   3240
agctaaccgc ttttttgcac aacatggggg atcatgtaac tcgccttgat cgttgggaac   3300
cggagctgaa tgaagccata ccaaacgacg agcgtgacac cacgatgcct gtagcaatgg   3360
caacaacgtt gcgcaaacta ttaactggcg aactacttac tctagcttcc cggcaacaat   3420
taatagactg gatggaggcg gataaagttg caggaccact tctgcgctcg gcccttccgg   3480
ctggctggtt tattgctgat aaatctggag ccggtgagcg tgggtctcgc ggtatcattg   3540
cagcactggg gccagatggt aagccctccc gtatcgtagt tatctacacg acggggagtc   3600
aggcaactat ggatgaacga aatagacaga tcgctgagat aggtgcctca ctgattaagc   3660
attggtaact gtcagaccaa gtttactcat atatacttta gattgattta aaacttcatt   3720
tttaatttaa aaggatctag gtgaagatcc tttttgataa tctcatgacc aaaatccctt   3780
aacgtgagtt ttcgttccac tgagcgtcag accccgtaga aaagatcaaa ggatcttctt   3840
gagatccttt ttttctgcgc gtaatctgct gcttgcaaac aaaaaaacca ccgctaccag   3900
cggtggtttg tttgccggat caagagctac caactctttt tccgaaggta actggcttca   3960
gcagagcgca gataccaaat actgtccttc tagtgtagcc gtagttaggc caccacttca   4020
agaactctgt agcaccgcct acatacctcg ctctgctaat cctgttacca gtggctgctg   4080
ccagtggcga taagtcgtgt cttaccgggt tggactcaag acgatagtta ccggataagg   4140
cgcagcggtc gggctgaacg gggggttcgt gcacacagcc cagcttggag cgaacgacct   4200
acaccgaact gagataccta cagcgtgagc attgagaaag cgccacgctt cccgaaggga   4260
gaaaggcgga caggtatccg gtaagcggca gggtcggaac aggagagcgc acgagggagc   4320
ttccaggggg gaacgcctgg tatctttata gtcctgtcgg gtttcgccac ctctgacttg   4380
agcgtcgatt tttgtgatgc tcgtcagggg ggccgagcct atggaaaaac gccagcaacg   4440
cggccttttt acggttcctg gccttttgct ggccttttgc tcacatgttc tttcctgcgt   4500
tatcccctga ttctgtggat aaccgtatta ccgcctttga gtgagctgat accgctcgcc   4560
gcagccgaac gaccgagcgc agcgagtcag tgagcgagga agcggaagag cgcccaatac   4620
gcaaaccgcc tctccccgcg cgttggccga ttcattaatg cagctggcac gacaggtttc   4680
```

```
ccgactggaa agcgggcagt gagcgcaacg caattaatgt gagttacctc actcattagg   4740

caccccaggc tttacacttt atgcttccgg ctcctatgtt gtgtggaatt gtgagcggat   4800

aacaatttca cacaggaaac agctatgacc atgattacgc caagctcgga attaaccctc   4860

actaaaggga acaaaagctg gctagt                                        4886
```

<210> SEQ ID NO 76
<211> LENGTH: 5801
<212> TYPE: DNA
<213> ORGANISM: artificial
<220> FEATURE:
<223> OTHER INFORMATION: vector pYD1gal

<400> SEQUENCE: 76

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt gctagccgct ggggccatgg    600

ttactgattg gcgcgccgga tccgatgtaa caaaatcgac tttgttccca ctgtactttt    660

agctcgtaca aaatacaata tacttttcat ttctccgtaa acaacatgtt ttcccatgta    720

atatcctttt ctatttttcg ttccgttacc aactttacac atactttata tagctattca    780

cttctataca ctaaaaaact aagacaattt taattttgct gcctgccata tttcaatttg    840

ttataaattc ctataattta tcctattagt agctaaaaaa agatgaatgt gaatcgaatc    900

ctaagagaat tgctgcagaa ttcacggatt agaagccgcc gagcgggtga cagccctccg    960

aaggaagact ctcctccgtg cgtcctcgtc ttcaccggtc gcgttcctga aacgcagatg   1020

tgcctcgcgc cgcactgctc cgaacaataa agattctaca atactagctt ttatggttat   1080

gaagaggaaa aattggcagt aacctggccc cacaaacctt caaatgaacg aatcaaatta   1140

acaaccatag gatgataatg cgattagttt tttagcctta tttctggggt aattaatcag   1200

cgaagcgatg atttttgatc tattaacaga tatataaatg caaaaactgc ataaccactt   1260

taactaatac tttcaacatt ttcggtttgt attacttctt attcaaatgt aataaaagta   1320

tcaacaaaaa attgttaata tacctctata ctttaacgtc aaggagaaaa aaccccggat   1380

cggactacta gcagctgtaa tacgactcac tatagggaat attaagctaa ttctacttca   1440

tacattttca attaagatgc agttacttcg ctgtttttca atattttctg ttattgcttc   1500

agttttagca caggaactga caactatatg cgagcaaatc ccctcaccaa ctttagaatc   1560

gacgccgtac tctttgtcaa cgactactat tttggccaac gggaaggcaa tgcaaggagt   1620

ttttgaatat tacaaatcag taacgtttgt cagtaattgc ggttctcacc cctcaacaac   1680

tagcaaaggc agccccataa acacacagta tgtttttaag cttctgcagg ctagtggtgg   1740

tggtggttct ggtggtggtg gttctggtgg tggtggttct gctagcatga ctggtggcca   1800

gcaaggccta attctgatgc ggccgcacat catcaccatc accattgatt aattaagttt   1860
```

```
aaacccgctg atctgataac aacagtgtag atgtaacaaa atcgactttg ttcccactgt   1920
acttttagct cgtacaaaat acaatatact tttcatttct ccgtaaacaa catgttttcc   1980
catgtaatat ccttttctat ttttcgttcc gttaccaact ttacacatac tttatatagc   2040
tattcacttc tatacactaa aaaactaaga caattttaat tttgctgcct gccatatttc   2100
aatttgttat aaattcctat aatttatcct attagtagct aaaaaaagat gaatgtgaat   2160
cgaatcctaa gagaattggg caagtgcaca aacaatactt aaataaatac tactcagtaa   2220
taacctattt cttagcattt ttgacgaaat ttgctatttt gttagagtct tttacaccat   2280
ttgtctccac acctccgctt acatcaacac caataacgcc atttaatcta agcgcatcac   2340
caacattttc tggcgtcagt ccaccagcta acataaaatg taagctctcg ggctctctt    2400
gccttccaac ccagtcagaa atcgagttcc aatccaaaag ttcacctgtc ccacctgctt   2460
ctgaatcaaa caagggaata aacgaatgag gtttctgtga agctgcactg agtagtatgt   2520
tgcagtcttt tggaaatacg agtcttttaa taactggcaa accgaggaac tcttggtatt   2580
cttgccacga ctcatctccg tgcagttgga cgatatcaat gccgtaatca ttgaccagag   2640
ccaaaacatc ctccttaggt tgattacgaa acacgccaac caagtatttc ggagtgcctg   2700
aactattttt atatgctttt acaagacttg aaattttcct tgcaataacc gggtcaattg   2760
ttctctttct attgggcaca catataatac ccagcaagtc agcatcggaa tctagagcac   2820
attctgcggc ctctgtgctc tgcaagccgc aaactttcac caatggacca gaactacctg   2880
tgaaattaat aacagacata ctccaagctg cctttgtgtg cttaatcacg tatactcacg   2940
tgctcaatag tcaccaatgc cctccctctt ggccctctcc ttttcttttt tcgaccgaat   3000
ttcttgaaga cgaaagggcc tcgtgatacg cctattttta taggttaatg tcatgataat   3060
aatggtttct taggacggat cgcttgcctg taacttacac gcgcctcgta tcttttaatg   3120
atggaataat ttgggaattt actctgtgtt tatttatttt tatgttttgt atttggattt   3180
tagaaagtaa ataaagaagg tagaagagtt acggaatgaa gaaaaaaaaa taaacaaagg   3240
tttaaaaaat ttcaacaaaa agcgtacttt acatatatat ttattagaca agaaaagcag   3300
attaaataga tatacattcg attaacgata agtaaaatgt aaaatcacag gattttcgtg   3360
tgtggtcttc tacacagaca agatgaaaca attcggcatt aatacctgag agcaggaaga   3420
gcaagataaa aggtagtatt tgttggcgat ccccctagag tcttttacat cttcggaaaa   3480
caaaaactat tttttcttta atttcttttt ttactttcta tttttaattt atatatttat   3540
attaaaaaat ttaaattata attattttta tagcacgtga tgaaaaggac ccaggtggca   3600
cttttcgggg aaatgtgcgc ggaacccta tttgtttatt tttctaaata cattcaaata   3660
tgtatccgct catgagacaa taaccctgat aaatgcttca ataatattga aaaaggaaga   3720
gtatgagtat tcaacatttc cgtgtcgccc ttattccctt ttttgcggca ttttgccttc   3780
ctgtttttgc tcacccagaa acgctggtga aagtaaaaga tgctgaagat cagttgggtg   3840
cacgagtggg ttacatcgaa ctggatctca acagcggtaa gatccttgag agttttcgcc   3900
ccgaagaacg ttttccaatg atgagcactt ttaaagttct gctatgtggc gcggtattat   3960
cccgtgttga cgccgggcaa gagcaactcg gtcgccgcat acactattct cagaatgact   4020
tggttgagta ctcaccagtc acagaaaagc atcttacgga tggcatgaca gtaagagaat   4080
tatgcagtgc tgccataacc atgagtgata acactgcggc caacttactt ctgacaacga   4140
tcggaggacc gaaggagcta accgcttttt tgcacaacat gggggatcat gtaactcgcc   4200
```

```
ttgatcgttg ggaaccggag ctgaatgaag ccataccaaa cgacgagcgt gacaccacga   4260
tgcctgtagc aatggcaaca acgttgcgca aactattaac tggcgaacta cttactctag   4320
cttcccggca acaattaata gactggatgg aggcggataa agttgcagga ccacttctgc   4380
gctcggccct tccggctggc tggtttattg ctgataaatc tggagccggt gagcgtgggt   4440
ctcgcggtat cattgcagca ctggggccag atggtaagcc ctcccgtatc gtagttatct   4500
acacgacggg cagtcaggca actatggatg aacgaaatag acagatcgct gagataggtg   4560
cctcactgat taagcattgg taactgtcag accaagttta ctcatatata ctttagattg   4620
atttaaaact tcatttttaa tttaaaagga tctaggtgaa gatccttttt gataatctca   4680
tgaccaaaat cccttaacgt gagttttcgt tccactgagc gtcagacccc gtagaaaaga   4740
tcaaaggatc ttcttgagat cctttttttc tgcgcgtaat ctgctgcttg caaacaaaaa   4800
aaccaccgct accagcggtg gtttgtttgc cggatcaaga gctaccaact ctttttccga   4860
aggtaactgg cttcagcaga gcgcagatac caaatactgt ccttctagtg tagccgtagt   4920
taggccacca cttcaagaac tctgtagcac cgcctacata cctcgctctg ctaatcctgt   4980
taccagtggc tgctgccagt ggcgataagt cgtgtcttac cgggttggac tcaagacgat   5040
agttaccgga taaggcgcag cggtcgggct gaacgggggg ttcgtgcaca cagcccagct   5100
tggagcgaac gacctacacc gaactgagat acctacagcg tgagcattga gaaagcgcca   5160
cgcttcccga agggagaaag gcggacaggt atccggtaag cggcagggtc ggaacaggag   5220
agcgcacgag ggagcttcca gggggaaacg cctggtatct ttatagtcct gtcgggtttc   5280
gccacctctg acttgagcgt cgatttttgt gatgctcgtc aggggggccg agcctatgga   5340
aaaacgccag caacgcggcc tttttacggt tcctggcctt ttgctggcct tttgctcaca   5400
tgttctttcc tgcgttatcc cctgattctg tggataaccg tattaccgcc tttgagtgag   5460
ctgataccgc tcgccgcagc cgaacgaccg agcgcagcga gtcagtgagc gaggaagcgg   5520
aagagcgccc aatacgcaaa ccgcctctcc ccgcgcgttg gccgattcat taatgcagct   5580
ggcacgacag gtttcccgac tggaaagcgg gcagtgagcg caacgcaatt aatgtgagtt   5640
acctcactca ttaggcaccc caggctttac actttatgct tccggctcct atgttgtgtg   5700
gaattgtgag cggataacaa tttcacacag gaaacagcta tgaccatgat tacgccaagc   5760
tcggaattaa ccctcactaa agggaacaaa agctggctag t                         5801
```

<210> SEQ ID NO 77
<211> LENGTH: 692
<212> TYPE: DNA
<213> ORGANISM: artificial
<220> FEATURE:
<223> OTHER INFORMATION: 4D5H

<400> SEQUENCE: 77

```
ggccagcaag gccaagaggt tcaactagtg gagtctggcg gtggcctggt gcagccaggg     60
ggctcactcc gtttgtcctg tgcagcttct ggcttcaaca ttaaagacac ctatatacac    120
tgggtgcgtc aggccccggg taagggcctg gaatgggttg caaggattta tcctacgaat    180
ggttatacta gatatgccga tagcgtcaag ggccgtttca ctataagcgc agacacatcc    240
aaaaacacag cctacctgca gatgaacagc ctgcgtgctg aggacactgc cgtctattat    300
tgttctagat ggggagggga cggcttctat gctatggact actggggtca aggaaccctg    360
gtcaccgtct cctcggctag caccaagggc cccagcgtgt tccctctggc ccccagctcc    420
aagagcacct ccggcggcac cgccgccctg ggctgcctgg tgaaggatta cttcccagag    480
```

```
cccgtgaccg tgagctggaa cagcggcgcc ctgaccagcg gcgtgcacac ctttcccgcc    540

gtgctgcagt ccagcggcct gtactccctg agcagcgtgg tgaccgtgcc cagcagcagc    600

ctgggcaccc agacctacat ctgcaatgtg aaccacaagc ccagcaatac caaggtggat    660

aagaaggtgg agcccaagag ctgcgcggcc gc                                  692
```

<210> SEQ ID NO 78
<211> LENGTH: 661
<212> TYPE: DNA
<213> ORGANISM: artificial
<220> FEATURE:
<223> OTHER INFORMATION: 4D5L

<400> SEQUENCE: 78

```
ccatggcgga tatccagatg acccagtccc cgagctccct gtccgcctct gtgggcgata     60

gggtcaccat cacctgccgt gccagtcagg atgtgaatac tgctgtagcc tggtatcaac    120

agaaaccagg aaaagctccg aaactactga tttactcggc atccttcctc tactctggag    180

tcccttctcg cttctctgga tccagatctg ggacggattt cactctgacc atcagcagtc    240

tgcagccgga agacttcgca acttattact gtcagcaaca ttatactact cctcccacgt    300

tcggacaggg taccaaggtg gagatcaaac gtacggtggc ggcgccatct gtcttcatct    360

tcccgccatc tgatgagcag cttaagtctg gaactgcctc tgttgtgtgc ctgctgaata    420

acttctatcc cagagaggcc aaagtacagt ggaaggtgga taacgccctc caatcgggta    480

actcccagga gagtgtcaca gagcaggaca gcaaggacag cacctacagc ctcagcagca    540

ccctgacgct gagcaaagca gactacgaga aacacaaagt ctacgcctgc gaagtcaccc    600

atcagggcct gagctcgccc gtcacaaaga gcttcaacag gggagagtgt tgaggcgcgc    660

c                                                                    661
```

<210> SEQ ID NO 79
<211> LENGTH: 6468
<212> TYPE: DNA
<213> ORGANISM: artificial
<220> FEATURE:
<223> OTHER INFORMATION: vector pYD4D5hc

<400> SEQUENCE: 79

```
acggattaga agccgccgag cgggtgacag ccctccgaag gaagactctc ctccgtgcgt     60

cctcgtcttc accggtcgcg ttcctgaaac gcagatgtgc ctcgcgccgc actgctccga    120

acaataaaga ttctacaata ctagctttta tggttatgaa gaggaaaaat tggcagtaac    180

ctggccccac aaaccttcaa atgaacgaat caaattaaca accataggat gataatgcga    240

ttagtttttt agccttattt ctggggtaat taatcagcga agcgatgatt tttgatctat    300

taacagatat ataaatgcaa aaactgcata accactttaa ctaatacttt caacattttc    360

ggtttgtatt acttcttatt caaatgtaat aaaagtatca acaaaaaatt gttaatatac    420

ctctatactt taacgtcaag gagaaaaaac cccggatcgg actactagca gctgtaatac    480

gactcactat agggaatatt aagctaattc tacttcatac attttcaatt aagatgcagt    540

tacttcgctg tttttcaata ttttctgtta ttgcttcagt gctagccgct ggggccatgg    600

ttactgattg gcgcgccgga tccgatgtaa caaaatcgac tttgttccca ctgtactttt    660

agctcgtaca aaatacaata tacttttcat ttctccgtaa acaacatgtt ttcccatgta    720

atatcctttt ctatttttcg ttccgttacc aactttacac atactttata tagctattca    780
```

-continued

```
cttctataca ctaaaaaact aagacaattt taattttgct gcctgccata tttcaatttg    840
ttataaattc ctataattta tcctattagt agctaaaaaa agatgaatgt gaatcgaatc    900
ctaagagaat tgctgcagaa ttcacggatt agaagccgcc gagcgggtga cagccctccg    960
aaggaagact ctcctccgtg cgtcctcgtc ttcaccggtc gcgttcctga aacgcagatg   1020
tgcctcgcgc cgcactgctc cgaacaataa agattctaca atactagctt ttatggttat   1080
gaagaggaaa aattggcagt aacctggccc cacaaacctt caaatgaacg aatcaaatta   1140
acaaccatag gatgataatg cgattagttt tttagcctta tttctggggt aattaatcag   1200
cgaagcgatg atttttgatc tattaacaga tatataaatg caaaaactgc ataaccactt   1260
taactaatac tttcaacatt ttcggtttgt attacttctt attcaaatgt aataaaagta   1320
tcaacaaaaa attgttaata tacctctata ctttaacgtc aaggagaaaa aaccccggat   1380
cggactacta gcagctgtaa tacgactcac tatagggaat attaagctaa ttctacttca   1440
tacattttca attaagatgc agttacttcg ctgtttttca atattttctg ttattgcttc   1500
agttttagca caggaactga caactatatg cgagcaaatc ccctcaccaa ctttagaatc   1560
gacgccgtac tctttgtcaa cgactactat tttggccaac gggaaggcaa tgcaaggagt   1620
ttttgaatat tacaaatcag taacgtttgt cagtaattgc ggttctcacc cctcaacaac   1680
tagcaaaggc agccccataa acacacagta tgtttttaag cttctgcagg ctagtggtgg   1740
tggtggttct ggtggtggtg gttctggtgg tggtggttct gctagcatga ctggtggcca   1800
gcaaggccaa ggttctgagg ttcaactagt ggagtctggc ggtggcctgg tgcagccagg   1860
gggctcactc cgtttgtcct gtgcagcttc tggcttcaac attaaagaca cctatataca   1920
ctgggtgcgt caggccccgg gtaagggcct ggaatgggtt gcaaggattt atcctacgaa   1980
tggttatact agatatgccg atagcgtcaa gggccgtttc actataagcg cagacacatc   2040
caaaaacaca gcctacctgc agatgaacag cctgcgtgct gaggacactg ccgtctatta   2100
ttgttctaga tggggagggg acggcttcta tgctatggac tactggggtc aaggaaccct   2160
ggtcaccgtc tcctcggcta gcaccaaggg ccccagcgtg ttccctctgg cccccagctc   2220
caagagcacc tccggcggca ccgccgccct gggctgcctg gtgaaggatt acttcccaga   2280
gcccgtgacc gtgagctgga acagcggcgc cctgaccagc ggcgtgcaca cctttcccgc   2340
cgtgctgcag tccagcggcc tgtactccct gagcagcgtg gtgaccgtgc ccagcagcag   2400
cctgggcacc cagacctaca tctgcaatgt gaaccacaag cccagcaata ccaaggtgga   2460
taagaaggtg gagcccaaga gctgcgcggc cgcacatcat caccatcacc attgattaat   2520
taagtttaaa cccgctgatc tgataacaac agtgtagatg taacaaaatc gactttgttc   2580
ccactgtact tttagctcgt acaaaataca atatactttt catttctccg taaacaacat   2640
gttttcccat gtaatatcct tttctatttt tcgttccgtt accaacttta cacatacttt   2700
atatagctat tcacttctat acactaaaaa actaagacaa ttttaatttt gctgcctgcc   2760
atatttcaat ttgttataaa ttcctataat ttatcctatt agtagctaaa aaaagatgaa   2820
tgtgaatcga atcctaagag aattgggcaa gtgcacaaac aatacttaaa taaatactac   2880
tcagtaataa cctatttctt agcatttttg acgaaatttg ctattttgtt agagtctttt   2940
acaccatttg tctccacacc tccgcttaca tcaacaccaa taacgccatt taatctaagc   3000
gcatcaccaa cattttctgg cgtcagtcca ccagctaaca taaaatgtaa gctctcgggg   3060
ctctcttgcc ttccaaccca gtcagaaatc gagttccaat ccaaaagttc acctgtccca   3120
cctgcttctg aatcaaacaa gggaataaac gaatgaggtt tctgtgaagc tgcactgagt   3180
```

```
agtatgttgc agtcttttgg aaatacgagt cttttaataa ctggcaaacc gaggaactct   3240
tggtattctt gccacgactc atctccgtgc agttggacga tatcaatgcc gtaatcattg   3300
accagagcca aaacatcctc cttaggttga ttacgaaaca cgccaaccaa gtatttcgga   3360
gtgcctgaac tatttttata tgcttttaca agacttgaaa ttttccttgc aataaccggg   3420
tcaattgttc tctttctatt gggcacacat ataataccca gcaagtcagc atcggaatct   3480
agagcacatt ctgcggcctc tgtgctctgc aagccgcaaa ctttcaccaa tggaccagaa   3540
ctacctgtga aattaataac agacatactc caagctgcct ttgtgtgctt aatcacgtat   3600
actcacgtgc tcaatagtca ccaatgccct ccctcttggc cctctccttt tctttttttcg  3660
accgaatttc ttgaagacga aagggcctcg tgatacgcct atttttatag gttaatgtca   3720
tgataataat ggtttcttag gacggatcgc ttgcctgtaa cttacacgcg cctcgtatct   3780
tttaatgatg gaataatttg ggaatttact ctgtgtttat ttatttttat gttttgtatt   3840
tggattttag aaagtaaata aagaaggtag aagagttacg gaatgaagaa aaaaaaataa   3900
acaaaggttt aaaaaatttc aacaaaaagc gtactttaca tatatattta ttagacaaga   3960
aaagcagatt aaatagatat acattcgatt aacgataagt aaaatgtaaa atcacaggat   4020
tttcgtgtgt ggtcttctac acagacaaga tgaaacaatt cggcattaat acctgagagc   4080
aggaagagca agataaaagg tagtatttgt tggcgatccc cctagagtct tttacatctt   4140
cggaaaacaa aaactatttt ttctttaatt tcttttttta ctttctattt ttaatttata   4200
tatttatatt aaaaaattta aattataatt atttttatag cacgtgatga aaaggaccca   4260
ggtggcactt ttcggggaaa tgtgcgcgga acccctattt gtttattttt ctaaatacat   4320
tcaaatatgt atccgctcat gagacaataa ccctgataaa tgcttcaata atattgaaaa   4380
aggaagagta tgagtattca acatttccgt gtcgccctta ttcccttttt tgcggcattt   4440
tgccttcctg tttttgctca cccagaaacg ctggtgaaag taaaagatgc tgaagatcag   4500
ttgggtgcac gagtgggtta catcgaactg gatctcaaca gcggtaagat ccttgagagt   4560
tttcgccccg aagaacgttt tccaatgatg agcactttta aagttctgct atgtggcgcg   4620
gtattatccc gtgttgacgc cgggcaagag caactcggtc gccgcataca ctattctcag   4680
aatgacttgg ttgagtactc accagtcaca gaaaagcatc ttacggatgg catgacagta   4740
agagaattat gcagtgctgc cataaccatg agtgataaca ctgcggccaa cttacttctg   4800
acaacgatcg gaggaccgaa ggagctaacc gcttttttgc acaacatggg ggatcatgta   4860
actcgccttg atcgttggga accggagctg aatgaagcca taccaaacga cgagcgtgac   4920
accacgatgc ctgtagcaat ggcaacaacg ttgcgcaaac tattaactgg cgaactactt   4980
actctagctt cccggcaaca attaatagac tggatggagg cggataaagt tgcaggacca   5040
cttctgcgct cggcccttcc ggctggctgg tttattgctg ataaatctgg agccggtgag   5100
cgtgggtctc gcggtatcat tgcagcactg gggccagatg gtaagccctc ccgtatcgta   5160
gttatctaca cgacgggcag tcaggcaact atggatgaac gaaatagaca gatcgctgag   5220
ataggtgcct cactgattaa gcattggtaa ctgtcagacc aagtttactc atatatactt   5280
tagattgatt taaaacttca tttttaattt aaaaggatct aggtgaagat cctttttgat   5340
aatctcatga ccaaaatccc ttaacgtgag ttttcgttcc actgagcgtc agaccccgta   5400
gaaaagatca aaggatcttc ttgagatcct ttttttctgc gcgtaatctg ctgcttgcaa   5460
acaaaaaaac caccgctacc agcggtggtt tgtttgccgg atcaagagct accaactctt   5520
```

```
tttccgaagg taactggctt cagcagagcg cagataccaa atactgtcct tctagtgtag   5580

ccgtagttag gccaccactt caagaactct gtagcaccgc ctacatacct cgctctgcta   5640

atcctgttac cagtggctgc tgccagtggc gataagtcgt gtcttaccgg gttggactca   5700

agacgatagt taccggataa ggcgcagcgg tcgggctgaa cggggggttc gtgcacacag   5760

cccagcttgg agcgaacgac ctacaccgaa ctgagatacc tacagcgtga gcattgagaa   5820

agcgccacgc ttcccgaagg gagaaaggcg gacaggtatc cggtaagcgg cagggtcgga   5880

acaggagagc gcacgaggga gcttccaggg ggaaacgcct ggtatcttta tagtcctgtc   5940

gggtttcgcc acctctgact tgagcgtcga tttttgtgat gctcgtcagg ggggcggagc   6000

ctatggaaaa acgccagcaa cgcggccttt ttacggttcc tggccttttg ctggcctttt   6060

gctcacatgt tctttcctgc gttatcccct gattctgtgg ataaccgtat taccgccttt   6120

gagtgagctg ataccgctcg ccgcagccga acgaccgagc gcagcgagtc agtgagcgag   6180

gaagcggaag agcgcccaat acgcaaaccg cctctccccg cgcgttggcc gattcattaa   6240

tgcagctggc acgacaggtt tcccgactgg aaagcgggca gtgagcgcaa cgcaattaat   6300

gtgagttacc tcactcatta ggcaccccag gctttacact ttatgcttcc ggctcctatg   6360

ttgtgtggaa ttgtgagcgg ataacaattt cacacaggaa acagctatga ccatgattac   6420

gccaagctcg gaattaaccc tcactaaagg gaacaaaagc tggctagt                6468
```

<210> SEQ ID NO 80
<211> LENGTH: 223
<212> TYPE: PRT
<213> ORGANISM: artificial
<220> FEATURE:
<223> OTHER INFORMATION: 4D5hp

<400> SEQUENCE: 80

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
```

```
        195                 200                 205

Pro Ser Asn Thr Lys Val Asp Lys Lys Val Glu Pro Lys Ser Cys
    210                 215                 220
```

<210> SEQ ID NO 81
<211> LENGTH: 7100
<212> TYPE: DNA
<213> ORGANISM: artificial
<220> FEATURE:
<223> OTHER INFORMATION: vector pYD4D5hl

<400> SEQUENCE: 81

```
acggattaga agccgccgag cgggtgacag ccctccgaag gaagactctc ctccgtgcgt      60

cctcgtcttc accggtcgcg ttcctgaaac gcagatgtgc ctcgcgccgc actgctccga     120

acaataaaga ttctacaata ctagctttta tggttatgaa gaggaaaaat tggcagtaac     180

ctggccccac aaaccttcaa atgaacgaat caaattaaca accataggat gataatgcga     240

ttagtttttt agccttattt ctggggtaat taatcagcga agcgatgatt tttgatctat     300

taacagatat ataaatgcaa aaactgcata accactttaa ctaatacttt caacattttc     360

ggtttgtatt acttcttatt caaatgtaat aaaagtatca acaaaaaatt gttaatatac     420

ctctatactt taacgtcaag gagaaaaaac cccggatcgg actactagca gctgtaatac     480

gactcactat agggaatatt aagctaattc tacttcatac attttcaatt aagatgcagt     540

tacttcgctg tttttcaata ttttctgtta ttgcttcagt gctagccgct ggggccatgg     600

cggatatcca gatgacccag tccccgagct ccctgtccgc ctctgtgggc gatagggtca     660

ccatcacctg ccgtgccagt caggatgtga atactgctgt agcctggtat caacagaaac     720

caggaaaagc tccgaaacta ctgatttact cggcatcctt cctctactct ggagtccctt     780

ctcgcttctc tggatccaga tctgggacgg atttcactct gaccatcagc agtctgcagc     840

cggaagactt cgcaacttat tactgtcagc aacattatac tactcctccc acgttcggac     900

agggtaccaa ggtggagatc aaacgtacgg tggcggcgcc atctgtcttc atcttcccgc     960

catctgatga gcagcttaag tctggaactg cctctgttgt gtgcctgctg aataacttct    1020

atcccagaga ggccaaagta cagtggaagg tggataacgc cctccaatcg ggtaactccc    1080

aggagagtgt cacagagcag gacagcaagg acagcaccta cagcctcagc agcaccctga    1140

cgctgagcaa agcagactac gagaaacaca aagtctacgc ctgcgaagtc acccatcagg    1200

gcctgagctc gcccgtcaca aagagcttca acaggggaga gtgttgaggc gcgccggatc    1260

cgatgtaaca aaatcgactt tgttcccact gtacttttag ctcgtacaaa atacaatata    1320

cttttcattt ctccgtaaac aacatgtttt cccatgtaat atccttttct atttttcgtt    1380

ccgttaccaa ctttacacat actttatata gctattcact tctatacact aaaaaactaa    1440

gacaatttta attttgctgc ctgccatatt tcaatttgtt ataaattcct ataatttatc    1500

ctattagtag ctaaaaaaag atgaatgtga atcgaatcct aagagaattg ctgcagaatt    1560

cacggattag aagccgccga gcgggtgaca gccctccgaa ggaagactct cctccgtgcg    1620

tcctcgtctt caccggtcgc gttcctgaaa cgcagatgtg cctcgcgccg cactgctccg    1680

aacaataaag attctacaat actagctttt atggttatga agaggaaaaa ttggcagtaa    1740

cctggcccca caaaccttca aatgaacgaa tcaaattaac aaccatagga tgataatgcg    1800

attagttttt tagccttatt tctggggtaa ttaatcagcg aagcgatgat ttttgatcta    1860

ttaacagata tataaatgca aaaactgcat aaccacttta actaatactt tcaacatttt    1920
```

```
cggtttgtat tacttcttat tcaaatgtaa taaaagtatc aacaaaaaat tgttaatata   1980
cctctatact ttaacgtcaa ggagaaaaaa ccccggatcg gactactagc agctgtaata   2040
cgactcacta tagggaatat taagctaatt ctacttcata cattttcaat taagatgcag   2100
ttacttcgct gtttttcaat attttctgtt attgcttcag ttttagcaca ggaactgaca   2160
actatatgcg agcaaatccc ctcaccaact ttagaatcga cgccgtactc tttgtcaacg   2220
actactattt tggccaacgg gaaggcaatg caaggagttt ttgaatatta caaatcagta   2280
acgtttgtca gtaattgcgg ttctcacccc tcaacaacta gcaaaggcag ccccataaac   2340
acacagtatg tttttaagct tctgcaggct agtggtggtg gtggttctgg tggtggtggt   2400
tctggtggtg gtggttctgc tagcatgact ggtggccagc aaggccaaga ggttcaacta   2460
gtggagtctg gcggtggcct ggtgcagcca gggggctcac tccgtttgtc ctgtgcagct   2520
tctggcttca acattaaaga cacctatata cactgggtgc gtcaggcccc gggtaagggc   2580
ctggaatggg ttgcaaggat ttatcctacg aatggttata ctagatatgc cgatagcgtc   2640
aagggccgtt tcactataag cgcagacaca tccaaaaaca cagcctacct gcagatgaac   2700
agcctgcgtg ctgaggacac tgccgtctat tattgttcta gatggggagg ggacggcttc   2760
tatgctatgg actactgggg tcaaggaacc ctggtcaccg tctcctcggc tagcaccaag   2820
ggccccagcg tgttccctct ggcccccagc tccaagagca cctccggcgg caccgccgcc   2880
ctgggctgcc tggtgaagga ttacttccca gagcccgtga ccgtgagctg gaacagcggc   2940
gccctgacca gcggcgtgca cacctttccc gccgtgctgc agtccagcgg cctgtactcc   3000
ctgagcagcg tggtgaccgt gcccagcagc agcctgggca cccagaccta catctgcaat   3060
gtgaaccaca agcccagcaa taccaaggtg gataagaagg tggagcccaa gagctgcgcg   3120
gccgcacatc atcaccatca ccattgatta attaagttta aacccgctga tctgataaca   3180
acagtgtaga tgtaacaaaa tcgactttgt tcccactgta cttttagctc gtacaaaata   3240
caatatactt ttcatttctc cgtaaacaac atgttttccc atgtaatatc cttttctatt   3300
tttcgttccg ttaccaactt tacacatact ttatatagct attcacttct atacactaaa   3360
aaactaagac aattttaatt ttgctgcctg ccatatttca atttgttata aattcctata   3420
atttatccta ttagtagcta aaaaaagatg aatgtgaatc gaatcctaag agaattgggc   3480
aagtgcacaa acaatactta aataaatact actcagtaat aacctatttc ttagcatttt   3540
tgacgaaatt tgctattttg ttagagtctt ttacaccatt tgtctccaca cctccgctta   3600
catcaacacc aataacgcca tttaatctaa gcgcatcacc aacattttct ggcgtcagtc   3660
caccagctaa cataaaatgt aagctctcgg ggctctcttg ccttccaacc cagtcagaaa   3720
tcgagttcca atccaaaagt tcacctgtcc cacctgcttc tgaatcaaac aagggaataa   3780
acgaatgagg tttctgtgaa gctgcactga gtagtatgtt gcagtctttt ggaaatacga   3840
gtcttttaat aactggcaaa ccgaggaact cttggtattc ttgccacgac tcatctccgt   3900
gcagttggac gatatcaatg ccgtaatcat tgaccagagc caaaacatcc tccttaggtt   3960
gattacgaaa cacgccaacc aagtatttcg gagtgcctga actattttta tatgctttta   4020
caagacttga aattttcctt gcaataaccg ggtcaattgt tctctttcta ttgggcacac   4080
atataatacc cagcaagtca gcatcggaat ctagagcaca ttctgcggcc tctgtgctct   4140
gcaagccgca aactttcacc aatggaccag aactacctgt gaaattaata acagacatac   4200
tccaagctgc ctttgtgtgc ttaatcacgt atactcacgt gctcaatagt caccaatgcc   4260
ctccctcttg gccctctcct ttcttttttt cgaccgaatt tcttgaagac gaaagggcct   4320
```

```
cgtgatacgc ctatttttat aggttaatgt catgataata atggtttctt aggacggatc   4380
gcttgcctgt aacttacacg cgcctcgtat cttttaatga tggaataatt tgggaattta   4440
ctctgtgttt atttattttt atgttttgta tttggatttt agaaagtaaa taaagaaggt   4500
agaagagtta cggaatgaag aaaaaaaaat aaacaaaggt ttaaaaaatt tcaacaaaaa   4560
gcgtacttta catatatatt tattagacaa gaaaagcaga ttaaatagat atacattcga   4620
ttaacgataa gtaaaatgta aaatcacagg attttcgtgt gtggtcttct acacagacaa   4680
gatgaaacaa ttcggcatta atacctgaga gcaggaagag caagataaaa ggtagtattt   4740
gttggcgatc cccctagagt cttttacatc ttcggaaaac aaaaactatt ttttctttaa   4800
tttctttttt tactttctat ttttaattta tatatttata ttaaaaaatt taaattataa   4860
ttatttttat agcacgtgat gaaaaggacc caggtggcac ttttcgggga aatgtgcgcg   4920
gaacccctat ttgtttattt ttctaaatac attcaaatat gtatccgctc atgagacaat   4980
aaccctgata aatgcttcaa taatattgaa aaaggaagag tatgagtatt caacatttcc   5040
gtgtcgccct tattcccttt tttgcggcat tttgccttcc tgtttttgct cacccagaaa   5100
cgctggtgaa agtaaaagat gctgaagatc agttgggtgc acgagtgggt tacatcgaac   5160
tggatctcaa cagcggtaag atccttgaga gttttcgccc cgaagaacgt tttccaatga   5220
tgagcacttt taaagttctg ctatgtggcg cggtattatc ccgtgttgac gccgggcaag   5280
agcaactcgg tcgccgcata cactattctc agaatgactt ggttgagtac tcaccagtca   5340
cagaaaagca tcttacggat ggcatgacag taagagaatt atgcagtgct gccataacca   5400
tgagtgataa cactgcggcc aacttacttc tgacaacgat cggaggaccg aaggagctaa   5460
ccgctttttt gcacaacatg ggggatcatg taactcgcct tgatcgttgg gaaccggagc   5520
tgaatgaagc cataccaaac gacgagcgtg acaccacgat gcctgtagca atggcaacaa   5580
cgttgcgcaa actattaact ggcgaactac ttactctagc ttcccggcaa caattaatag   5640
actggatgga ggcggataaa gttgcaggac cacttctgcg ctcggccctt ccggctggct   5700
ggtttattgc tgataaatct ggagccggtg agcgtgggtc tcgcggtatc attgcagcac   5760
tggggccaga tggtaagccc tcccgtatcg tagttatcta cacgacgggc agtcaggcaa   5820
ctatggatga acgaaataga cagatcgctg agataggtgc ctcactgatt aagcattggt   5880
aactgtcaga ccaagtttac tcatatatac tttagattga tttaaaactt catttttaat   5940
ttaaaaggat ctaggtgaag atcctttttg ataatctcat gaccaaaatc ccttaacgtg   6000
agttttcgtt ccactgagcg tcagaccccg tagaaaagat caaaggatct tcttgagatc   6060
ctttttttct gcgcgtaatc tgctgcttgc aaacaaaaaa accaccgcta ccagcggtgg   6120
tttgtttgcc ggatcaagag ctaccaactc tttttccgaa ggtaactggc ttcagcagag   6180
cgcagatacc aaatactgtc cttctagtgt agccgtagtt aggccaccac ttcaagaact   6240
ctgtagcacc gcctacatac ctcgctctgc taatcctgtt accagtggct gctgccagtg   6300
gcgataagtc gtgtcttacc gggttggact caagacgata gttaccggat aaggcgcagc   6360
ggtcgggctg aacggggggt tcgtgcacac agcccagctt ggagcgaacg acctacaccg   6420
aactgagata cctacagcgt gagcattgag aaagcgccac gcttcccgaa gggagaaagg   6480
cggacaggta tccggtaagc ggcagggtcg gaacaggaga gcgcacgagg gagcttccag   6540
ggggaaacgc ctggtatctt tatagtcctg tcgggtttcg ccacctctga cttgagcgtc   6600
gatttttgtg atgctcgtca ggggggccga gcctatggaa aaacgccagc aacgcggcct   6660
```

```
ttttacggtt cctggccttt tgctggcctt ttgctcacat gttctttcct gcgttatccc   6720

ctgattctgt ggataaccgt attaccgcct ttgagtgagc tgataccgct cgccgcagcc   6780

gaacgaccga gcgcagcgag tcagtgagcg aggaagcgga agagcgccca atacgcaaac   6840

cgcctctccc cgcgcgttgg ccgattcatt aatgcagctg gcacgacagg tttcccgact   6900

ggaaagcggg cagtgagcgc aacgcaatta atgtgagtta cctcactcat taggcacccc   6960

aggctttaca ctttatgctt ccggctccta tgttgtgtgg aattgtgagc ggataacaat   7020

ttcacacagg aaacagctat gaccatgatt acgccaagct cggaattaac cctcactaaa   7080

gggaacaaaa gctggctagt                                               7100
```

<210> SEQ ID NO 82
<211> LENGTH: 214
<212> TYPE: PRT
<213> ORGANISM: artificial
<220> FEATURE:
<223> OTHER INFORMATION: 4D5lp

<400> SEQUENCE: 82

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 83
<211> LENGTH: 13
<212> TYPE: PRT
<213> ORGANISM: artificial
<220> FEATURE:
<223> OTHER INFORMATION: EF-loop sequence AA198ff

<400> SEQUENCE: 83

```
Val Ala Arg Asn Ser Pro Ser Met Trp Arg Trp Ala His
```

1 5 10

<210> SEQ ID NO 84
<211> LENGTH: 13
<212> TYPE: PRT
<213> ORGANISM: artificial
<220> FEATURE:
<223> OTHER INFORMATION: EF-loop sequence AA198ff

<400> SEQUENCE: 84

Val Ala Arg Trp Ser Pro Ser Met Val Arg Trp Ala His
1 5 10

<210> SEQ ID NO 85
<211> LENGTH: 13
<212> TYPE: PRT
<213> ORGANISM: artificial
<220> FEATURE:
<223> OTHER INFORMATION: EF-loop sequence AA198ff

<400> SEQUENCE: 85

Val Ala Arg Lys Asn His Arg Lys Trp Arg Arg Thr His
1 5 10

<210> SEQ ID NO 86
<211> LENGTH: 13
<212> TYPE: PRT
<213> ORGANISM: artificial
<220> FEATURE:
<223> OTHER INFORMATION: EF-loop sequence AA198ff

<400> SEQUENCE: 86

Val Ser Arg Tyr Ser Pro Thr Met Trp Gln Trp Ala His
1 5 10

<210> SEQ ID NO 87
<211> LENGTH: 13
<212> TYPE: PRT
<213> ORGANISM: artificial
<220> FEATURE:
<223> OTHER INFORMATION: EF-loop sequence AA198ff

<400> SEQUENCE: 87

Val Ala Arg His Ser Leu Ser Met Trp Arg Trp Ala His
1 5 10

<210> SEQ ID NO 88
<211> LENGTH: 13
<212> TYPE: PRT
<213> ORGANISM: artificial
<220> FEATURE:
<223> OTHER INFORMATION: EF-loop sequence AA198ff

<400> SEQUENCE: 88

Val Ala Arg Tyr Ser Gln Thr Met Trp Arg Trp Ala His
1 5 10

<210> SEQ ID NO 89
<211> LENGTH: 13
<212> TYPE: PRT
<213> ORGANISM: artificial
<220> FEATURE:
<223> OTHER INFORMATION: EF-loop sequence AA198ff

<400> SEQUENCE: 89

Met Pro Arg Phe Ser Pro Ser Met Trp Arg Trp Ala His
1 5 10

<210> SEQ ID NO 90
<211> LENGTH: 13
<212> TYPE: PRT
<213> ORGANISM: artificial
<220> FEATURE:
<223> OTHER INFORMATION: EF-loop sequence AA198ff

<400> SEQUENCE: 90

Val Thr Arg Tyr Ser Gln Ser Met Trp Arg Trp Ala His
1               5                   10

<210> SEQ ID NO 91
<211> LENGTH: 13
<212> TYPE: PRT
<213> ORGANISM: artificial
<220> FEATURE:
<223> OTHER INFORMATION: EF-loop sequence AA198ff

<400> SEQUENCE: 91

Ile Glu Arg Tyr Ser Thr Arg Met Trp Ser Trp Ala His
1               5                   10

<210> SEQ ID NO 92
<211> LENGTH: 13
<212> TYPE: PRT
<213> ORGANISM: artificial
<220> FEATURE:
<223> OTHER INFORMATION: EF-loop sequence AA198ff

<400> SEQUENCE: 92

Val Ala Arg His Ser Pro Glu Met Trp His Trp Ala His
1               5                   10

<210> SEQ ID NO 93
<211> LENGTH: 13
<212> TYPE: PRT
<213> ORGANISM: artificial
<220> FEATURE:
<223> OTHER INFORMATION: EF-loop sequence AA198ff

<400> SEQUENCE: 93

Val Ala Arg Gly Ser Pro Ser Met Trp Ser Trp Gly His
1               5                   10

<210> SEQ ID NO 94
<211> LENGTH: 13
<212> TYPE: PRT
<213> ORGANISM: artificial
<220> FEATURE:
<223> OTHER INFORMATION: EF-loop sequence AA198ff

<400> SEQUENCE: 94

Val Ala Arg His Ser Gln Thr Met Trp His Trp Ala His
1               5                   10

<210> SEQ ID NO 95
<211> LENGTH: 13
<212> TYPE: PRT
<213> ORGANISM: artificial
<220> FEATURE:
<223> OTHER INFORMATION: EF-loop sequence AA198ff

<400> SEQUENCE: 95

Leu Ala Arg Tyr Ser Pro Gly Met Trp Arg Trp Ala His
1               5                   10

<210> SEQ ID NO 96
<211> LENGTH: 13
<212> TYPE: PRT
<213> ORGANISM: artificial
<220> FEATURE:
<223> OTHER INFORMATION: EF-loop sequence AA198ff

<400> SEQUENCE: 96

Val Pro Arg Phe Ser Pro Thr Met Trp Lys Trp Ala His
1 5 10

<210> SEQ ID NO 97
<211> LENGTH: 13
<212> TYPE: PRT
<213> ORGANISM: artificial
<220> FEATURE:
<223> OTHER INFORMATION: EF-loop sequence AA198ff

<400> SEQUENCE: 97

Val Pro Arg Trp Ser Arg Thr Met Leu Arg Trp Ala His
1 5 10

<210> SEQ ID NO 98
<211> LENGTH: 13
<212> TYPE: PRT
<213> ORGANISM: artificial
<220> FEATURE:
<223> OTHER INFORMATION: EF-loop sequence AA198ff

<400> SEQUENCE: 98

Val Pro Arg Tyr Ser Pro Arg Met Trp Arg Trp Ala His
1 5 10

<210> SEQ ID NO 99
<211> LENGTH: 13
<212> TYPE: PRT
<213> ORGANISM: artificial
<220> FEATURE:
<223> OTHER INFORMATION: EF-loop sequence AA198ff

<400> SEQUENCE: 99

Ile Ala Arg His Ser Lys Ser Met Trp Ser Trp Ala His
1 5 10

<210> SEQ ID NO 100
<211> LENGTH: 13
<212> TYPE: PRT
<213> ORGANISM: artificial
<220> FEATURE:
<223> OTHER INFORMATION: EF-loop sequence AA198ff

<400> SEQUENCE: 100

Met Pro Arg Trp Ser Lys Ser Leu Ser Gly Trp Ala His
1 5 10

<210> SEQ ID NO 101
<211> LENGTH: 13
<212> TYPE: PRT
<213> ORGANISM: artificial
<220> FEATURE:
<223> OTHER INFORMATION: EF-loop sequence AA198ff

<400> SEQUENCE: 101

Val Ala Arg Tyr Thr Pro Ser Met Trp Arg Trp Ala His
1 5 10

<210> SEQ ID NO 102
<211> LENGTH: 13
<212> TYPE: PRT
<213> ORGANISM: artificial
<220> FEATURE:
<223> OTHER INFORMATION: EF-loop sequence AA198ff

<400> SEQUENCE: 102

Val Ala Arg Asn Ser Leu Thr Met Trp Arg Trp Ala His
1 5 10

<210> SEQ ID NO 103
<211> LENGTH: 13
<212> TYPE: PRT
<213> ORGANISM: artificial
<220> FEATURE:
<223> OTHER INFORMATION: EF-loop sequence AA198ff

<400> SEQUENCE: 103

Val Ala Arg Tyr Ser Pro Ser Met Trp Lys Trp Ala His
1 5 10

<210> SEQ ID NO 104
<211> LENGTH: 13
<212> TYPE: PRT
<213> ORGANISM: artificial
<220> FEATURE:
<223> OTHER INFORMATION: EF-loop sequence AA198ff

<400> SEQUENCE: 104

Val Ala Arg Phe Ser Pro Ser Met Trp Arg Trp Ala His
1 5 10

<210> SEQ ID NO 105
<211> LENGTH: 13
<212> TYPE: PRT
<213> ORGANISM: artificial
<220> FEATURE:
<223> OTHER INFORMATION: EF-loop sequence AA198ff

<400> SEQUENCE: 105

Leu Ala Arg Trp Ser Pro Ser Leu Ser Arg Trp Ala His
1 5 10

<210> SEQ ID NO 106
<211> LENGTH: 13
<212> TYPE: PRT
<213> ORGANISM: artificial
<220> FEATURE:
<223> OTHER INFORMATION: EF-loop sequence AA198ff

<400> SEQUENCE: 106

Val Ala Arg Tyr Ser Pro Ser Met Trp Arg Trp Ala His
1 5 10

<210> SEQ ID NO 107
<211> LENGTH: 13
<212> TYPE: PRT
<213> ORGANISM: artificial
<220> FEATURE:
<223> OTHER INFORMATION: EF-loop sequence AA198ff

<400> SEQUENCE: 107

Val Pro Arg Ser Ser Leu Thr Met Trp Lys Trp Ala His
1 5 10

<210> SEQ ID NO 108

<211> LENGTH: 13
<212> TYPE: PRT
<213> ORGANISM: artificial
<220> FEATURE:
<223> OTHER INFORMATION: EF-loop sequence AA198ff

<400> SEQUENCE: 108

Val Pro Arg His Ser Thr Arg Met Trp Lys Trp Ala His
1 5 10

<210> SEQ ID NO 109
<211> LENGTH: 13
<212> TYPE: PRT
<213> ORGANISM: artificial
<220> FEATURE:
<223> OTHER INFORMATION: EF-loop sequence AA198ff

<400> SEQUENCE: 109

Val Pro Arg His Ser Arg Arg Met Trp Arg Trp Ala His
1 5 10

<210> SEQ ID NO 110
<211> LENGTH: 13
<212> TYPE: PRT
<213> ORGANISM: artificial
<220> FEATURE:
<223> OTHER INFORMATION: EF-loop sequence AA198ff

<400> SEQUENCE: 110

Val Thr Arg Tyr Ser Pro Ser Met Trp Arg Trp Ala His
1 5 10

<210> SEQ ID NO 111
<211> LENGTH: 13
<212> TYPE: PRT
<213> ORGANISM: artificial
<220> FEATURE:
<223> OTHER INFORMATION: EF-loop sequence AA198ff

<400> SEQUENCE: 111

Val Thr Arg His Ser Ser Ser Met Trp Arg Trp Ala His
1 5 10

<210> SEQ ID NO 112
<211> LENGTH: 13
<212> TYPE: PRT
<213> ORGANISM: artificial
<220> FEATURE:
<223> OTHER INFORMATION: EF-loop sequence AA198ff

<400> SEQUENCE: 112

Val Ala Arg Tyr Ser Arg Ser Met Lys Lys Trp Ala His
1 5 10

<210> SEQ ID NO 113
<211> LENGTH: 13
<212> TYPE: PRT
<213> ORGANISM: artificial
<220> FEATURE:
<223> OTHER INFORMATION: EF-loop sequence AA198ff

<400> SEQUENCE: 113

Val Ala Arg Gly Ser Thr Thr Met Trp Arg Trp Gly His
1 5 10

<210> SEQ ID NO 114
<211> LENGTH: 13

<212> TYPE: PRT
<213> ORGANISM: artificial
<220> FEATURE:
<223> OTHER INFORMATION: EF-loop sequence AA198ff

<400> SEQUENCE: 114

Val Ala Arg Ser Ser Pro Glu Met Trp Arg Trp Ala His
1 5 10

<210> SEQ ID NO 115
<211> LENGTH: 13
<212> TYPE: PRT
<213> ORGANISM: artificial
<220> FEATURE:
<223> OTHER INFORMATION: EF-loop sequence AA198ff

<400> SEQUENCE: 115

Val Ala Arg Tyr Ser Thr Gly Met Trp Asn Trp Ala His
1 5 10

<210> SEQ ID NO 116
<211> LENGTH: 13
<212> TYPE: PRT
<213> ORGANISM: artificial
<220> FEATURE:
<223> OTHER INFORMATION: EF-loop sequence AA198ff

<400> SEQUENCE: 116

Val Pro Arg Tyr Ser Gln Arg Met Trp Arg Trp Ala His
1 5 10

<210> SEQ ID NO 117
<211> LENGTH: 13
<212> TYPE: PRT
<213> ORGANISM: artificial
<220> FEATURE:
<223> OTHER INFORMATION: EF-loop sequence AA198ff

<400> SEQUENCE: 117

Val Pro Arg Asn Ser Pro Arg Met Trp Arg Trp Ala His
1 5 10

<210> SEQ ID NO 118
<211> LENGTH: 13
<212> TYPE: PRT
<213> ORGANISM: artificial
<220> FEATURE:
<223> OTHER INFORMATION: EF-loop sequence AA198ff

<400> SEQUENCE: 118

Leu Ala Arg Trp Ser Pro Ser Met Ser Arg Trp Ala His
1 5 10

<210> SEQ ID NO 119
<211> LENGTH: 13
<212> TYPE: PRT
<213> ORGANISM: artificial
<220> FEATURE:
<223> OTHER INFORMATION: EF-loop sequence AA198ff

<400> SEQUENCE: 119

Leu Ala Arg Trp Ser Pro Ser Met Lys Ser Trp Ala His
1 5 10

<210> SEQ ID NO 120
<211> LENGTH: 13
<212> TYPE: PRT

<213> ORGANISM: artificial
<220> FEATURE:
<223> OTHER INFORMATION: EF-loop sequence AA198ff

<400> SEQUENCE: 120

Leu Pro Arg Tyr Ser Thr Lys Met Lys Arg Trp Ala His
1               5                   10

<210> SEQ ID NO 121
<211> LENGTH: 13
<212> TYPE: PRT
<213> ORGANISM: artificial
<220> FEATURE:
<223> OTHER INFORMATION: EF-loop sequence AA198ff

<400> SEQUENCE: 121

Leu Ala Arg Tyr Ser Gly Arg Met Lys Arg Trp Ala His
1               5                   10

<210> SEQ ID NO 122
<211> LENGTH: 13
<212> TYPE: PRT
<213> ORGANISM: artificial
<220> FEATURE:
<223> OTHER INFORMATION: EF-loop sequence AA198ff

<400> SEQUENCE: 122

Ile Pro Arg Trp Ser Gln Gln Met Ser Arg Trp Ala His
1               5                   10

<210> SEQ ID NO 123
<211> LENGTH: 13
<212> TYPE: PRT
<213> ORGANISM: artificial
<220> FEATURE:
<223> OTHER INFORMATION: EF-loop sequence AA198ff

<400> SEQUENCE: 123

Val Gly Arg Trp Thr Pro Ser Met Trp Arg Trp Ala His
1               5                   10

<210> SEQ ID NO 124
<211> LENGTH: 13
<212> TYPE: PRT
<213> ORGANISM: artificial
<220> FEATURE:
<223> OTHER INFORMATION: EF-loop sequence AA198ff

<400> SEQUENCE: 124

Val Lys Arg Ser Ser Pro Ser Met Trp Arg Trp Ala His
1               5                   10

<210> SEQ ID NO 125
<211> LENGTH: 13
<212> TYPE: PRT
<213> ORGANISM: artificial
<220> FEATURE:
<223> OTHER INFORMATION: EF-loop sequence AA198ff

<400> SEQUENCE: 125

Leu Ala Arg Tyr Ser Pro Gly Met Trp Asn Trp Ala His
1               5                   10

<210> SEQ ID NO 126
<211> LENGTH: 13
<212> TYPE: PRT
<213> ORGANISM: artificial

<220> FEATURE:
<223> OTHER INFORMATION: EF-loop sequence AA198ff

<400> SEQUENCE: 126

Ile Ala Arg Tyr Ser Pro Asn Met Trp Asn Trp Ala His
1 5 10

<210> SEQ ID NO 127
<211> LENGTH: 13
<212> TYPE: PRT
<213> ORGANISM: artificial
<220> FEATURE:
<223> OTHER INFORMATION: EF-loop sequence AA198ff

<400> SEQUENCE: 127

Ile Ala Arg Tyr Ser Pro Ser Met Trp Arg Trp Ala His
1 5 10

<210> SEQ ID NO 128
<211> LENGTH: 13
<212> TYPE: PRT
<213> ORGANISM: artificial
<220> FEATURE:
<223> OTHER INFORMATION: EF-loop sequence AA198ff

<400> SEQUENCE: 128

Val Ala Arg Phe Ser Pro Ser Met Leu Lys Trp Ala His
1 5 10

<210> SEQ ID NO 129
<211> LENGTH: 13
<212> TYPE: PRT
<213> ORGANISM: artificial
<220> FEATURE:
<223> OTHER INFORMATION: EF-loop sequence AA198ff

<400> SEQUENCE: 129

Val Ala Arg Tyr Ser Lys Ser Met Leu Lys Trp Ala His
1 5 10

<210> SEQ ID NO 130
<211> LENGTH: 13
<212> TYPE: PRT
<213> ORGANISM: artificial
<220> FEATURE:
<223> OTHER INFORMATION: EF-loop sequence AA198ff

<400> SEQUENCE: 130

Val Ala Arg His Ser Arg Thr Met Trp Arg Trp Gly His
1 5 10

<210> SEQ ID NO 131
<211> LENGTH: 13
<212> TYPE: PRT
<213> ORGANISM: artificial
<220> FEATURE:
<223> OTHER INFORMATION: EF-loop sequence AA198ff

<400> SEQUENCE: 131

Ile Ala Arg His Ser Arg Glu Met Leu Arg Trp Ala His
1 5 10

<210> SEQ ID NO 132
<211> LENGTH: 13
<212> TYPE: PRT
<213> ORGANISM: artificial
<220> FEATURE:

<223> OTHER INFORMATION: EF-loop sequence AA198ff

<400> SEQUENCE: 132

Val Ala Arg Tyr Ser Ser Thr Met Ser Arg Trp Ala His
1               5                   10

<210> SEQ ID NO 133
<211> LENGTH: 13
<212> TYPE: PRT
<213> ORGANISM: artificial
<220> FEATURE:
<223> OTHER INFORMATION: EF-loop sequence AA198ff

<400> SEQUENCE: 133

Val Pro Arg His Ser Leu Lys Lys Leu Gln Arg Lys His
1               5                   10

<210> SEQ ID NO 134
<211> LENGTH: 13
<212> TYPE: PRT
<213> ORGANISM: artificial
<220> FEATURE:
<223> OTHER INFORMATION: EF-loop sequence AA198ff

<400> SEQUENCE: 134

Val Ala Arg Tyr Ser Pro Ser Met Trp Asn Trp Ala His
1               5                   10

<210> SEQ ID NO 135
<211> LENGTH: 13
<212> TYPE: PRT
<213> ORGANISM: artificial
<220> FEATURE:
<223> OTHER INFORMATION: EF-loop sequence AA198ff

<400> SEQUENCE: 135

Val Ala Arg Tyr Ser Pro Ser Met Trp Arg Trp Gly His
1               5                   10

<210> SEQ ID NO 136
<211> LENGTH: 13
<212> TYPE: PRT
<213> ORGANISM: artificial
<220> FEATURE:
<223> OTHER INFORMATION: EF-loop sequence AA198ff

<400> SEQUENCE: 136

Val Pro Arg Tyr Ser Ala Ser Met Trp Arg Trp Gly His
1               5                   10

<210> SEQ ID NO 137
<211> LENGTH: 13
<212> TYPE: PRT
<213> ORGANISM: artificial
<220> FEATURE:
<223> OTHER INFORMATION: EF-loop sequence AA198ff

<400> SEQUENCE: 137

Val Pro Arg Tyr Ser Ala Ser Met Trp Arg Trp Ala His
1               5                   10

<210> SEQ ID NO 138
<211> LENGTH: 13
<212> TYPE: PRT
<213> ORGANISM: artificial
<220> FEATURE:
<223> OTHER INFORMATION: EF-loop sequence AA198ff

<400> SEQUENCE: 138

Leu Pro Arg Tyr Ser Pro Gly Met Trp Arg Trp Ala His
1 5 10

<210> SEQ ID NO 139
<211> LENGTH: 13
<212> TYPE: PRT
<213> ORGANISM: artificial
<220> FEATURE:
<223> OTHER INFORMATION: EF-loop sequence AA198ff

<400> SEQUENCE: 139

Val Ala Arg Tyr Ser Gln Thr Met Ser Arg Trp Ala His
1 5 10

<210> SEQ ID NO 140
<211> LENGTH: 13
<212> TYPE: PRT
<213> ORGANISM: artificial
<220> FEATURE:
<223> OTHER INFORMATION: EF-loop sequence AA198ff

<400> SEQUENCE: 140

Val Ala Gly Tyr Arg Pro Arg Arg Ser Gly Ser Ser His
1 5 10

<210> SEQ ID NO 141
<211> LENGTH: 13
<212> TYPE: PRT
<213> ORGANISM: artificial
<220> FEATURE:
<223> OTHER INFORMATION: EF-loop sequence AA198ff

<400> SEQUENCE: 141

Leu Ala Arg His Ser Ala Asn Met Leu Arg Trp Ala His
1 5 10

<210> SEQ ID NO 142
<211> LENGTH: 13
<212> TYPE: PRT
<213> ORGANISM: artificial
<220> FEATURE:
<223> OTHER INFORMATION: EF-loop sequence AA198ff

<400> SEQUENCE: 142

Val Ala Arg His Ser Pro Ser Met Trp Ser Trp Ala His
1 5 10

<210> SEQ ID NO 143
<211> LENGTH: 13
<212> TYPE: PRT
<213> ORGANISM: artificial
<220> FEATURE:
<223> OTHER INFORMATION: EF-loop sequence AA198ff

<400> SEQUENCE: 143

Val Ala Arg Trp Ser Pro Ser Met Phe Arg Trp Ala His
1 5 10

<210> SEQ ID NO 144
<211> LENGTH: 13
<212> TYPE: PRT
<213> ORGANISM: artificial
<220> FEATURE:
<223> OTHER INFORMATION: EF-loop sequence AA198ff

<400> SEQUENCE: 144

Val Ala Arg Trp Ser Pro Ser Met Leu Arg Trp Ala His
1 5 10

<210> SEQ ID NO 145
<211> LENGTH: 13
<212> TYPE: PRT
<213> ORGANISM: artificial
<220> FEATURE:
<223> OTHER INFORMATION: EF-loop sequence AA198ff

<400> SEQUENCE: 145

Val Ala Arg Ser Ser Pro Thr Met Trp Arg Trp Ala His
1 5 10

<210> SEQ ID NO 146
<211> LENGTH: 13
<212> TYPE: PRT
<213> ORGANISM: artificial
<220> FEATURE:
<223> OTHER INFORMATION: EF-loop sequence AA198ff

<400> SEQUENCE: 146

Val Thr Arg Trp Ser Pro Thr Met Trp Arg Trp Ala His
1 5 10

<210> SEQ ID NO 147
<211> LENGTH: 13
<212> TYPE: PRT
<213> ORGANISM: artificial
<220> FEATURE:
<223> OTHER INFORMATION: EF-loop sequence AA198ff

<400> SEQUENCE: 147

Val Ala Arg Ser Ser Pro Ser Met Trp Arg Trp Ala His
1 5 10

<210> SEQ ID NO 148
<211> LENGTH: 13
<212> TYPE: PRT
<213> ORGANISM: artificial
<220> FEATURE:
<223> OTHER INFORMATION: EF-loop sequence AA198ff

<400> SEQUENCE: 148

Val Ala Arg Tyr Ser Pro Thr Met Trp Lys Trp Ala His
1 5 10

<210> SEQ ID NO 149
<211> LENGTH: 13
<212> TYPE: PRT
<213> ORGANISM: artificial
<220> FEATURE:
<223> OTHER INFORMATION: EF-loop sequence AA198ff

<400> SEQUENCE: 149

Val Ser Arg Phe Ser Pro Ser Met Trp Arg Trp Ala His
1 5 10

<210> SEQ ID NO 150
<211> LENGTH: 13
<212> TYPE: PRT
<213> ORGANISM: artificial
<220> FEATURE:
<223> OTHER INFORMATION: EF-loop sequence AA198ff

<400> SEQUENCE: 150

Ile Pro Arg Tyr Thr Pro Ser Met Trp Arg Trp Ala His
1 5 10

<210> SEQ ID NO 151
<211> LENGTH: 13
<212> TYPE: PRT
<213> ORGANISM: artificial
<220> FEATURE:
<223> OTHER INFORMATION: EF-loop sequence AA198ff

<400> SEQUENCE: 151

Val Pro Arg Tyr Ser Thr Leu Met Trp Arg Trp Ala His
1 5 10

<210> SEQ ID NO 152
<211> LENGTH: 13
<212> TYPE: PRT
<213> ORGANISM: artificial
<220> FEATURE:
<223> OTHER INFORMATION: EF-loop sequence AA198ff

<400> SEQUENCE: 152

Leu Pro Arg His Ser Arg Arg Met Trp Arg Trp Ala His
1 5 10

<210> SEQ ID NO 153
<211> LENGTH: 13
<212> TYPE: PRT
<213> ORGANISM: artificial
<220> FEATURE:
<223> OTHER INFORMATION: EF-loop sequence AA198ff

<400> SEQUENCE: 153

Leu Ala Arg Trp Ser Pro Ser Met Leu Arg Trp Ala His
1 5 10

<210> SEQ ID NO 154
<211> LENGTH: 13
<212> TYPE: PRT
<213> ORGANISM: artificial
<220> FEATURE:
<223> OTHER INFORMATION: EF-loop sequence AA198ff

<400> SEQUENCE: 154

Val Ala Arg His Ser Pro Ala Met Trp Arg Trp Ala His
1 5 10

<210> SEQ ID NO 155
<211> LENGTH: 13
<212> TYPE: PRT
<213> ORGANISM: artificial
<220> FEATURE:
<223> OTHER INFORMATION: EF-loop sequence AA198ff

<400> SEQUENCE: 155

Val Pro Arg His Ser Ala Arg Met Trp Arg Trp Ala His
1 5 10

<210> SEQ ID NO 156
<211> LENGTH: 13
<212> TYPE: PRT
<213> ORGANISM: artificial
<220> FEATURE:
<223> OTHER INFORMATION: EF-loop sequence AA198ff

<400> SEQUENCE: 156

Val Pro Arg Tyr Ser Ala Arg Met Trp Arg Trp Ala His
1 5 10

<210> SEQ ID NO 157
<211> LENGTH: 13
<212> TYPE: PRT
<213> ORGANISM: artificial
<220> FEATURE:
<223> OTHER INFORMATION: EF-loop sequence AA198ff

<400> SEQUENCE: 157

Val Ala Arg Tyr Ser Pro Arg Met Trp Arg Trp Ala His
1 5 10

<210> SEQ ID NO 158
<211> LENGTH: 13
<212> TYPE: PRT
<213> ORGANISM: artificial
<220> FEATURE:
<223> OTHER INFORMATION: EF-loop sequence AA198ff

<400> SEQUENCE: 158

Val Ala Arg Tyr Ser Arg Lys Met Ser Ser Trp Gly His
1 5 10

<210> SEQ ID NO 159
<211> LENGTH: 13
<212> TYPE: PRT
<213> ORGANISM: artificial
<220> FEATURE:
<223> OTHER INFORMATION: EF-loop sequence AA198ff

<400> SEQUENCE: 159

Leu Ala Ser Tyr Ser Pro Ser Met Trp Arg Trp Gly His
1 5 10

<210> SEQ ID NO 160
<211> LENGTH: 13
<212> TYPE: PRT
<213> ORGANISM: artificial
<220> FEATURE:
<223> OTHER INFORMATION: EF-loop sequence AA198ff

<400> SEQUENCE: 160

Val Ala Arg Tyr Ser Pro Thr Met Lys Arg Trp Ala His
1 5 10

<210> SEQ ID NO 161
<211> LENGTH: 5
<212> TYPE: PRT
<213> ORGANISM: artificial
<220> FEATURE:
<223> OTHER INFORMATION: AB-loop sequence AA143ff

<400> SEQUENCE: 161

Tyr Leu His Gly Asp
1 5

<210> SEQ ID NO 162
<211> LENGTH: 5
<212> TYPE: PRT
<213> ORGANISM: artificial
<220> FEATURE:
<223> OTHER INFORMATION: AB-loop sequence AA143ff

<400> SEQUENCE: 162

Tyr Leu Tyr Gly Asp 1 5

<210> SEQ ID NO 163
<211> LENGTH: 5
<212> TYPE: PRT
<213> ORGANISM: artificial
<220> FEATURE:
<223> OTHER INFORMATION: AB-loop sequence AA143ff

<400> SEQUENCE: 163

Tyr Leu Ser Ala Asp
1 5

<210> SEQ ID NO 164
<211> LENGTH: 5
<212> TYPE: PRT
<213> ORGANISM: artificial
<220> FEATURE:
<223> OTHER INFORMATION: AB-loop sequence AA143ff

<400> SEQUENCE: 164

Leu Ser Leu Pro Cys
1 5

<210> SEQ ID NO 165
<211> LENGTH: 5
<212> TYPE: PRT
<213> ORGANISM: artificial
<220> FEATURE:
<223> OTHER INFORMATION: AB-loop sequence AA143ff

<400> SEQUENCE: 165

Arg Glu Gly Gly Arg
1 5

<210> SEQ ID NO 166
<211> LENGTH: 5
<212> TYPE: PRT
<213> ORGANISM: artificial
<220> FEATURE:
<223> OTHER INFORMATION: AB-loop sequence AA143ff

<400> SEQUENCE: 166

Leu Thr Lys Asn Gln
1 5

<210> SEQ ID NO 167
<211> LENGTH: 5
<212> TYPE: PRT
<213> ORGANISM: artificial
<220> FEATURE:
<223> OTHER INFORMATION: AB-loop sequence AA143ff

<400> SEQUENCE: 167

Thr Lys Ala Phe Tyr
1 5

<210> SEQ ID NO 168
<211> LENGTH: 5
<212> TYPE: PRT
<213> ORGANISM: artificial
<220> FEATURE:
<223> OTHER INFORMATION: AB-loop sequence AA143ff

<400> SEQUENCE: 168

Trp Trp Leu Phe Gly
1 5

<210> SEQ ID NO 169
<211> LENGTH: 5
<212> TYPE: PRT
<213> ORGANISM: artificial
<220> FEATURE:
<223> OTHER INFORMATION: AB-loop sequence AA143ff

<400> SEQUENCE: 169

Ile Lys Lys Lys Lys
1               5

<210> SEQ ID NO 170
<211> LENGTH: 5
<212> TYPE: PRT
<213> ORGANISM: artificial
<220> FEATURE:
<223> OTHER INFORMATION: AB-loop sequence AA143ff

<400> SEQUENCE: 170

Lys Trp Asn Lys Lys
1               5

<210> SEQ ID NO 171
<211> LENGTH: 5
<212> TYPE: PRT
<213> ORGANISM: artificial
<220> FEATURE:
<223> OTHER INFORMATION: AB-loop sequence AA143ff

<400> SEQUENCE: 171

Lys Lys Lys Lys Lys
1               5

<210> SEQ ID NO 172
<211> LENGTH: 4
<212> TYPE: PRT
<213> ORGANISM: artificial
<220> FEATURE:
<223> OTHER INFORMATION: AB-loop sequence AA143ff

<400> SEQUENCE: 172

Thr Lys Gly Leu
1

<210> SEQ ID NO 173
<211> LENGTH: 5
<212> TYPE: PRT
<213> ORGANISM: artificial
<220> FEATURE:
<223> OTHER INFORMATION: AB-loop sequence AA143ff

<400> SEQUENCE: 173

Tyr Lys Thr Lys Asp
1               5

<210> SEQ ID NO 174
<211> LENGTH: 5
<212> TYPE: PRT
<213> ORGANISM: artificial
<220> FEATURE:
<223> OTHER INFORMATION: AB-loop sequence AA143ff

<400> SEQUENCE: 174

Arg Lys Glu Lys Lys
1               5

<210> SEQ ID NO 175
<211> LENGTH: 5
<212> TYPE: PRT
<213> ORGANISM: artificial
<220> FEATURE:
<223> OTHER INFORMATION: AB-loop sequence AA143ff

<400> SEQUENCE: 175

Trp Trp Val Gly Gly
1               5

<210> SEQ ID NO 176
<211> LENGTH: 5
<212> TYPE: PRT
<213> ORGANISM: artificial
<220> FEATURE:
<223> OTHER INFORMATION: AB-loop sequence AA143ff

<400> SEQUENCE: 176

Trp Trp Arg Gly Gly
1               5

<210> SEQ ID NO 177
<211> LENGTH: 5
<212> TYPE: PRT
<213> ORGANISM: artificial
<220> FEATURE:
<223> OTHER INFORMATION: AB-loop sequence AA143ff

<400> SEQUENCE: 177

Tyr Gly His Lys Tyr
1               5

<210> SEQ ID NO 178
<211> LENGTH: 5
<212> TYPE: PRT
<213> ORGANISM: artificial
<220> FEATURE:
<223> OTHER INFORMATION: AB-loop sequence AA143ff

<400> SEQUENCE: 178

Thr Lys Lys Glu Thr
1               5

<210> SEQ ID NO 179
<211> LENGTH: 5
<212> TYPE: PRT
<213> ORGANISM: artificial
<220> FEATURE:
<223> OTHER INFORMATION: AB-loop sequence AA143ff

<400> SEQUENCE: 179

Thr Gly Gly Asn Lys
1               5

<210> SEQ ID NO 180
<211> LENGTH: 5
<212> TYPE: PRT
<213> ORGANISM: artificial
<220> FEATURE:
<223> OTHER INFORMATION: AB-loop sequence AA143ff

<400> SEQUENCE: 180

Leu Asp Gly Asp Gln
1               5

<210> SEQ ID NO 181
<211> LENGTH: 5
<212> TYPE: PRT
<213> ORGANISM: artificial
<220> FEATURE:
<223> OTHER INFORMATION: AB-loop sequence AA143ff

<400> SEQUENCE: 181

Phe Ile Pro His Asn
1 5

<210> SEQ ID NO 182
<211> LENGTH: 5
<212> TYPE: PRT
<213> ORGANISM: artificial
<220> FEATURE:
<223> OTHER INFORMATION: AB-loop sequence AA143ff

<400> SEQUENCE: 182

Lys Lys Lys Gly Lys
1 5

<210> SEQ ID NO 183
<211> LENGTH: 5
<212> TYPE: PRT
<213> ORGANISM: artificial
<220> FEATURE:
<223> OTHER INFORMATION: AB-loop sequence AA143ff

<400> SEQUENCE: 183

Lys Asn Lys Lys Lys
1 5

<210> SEQ ID NO 184
<211> LENGTH: 5
<212> TYPE: PRT
<213> ORGANISM: artificial
<220> FEATURE:
<223> OTHER INFORMATION: AB-loop sequence AA143ff

<400> SEQUENCE: 184

Lys Lys Lys Asn Asn
1 5

<210> SEQ ID NO 185
<211> LENGTH: 5
<212> TYPE: PRT
<213> ORGANISM: artificial
<220> FEATURE:
<223> OTHER INFORMATION: AB-loop sequence AA143ff

<400> SEQUENCE: 185

Lys Lys Lys Lys Arg
1 5

<210> SEQ ID NO 186
<211> LENGTH: 5
<212> TYPE: PRT
<213> ORGANISM: artificial
<220> FEATURE:
<223> OTHER INFORMATION: AB-loop sequence AA143ff

<400> SEQUENCE: 186

Leu Lys Lys Lys Thr
1 5

<210> SEQ ID NO 187

<211> LENGTH: 5
<212> TYPE: PRT
<213> ORGANISM: artificial
<220> FEATURE:
<223> OTHER INFORMATION: AB-loop sequence AA143ff

<400> SEQUENCE: 187

Thr Lys Gly Arg Trp
1 5

<210> SEQ ID NO 188
<211> LENGTH: 5
<212> TYPE: PRT
<213> ORGANISM: artificial
<220> FEATURE:
<223> OTHER INFORMATION: AB-loop sequence AA143ff

<400> SEQUENCE: 188

Lys Lys Lys Asn Lys
1 5

<210> SEQ ID NO 189
<211> LENGTH: 5
<212> TYPE: PRT
<213> ORGANISM: artificial
<220> FEATURE:
<223> OTHER INFORMATION: AB-loop sequence AA143ff

<400> SEQUENCE: 189

Lys His Ala Glu Thr
1 5

<210> SEQ ID NO 190
<211> LENGTH: 4
<212> TYPE: PRT
<213> ORGANISM: artificial
<220> FEATURE:
<223> OTHER INFORMATION: AB-loop sequence AA144ff

<400> SEQUENCE: 190

Lys Lys Lys Lys
1

<210> SEQ ID NO 191
<211> LENGTH: 5
<212> TYPE: PRT
<213> ORGANISM: artificial
<220> FEATURE:
<223> OTHER INFORMATION: AB-loop sequence AA143ff

<400> SEQUENCE: 191

Phe Phe Thr Tyr Trp
1 5

<210> SEQ ID NO 192
<211> LENGTH: 5
<212> TYPE: PRT
<213> ORGANISM: artificial
<220> FEATURE:
<223> OTHER INFORMATION: AB-loop sequence AA143ff

<400> SEQUENCE: 192

Glu Gly Lys Arg Lys
1 5

<210> SEQ ID NO 193
<211> LENGTH: 5

<212> TYPE: PRT
<213> ORGANISM: artificial
<220> FEATURE:
<223> OTHER INFORMATION: AB-loop sequence AA143ff

<400> SEQUENCE: 193

Arg His Gly Gly Trp
1               5

<210> SEQ ID NO 194
<211> LENGTH: 4
<212> TYPE: PRT
<213> ORGANISM: artificial
<220> FEATURE:
<223> OTHER INFORMATION: AB-loop sequence AA144ff

<400> SEQUENCE: 194

Lys Ser Gly Tyr
1

<210> SEQ ID NO 195
<211> LENGTH: 5
<212> TYPE: PRT
<213> ORGANISM: artificial
<220> FEATURE:
<223> OTHER INFORMATION: AB-loop sequence AA143ff

<400> SEQUENCE: 195

Ala Lys Glu Gly Gly
1               5

<210> SEQ ID NO 196
<211> LENGTH: 5
<212> TYPE: PRT
<213> ORGANISM: artificial
<220> FEATURE:
<223> OTHER INFORMATION: AB-loop sequence AA143ff

<400> SEQUENCE: 196

Lys Tyr Trp Met Ala
1               5

<210> SEQ ID NO 197
<211> LENGTH: 5
<212> TYPE: PRT
<213> ORGANISM: artificial
<220> FEATURE:
<223> OTHER INFORMATION: AB-loop sequence AA143ff

<400> SEQUENCE: 197

Gln Leu Arg Asn Lys
1               5

<210> SEQ ID NO 198
<211> LENGTH: 5
<212> TYPE: PRT
<213> ORGANISM: artificial
<220> FEATURE:
<223> OTHER INFORMATION: AB-loop sequence AA143ff

<400> SEQUENCE: 198

Gln Arg Gly Arg Met
1               5

<210> SEQ ID NO 199
<211> LENGTH: 5
<212> TYPE: PRT

<213> ORGANISM: artificial
<220> FEATURE:
<223> OTHER INFORMATION: AB-loop sequence AA143ff

<400> SEQUENCE: 199

Lys Asn His Asn Thr
1               5

<210> SEQ ID NO 200
<211> LENGTH: 5
<212> TYPE: PRT
<213> ORGANISM: artificial
<220> FEATURE:
<223> OTHER INFORMATION: AB-loop sequence AA143ff

<400> SEQUENCE: 200

Met Ser Glu Asn Glu
1               5

<210> SEQ ID NO 201
<211> LENGTH: 5
<212> TYPE: PRT
<213> ORGANISM: artificial
<220> FEATURE:
<223> OTHER INFORMATION: AB-loop sequence AA143ff

<400> SEQUENCE: 201

Trp Trp Met Asp Tyr
1               5

<210> SEQ ID NO 202
<211> LENGTH: 5
<212> TYPE: PRT
<213> ORGANISM: artificial
<220> FEATURE:
<223> OTHER INFORMATION: AB-loop sequence AA143ff

<400> SEQUENCE: 202

Met Lys Lys Asn Lys
1               5

<210> SEQ ID NO 203
<211> LENGTH: 5
<212> TYPE: PRT
<213> ORGANISM: artificial
<220> FEATURE:
<223> OTHER INFORMATION: AB-loop sequence AA143ff

<400> SEQUENCE: 203

Glu Tyr Phe Arg His
1               5

<210> SEQ ID NO 204
<211> LENGTH: 5
<212> TYPE: PRT
<213> ORGANISM: artificial
<220> FEATURE:
<223> OTHER INFORMATION: AB-loop sequence AA143ff

<400> SEQUENCE: 204

Phe Asp Met Arg Asp
1               5

<210> SEQ ID NO 205
<211> LENGTH: 5
<212> TYPE: PRT
<213> ORGANISM: artificial

<220> FEATURE:
<223> OTHER INFORMATION: AB-loop sequence AA143ff

<400> SEQUENCE: 205

Met Lys Lys Pro Tyr
1 5

<210> SEQ ID NO 206
<211> LENGTH: 5
<212> TYPE: PRT
<213> ORGANISM: artificial
<220> FEATURE:
<223> OTHER INFORMATION: AB-loop sequence AA143ff

<400> SEQUENCE: 206

Phe Glu Met Pro Tyr
1 5

<210> SEQ ID NO 207
<211> LENGTH: 5
<212> TYPE: PRT
<213> ORGANISM: artificial
<220> FEATURE:
<223> OTHER INFORMATION: AB-loop sequence AA143ff

<400> SEQUENCE: 207

Lys Lys Lys Asn His
1 5

<210> SEQ ID NO 208
<211> LENGTH: 5
<212> TYPE: PRT
<213> ORGANISM: artificial
<220> FEATURE:
<223> OTHER INFORMATION: AB-loop sequence AA143ff

<400> SEQUENCE: 208

Met Trp Glu Pro Ser
1 5

<210> SEQ ID NO 209
<211> LENGTH: 5
<212> TYPE: PRT
<213> ORGANISM: artificial
<220> FEATURE:
<223> OTHER INFORMATION: AB-loop sequence AA143ff

<400> SEQUENCE: 209

Leu Arg Gly Ser Thr
1 5

<210> SEQ ID NO 210
<211> LENGTH: 5
<212> TYPE: PRT
<213> ORGANISM: artificial
<220> FEATURE:
<223> OTHER INFORMATION: AB-loop sequence AA143ff

<400> SEQUENCE: 210

Asp Ser Tyr Met Ile
1 5

<210> SEQ ID NO 211
<211> LENGTH: 5
<212> TYPE: PRT
<213> ORGANISM: artificial
<220> FEATURE:

<223> OTHER INFORMATION: AB-loop sequence AA143ff

<400> SEQUENCE: 211

Met Glu Gln His Ser
1 5

<210> SEQ ID NO 212
<211> LENGTH: 5
<212> TYPE: PRT
<213> ORGANISM: artificial
<220> FEATURE:
<223> OTHER INFORMATION: AB-loop sequence AA143ff

<400> SEQUENCE: 212

Lys Lys Lys Lys His
1 5

<210> SEQ ID NO 213
<211> LENGTH: 5
<212> TYPE: PRT
<213> ORGANISM: artificial
<220> FEATURE:
<223> OTHER INFORMATION: AB-loop sequence AA143ff

<400> SEQUENCE: 213

Asn Lys Lys Lys Lys
1 5

<210> SEQ ID NO 214
<211> LENGTH: 5
<212> TYPE: PRT
<213> ORGANISM: artificial
<220> FEATURE:
<223> OTHER INFORMATION: AB-loop sequence AA143ff

<400> SEQUENCE: 214

Ile Met Asn Asp Trp
1 5

<210> SEQ ID NO 215
<211> LENGTH: 5
<212> TYPE: PRT
<213> ORGANISM: artificial
<220> FEATURE:
<223> OTHER INFORMATION: AB-loop sequence AA143ff

<400> SEQUENCE: 215

Trp Thr Asn Gly Asp
1 5

<210> SEQ ID NO 216
<211> LENGTH: 5
<212> TYPE: PRT
<213> ORGANISM: artificial
<220> FEATURE:
<223> OTHER INFORMATION: AB-loop sequence AA143ff

<400> SEQUENCE: 216

Trp Trp His Asp Met
1 5

<210> SEQ ID NO 217
<211> LENGTH: 5
<212> TYPE: PRT
<213> ORGANISM: artificial
<220> FEATURE:
<223> OTHER INFORMATION: AB-loop sequence AA143ff

<400> SEQUENCE: 217

Trp Glu Asn Pro His
1 5

<210> SEQ ID NO 218
<211> LENGTH: 5
<212> TYPE: PRT
<213> ORGANISM: artificial
<220> FEATURE:
<223> OTHER INFORMATION: AB-loop sequence AA143ff

<400> SEQUENCE: 218

Leu Tyr His Glu His
1 5

<210> SEQ ID NO 219
<211> LENGTH: 5
<212> TYPE: PRT
<213> ORGANISM: artificial
<220> FEATURE:
<223> OTHER INFORMATION: AB-loop sequence AA143ff

<400> SEQUENCE: 219

Gly Gly Asp Gln His
1 5

<210> SEQ ID NO 220
<211> LENGTH: 5
<212> TYPE: PRT
<213> ORGANISM: artificial
<220> FEATURE:
<223> OTHER INFORMATION: AB-loop sequence AA143ff

<400> SEQUENCE: 220

Ile Tyr Val Pro Tyr
1 5

<210> SEQ ID NO 221
<211> LENGTH: 5
<212> TYPE: PRT
<213> ORGANISM: artificial
<220> FEATURE:
<223> OTHER INFORMATION: AB-loop sequence AA143ff

<400> SEQUENCE: 221

Val Val Thr Ser Gln
1 5

<210> SEQ ID NO 222
<211> LENGTH: 5
<212> TYPE: PRT
<213> ORGANISM: artificial
<220> FEATURE:
<223> OTHER INFORMATION: AB-loop sequence AA143ff

<400> SEQUENCE: 222

Trp Trp Asn Ser Lys
1 5

<210> SEQ ID NO 223
<211> LENGTH: 5
<212> TYPE: PRT
<213> ORGANISM: artificial
<220> FEATURE:
<223> OTHER INFORMATION: AB-loop sequence AA143ff

<400> SEQUENCE: 223

Met Thr Gly Pro Gly
1 5

<210> SEQ ID NO 224
<211> LENGTH: 5
<212> TYPE: PRT
<213> ORGANISM: artificial
<220> FEATURE:
<223> OTHER INFORMATION: AB-loop sequence AA143ff

<400> SEQUENCE: 224

Asp Thr Tyr His Asp
1 5

<210> SEQ ID NO 225
<211> LENGTH: 5
<212> TYPE: PRT
<213> ORGANISM: artificial
<220> FEATURE:
<223> OTHER INFORMATION: AB-loop sequence AA143ff

<400> SEQUENCE: 225

Gln Asp Glu Lys Thr
1 5

<210> SEQ ID NO 226
<211> LENGTH: 5
<212> TYPE: PRT
<213> ORGANISM: artificial
<220> FEATURE:
<223> OTHER INFORMATION: AB-loop sequence AA143ff

<400> SEQUENCE: 226

Gly Asp His Arg Ile
1 5

<210> SEQ ID NO 227
<211> LENGTH: 5
<212> TYPE: PRT
<213> ORGANISM: artificial
<220> FEATURE:
<223> OTHER INFORMATION: AB-loop sequence AA143ff

<400> SEQUENCE: 227

Arg Asn Ser Asn Ser
1 5

<210> SEQ ID NO 228
<211> LENGTH: 5
<212> TYPE: PRT
<213> ORGANISM: artificial
<220> FEATURE:
<223> OTHER INFORMATION: AB-loop sequence AA143ff

<400> SEQUENCE: 228

Arg Glu Asn Thr Met
1 5

<210> SEQ ID NO 229
<211> LENGTH: 5
<212> TYPE: PRT
<213> ORGANISM: artificial
<220> FEATURE:
<223> OTHER INFORMATION: AB-loop sequence AA143ff

<400> SEQUENCE: 229

Val Asn Asp Lys Met
1 5

<210> SEQ ID NO 230
<211> LENGTH: 5
<212> TYPE: PRT
<213> ORGANISM: artificial
<220> FEATURE:
<223> OTHER INFORMATION: AB-loop sequence AA143ff

<400> SEQUENCE: 230

Arg Lys Lys Asp Glu
1 5

<210> SEQ ID NO 231
<211> LENGTH: 5
<212> TYPE: PRT
<213> ORGANISM: artificial
<220> FEATURE:
<223> OTHER INFORMATION: AB-loop sequence AA143ff

<400> SEQUENCE: 231

Ser Asn Ser Gly Tyr
1 5

<210> SEQ ID NO 232
<211> LENGTH: 5
<212> TYPE: PRT
<213> ORGANISM: artificial
<220> FEATURE:
<223> OTHER INFORMATION: AB-loop sequence AA143ff

<400> SEQUENCE: 232

Phe Glu Tyr Arg His
1 5

<210> SEQ ID NO 233
<211> LENGTH: 5
<212> TYPE: PRT
<213> ORGANISM: artificial
<220> FEATURE:
<223> OTHER INFORMATION: AB-loop sequence AA143ff

<400> SEQUENCE: 233

Arg Lys Lys Lys Lys
1 5

<210> SEQ ID NO 234
<211> LENGTH: 5
<212> TYPE: PRT
<213> ORGANISM: artificial
<220> FEATURE:
<223> OTHER INFORMATION: AB-loop sequence AA143ff

<400> SEQUENCE: 234

Tyr Gly Asn Ser Tyr
1 5

<210> SEQ ID NO 235
<211> LENGTH: 5
<212> TYPE: PRT
<213> ORGANISM: artificial
<220> FEATURE:
<223> OTHER INFORMATION: AB-loop sequence AA143ff

<400> SEQUENCE: 235

Arg Asn Arg Lys Lys
1 5

<210> SEQ ID NO 236
<211> LENGTH: 5
<212> TYPE: PRT
<213> ORGANISM: artificial
<220> FEATURE:
<223> OTHER INFORMATION: AB-loop sequence AA143ff

<400> SEQUENCE: 236

Trp Asp His Gly Ser
1 5

<210> SEQ ID NO 237
<211> LENGTH: 5
<212> TYPE: PRT
<213> ORGANISM: artificial
<220> FEATURE:
<223> OTHER INFORMATION: AB-loop sequence AA143ff

<400> SEQUENCE: 237

Phe Ala Lys Arg Thr
1 5

<210> SEQ ID NO 238
<211> LENGTH: 5
<212> TYPE: PRT
<213> ORGANISM: artificial
<220> FEATURE:
<223> OTHER INFORMATION: AB-loop sequence AA143ff

<400> SEQUENCE: 238

Ser Met Asp Lys Val
1 5

<210> SEQ ID NO 239
<211> LENGTH: 5
<212> TYPE: PRT
<213> ORGANISM: artificial
<220> FEATURE:
<223> OTHER INFORMATION: AB-loop sequence AA143ff

<400> SEQUENCE: 239

Arg His Gln Asp Arg
1 5

<210> SEQ ID NO 240
<211> LENGTH: 5
<212> TYPE: PRT
<213> ORGANISM: artificial
<220> FEATURE:
<223> OTHER INFORMATION: CD-loop sequence AA169ff

<400> SEQUENCE: 240

Ile Ser Gly Pro Glu
1 5

<210> SEQ ID NO 241
<211> LENGTH: 5
<212> TYPE: PRT
<213> ORGANISM: artificial
<220> FEATURE:
<223> OTHER INFORMATION: CD-loop sequence AA169ff

<400> SEQUENCE: 241

Asn Gly Gln Pro Glu

```
1               5


<210> SEQ ID NO 242
<211> LENGTH: 5
<212> TYPE: PRT
<213> ORGANISM: artificial
<220> FEATURE:
<223> OTHER INFORMATION: CD-loop sequence AA169ff

<400> SEQUENCE: 242

Asp Gly Arg Pro Glu
1               5


<210> SEQ ID NO 243
<211> LENGTH: 5
<212> TYPE: PRT
<213> ORGANISM: artificial
<220> FEATURE:
<223> OTHER INFORMATION: CD-loop sequence AA169ff

<400> SEQUENCE: 243

Asp Ala Gly Pro Glu
1               5


<210> SEQ ID NO 244
<211> LENGTH: 5
<212> TYPE: PRT
<213> ORGANISM: artificial
<220> FEATURE:
<223> OTHER INFORMATION: CD-loop sequence AA169ff

<400> SEQUENCE: 244

Asn Lys Gln Asn His
1               5


<210> SEQ ID NO 245
<211> LENGTH: 5
<212> TYPE: PRT
<213> ORGANISM: artificial
<220> FEATURE:
<223> OTHER INFORMATION: CD-loop sequence AA169ff

<400> SEQUENCE: 245

Asn Met Gly Pro Glu
1               5


<210> SEQ ID NO 246
<211> LENGTH: 5
<212> TYPE: PRT
<213> ORGANISM: artificial
<220> FEATURE:
<223> OTHER INFORMATION: CD-loop sequence AA169ff

<400> SEQUENCE: 246

Asp Cys Gly Pro Glu
1               5


<210> SEQ ID NO 247
<211> LENGTH: 5
<212> TYPE: PRT
<213> ORGANISM: artificial
<220> FEATURE:
<223> OTHER INFORMATION: CD-loop sequence AA169ff

<400> SEQUENCE: 247

Met Asp Gly Pro Glu
1               5
```

<210> SEQ ID NO 248
<211> LENGTH: 5
<212> TYPE: PRT
<213> ORGANISM: artificial
<220> FEATURE:
<223> OTHER INFORMATION: CD-loop sequence AA169ff

<400> SEQUENCE: 248

Tyr Pro Glu Lys His
1               5

<210> SEQ ID NO 249
<211> LENGTH: 5
<212> TYPE: PRT
<213> ORGANISM: artificial
<220> FEATURE:
<223> OTHER INFORMATION: CD-loop sequence AA169ff

<400> SEQUENCE: 249

Asn Gly Ala Pro Gln
1               5

<210> SEQ ID NO 250
<211> LENGTH: 5
<212> TYPE: PRT
<213> ORGANISM: artificial
<220> FEATURE:
<223> OTHER INFORMATION: CD-loop sequence AA169ff

<400> SEQUENCE: 250

Asp Tyr Gly Pro Met
1               5

<210> SEQ ID NO 251
<211> LENGTH: 5
<212> TYPE: PRT
<213> ORGANISM: artificial
<220> FEATURE:
<223> OTHER INFORMATION: CD-loop sequence AA169ff

<400> SEQUENCE: 251

Arg Lys Lys Lys Glu
1               5

<210> SEQ ID NO 252
<211> LENGTH: 5
<212> TYPE: PRT
<213> ORGANISM: artificial
<220> FEATURE:
<223> OTHER INFORMATION: CD-loop sequence AA169ff

<400> SEQUENCE: 252

Lys Gly Gly Arg Glu
1               5

<210> SEQ ID NO 253
<211> LENGTH: 5
<212> TYPE: PRT
<213> ORGANISM: artificial
<220> FEATURE:
<223> OTHER INFORMATION: CD-loop sequence AA169ff

<400> SEQUENCE: 253

Gly Asn Trp Gln Pro
1               5

<210> SEQ ID NO 254
<211> LENGTH: 5
<212> TYPE: PRT
<213> ORGANISM: artificial
<220> FEATURE:
<223> OTHER INFORMATION: CD-loop sequence AA169ff

<400> SEQUENCE: 254

Thr Thr Gly Pro Tyr
1 5

<210> SEQ ID NO 255
<211> LENGTH: 5
<212> TYPE: PRT
<213> ORGANISM: artificial
<220> FEATURE:
<223> OTHER INFORMATION: CD-loop sequence AA169ff

<400> SEQUENCE: 255

Asp Met Asn Gln Pro
1 5

<210> SEQ ID NO 256
<211> LENGTH: 5
<212> TYPE: PRT
<213> ORGANISM: artificial
<220> FEATURE:
<223> OTHER INFORMATION: CD-loop sequence AA169ff

<400> SEQUENCE: 256

Lys Trp Pro Met Phe
1 5

<210> SEQ ID NO 257
<211> LENGTH: 5
<212> TYPE: PRT
<213> ORGANISM: artificial
<220> FEATURE:
<223> OTHER INFORMATION: CD-loop sequence AA169ff

<400> SEQUENCE: 257

His Asp Gln Arg His
1 5

<210> SEQ ID NO 258
<211> LENGTH: 5
<212> TYPE: PRT
<213> ORGANISM: artificial
<220> FEATURE:
<223> OTHER INFORMATION: CD-loop sequence AA169ff

<400> SEQUENCE: 258

Leu Gly Met Tyr Met
1 5

<210> SEQ ID NO 259
<211> LENGTH: 5
<212> TYPE: PRT
<213> ORGANISM: artificial
<220> FEATURE:
<223> OTHER INFORMATION: CD-loop sequence AA169ff

<400> SEQUENCE: 259

Asn Lys Met Phe Thr
1 5

<210> SEQ ID NO 260
<211> LENGTH: 5
<212> TYPE: PRT
<213> ORGANISM: artificial
<220> FEATURE:
<223> OTHER INFORMATION: CD-loop sequence AA169ff

<400> SEQUENCE: 260

Leu Gly Tyr Pro Glu
1 5

<210> SEQ ID NO 261
<211> LENGTH: 5
<212> TYPE: PRT
<213> ORGANISM: artificial
<220> FEATURE:
<223> OTHER INFORMATION: CD-loop sequence AA169ff

<400> SEQUENCE: 261

His Gly Tyr Gln Leu
1 5

<210> SEQ ID NO 262
<211> LENGTH: 5
<212> TYPE: PRT
<213> ORGANISM: artificial
<220> FEATURE:
<223> OTHER INFORMATION: CD-loop sequence AA169ff

<400> SEQUENCE: 262

Asn Val Phe Ile Glu
1 5

<210> SEQ ID NO 263
<211> LENGTH: 5
<212> TYPE: PRT
<213> ORGANISM: artificial
<220> FEATURE:
<223> OTHER INFORMATION: CD-loop sequence AA169ff

<400> SEQUENCE: 263

Asn Arg Gly Trp His
1 5

<210> SEQ ID NO 264
<211> LENGTH: 5
<212> TYPE: PRT
<213> ORGANISM: artificial
<220> FEATURE:
<223> OTHER INFORMATION: CD-loop sequence AA169ff

<400> SEQUENCE: 264

Pro Phe Thr Leu Lys
1 5

<210> SEQ ID NO 265
<211> LENGTH: 5
<212> TYPE: PRT
<213> ORGANISM: artificial
<220> FEATURE:
<223> OTHER INFORMATION: CD-loop sequence AA169ff

<400> SEQUENCE: 265

Ser Thr Thr Arg Val
1 5

<210> SEQ ID NO 266

<211> LENGTH: 5
<212> TYPE: PRT
<213> ORGANISM: artificial
<220> FEATURE:
<223> OTHER INFORMATION: CD-loop sequence AA169ff

<400> SEQUENCE: 266

Trp Asp Gln His Gln
1               5

<210> SEQ ID NO 267
<211> LENGTH: 5
<212> TYPE: PRT
<213> ORGANISM: artificial
<220> FEATURE:
<223> OTHER INFORMATION: CD-loop sequence AA169ff

<400> SEQUENCE: 267

Ser Gly Trp Met Met
1               5

<210> SEQ ID NO 268
<211> LENGTH: 5
<212> TYPE: PRT
<213> ORGANISM: artificial
<220> FEATURE:
<223> OTHER INFORMATION: CD-loop sequence AA169ff

<400> SEQUENCE: 268

Trp Arg Lys Met Thr
1               5

<210> SEQ ID NO 269
<211> LENGTH: 5
<212> TYPE: PRT
<213> ORGANISM: artificial
<220> FEATURE:
<223> OTHER INFORMATION: CD-loop sequence AA169ff

<400> SEQUENCE: 269

Phe Pro Lys Lys Tyr
1               5

<210> SEQ ID NO 270
<211> LENGTH: 5
<212> TYPE: PRT
<213> ORGANISM: artificial
<220> FEATURE:
<223> OTHER INFORMATION: CD-loop sequence AA169ff

<400> SEQUENCE: 270

Ser Pro Tyr Phe Val
1               5

<210> SEQ ID NO 271
<211> LENGTH: 5
<212> TYPE: PRT
<213> ORGANISM: artificial
<220> FEATURE:
<223> OTHER INFORMATION: CD-loop sequence AA169ff

<400> SEQUENCE: 271

Ile Arg Gly Thr Ser
1               5

<210> SEQ ID NO 272
<211> LENGTH: 5

<212> TYPE: PRT
<213> ORGANISM: artificial
<220> FEATURE:
<223> OTHER INFORMATION: CD-loop sequence AA169ff

<400> SEQUENCE: 272

Gln Val Pro Gly Trp
1               5

<210> SEQ ID NO 273
<211> LENGTH: 5
<212> TYPE: PRT
<213> ORGANISM: artificial
<220> FEATURE:
<223> OTHER INFORMATION: CD-loop sequence AA169ff

<400> SEQUENCE: 273

Asp Leu Pro Tyr Gln
1               5

<210> SEQ ID NO 274
<211> LENGTH: 5
<212> TYPE: PRT
<213> ORGANISM: artificial
<220> FEATURE:
<223> OTHER INFORMATION: CD-loop sequence AA169ff

<400> SEQUENCE: 274

Pro Arg Ser His Trp
1               5

<210> SEQ ID NO 275
<211> LENGTH: 5
<212> TYPE: PRT
<213> ORGANISM: artificial
<220> FEATURE:
<223> OTHER INFORMATION: CD-loop sequence AA169ff

<400> SEQUENCE: 275

Leu Tyr Gly His Ala
1               5

<210> SEQ ID NO 276
<211> LENGTH: 5
<212> TYPE: PRT
<213> ORGANISM: artificial
<220> FEATURE:
<223> OTHER INFORMATION: CD-loop sequence AA169ff

<400> SEQUENCE: 276

Ala Pro Tyr Val His
1               5

<210> SEQ ID NO 277
<211> LENGTH: 5
<212> TYPE: PRT
<213> ORGANISM: artificial
<220> FEATURE:
<223> OTHER INFORMATION: CD-loop sequence AA169ff

<400> SEQUENCE: 277

Arg Thr Gly Gln Lys
1               5

<210> SEQ ID NO 278
<211> LENGTH: 5
<212> TYPE: PRT

<213> ORGANISM: artificial
<220> FEATURE:
<223> OTHER INFORMATION: CD-loop sequence AA169ff

<400> SEQUENCE: 278

Pro Thr Tyr Trp Tyr
1 5

<210> SEQ ID NO 279
<211> LENGTH: 5
<212> TYPE: PRT
<213> ORGANISM: artificial
<220> FEATURE:
<223> OTHER INFORMATION: CD-loop sequence AA169ff

<400> SEQUENCE: 279

Glu Gly Met Glu Ile
1 5

<210> SEQ ID NO 280
<211> LENGTH: 5
<212> TYPE: PRT
<213> ORGANISM: artificial
<220> FEATURE:
<223> OTHER INFORMATION: CD-loop sequence AA169ff

<400> SEQUENCE: 280

Pro Val Val Gly Ala
1 5

<210> SEQ ID NO 281
<211> LENGTH: 5
<212> TYPE: PRT
<213> ORGANISM: artificial
<220> FEATURE:
<223> OTHER INFORMATION: CD-loop sequence AA169ff

<400> SEQUENCE: 281

Pro Leu Met Val Asp
1 5

<210> SEQ ID NO 282
<211> LENGTH: 5
<212> TYPE: PRT
<213> ORGANISM: artificial
<220> FEATURE:
<223> OTHER INFORMATION: CD-loop sequence AA169ff

<400> SEQUENCE: 282

Lys Tyr Gly Ser Gln
1 5

<210> SEQ ID NO 283
<211> LENGTH: 5
<212> TYPE: PRT
<213> ORGANISM: artificial
<220> FEATURE:
<223> OTHER INFORMATION: CD-loop sequence AA169ff

<400> SEQUENCE: 283

Arg Trp Asn Asn Gln
1 5

<210> SEQ ID NO 284
<211> LENGTH: 5
<212> TYPE: PRT
<213> ORGANISM: artificial

<220> FEATURE:
<223> OTHER INFORMATION: CD-loop sequence AA169ff

<400> SEQUENCE: 284

Val Tyr Lys Gln Asp
1 5

<210> SEQ ID NO 285
<211> LENGTH: 5
<212> TYPE: PRT
<213> ORGANISM: artificial
<220> FEATURE:
<223> OTHER INFORMATION: CD-loop sequence AA169ff

<400> SEQUENCE: 285

Asn Gln Met Lys Phe
1 5

<210> SEQ ID NO 286
<211> LENGTH: 5
<212> TYPE: PRT
<213> ORGANISM: artificial
<220> FEATURE:
<223> OTHER INFORMATION: CD-loop sequence AA169ff

<400> SEQUENCE: 286

Asn His Gln His Thr
1 5

<210> SEQ ID NO 287
<211> LENGTH: 5
<212> TYPE: PRT
<213> ORGANISM: artificial
<220> FEATURE:
<223> OTHER INFORMATION: CD-loop sequence AA169ff

<400> SEQUENCE: 287

Lys Arg Phe Val Asp
1 5

<210> SEQ ID NO 288
<211> LENGTH: 5
<212> TYPE: PRT
<213> ORGANISM: artificial
<220> FEATURE:
<223> OTHER INFORMATION: CD-loop sequence AA169ff

<400> SEQUENCE: 288

His His Glu Pro Leu
1 5

<210> SEQ ID NO 289
<211> LENGTH: 5
<212> TYPE: PRT
<213> ORGANISM: artificial
<220> FEATURE:
<223> OTHER INFORMATION: CD-loop sequence AA169ff

<400> SEQUENCE: 289

Pro Lys Met Pro Tyr
1 5

<210> SEQ ID NO 290
<211> LENGTH: 5
<212> TYPE: PRT
<213> ORGANISM: artificial
<220> FEATURE:

<223> OTHER INFORMATION: CD-loop sequence AA169ff

<400> SEQUENCE: 290

Pro Lys Asp His Glu
1 5

<210> SEQ ID NO 291
<211> LENGTH: 5
<212> TYPE: PRT
<213> ORGANISM: artificial
<220> FEATURE:
<223> OTHER INFORMATION: CD-loop sequence AA169ff

<400> SEQUENCE: 291

Ala Lys Gly Ser Ile
1 5

<210> SEQ ID NO 292
<211> LENGTH: 5
<212> TYPE: PRT
<213> ORGANISM: artificial
<220> FEATURE:
<223> OTHER INFORMATION: CD-loop sequence AA169ff

<400> SEQUENCE: 292

Glu Asp Pro Glu Met
1 5

<210> SEQ ID NO 293
<211> LENGTH: 5
<212> TYPE: PRT
<213> ORGANISM: artificial
<220> FEATURE:
<223> OTHER INFORMATION: CD-loop sequence AA169ff

<400> SEQUENCE: 293

Glu Phe Asp His Gln
1 5

<210> SEQ ID NO 294
<211> LENGTH: 5
<212> TYPE: PRT
<213> ORGANISM: artificial
<220> FEATURE:
<223> OTHER INFORMATION: CD-loop sequence AA169ff

<400> SEQUENCE: 294

Asn Glu Lys Gln Asp
1 5

<210> SEQ ID NO 295
<211> LENGTH: 5
<212> TYPE: PRT
<213> ORGANISM: artificial
<220> FEATURE:
<223> OTHER INFORMATION: CD-loop sequence AA169ff

<400> SEQUENCE: 295

Ala Pro His Tyr Tyr
1 5

<210> SEQ ID NO 296
<211> LENGTH: 5
<212> TYPE: PRT
<213> ORGANISM: artificial
<220> FEATURE:
<223> OTHER INFORMATION: CD-loop sequence AA169ff

<400> SEQUENCE: 296

Pro Gln Leu His Leu
1 5

<210> SEQ ID NO 297
<211> LENGTH: 5
<212> TYPE: PRT
<213> ORGANISM: artificial
<220> FEATURE:
<223> OTHER INFORMATION: CD-loop sequence AA169ff

<400> SEQUENCE: 297

Asn Trp Arg Ala Glu
1 5

<210> SEQ ID NO 298
<211> LENGTH: 5
<212> TYPE: PRT
<213> ORGANISM: artificial
<220> FEATURE:
<223> OTHER INFORMATION: CD-loop sequence AA169ff

<400> SEQUENCE: 298

Asn Asn Gln Tyr Lys
1 5

<210> SEQ ID NO 299
<211> LENGTH: 4
<212> TYPE: PRT
<213> ORGANISM: artificial
<220> FEATURE:
<223> OTHER INFORMATION: CD-loop sequence AA170ff

<400> SEQUENCE: 299

Arg Ser Ile His
1

<210> SEQ ID NO 300
<211> LENGTH: 5
<212> TYPE: PRT
<213> ORGANISM: artificial
<220> FEATURE:
<223> OTHER INFORMATION: CD-loop sequence AA169ff

<400> SEQUENCE: 300

Arg Asp Arg Ile Met
1 5

<210> SEQ ID NO 301
<211> LENGTH: 5
<212> TYPE: PRT
<213> ORGANISM: artificial
<220> FEATURE:
<223> OTHER INFORMATION: CD-loop sequence AA169ff

<400> SEQUENCE: 301

Tyr Gly Lys Gly His
1 5

<210> SEQ ID NO 302
<211> LENGTH: 5
<212> TYPE: PRT
<213> ORGANISM: artificial
<220> FEATURE:
<223> OTHER INFORMATION: CD-loop sequence AA169ff

<400> SEQUENCE: 302

Gly Lys Gly Gly Lys
1 5

<210> SEQ ID NO 303
<211> LENGTH: 5
<212> TYPE: PRT
<213> ORGANISM: artificial
<220> FEATURE:
<223> OTHER INFORMATION: CD-loop sequence AA169ff

<400> SEQUENCE: 303

Arg His Ile Gly Lys
1 5

<210> SEQ ID NO 304
<211> LENGTH: 5
<212> TYPE: PRT
<213> ORGANISM: artificial
<220> FEATURE:
<223> OTHER INFORMATION: CD-loop sequence AA169ff

<400> SEQUENCE: 304

Gln Tyr Thr Tyr His
1 5

<210> SEQ ID NO 305
<211> LENGTH: 5
<212> TYPE: PRT
<213> ORGANISM: artificial
<220> FEATURE:
<223> OTHER INFORMATION: CD-loop sequence AA169ff

<400> SEQUENCE: 305

Leu His Ser His Val
1 5

<210> SEQ ID NO 306
<211> LENGTH: 5
<212> TYPE: PRT
<213> ORGANISM: artificial
<220> FEATURE:
<223> OTHER INFORMATION: CD-loop sequence AA169ff

<400> SEQUENCE: 306

Ala Arg Asp Lys Arg
1 5

<210> SEQ ID NO 307
<211> LENGTH: 5
<212> TYPE: PRT
<213> ORGANISM: artificial
<220> FEATURE:
<223> OTHER INFORMATION: CD-loop sequence AA169ff

<400> SEQUENCE: 307

Glu His Lys Lys Thr
1 5

<210> SEQ ID NO 308
<211> LENGTH: 5
<212> TYPE: PRT
<213> ORGANISM: artificial
<220> FEATURE:
<223> OTHER INFORMATION: CD-loop sequence AA169ff

<400> SEQUENCE: 308

Met Asp Glu Val Pro
1 5

<210> SEQ ID NO 309
<211> LENGTH: 5
<212> TYPE: PRT
<213> ORGANISM: artificial
<220> FEATURE:
<223> OTHER INFORMATION: CD-loop sequence AA169ff

<400> SEQUENCE: 309

Gln Asp Trp Gln Arg
1 5

<210> SEQ ID NO 310
<211> LENGTH: 5
<212> TYPE: PRT
<213> ORGANISM: artificial
<220> FEATURE:
<223> OTHER INFORMATION: CD-loop sequence AA169ff

<400> SEQUENCE: 310

Pro Ser Asp Arg Glu
1 5

<210> SEQ ID NO 311
<211> LENGTH: 5
<212> TYPE: PRT
<213> ORGANISM: artificial
<220> FEATURE:
<223> OTHER INFORMATION: CD-loop sequence AA169ff

<400> SEQUENCE: 311

Gln Asn Thr Arg Trp
1 5

<210> SEQ ID NO 312
<211> LENGTH: 5
<212> TYPE: PRT
<213> ORGANISM: artificial
<220> FEATURE:
<223> OTHER INFORMATION: CD-loop sequence AA169ff

<400> SEQUENCE: 312

Asp Glu Gly Leu His
1 5

<210> SEQ ID NO 313
<211> LENGTH: 5
<212> TYPE: PRT
<213> ORGANISM: artificial
<220> FEATURE:
<223> OTHER INFORMATION: CD-loop sequence AA169ff

<400> SEQUENCE: 313

Trp Pro Asn Met Glu
1 5

<210> SEQ ID NO 314
<211> LENGTH: 5
<212> TYPE: PRT
<213> ORGANISM: artificial
<220> FEATURE:
<223> OTHER INFORMATION: CD-loop sequence AA169ff

<400> SEQUENCE: 314

Met Thr Gly Arg Val
1 5

<210> SEQ ID NO 315
<211> LENGTH: 5
<212> TYPE: PRT
<213> ORGANISM: artificial
<220> FEATURE:
<223> OTHER INFORMATION: CD-loop sequence AA169ff

<400> SEQUENCE: 315

Gly Lys Tyr Asn Ile
1 5

<210> SEQ ID NO 316
<211> LENGTH: 5
<212> TYPE: PRT
<213> ORGANISM: artificial
<220> FEATURE:
<223> OTHER INFORMATION: CD-loop sequence AA169ff

<400> SEQUENCE: 316

Asn Ala Tyr Leu Leu
1 5

<210> SEQ ID NO 317
<211> LENGTH: 5
<212> TYPE: PRT
<213> ORGANISM: artificial
<220> FEATURE:
<223> OTHER INFORMATION: CD-loop sequence AA169ff

<400> SEQUENCE: 317

Ala Gln Tyr Asn Val
1 5

<210> SEQ ID NO 318
<211> LENGTH: 5
<212> TYPE: PRT
<213> ORGANISM: artificial
<220> FEATURE:
<223> OTHER INFORMATION: CD-loop sequence AA169ff

<400> SEQUENCE: 318

Asn Gln Val Met Thr
1 5

<210> SEQ ID NO 319
<211> LENGTH: 5
<212> TYPE: PRT
<213> ORGANISM: artificial
<220> FEATURE:
<223> OTHER INFORMATION: CD-loop sequence AA169ff

<400> SEQUENCE: 319

Val Val His Asp Thr
1 5

<210> SEQ ID NO 320
<211> LENGTH: 5
<212> TYPE: PRT
<213> ORGANISM: artificial
<220> FEATURE:
<223> OTHER INFORMATION: CD-loop sequence AA169ff

<400> SEQUENCE: 320

Asn Ile Trp His Gln 1 5

<210> SEQ ID NO 321
<211> LENGTH: 5
<212> TYPE: PRT
<213> ORGANISM: artificial
<220> FEATURE:
<223> OTHER INFORMATION: CD-loop sequence AA169ff

<400> SEQUENCE: 321

Gln Trp Gly Asn Met
1 5

<210> SEQ ID NO 322
<211> LENGTH: 5
<212> TYPE: PRT
<213> ORGANISM: artificial
<220> FEATURE:
<223> OTHER INFORMATION: CD-loop sequence AA169ff

<400> SEQUENCE: 322

Met His Val Lys Ser
1 5

<210> SEQ ID NO 323
<211> LENGTH: 5
<212> TYPE: PRT
<213> ORGANISM: artificial
<220> FEATURE:
<223> OTHER INFORMATION: CD-loop sequence AA169ff

<400> SEQUENCE: 323

Glu Tyr Thr Val Val
1 5

<210> SEQ ID NO 324
<211> LENGTH: 5
<212> TYPE: PRT
<213> ORGANISM: artificial
<220> FEATURE:
<223> OTHER INFORMATION: CD-loop sequence AA169ff

<400> SEQUENCE: 324

Gly Pro Tyr Gln Asp
1 5

<210> SEQ ID NO 325
<211> LENGTH: 5
<212> TYPE: PRT
<213> ORGANISM: artificial
<220> FEATURE:
<223> OTHER INFORMATION: CD-loop sequence AA169ff

<400> SEQUENCE: 325

Gln Gly Val Leu Glu
1 5

<210> SEQ ID NO 326
<211> LENGTH: 5
<212> TYPE: PRT
<213> ORGANISM: artificial
<220> FEATURE:
<223> OTHER INFORMATION: CD-loop sequence AA169ff

<400> SEQUENCE: 326

Gln Gln Pro Gly Val
1 5

<210> SEQ ID NO 327
<211> LENGTH: 5
<212> TYPE: PRT
<213> ORGANISM: artificial
<220> FEATURE:
<223> OTHER INFORMATION: CD-loop sequence AA169ff

<400> SEQUENCE: 327

Asn Gln Val Arg Gly
1               5

<210> SEQ ID NO 328
<211> LENGTH: 5
<212> TYPE: PRT
<213> ORGANISM: artificial
<220> FEATURE:
<223> OTHER INFORMATION: CD-loop sequence AA169ff

<400> SEQUENCE: 328

Val Pro His Val Leu
1               5

<210> SEQ ID NO 329
<211> LENGTH: 5
<212> TYPE: PRT
<213> ORGANISM: artificial
<220> FEATURE:
<223> OTHER INFORMATION: CD-loop sequence AA169ff

<400> SEQUENCE: 329

Asp Gly Arg Lys Gln
1               5

<210> SEQ ID NO 330
<211> LENGTH: 5
<212> TYPE: PRT
<213> ORGANISM: artificial
<220> FEATURE:
<223> OTHER INFORMATION: CD-loop sequence AA169ff

<400> SEQUENCE: 330

Asn Ala Ser Phe Glu
1               5

<210> SEQ ID NO 331
<211> LENGTH: 5
<212> TYPE: PRT
<213> ORGANISM: artificial
<220> FEATURE:
<223> OTHER INFORMATION: CD-loop sequence AA169ff

<400> SEQUENCE: 331

Lys Lys Arg Val Val
1               5

<210> SEQ ID NO 332
<211> LENGTH: 5
<212> TYPE: PRT
<213> ORGANISM: artificial
<220> FEATURE:
<223> OTHER INFORMATION: CD-loop sequence AA169ff

<400> SEQUENCE: 332

Lys Gly Ile Lys Lys
1               5

<210> SEQ ID NO 333
<211> LENGTH: 5
<212> TYPE: PRT
<213> ORGANISM: artificial
<220> FEATURE:
<223> OTHER INFORMATION: CD-loop sequence AA169ff

<400> SEQUENCE: 333

Pro Met Gly Met Gly
1 5

<210> SEQ ID NO 334
<211> LENGTH: 5
<212> TYPE: PRT
<213> ORGANISM: artificial
<220> FEATURE:
<223> OTHER INFORMATION: CD-loop sequence AA169ff

<400> SEQUENCE: 334

Pro Met Gly Lys Tyr
1 5

<210> SEQ ID NO 335
<211> LENGTH: 5
<212> TYPE: PRT
<213> ORGANISM: artificial
<220> FEATURE:
<223> OTHER INFORMATION: CD-loop sequence AA169ff

<400> SEQUENCE: 335

Arg Gly Ile Ala Lys
1 5

<210> SEQ ID NO 336
<211> LENGTH: 5
<212> TYPE: PRT
<213> ORGANISM: artificial
<220> FEATURE:
<223> OTHER INFORMATION: CD-loop sequence AA169ff

<400> SEQUENCE: 336

Leu Trp Gly Gly Met
1 5

<210> SEQ ID NO 337
<211> LENGTH: 5
<212> TYPE: PRT
<213> ORGANISM: artificial
<220> FEATURE:
<223> OTHER INFORMATION: CD-loop sequence AA169ff

<400> SEQUENCE: 337

Asn Ala His Tyr Ile
1 5

<210> SEQ ID NO 338
<211> LENGTH: 5
<212> TYPE: PRT
<213> ORGANISM: artificial
<220> FEATURE:
<223> OTHER INFORMATION: CD-loop sequence AA169ff

<400> SEQUENCE: 338

Ser Gly Thr Arg Leu
1 5

<210> SEQ ID NO 339
<211> LENGTH: 5
<212> TYPE: PRT
<213> ORGANISM: artificial
<220> FEATURE:
<223> OTHER INFORMATION: CD-loop sequence AA169ff

<400> SEQUENCE: 339

Asn Leu Gly Pro Glu
1 5

<210> SEQ ID NO 340
<211> LENGTH: 7
<212> TYPE: PRT
<213> ORGANISM: artificial
<220> FEATURE:
<223> OTHER INFORMATION: EF-loop sequence AA198ff

<400> SEQUENCE: 340

Pro Gln Thr Pro Pro Ser Gln
1 5

<210> SEQ ID NO 341
<211> LENGTH: 7
<212> TYPE: PRT
<213> ORGANISM: artificial
<220> FEATURE:
<223> OTHER INFORMATION: EF-loop sequence AA198ff

<400> SEQUENCE: 341

Pro Pro Ser Pro Pro Arg Thr
1 5

<210> SEQ ID NO 342
<211> LENGTH: 7
<212> TYPE: PRT
<213> ORGANISM: artificial
<220> FEATURE:
<223> OTHER INFORMATION: EF-loop sequence AA198ff

<400> SEQUENCE: 342

Pro Trp Val Arg Trp Met Gln
1 5

<210> SEQ ID NO 343
<211> LENGTH: 7
<212> TYPE: PRT
<213> ORGANISM: artificial
<220> FEATURE:
<223> OTHER INFORMATION: EF-loop sequence AA198ff

<400> SEQUENCE: 343

Ser Arg Ala Arg Trp Arg His
1 5

<210> SEQ ID NO 344
<211> LENGTH: 7
<212> TYPE: PRT
<213> ORGANISM: artificial
<220> FEATURE:
<223> OTHER INFORMATION: EF-loop sequence AA198ff

<400> SEQUENCE: 344

Ser Arg Ser Arg Trp Arg Gly
1 5

<210> SEQ ID NO 345

<211> LENGTH: 5
<212> TYPE: PRT
<213> ORGANISM: artificial
<220> FEATURE:
<223> OTHER INFORMATION: EF-loop sequence AA198ff

<400> SEQUENCE: 345

Pro Arg Trp Lys Met
1               5

<210> SEQ ID NO 346
<211> LENGTH: 12
<212> TYPE: PRT
<213> ORGANISM: artificial
<220> FEATURE:
<223> OTHER INFORMATION: EF-loop sequence AA198ff

<400> SEQUENCE: 346

Lys Arg Tyr Asn Pro Arg Met Val Arg Trp Ala His
1               5                   10

<210> SEQ ID NO 347
<211> LENGTH: 7
<212> TYPE: PRT
<213> ORGANISM: artificial
<220> FEATURE:
<223> OTHER INFORMATION: EF-loop sequence AA198ff

<400> SEQUENCE: 347

Pro Gln Ser Arg Trp Tyr Asn
1               5

<210> SEQ ID NO 348
<211> LENGTH: 7
<212> TYPE: PRT
<213> ORGANISM: artificial
<220> FEATURE:
<223> OTHER INFORMATION: EF-loop sequence AA198ff

<400> SEQUENCE: 348

Pro Trp Ser Arg Trp Arg Leu
1               5

<210> SEQ ID NO 349
<211> LENGTH: 7
<212> TYPE: PRT
<213> ORGANISM: artificial
<220> FEATURE:
<223> OTHER INFORMATION: EF-loop sequence AA198ff

<400> SEQUENCE: 349

Pro Gln Lys Arg Trp Arg Ser
1               5

<210> SEQ ID NO 350
<211> LENGTH: 7
<212> TYPE: PRT
<213> ORGANISM: artificial
<220> FEATURE:
<223> OTHER INFORMATION: EF-loop sequence AA198ff

<400> SEQUENCE: 350

Pro Trp Val Arg Trp Leu Gln
1               5

<210> SEQ ID NO 351
<211> LENGTH: 7

<212> TYPE: PRT
<213> ORGANISM: artificial
<220> FEATURE:
<223> OTHER INFORMATION: EF-loop sequence AA198ff

<400> SEQUENCE: 351

Glu Leu Glu Gly Glu Glu Gln
1 5

<210> SEQ ID NO 352
<211> LENGTH: 7
<212> TYPE: PRT
<213> ORGANISM: artificial
<220> FEATURE:
<223> OTHER INFORMATION: EF-loop sequence AA198ff

<400> SEQUENCE: 352

Asn Arg Ser Arg Trp Gln Gln
1 5

<210> SEQ ID NO 353
<211> LENGTH: 7
<212> TYPE: PRT
<213> ORGANISM: artificial
<220> FEATURE:
<223> OTHER INFORMATION: EF-loop sequence AA198ff

<400> SEQUENCE: 353

Lys Lys Lys Lys Leu Lys Gln
1 5

<210> SEQ ID NO 354
<211> LENGTH: 7
<212> TYPE: PRT
<213> ORGANISM: artificial
<220> FEATURE:
<223> OTHER INFORMATION: EF-loop sequence AA198ff

<400> SEQUENCE: 354

Lys Lys Lys Gln Leu Lys Lys
1 5

<210> SEQ ID NO 355
<211> LENGTH: 9
<212> TYPE: PRT
<213> ORGANISM: artificial
<220> FEATURE:
<223> OTHER INFORMATION: EF-loop sequence AA198ff

<400> SEQUENCE: 355

Gln Gln Lys Lys Arg Lys Lys Lys Lys
1 5

<210> SEQ ID NO 356
<211> LENGTH: 7
<212> TYPE: PRT
<213> ORGANISM: artificial
<220> FEATURE:
<223> OTHER INFORMATION: EF-loop sequence AA198ff

<400> SEQUENCE: 356

Pro Pro Pro Leu Cys Ala Pro
1 5

<210> SEQ ID NO 357
<211> LENGTH: 7
<212> TYPE: PRT

<213> ORGANISM: artificial
<220> FEATURE:
<223> OTHER INFORMATION: EF-loop sequence AA198ff

<400> SEQUENCE: 357

Ser Leu Asn Arg Trp Lys Arg
1 5

<210> SEQ ID NO 358
<211> LENGTH: 7
<212> TYPE: PRT
<213> ORGANISM: artificial
<220> FEATURE:
<223> OTHER INFORMATION: EF-loop sequence AA198ff

<400> SEQUENCE: 358

Lys Asn Lys Lys Lys Arg Lys
1 5

<210> SEQ ID NO 359
<211> LENGTH: 7
<212> TYPE: PRT
<213> ORGANISM: artificial
<220> FEATURE:
<223> OTHER INFORMATION: EF-loop sequence AA198ff

<400> SEQUENCE: 359

Lys Lys Lys Lys Ile Lys Lys
1 5

<210> SEQ ID NO 360
<211> LENGTH: 7
<212> TYPE: PRT
<213> ORGANISM: artificial
<220> FEATURE:
<223> OTHER INFORMATION: EF-loop sequence AA198ff

<400> SEQUENCE: 360

Lys Lys Lys Lys Met Lys Lys
1 5

<210> SEQ ID NO 361
<211> LENGTH: 7
<212> TYPE: PRT
<213> ORGANISM: artificial
<220> FEATURE:
<223> OTHER INFORMATION: EF-loop sequence AA198ff

<400> SEQUENCE: 361

Lys Arg Lys Lys Leu Lys Lys
1 5

<210> SEQ ID NO 362
<211> LENGTH: 7
<212> TYPE: PRT
<213> ORGANISM: artificial
<220> FEATURE:
<223> OTHER INFORMATION: EF-loop sequence AA198ff

<400> SEQUENCE: 362

Arg Glu Arg Glu Trp Arg Lys
1 5

<210> SEQ ID NO 363
<211> LENGTH: 7
<212> TYPE: PRT
<213> ORGANISM: artificial

<220> FEATURE:
<223> OTHER INFORMATION: EF-loop sequence AA198ff

<400> SEQUENCE: 363

Asp Lys Ser Arg Trp Gln Gln
1               5

<210> SEQ ID NO 364
<211> LENGTH: 7
<212> TYPE: PRT
<213> ORGANISM: artificial
<220> FEATURE:
<223> OTHER INFORMATION: EF-loop sequence AA198ff

<400> SEQUENCE: 364

Pro Leu Arg Leu Pro Pro Met
1               5

<210> SEQ ID NO 365
<211> LENGTH: 12
<212> TYPE: PRT
<213> ORGANISM: artificial
<220> FEATURE:
<223> OTHER INFORMATION: EF-loop sequence AA198ff

<400> SEQUENCE: 365

Pro Arg Ser Asn Trp Tyr Gly Asn Arg Trp Arg Arg
1               5                   10

<210> SEQ ID NO 366
<211> LENGTH: 7
<212> TYPE: PRT
<213> ORGANISM: artificial
<220> FEATURE:
<223> OTHER INFORMATION: EF-loop sequence AA198ff

<400> SEQUENCE: 366

Thr Pro Gly Asn Leu Ala Leu
1               5

<210> SEQ ID NO 367
<211> LENGTH: 7
<212> TYPE: PRT
<213> ORGANISM: artificial
<220> FEATURE:
<223> OTHER INFORMATION: EF-loop sequence AA198ff

<400> SEQUENCE: 367

Ser Arg Glu Asp Phe Arg Ala
1               5

<210> SEQ ID NO 368
<211> LENGTH: 7
<212> TYPE: PRT
<213> ORGANISM: artificial
<220> FEATURE:
<223> OTHER INFORMATION: EF-loop sequence AA198ff

<400> SEQUENCE: 368

Leu Val Ser Ile Ser Val Gly
1               5

<210> SEQ ID NO 369
<211> LENGTH: 7
<212> TYPE: PRT
<213> ORGANISM: artificial
<220> FEATURE:

<223> OTHER INFORMATION: EF-loop sequence AA198ff

<400> SEQUENCE: 369

Pro Ser Arg Arg Trp Arg Glu
1               5

<210> SEQ ID NO 370
<211> LENGTH: 7
<212> TYPE: PRT
<213> ORGANISM: artificial
<220> FEATURE:
<223> OTHER INFORMATION: EF-loop sequence AA198ff

<400> SEQUENCE: 370

Asp Arg Arg Arg Trp Thr Ala
1               5

<210> SEQ ID NO 371
<211> LENGTH: 7
<212> TYPE: PRT
<213> ORGANISM: artificial
<220> FEATURE:
<223> OTHER INFORMATION: EF-loop sequence AA198ff

<400> SEQUENCE: 371

Asp Leu Gln Asp Lys Lys Tyr
1               5

<210> SEQ ID NO 372
<211> LENGTH: 7
<212> TYPE: PRT
<213> ORGANISM: artificial
<220> FEATURE:
<223> OTHER INFORMATION: EF-loop sequence AA198ff

<400> SEQUENCE: 372

Ile Ser Val Pro Pro Asp Glu
1               5

<210> SEQ ID NO 373
<211> LENGTH: 7
<212> TYPE: PRT
<213> ORGANISM: artificial
<220> FEATURE:
<223> OTHER INFORMATION: EF-loop sequence AA198ff

<400> SEQUENCE: 373

Thr Gly Pro Asp Ile Thr Val
1               5

<210> SEQ ID NO 374
<211> LENGTH: 7
<212> TYPE: PRT
<213> ORGANISM: artificial
<220> FEATURE:
<223> OTHER INFORMATION: EF-loop sequence AA198ff

<400> SEQUENCE: 374

Ile Val Leu Ser Gly Phe Arg
1               5

<210> SEQ ID NO 375
<211> LENGTH: 7
<212> TYPE: PRT
<213> ORGANISM: artificial
<220> FEATURE:
<223> OTHER INFORMATION: EF-loop sequence AA198ff

<400> SEQUENCE: 375

Met Gly Ile His Asn Ile Asn
1 5

<210> SEQ ID NO 376
<211> LENGTH: 7
<212> TYPE: PRT
<213> ORGANISM: artificial
<220> FEATURE:
<223> OTHER INFORMATION: EF-loop sequence AA198ff

<400> SEQUENCE: 376

Met Lys Gln Asp Glu Met Ala
1 5

<210> SEQ ID NO 377
<211> LENGTH: 7
<212> TYPE: PRT
<213> ORGANISM: artificial
<220> FEATURE:
<223> OTHER INFORMATION: EF-loop sequence AA198ff

<400> SEQUENCE: 377

Pro Gln Trp Arg Leu Gln Trp
1 5

<210> SEQ ID NO 378
<211> LENGTH: 7
<212> TYPE: PRT
<213> ORGANISM: artificial
<220> FEATURE:
<223> OTHER INFORMATION: EF-loop sequence AA198ff

<400> SEQUENCE: 378

His Arg Arg Leu Val Ala Arg
1 5

<210> SEQ ID NO 379
<211> LENGTH: 7
<212> TYPE: PRT
<213> ORGANISM: artificial
<220> FEATURE:
<223> OTHER INFORMATION: EF-loop sequence AA198ff

<400> SEQUENCE: 379

Lys Gln Asn Leu Arg Arg Lys
1 5

<210> SEQ ID NO 380
<211> LENGTH: 12
<212> TYPE: PRT
<213> ORGANISM: artificial
<220> FEATURE:
<223> OTHER INFORMATION: EF-loop sequence AA198ff

<400> SEQUENCE: 380

Ser Arg Ser Arg Leu His Gly Asn Arg Trp Arg Arg
1 5 10

<210> SEQ ID NO 381
<211> LENGTH: 7
<212> TYPE: PRT
<213> ORGANISM: artificial
<220> FEATURE:
<223> OTHER INFORMATION: EF-loop sequence AA198ff

<400> SEQUENCE: 381

Asn Arg Glu Arg Trp Arg Arg
1               5

<210> SEQ ID NO 382
<211> LENGTH: 7
<212> TYPE: PRT
<213> ORGANISM: artificial
<220> FEATURE:
<223> OTHER INFORMATION: EF-loop sequence AA198ff

<400> SEQUENCE: 382

Thr Trp Val Arg Trp Met Gln
1               5

<210> SEQ ID NO 383
<211> LENGTH: 7
<212> TYPE: PRT
<213> ORGANISM: artificial
<220> FEATURE:
<223> OTHER INFORMATION: EF-loop sequence AA198ff

<400> SEQUENCE: 383

Pro His Trp Gln Trp Lys Trp
1               5

<210> SEQ ID NO 384
<211> LENGTH: 7
<212> TYPE: PRT
<213> ORGANISM: artificial
<220> FEATURE:
<223> OTHER INFORMATION: EF-loop sequence AA198ff

<400> SEQUENCE: 384

Ser Lys Lys Lys Leu Arg Lys
1               5

<210> SEQ ID NO 385
<211> LENGTH: 7
<212> TYPE: PRT
<213> ORGANISM: artificial
<220> FEATURE:
<223> OTHER INFORMATION: EF-loop sequence AA198ff

<400> SEQUENCE: 385

Pro Trp Lys Arg Leu Arg Lys
1               5

<210> SEQ ID NO 386
<211> LENGTH: 7
<212> TYPE: PRT
<213> ORGANISM: artificial
<220> FEATURE:
<223> OTHER INFORMATION: EF-loop sequence AA198ff

<400> SEQUENCE: 386

Thr Gln Lys Arg Trp Arg Ser
1               5

<210> SEQ ID NO 387
<211> LENGTH: 7
<212> TYPE: PRT
<213> ORGANISM: artificial
<220> FEATURE:
<223> OTHER INFORMATION: EF-loop sequence AA198ff

<400> SEQUENCE: 387

Asn Arg Lys His Leu Arg Ala
1 5

<210> SEQ ID NO 388
<211> LENGTH: 7
<212> TYPE: PRT
<213> ORGANISM: artificial
<220> FEATURE:
<223> OTHER INFORMATION: EF-loop sequence AA198ff

<400> SEQUENCE: 388

Thr Arg Arg Arg Trp Thr Arg
1 5

<210> SEQ ID NO 389
<211> LENGTH: 7
<212> TYPE: PRT
<213> ORGANISM: artificial
<220> FEATURE:
<223> OTHER INFORMATION: EF-loop sequence AA198ff

<400> SEQUENCE: 389

Asp His Arg Arg Ile Asn Arg
1 5

<210> SEQ ID NO 390
<211> LENGTH: 7
<212> TYPE: PRT
<213> ORGANISM: artificial
<220> FEATURE:
<223> OTHER INFORMATION: EF-loop sequence AA198ff

<400> SEQUENCE: 390

Lys Lys Lys Lys Tyr His Lys
1 5

<210> SEQ ID NO 391
<211> LENGTH: 7
<212> TYPE: PRT
<213> ORGANISM: artificial
<220> FEATURE:
<223> OTHER INFORMATION: EF-loop sequence AA198ff

<400> SEQUENCE: 391

Gln Lys Lys Lys Leu Lys Lys
1 5

<210> SEQ ID NO 392
<211> LENGTH: 7
<212> TYPE: PRT
<213> ORGANISM: artificial
<220> FEATURE:
<223> OTHER INFORMATION: EF-loop sequence AA198ff

<400> SEQUENCE: 392

Pro Gln Lys Lys Leu Arg Lys
1 5

<210> SEQ ID NO 393
<211> LENGTH: 7
<212> TYPE: PRT
<213> ORGANISM: artificial
<220> FEATURE:
<223> OTHER INFORMATION: EF-loop sequence AA198ff

<400> SEQUENCE: 393

Asp Lys Arg Gly Ile Arg Lys
1 5

<210> SEQ ID NO 394
<211> LENGTH: 7
<212> TYPE: PRT
<213> ORGANISM: artificial
<220> FEATURE:
<223> OTHER INFORMATION: EF-loop sequence AA198ff

<400> SEQUENCE: 394

Glu Lys Lys Arg Trp Lys Glu
1 5

<210> SEQ ID NO 395
<211> LENGTH: 7
<212> TYPE: PRT
<213> ORGANISM: artificial
<220> FEATURE:
<223> OTHER INFORMATION: EF-loop sequence AA198ff

<400> SEQUENCE: 395

Thr Ser Arg Arg Trp Arg Glu
1 5

<210> SEQ ID NO 396
<211> LENGTH: 7
<212> TYPE: PRT
<213> ORGANISM: artificial
<220> FEATURE:
<223> OTHER INFORMATION: EF-loop sequence AA198ff

<400> SEQUENCE: 396

Lys Lys Glu Lys Leu Arg Lys
1 5

<210> SEQ ID NO 397
<211> LENGTH: 7
<212> TYPE: PRT
<213> ORGANISM: artificial
<220> FEATURE:
<223> OTHER INFORMATION: EF-loop sequence AA198ff

<400> SEQUENCE: 397

Lys Lys Lys Lys Leu Lys Lys
1 5

<210> SEQ ID NO 398
<211> LENGTH: 7
<212> TYPE: PRT
<213> ORGANISM: artificial
<220> FEATURE:
<223> OTHER INFORMATION: EF-loop sequence AA198ff

<400> SEQUENCE: 398

Lys Lys Lys Lys Ile Met Lys
1 5

<210> SEQ ID NO 399
<211> LENGTH: 7
<212> TYPE: PRT
<213> ORGANISM: artificial
<220> FEATURE:
<223> OTHER INFORMATION: EF-loop sequence AA198ff

<400> SEQUENCE: 399

Asp Gln Thr Arg Trp Arg Arg

```
1               5


<210> SEQ ID NO 400
<211> LENGTH: 7
<212> TYPE: PRT
<213> ORGANISM: artificial
<220> FEATURE:
<223> OTHER INFORMATION: EF-loop sequence AA198ff

<400> SEQUENCE: 400

Lys Lys Lys Glu Ile Lys Lys
1               5


<210> SEQ ID NO 401
<211> LENGTH: 7
<212> TYPE: PRT
<213> ORGANISM: artificial
<220> FEATURE:
<223> OTHER INFORMATION: EF-loop sequence AA198ff

<400> SEQUENCE: 401

Lys Lys Asn Lys Leu Lys Lys
1               5


<210> SEQ ID NO 402
<211> LENGTH: 7
<212> TYPE: PRT
<213> ORGANISM: artificial
<220> FEATURE:
<223> OTHER INFORMATION: EF-loop sequence AA198ff

<400> SEQUENCE: 402

Pro Trp Trp Gln Phe Arg Gln
1               5


<210> SEQ ID NO 403
<211> LENGTH: 12
<212> TYPE: PRT
<213> ORGANISM: artificial
<220> FEATURE:
<223> OTHER INFORMATION: EF-loop sequence AA198ff

<400> SEQUENCE: 403

Asp Gln Ser Lys Leu Ser Ser Leu Arg Trp Lys Lys
1               5                   10


<210> SEQ ID NO 404
<211> LENGTH: 7
<212> TYPE: PRT
<213> ORGANISM: artificial
<220> FEATURE:
<223> OTHER INFORMATION: EF-loop sequence AA198ff

<400> SEQUENCE: 404

Pro Asn Glu Lys Leu Lys Lys
1               5


<210> SEQ ID NO 405
<211> LENGTH: 7
<212> TYPE: PRT
<213> ORGANISM: artificial
<220> FEATURE:
<223> OTHER INFORMATION: EF-loop sequence AA198ff

<400> SEQUENCE: 405

Pro Leu Ser Arg Trp Lys Arg
1               5
```

<210> SEQ ID NO 406
<211> LENGTH: 7
<212> TYPE: PRT
<213> ORGANISM: artificial
<220> FEATURE:
<223> OTHER INFORMATION: EF-loop sequence AA198ff

<400> SEQUENCE: 406

Thr Gln Asn Gln Ile Lys Lys
1               5

<210> SEQ ID NO 407
<211> LENGTH: 7
<212> TYPE: PRT
<213> ORGANISM: artificial
<220> FEATURE:
<223> OTHER INFORMATION: EF-loop sequence AA198ff

<400> SEQUENCE: 407

Asp Arg Glu Arg Trp Arg Arg
1               5

<210> SEQ ID NO 408
<211> LENGTH: 7
<212> TYPE: PRT
<213> ORGANISM: artificial
<220> FEATURE:
<223> OTHER INFORMATION: EF-loop sequence AA198ff

<400> SEQUENCE: 408

Ala Arg Ser Arg Trp Arg Lys
1               5

<210> SEQ ID NO 409
<211> LENGTH: 7
<212> TYPE: PRT
<213> ORGANISM: artificial
<220> FEATURE:
<223> OTHER INFORMATION: EF-loop sequence AA198ff

<400> SEQUENCE: 409

Pro Lys Lys Arg Leu Arg Arg
1               5

<210> SEQ ID NO 410
<211> LENGTH: 7
<212> TYPE: PRT
<213> ORGANISM: artificial
<220> FEATURE:
<223> OTHER INFORMATION: EF-loop sequence AA198ff

<400> SEQUENCE: 410

Lys Asn Lys Lys Arg Lys Lys
1               5

<210> SEQ ID NO 411
<211> LENGTH: 7
<212> TYPE: PRT
<213> ORGANISM: artificial
<220> FEATURE:
<223> OTHER INFORMATION: EF-loop sequence AA198ff

<400> SEQUENCE: 411

Asn Thr Lys Lys Leu Lys Lys
1               5

<210> SEQ ID NO 412
<211> LENGTH: 7
<212> TYPE: PRT
<213> ORGANISM: artificial
<220> FEATURE:
<223> OTHER INFORMATION: EF-loop sequence AA198ff

<400> SEQUENCE: 412

Asn Arg Lys Arg Ile Arg Lys
1               5

<210> SEQ ID NO 413
<211> LENGTH: 7
<212> TYPE: PRT
<213> ORGANISM: artificial
<220> FEATURE:
<223> OTHER INFORMATION: EF-loop sequence AA198ff

<400> SEQUENCE: 413

Ser Arg Lys Arg Phe Arg Ser
1               5

<210> SEQ ID NO 414
<211> LENGTH: 7
<212> TYPE: PRT
<213> ORGANISM: artificial
<220> FEATURE:
<223> OTHER INFORMATION: EF-loop sequence AA198ff

<400> SEQUENCE: 414

Pro Phe Arg Arg Trp Val Lys
1               5

<210> SEQ ID NO 415
<211> LENGTH: 7
<212> TYPE: PRT
<213> ORGANISM: artificial
<220> FEATURE:
<223> OTHER INFORMATION: EF-loop sequence AA198ff

<400> SEQUENCE: 415

Asn Lys Lys Lys Lys Lys Lys
1               5

<210> SEQ ID NO 416
<211> LENGTH: 7
<212> TYPE: PRT
<213> ORGANISM: artificial
<220> FEATURE:
<223> OTHER INFORMATION: EF-loop sequence AA198ff

<400> SEQUENCE: 416

Asn Gly Lys Arg Leu His Ser
1               5

<210> SEQ ID NO 417
<211> LENGTH: 7
<212> TYPE: PRT
<213> ORGANISM: artificial
<220> FEATURE:
<223> OTHER INFORMATION: EF-loop sequence AA198ff

<400> SEQUENCE: 417

Pro Lys Trp Leu Trp His Gln
1               5

<210> SEQ ID NO 418
<211> LENGTH: 7
<212> TYPE: PRT
<213> ORGANISM: artificial
<220> FEATURE:
<223> OTHER INFORMATION: EF-loop sequence AA198ff

<400> SEQUENCE: 418

Pro Trp Trp Lys His His Val
1               5

<210> SEQ ID NO 419
<211> LENGTH: 7
<212> TYPE: PRT
<213> ORGANISM: artificial
<220> FEATURE:
<223> OTHER INFORMATION: EF-loop sequence AA198ff

<400> SEQUENCE: 419

Pro Asn Trp Lys Tyr Gln Trp
1               5

<210> SEQ ID NO 420
<211> LENGTH: 7
<212> TYPE: PRT
<213> ORGANISM: artificial
<220> FEATURE:
<223> OTHER INFORMATION: EF-loop sequence AA198ff

<400> SEQUENCE: 420

Pro Gln Arg Lys Val Ala Pro
1               5

<210> SEQ ID NO 421
<211> LENGTH: 7
<212> TYPE: PRT
<213> ORGANISM: artificial
<220> FEATURE:
<223> OTHER INFORMATION: EF-loop sequence AA198ff

<400> SEQUENCE: 421

Pro Trp Tyr Lys Val Leu Met
1               5

<210> SEQ ID NO 422
<211> LENGTH: 7
<212> TYPE: PRT
<213> ORGANISM: artificial
<220> FEATURE:
<223> OTHER INFORMATION: EF-loop sequence AA198ff

<400> SEQUENCE: 422

Asp Arg Lys Trp Trp Thr Phe
1               5

<210> SEQ ID NO 423
<211> LENGTH: 7
<212> TYPE: PRT
<213> ORGANISM: artificial
<220> FEATURE:
<223> OTHER INFORMATION: EF-loop sequence AA198ff

<400> SEQUENCE: 423

Pro Arg His Glu Trp Val Met
1               5

<210> SEQ ID NO 424

<211> LENGTH: 7
<212> TYPE: PRT
<213> ORGANISM: artificial
<220> FEATURE:
<223> OTHER INFORMATION: EF-loop sequence AA198ff

<400> SEQUENCE: 424

Pro Trp Ser Arg Trp Met Gln
1               5

<210> SEQ ID NO 425
<211> LENGTH: 7
<212> TYPE: PRT
<213> ORGANISM: artificial
<220> FEATURE:
<223> OTHER INFORMATION: EF-loop sequence AA198ff

<400> SEQUENCE: 425

Ser Arg Ala Arg Trp Leu His
1               5

<210> SEQ ID NO 426
<211> LENGTH: 12
<212> TYPE: PRT
<213> ORGANISM: artificial
<220> FEATURE:
<223> OTHER INFORMATION: EF-loop sequence AA198ff

<400> SEQUENCE: 426

Asn Arg Ser Arg Leu His Gly Asn Arg Trp Arg Arg
1               5                   10

<210> SEQ ID NO 427
<211> LENGTH: 5473
<212> TYPE: DNA
<213> ORGANISM: artificial
<220> FEATURE:
<223> OTHER INFORMATION: plasmid pYD1dX_dCH1dCH3_Fcab_wt

<400> SEQUENCE: 427
acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgcttcagt tttagcacag gaactgacaa 600
ctatatgcga gcaaatcccc tcaccaactt tagaatcgac gccgtactct ttgtcaacga 660
ctactatttt ggccaacggg aaggcaatgc aaggagtttt tgaatattac aaatcagtaa 720
cgtttgtcag taattgcggt tctcacccct caacaactag caaaggcagc cccataaaca 780
cacagtatgt ttttaagctt ctgcaggcta gtggtggtgg tggttctggt ggtggtggtt 840
ctggtggtgg tggttctgct agcatgactg gtggacagca aatgggtcgg gatctgtacg 900
acgatgacga taaggtacca ggatccgagc ccaagagcag cgacaagaca cacacgtgtc 960

```
ccccatgtcc cgcccctgag ctgctgggcg gcccttccgt gttcctgttc cctcccaagc   1020
caaaggacac cctgatgatc tcccggaccc ctgaggtgac ctgtgtggtg gtggacgtga   1080
gccacgagga cccagaggtg aagttcaact ggtacgtgga cggcgtggag gtgcacaacg   1140
ccaagaccaa gcctagagag gagcagtaca acagcaccta ccgcgtggtg agcgtgctga   1200
ccgtgctgca ccaggattgg ctgaatggca aggagtacaa gtgcaaggtg agcaacaagg   1260
ccctgcctgc ccccatcgag aagaccatct ccaaggccaa gggccagcct cgagaaggta   1320
agcctatccc taaccctctc ctcggtctcg attctacgcg taccggtcat catcaccatc   1380
accattgagt ttaaacccgc tgatctgata acaacagtgt agcggccgct cgatcgagtc   1440
tagagggccc ttcgaaggta agcctatccc taaccctctc ctcggtctcg attctacgcg   1500
taccggtcat catcaccatc accattgagt ttaaacccgc tgatctgata acaacagtgt   1560
agatgtaaca aaatcgactt tgttcccact gtacttttag ctcgtacaaa atacaatata   1620
cttttcattt ctccgtaaac aacatgtttt cccatgtaat atccttttct atttttcgtt   1680
ccgttaccaa ctttacacat actttatata gctattcact tctatacact aaaaaactaa   1740
gacaatttta attttgctgc ctgccatatt tcaatttgtt ataaattcct ataatttatc   1800
ctattagtag ctaaaaaaag atgaatgtga atcgaatcct aagagaattg ggcaagtgca   1860
caaacaatac ttaaataaat actactcagt aataacctat ttcttagcat ttttgacgaa   1920
atttgctatt ttgttagagt cttttacacc atttgtctcc acacctccgc ttacatcaac   1980
accaataacg ccatttaatc taagcgcatc accaacattt tctggcgtca gtccaccagc   2040
taacataaaa tgtaagctct cggggctctc ttgccttcca acccagtcag aaatcgagtt   2100
ccaatccaaa agttcacctg tcccacctgc ttctgaatca aacaagggaa taaacgaatg   2160
aggtttctgt gaagctgcac tgagtagtat gttgcagtct tttggaaata cgagtctttt   2220
aataactggc aaaccgagga actcttggta ttcttgccac gactcatctc cgtgcagttg   2280
gacgatatca atgccgtaat cattgaccag agccaaaaca tcctccttag gttgattacg   2340
aaacacgcca accaagtatt tcggagtgcc tgaactattt ttatatgctt ttacaagact   2400
tgaaattttc cttgcaataa ccgggtcaat tgttctcttt ctattgggca cacatataat   2460
acccagcaag tcagcatcgg aatctagagc acattctgcg gcctctgtgc tctgcaagcc   2520
gcaaactttc accaatggac cagaactacc tgtgaaatta ataacagaca tactccaagc   2580
tgcctttgtg tgcttaatca cgtatactca cgtgctcaat agtcaccaat gccctccctc   2640
ttggccctct ccttttcttt tttcgaccga atttcttgaa gacgaaaggg cctcgtgata   2700
cgcctatttt tataggttaa tgtcatgata ataatggttt cttaggacgg atcgcttgcc   2760
tgtaacttac acgcgcctcg tatcttttaa tgatggaata atttgggaat ttactctgtg   2820
tttatttatt tttatgtttt gtatttggat tttagaaagt aaataaagaa ggtagaagag   2880
ttacggaatg aagaaaaaaa aataaacaaa ggtttaaaaa atttcaacaa aaagcgtact   2940
ttacatatat atttattaga caagaaaagc agattaaata gatatacatt cgattaacga   3000
taagtaaaat gtaaaatcac aggattttcg tgtgtggtct tctacacaga caagatgaaa   3060
caattcggca ttaatacctg agagcaggaa gagcaagata aaaggtagta tttgttggcg   3120
atccccctag agtcttttac atcttcggaa aacaaaaact atttttttctt taatttcttt   3180
ttttactttc tatttttaat ttatatattt atattaaaaa atttaaatta taattatttt   3240
tatagcacgt gatgaaaagg acccaggtgg cacttttcgg ggaaatgtgc gcggaacccc   3300
tatttgttta tttttctaaa tacattcaaa tatgtatccg ctcatgagac aataaccctg   3360
```

```
ataaatgctt caataatatt gaaaaaggaa gagtatgagt attcaacatt tccgtgtcgc   3420
ccttattccc ttttttgcgg cattttgcct tcctgttttt gctcacccag aaacgctggt   3480
gaaagtaaaa gatgctgaag atcagttggg tgcacgagtg ggttacatcg aactggatct   3540
caacagcggt aagatccttg agagttttcg ccccgaagaa cgttttccaa tgatgagcac   3600
ttttaaagtt ctgctatgtg gcgcggtatt atcccgtgtt gacgccgggc aagagcaact   3660
cggtcgccgc atacactatt ctcagaatga cttggttgag tactcaccag tcacagaaaa   3720
gcatcttacg gatggcatga cagtaagaga attatgcagt gctgccataa ccatgagtga   3780
taacactgcg gccaacttac ttctgacaac gatcggagga ccgaaggagc taaccgcttt   3840
tttgcacaac atgggggatc atgtaactcg ccttgatcgt tgggaaccgg agctgaatga   3900
agccatacca aacgacgagc gtgacaccac gatgcctgta gcaatggcaa caacgttgcg   3960
caaactatta actggcgaac tacttactct agcttcccgg caacaattaa tagactggat   4020
ggaggcggat aaagttgcag gaccacttct gcgctcggcc cttccggctg gctggtttat   4080
tgctgataaa tctggagccg gtgagcgtgg gtctcgcggt atcattgcag cactggggcc   4140
agatggtaag ccctcccgta tcgtagttat ctacacgacg ggcagtcagg caactatgga   4200
tgaacgaaat agacagatcg ctgagatagg tgcctcactg attaagcatt ggtaactgtc   4260
agaccaagtt tactcatata tactttagat tgatttaaaa cttcattttt aatttaaaag   4320
gatctaggtg aagatccttt ttgataatct catgaccaaa atcccttaac gtgagttttc   4380
gttccactga gcgtcagacc ccgtagaaaa gatcaaagga tcttcttgag atcctttttt   4440
tctgcgcgta atctgctgct tgcaaacaaa aaaaccaccg ctaccagcgg tggtttgttt   4500
gccggatcaa gagctaccaa ctctttttcc gaaggtaact ggcttcagca gagcgcagat   4560
accaaatact gtccttctag tgtagccgta gttaggccac cacttcaaga actctgtagc   4620
accgcctaca tacctcgctc tgctaatcct gttaccagtg gctgctgcca gtggcgataa   4680
gtcgtgtctt accgggttgg actcaagacg atagttaccg gataaggcgc agcggtcggg   4740
ctgaacgggg ggttcgtgca cacagcccag cttggagcga acgacctaca ccgaactgag   4800
atacctacag cgtgagcatt gagaaagcgc cacgcttccc gaagggagaa aggcggacag   4860
gtatccggta agcggcaggg tcggaacagg agagcgcacg agggagcttc cagggggaaa   4920
cgcctggtat ctttatagtc ctgtcgggtt tcgccacctc tgacttgagc gtcgattttt   4980
gtgatgctcg tcaggggggc ggagcctatg gaaaaacgcc agcaacgcgg cctttttacg   5040
gttcctggcc ttttgctggc cttttgctca catgttcttt cctgcgttat cccctgattc   5100
tgtggataac cgtattaccg cctttgagtg agctgatacc gctcgccgca gccgaacgac   5160
cgagcgcagc gagtcagtga gcgaggaagc ggaagagcgc ccaatacgca aaccgcctct   5220
ccccgcgcgt tggccgattc attaatgcag ctggcacgac aggtttcccg actggaaagc   5280
gggcagtgag cgcaacgcaa ttaatgtgag ttacctcact cattaggcac cccaggcttt   5340
acactttatg cttccggctc ctatgttgtg tggaattgtg agcggataac aatttcacac   5400
aggaaacagc tatgaccatg attacgccaa gctcggaatt aaccctcact aaagggaaca   5460
aaagctggct agt                                                       5473
```

<210> SEQ ID NO 428
<211> LENGTH: 5677
<212> TYPE: DNA
<213> ORGANISM: artificial
<220> FEATURE:

<223> OTHER INFORMATION: PYD1dX_dCH1_Fcab_wt

<400> SEQUENCE: 428
acggattaga agccgccgag cgggtgacag ccctccgaag gaagactctc ctccgtgcgt 60
cctcgtcttc accggtcgcg ttcctgaaac gcagatgtgc ctcgcgccgc actgctccga 120
acaataaaga ttctacaata ctagctttta tggttatgaa gaggaaaaat tggcagtaac 180
ctggccccac aaaccttcaa atgaacgaat caaattaaca accataggat gataatgcga 240
ttagtttttt agccttattt ctggggtaat taatcagcga agcgatgatt tttgatctat 300
taacagatat ataaatgcaa aaactgcata accactttaa ctaatacttt caacattttc 360
ggtttgtatt acttcttatt caaatgtaat aaaagtatca acaaaaaatt gttaatatac 420
ctctatactt taacgtcaag gagaaaaaac cccggatcgg actactagca gctgtaatac 480
gactcactat agggaatatt aagctaattc tacttcatac attttcaatt aagatgcagt 540
tacttcgctg tttttcaata ttttctgtta ttgcttcagt tttagcacag gaactgacaa 600
ctatatgcga gcaaatcccc tcaccaactt tagaatcgac gccgtactct ttgtcaacga 660
ctactatttt ggccaacggg aaggcaatgc aaggagtttt tgaatattac aaatcagtaa 720
cgtttgtcag taattgcggt tctcacccct caacaactag caaaggcagc cccataaaca 780
cacagtatgt ttttaagctt ctgcaggcta gtggtggtgg tggttctggt ggtggtggtt 840
ctggtggtgg tggttctgct agcatgactg gtggacagca aatgggtcgg gatctgtacg 900
acgatgacga taaggtacca ggatccgagc ccaagagcag cgacaagaca cacacgtgtc 960
ccccatgtcc cgcccctgag ctgctgggcg gcccttccgt gttcctgttc cctcccaagc 1020
caaaggacac cctgatgatc tcccggaccc ctgaggtgac ctgtgtggtg gtggacgtga 1080
gccacgagga cccagaggtg aagttcaact ggtacgtgga cggcgtggag gtgcacaacg 1140
ccaagaccaa gcctagagag gagcagtaca acagcaccta ccgcgtggtg agcgtgctga 1200
ccgtgctgca ccaggattgg ctgaatggca aggagtacaa gtgcaaggtg agcaacaagg 1260
ccctgcctgc ccccatcgag aagaccatct ccaaggccaa gggccagcct cgagaaccac 1320
aggtgtacac cctgccccca tcccgggatg agctgaccaa gaaccaggtc agcctgacct 1380
gcctggtcaa aggcttctat cccagcgaca tcgccgtgga gtgggagagc aatgggcagc 1440
cggagaacaa ctacaagacc acgcctcccg tgctggactc cgacggctcc ttcttcctct 1500
acagcaagct caccgtggac aagagcaggt ggcagcaggg gaacgtcttc tcatgctccg 1560
tgatgcatga ggctctgcac aaccactaca cacagaagag cctctccctg tctccgggta 1620
aatgagcggc cgctcgatcg agtctagagg gcccttcgaa ggtaagccta tccctaaccc 1680
tctcctcggt ctcgattcta cgcgtaccgg tcatcatcac catcaccatt gagtttaaac 1740
ccgctgatct gataacaaca gtgtagatgt aacaaaatcg actttgttcc cactgtactt 1800
ttagctcgta caaaatacaa tatacttttc atttctccgt aaacaacatg ttttcccatg 1860
taatatcctt ttctattttt cgttccgtta ccaactttac acatacttta tatagctatt 1920
cacttctata cactaaaaaa ctaagacaat tttaattttg ctgcctgcca tatttcaatt 1980
tgttataaat tcctataatt tatcctatta gtagctaaaa aaagatgaat gtgaatcgaa 2040
tcctaagaga attgggcaag tgcacaaaca atacttaaat aaatactact cagtaataac 2100
ctatttctta gcatttttga cgaaatttgc tattttgtta gagtctttta caccatttgt 2160
ctccacacct ccgcttacat caacaccaat aacgccattt aatctaagcg catcaccaac 2220
attttctggc gtcagtccac cagctaacat aaaatgtaag ctctcggggc tctcttgcct 2280

```
tccaacccag tcagaaatcg agttccaatc caaaagttca cctgtcccac ctgcttctga   2340
atcaaacaag ggaataaacg aatgaggttt ctgtgaagct gcactgagta gtatgttgca   2400
gtcttttgga aatacgagtc ttttaataac tggcaaaccg aggaactctt ggtattcttg   2460
ccacgactca tctccgtgca gttggacgat atcaatgccg taatcattga ccagagccaa   2520
aacatcctcc ttaggttgat tacgaaacac gccaaccaag tatttcggag tgcctgaact   2580
atttttatat gcttttacaa gacttgaaat tttccttgca ataaccgggt caattgttct   2640
ctttctattg ggcacacata taatacccag caagtcagca tcggaatcta gagcacattc   2700
tgcggcctct gtgctctgca agccgcaaac tttcaccaat ggaccagaac tacctgtgaa   2760
attaataaca gacatactcc aagctgcctt tgtgtgctta atcacgtata ctcacgtgct   2820
caatagtcac caatgccctc cctcttggcc ctctcctttt cttttttcga ccgaatttct   2880
tgaagacgaa agggcctcgt gatacgccta tttttatagg ttaatgtcat gataataatg   2940
gtttcttagg acggatcgct tgcctgtaac ttacacgcgc ctcgtatctt ttaatgatgg   3000
aataatttgg gaatttactc tgtgtttatt tatttttatg ttttgtattt ggattttaga   3060
aagtaaataa agaaggtaga agagttacgg aatgaagaaa aaaaaataaa caaaggttta   3120
aaaaatttca acaaaaagcg tactttacat atatatttat tagacaagaa aagcagatta   3180
aatagatata cattcgatta acgataagta aaatgtaaaa tcacaggatt ttcgtgtgtg   3240
gtcttctaca cagacaagat gaaacaattc ggcattaata cctgagagca ggaagagcaa   3300
gataaaaggt agtatttgtt ggcgatcccc ctagagtctt ttacatcttc ggaaaacaaa   3360
aactattttt tctttaattt ctttttttac tttctatttt taatttatat atttatatta   3420
aaaaatttaa attataatta tttttatagc acgtgatgaa aaggacccag gtggcacttt   3480
tcggggaaat gtgcgcggaa cccctatttg tttatttttc taaatacatt caaatatgta   3540
tccgctcatg agacaataac cctgataaat gcttcaataa tattgaaaaa ggaagagtat   3600
gagtattcaa catttccgtg tcgcccttat tccctttttt gcggcatttt gccttcctgt   3660
ttttgctcac ccagaaacgc tggtgaaagt aaaagatgct gaagatcagt tgggtgcacg   3720
agtgggttac atcgaactgg atctcaacag cggtaagatc cttgagagtt ttcgccccga   3780
agaacgtttt ccaatgatga gcacttttaa agttctgcta tgtggcgcgg tattatcccg   3840
tgttgacgcc gggcaagagc aactcggtcg ccgcatacac tattctcaga atgacttggt   3900
tgagtactca ccagtcacag aaaagcatct tacggatggc atgacagtaa gagaattatg   3960
cagtgctgcc ataaccatga gtgataacac tgcggccaac ttacttctga caacgatcgg   4020
aggaccgaag gagctaaccg cttttttgca caacatgggg gatcatgtaa ctcgccttga   4080
tcgttgggaa ccggagctga atgaagccat accaaacgac gagcgtgaca ccacgatgcc   4140
tgtagcaatg gcaacaacgt tgcgcaaact attaactggc gaactactta ctctagcttc   4200
ccggcaacaa ttaatagact ggatggaggc ggataaagtt gcaggaccac ttctgcgctc   4260
ggcccttccg gctggctggt ttattgctga taaatctgga gccggtgagc gtgggtctcg   4320
cggtatcatt gcagcactgg ggccagatgg taagccctcc cgtatcgtag ttatctacac   4380
gacgggcagt caggcaacta tggatgaacg aaatagacag atcgctgaga taggtgcctc   4440
actgattaag cattggtaac tgtcagacca agtttactca tatatacttt agattgattt   4500
aaaacttcat ttttaattta aaaggatcta ggtgaagatc ctttttgata atctcatgac   4560
caaaatccct taacgtgagt tttcgttcca ctgagcgtca gaccccgtag aaaagatcaa   4620
```

aggatcttct tgagatcctt tttttctgcg cgtaatctgc tgcttgcaaa caaaaaaacc 4680
accgctacca gcggtggttt gtttgccgga tcaagagcta ccaactcttt ttccgaaggt 4740
aactggcttc agcagagcgc agataccaaa tactgtcctt ctagtgtagc cgtagttagg 4800
ccaccacttc aagaactctg tagcaccgcc tacatacctc gctctgctaa tcctgttacc 4860
agtggctgct gccagtggcg ataagtcgtg tcttaccggg ttggactcaa gacgatagtt 4920
accggataag gcgcagcggt cgggctgaac ggggggttcg tgcacacagc ccagcttgga 4980
gcgaacgacc tacaccgaac tgagatacct acagcgtgag cattgagaaa gcgccacgct 5040
tcccgaaggg agaaaggcgg acaggtatcc ggtaagcggc agggtcggaa caggagagcg 5100
cacgagggag cttccagggg ggaacgcctg gtatctttat agtcctgtcg ggtttcgcca 5160
cctctgactt gagcgtcgat ttttgtgatg ctcgtcaggg gggccgagcc tatggaaaaa 5220
cgccagcaac gcggcctttt tacggttcct ggccttttgc tggccttttg ctcacatgtt 5280
ctttcctgcg ttatcccctg attctgtgga taaccgtatt accgcctttg agtgagctga 5340
taccgctcgc cgcagccgaa cgaccgagcg cagcgagtca gtgagcgagg aagcggaaga 5400
gcgcccaata cgcaaaccgc ctctccccgc gcgttggccg attcattaat gcagctggca 5460
cgacaggttt cccgactgga aagcgggcag tgagcgcaac gcaattaatg tgagttacct 5520
cactcattag gcaccccagg ctttacactt tatgcttccg gctcctatgt tgtgtggaat 5580
tgtgagcgga taacaatttc acacaggaaa cagctatgac catgattacg ccaagctcgg 5640
aattaaccct cactaaaggg aacaaaagct ggctagt 5677

<210> SEQ ID NO 429
<211> LENGTH: 19
<212> TYPE: DNA
<213> ORGANISM: artificial
<220> FEATURE:
<223> OTHER INFORMATION: primer CH3seqs/2

<400> SEQUENCE: 429
aaggagtaca agtgcaagg 19

<210> SEQ ID NO 430
<211> LENGTH: 16
<212> TYPE: DNA
<213> ORGANISM: artificial
<220> FEATURE:
<223> OTHER INFORMATION: primer CDmut_back

<400> SEQUENCE: 430
gctctcccac tccacg 16

<210> SEQ ID NO 431
<211> LENGTH: 21
<212> TYPE: DNA
<213> ORGANISM: artificial
<220> FEATURE:
<223> OTHER INFORMATION: primer EFmut_back

<400> SEQUENCE: 431
cacggtgagc ttgctgtaga g 21

<210> SEQ ID NO 432
<211> LENGTH: 16
<212> TYPE: DNA
<213> ORGANISM: artificial
<220> FEATURE:
<223> OTHER INFORMATION: primer ABMUT5/2_back

<400> SEQUENCE: 432
ctcatcccgg gatggg 16

<210> SEQ ID NO 433
<211> LENGTH: 48
<212> TYPE: DNA
<213> ORGANISM: artificial
<220> FEATURE:
<223> OTHER INFORMATION: primer CDmut5cod_for
<220> FEATURE:
<221> NAME/KEY: misc_feature
<222> LOCATION: (16)..(30)
<223> OTHER INFORMATION: n is a, c, g, or t

<400> SEQUENCE: 433
gtggagtggg agagcnnnnn nnnnnnnnnn aacaactaca agaccacg 48

<210> SEQ ID NO 434
<211> LENGTH: 54
<212> TYPE: DNA
<213> ORGANISM: artificial
<220> FEATURE:
<223> OTHER INFORMATION: primer EFMUT7cod_for
<220> FEATURE:
<221> NAME/KEY: misc_feature
<222> LOCATION: (16)..(36)
<223> OTHER INFORMATION: n is a, c, g, or t

<400> SEQUENCE: 434
agcaagctca ccgtgnnnnn nnnnnnnnnn nnnnnnggga acgtcttctc atgc 54

<210> SEQ ID NO 435
<211> LENGTH: 54
<212> TYPE: DNA
<213> ORGANISM: artificial
<220> FEATURE:
<223> OTHER INFORMATION: primer EFMUT3+2_for
<220> FEATURE:
<221> NAME/KEY: misc_feature
<222> LOCATION: (16)..(24)
<223> OTHER INFORMATION: n is a, c, g, or t
<220> FEATURE:
<221> NAME/KEY: misc_feature
<222> LOCATION: (31)..(36)
<223> OTHER INFORMATION: n is a, c, g, or t

<400> SEQUENCE: 435
agcaagctca ccgtgnnnnn nnnnaggtgg nnnnnnggga acgtcttctc atgc 54

<210> SEQ ID NO 436
<211> LENGTH: 49
<212> TYPE: DNA
<213> ORGANISM: artificial
<220> FEATURE:
<223> OTHER INFORMATION: primer ABMUT5 (wt)_for
<220> FEATURE:
<221> NAME/KEY: misc_feature
<222> LOCATION: (16)..(30)
<223> OTHER INFORMATION: n is a, c, g, or t

<400> SEQUENCE: 436
ccatcccggg atgagnnnnn nnnnnnnnnn gtcagcctga cctgcctgg 49

<210> SEQ ID NO 437
<211> LENGTH: 17
<212> TYPE: DNA
<213> ORGANISM: artificial
<220> FEATURE:

```
<223> OTHER INFORMATION: primer CH3seqAS

<400> SEQUENCE: 437

tagaatcgag accgagg                                                  17


<210> SEQ ID NO 438
<211> LENGTH: 19
<212> TYPE: DNA
<213> ORGANISM: artificial
<220> FEATURE:
<223> OTHER INFORMATION: primer YCH3.25rec.opt.for

<400> SEQUENCE: 438

accatctcca aggccaagg                                                19


<210> SEQ ID NO 439
<211> LENGTH: 18
<212> TYPE: DNA
<213> ORGANISM: artificial
<220> FEATURE:
<223> OTHER INFORMATION: primer Ych3.25rec.back

<400> SEQUENCE: 439

aagggccctc tagactcg                                                 18


<210> SEQ ID NO 440
<211> LENGTH: 105
<212> TYPE: PRT
<213> ORGANISM: artificial
<220> FEATURE:
<223> OTHER INFORMATION: cH3 constant domain sequence

<400> SEQUENCE: 440

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro
            100                 105


<210> SEQ ID NO 441
<211> LENGTH: 15
<212> TYPE: PRT
<213> ORGANISM: artificial
<220> FEATURE:
<223> OTHER INFORMATION: human IgG hinge

<400> SEQUENCE: 441

Glu Pro Lys Ser Cys Asp Lys Thr His Thr Cys Pro Pro Cys Pro
1               5                   10                  15


<210> SEQ ID NO 442
<211> LENGTH: 4
<212> TYPE: PRT
<213> ORGANISM: artificial
```

<220> FEATURE:
<223> OTHER INFORMATION: residues 1-4 of SEQ ID NO:10

<400> SEQUENCE: 442

Ser Pro Gly Lys
1

<210> SEQ ID NO 443
<211> LENGTH: 10
<212> TYPE: PRT
<213> ORGANISM: artificial
<220> FEATURE:
<223> OTHER INFORMATION: residues 8-17 of SEQ ID NO:10

<400> SEQUENCE: 443

Glu Gln Lys Leu Ile Ser Glu Glu Asp Leu
1               5                   10

<210> SEQ ID NO 444
<211> LENGTH: 4
<212> TYPE: PRT
<213> ORGANISM: artificial
<220> FEATURE:
<223> OTHER INFORMATION: residues 22-25 of SEQ ID NO:10

<400> SEQUENCE: 444

Thr Val Glu Ser
1

<210> SEQ ID NO 445
<211> LENGTH: 4
<212> TYPE: PRT
<213> ORGANISM: artificial
<220> FEATURE:
<223> OTHER INFORMATION: residues 18-21 of SEQ ID NO:10

<400> SEQUENCE: 445

Asn Gly Ala Ala
1

<210> SEQ ID NO 446
<211> LENGTH: 5
<212> TYPE: PRT
<213> ORGANISM: artificial
<220> FEATURE:
<223> OTHER INFORMATION: AB loop cH3 constant domain sequence

<400> SEQUENCE: 446

Leu Thr Lys Asn Gln
1               5

<210> SEQ ID NO 447
<211> LENGTH: 5
<212> TYPE: PRT
<213> ORGANISM: artificial
<220> FEATURE:
<223> OTHER INFORMATION: CD loop cH3 constant domain sequence

<400> SEQUENCE: 447

Asn Gly Gln Pro Glu
1               5

<210> SEQ ID NO 448
<211> LENGTH: 7
<212> TYPE: PRT
<213> ORGANISM: artificial
<220> FEATURE:

```
<223> OTHER INFORMATION: EF loop cH3 constant domain sequence

<400> SEQUENCE: 448

Asp Lys Ser Arg Trp Gln Gln
1               5
```